(12) United States Patent
Endo et al.

(10) Patent No.: US 8,993,129 B2
(45) Date of Patent: Mar. 31, 2015

(54) FLUORESCENCE AND DELAYED FLUORESCENCE-TYPE ORGANIC LIGHT-EMITTING MATERIAL AND ELEMENT

(75) Inventors: Ayataka Endo, Fukuoka (JP); Chihaya Adachi, Fukuoka (JP); Kazuaki Yoshimura, Kitakyushu (JP); Atsushi Kawada, Kitakyushu (JP); Hiroshi Miyazaki, Kitakyushu (JP); Takahiro Kai, Kitakyushu (JP)

(73) Assignees: Nippon Steel & Sumikin Chemical Co., Ltd., Tokyo (JP); Kyushu University, National University Corporation, Fukuoka (JP)

( * ) Notice: Subject to any disclaimer, the term of this patent is extended or adjusted under 35 U.S.C. 154(b) by 0 days.

(21) Appl. No.: 13/514,248

(22) PCT Filed: Dec. 2, 2010

(86) PCT No.: PCT/JP2010/071568
§ 371 (c)(1),
(2), (4) Date: Jun. 6, 2012

(87) PCT Pub. No.: WO2011/070963
PCT Pub. Date: Jun. 16, 2011

(65) Prior Publication Data
US 2012/0241732 A1    Sep. 27, 2012

(30) Foreign Application Priority Data

Dec. 7, 2009  (JP) .................................. 2009-277838
Feb. 25, 2010  (JP) .................................. 2010-040036

(51) Int. Cl.
| | | |
|---|---|---|
| H01L 51/54 | (2006.01) | |
| C09K 11/06 | (2006.01) | |
| H05B 33/10 | (2006.01) | |
| C09B 57/00 | (2006.01) | |
| H01L 51/00 | (2006.01) | |
| H01L 51/50 | (2006.01) | |

(52) U.S. Cl.
CPC ............... *H05B 33/10* (2013.01); *C09B 57/00* (2013.01); *C09K 11/06* (2013.01); *H01L 51/0072* (2013.01); *H01L 51/5012* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *Y10S 428/917* (2013.01)
USPC ...... 428/690; 428/917; 257/40; 257/E51.026; 313/504

(58) Field of Classification Search
None
See application file for complete search history.

(56) References Cited

U.S. PATENT DOCUMENTS

| | | | |
|---|---|---|---|
| 5,952,115 A | 9/1999 | Hu et al. | |
| 7,993,760 B2 * | 8/2011 | Komori et al. | ................. 428/690 |
| 8,008,657 B2 * | 8/2011 | Kai et al. | .......................... 257/40 |
| 8,013,330 B2 * | 9/2011 | Komori et al. | ................... 257/40 |
| 8,062,769 B2 * | 11/2011 | Kai et al. | ....................... 428/690 |
| 2002/0146589 A1 | 10/2002 | Akiyama et al. | |
| 2004/0150327 A1 † | 8/2004 | Kawai et al. | |
| 2007/0072001 A1 * | 3/2007 | Tsuboyama et al. | ........... 428/690 |
| 2008/0220285 A1 † | 9/2008 | Vestweber et al. | |
| 2009/0295276 A1 * | 12/2009 | Asari et al. | ...................... 313/504 |
| 2009/0302742 A1 | 12/2009 | Komori et al. | |
| 2010/0090209 A1 * | 4/2010 | Ikari et al. | ........................ 257/40 |

(Continued)

FOREIGN PATENT DOCUMENTS

| | | | |
|---|---|---|---|
| JP | 11-162650 A | 6/1999 | |
| JP | 2002-50483 A | 2/2002 | |

(Continued)

OTHER PUBLICATIONS

Thompson et al. Final report on Novel Materials for High Efficiency White Phosphorescent OLED. 17 pages. Date of publication: Oct. 31, 2008.*

(Continued)

*Primary Examiner* — Andrew K Bohaty
(74) *Attorney, Agent, or Firm* — Birch, Stewart, Kolasch & Birch, LLP

(57) ABSTRACT

Fluorescence-emitting material which improves luminous efficiency of an organic light-emitting element such as an organic EL element or an organic PL element and an organic light-emitting element using the fluorescence-emitting material. The fluorescence-emitting material includes a compound having an indolocarbazole skeleton represented by the following general formula (1), as defined in the specification.

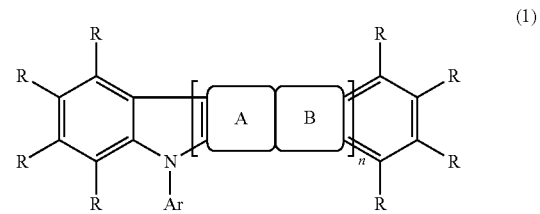

(1)

The organic light-emitting element includes an organic EL element including: a substrate; an anode; a cathode; and a light-emitting layer, the anode and the cathode being laminated on the substrate and the light-emitting layer being sandwiched between the anode and the cathode, in which the light-emitting layer includes: the organic light-emitting material; and as a host material, an organic compound having excited triplet energy higher than that of the organic light-emitting material.

16 Claims, 1 Drawing Sheet

(56) References Cited

U.S. PATENT DOCUMENTS

2010/0090593 A1     4/2010    Mori et al.
2010/0187977 A1†   7/2010    Kai et al.

FOREIGN PATENT DOCUMENTS

| | | |
|---|---|---|
| JP | 2004-214180 A | 7/2004 |
| JP | 2004-241374 A | 8/2004 |
| JP | 2006-24830 A | 1/2006 |
| JP | 2007217312 A † | 8/2007 |
| JP | 2008-545630 A | 12/2008 |
| JP | 2010-93181 A | 4/2010 |
| JP | 2010-114429 A | 5/2010 |
| WO | WO 2007/063754 A1 | 6/2007 |
| WO | WO 2007063796 A1 * | 6/2007 |

OTHER PUBLICATIONS

English translation of the International Preliminary Report on Patentability dated Jul. 5, 2012 for International Application No. PCT/JP2010/071568.

Response to Written Opinion, filed Aug. 25, 2011, in PCT/JP2010/071568 (English translation).

Endo et al., "Thermally Activated Delayed Flurescence from Sn4+-Porphyrin Complexes and Their Application to Organic Light-Emitting Diodes—A Novel Mechanism for Electroluminescence," Adv. Mater., 2009, No. 21, pp. 4802-4805.

Ayataka Endo et al, Thermally Activated Delayed Fluorescence from Sn4+-Porphyrin Complexes and Their Application to Organic Light . . . , Advanced Materials, 2009, 21, pp. 4802-4806.†

\* cited by examiner
† cited by third party

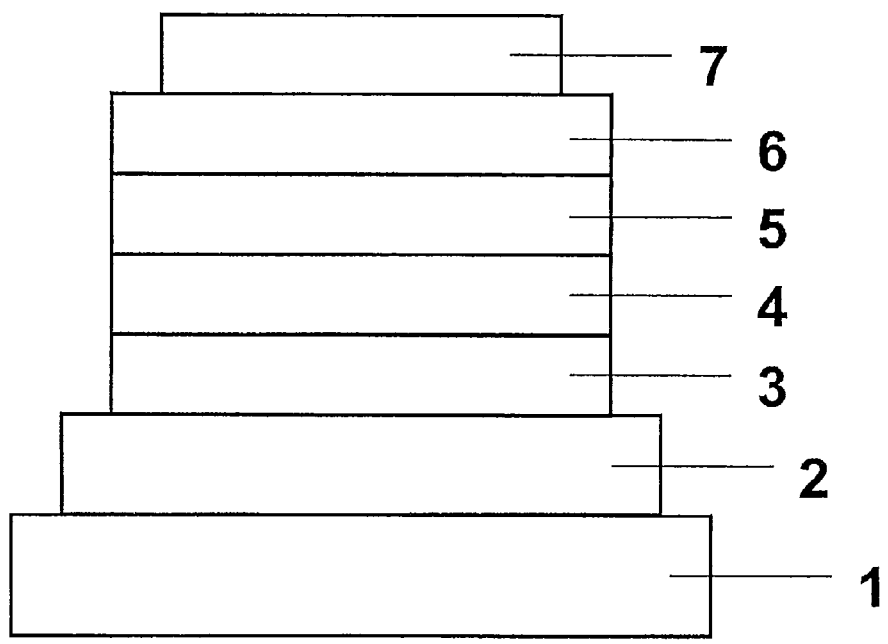

FLUORESCENCE AND DELAYED FLUORESCENCE-TYPE ORGANIC LIGHT-EMITTING MATERIAL AND ELEMENT

TECHNICAL FIELD

The present invention relates to a novel organic light-emitting material which emits fluorescence and delayed fluorescence and an organic light-emitting element using the organic light-emitting material.

BACKGROUND ART

In general, an organic light-emitting element has such a configuration that a thin film including an organic light-emitting material is formed on a substrate as its simplest structure. The organic light-emitting element is subjected to optical and electrical excitation so as to emit light. As a result, light is emitted from the organic light-emitting element. A photo luminescence element (PL element), in which optical excitation is performed, serves as the organic light-emitting element as long as at least the above-mentioned element configuration is satisfied. That is, the PL element utilizes a phenomenon in which an organic light-emitting material is excited by being irradiated with light depending on a light absorption wavelength of the organic light-emitting material, and light is then emitted as energy upon return from a conduction band to a valence band. On the other hand, an organic electroluminescence element (hereinafter, referred to as "organic EL element"), in which electrical excitation is performed, includes a light-emitting layer and a pair of counter electrodes sandwiching the light-emitting layer therebetween as its simplest structure. That is, the organic EL element utilizes a phenomenon in which electrons are injected from an cathode and holes are injected from an anode when an electric field is applied between both the electrodes, and light is emitted as energy upon return from a conduction band to a valence band of an energy level at which the electrons and the holes recombine with each other in a light-emitting layer.

In recent years, in particular, the organic EL element has increasingly been expected to find practical applications in energy-saving displays and lighting. In such circumstances, an organic EL element using an organic thin film has been developed actively. As a fluorescent organic compound to be used as a material for such organic EL element, there are known, for example, perylene, a thiazole derivative, a quinacridone derivative, rubrene, a benzophenone derivative, and a coumarin derivative. However, a conventional fluorescent organic compound involves the following fundamental problem in terms of excitation efficiency of the compound. That is, upon recombination of electrons and holes in a light-emitting layer of an organic EL element, singlet excitons as fluorescence-emitting excitons are formed only at a ratio of 25% of all excitons, yielding an internal quantum efficiency of 25% at the highest and a luminous efficiency of the organic EL element of about 5% at the highest (Non Patent Literature 1).

It has recently been found that when a specific porphyrin-based metal complex as a fluorescent organic compound is used as the light-emitting material for the organic EL element, the porphyrin-based metal complex emits thermally activated delayed fluorescence, leading to an improvement in exciton generation efficiency of the element (Patent Literatures 1 and 2 and Non Patent Literature 1).

Patent Literatures 1 and 2 disclose the following matters. In an organic EL element, carriers are injected from each of both electrodes, i.e., positive and negative electrodes to a light-emitting substance to generate a light-emitting substance in an excited state so as to emit light. It is generally said that in the case of a carrier injection type organic EL element, 25% of generated excitons are excited to an excited singlet state and the remaining 75% are excited to an excited triplet state. Accordingly, it is conceivable that utilization of light to be emitted from the excited triplet state, i.e., phosphorescence should provide higher energy use efficiency. However, in the phosphorescence, the excited triplet state has a long lifetime, and hence deactivation of energy occurs through saturation of an excited state and interactions with excitons in an excited triplet state, with the result that a high quantum yield is not obtained in many cases in general. In view of the foregoing, an organic EL element utilizing a material which emits delayed fluorescence is conceivable. A certain kind of fluorescent substance emits fluorescence via intersystem crossing or the like leading to energy transition to an excited triplet state and the subsequent reverse intersystem crossing to an excited singlet state through triplet-triplet annihilation or thermal energy absorption. In the organic EL element, it is considered that the latter material which emits thermally activated delayed fluorescence is particularly useful. In this case, when a delayed fluorescent material is utilized in the organic EL element, excitons in an excited singlet state emit fluorescence as per normal. On the other hand, excitons in an excited triplet state absorb heat produced from a device and undergo intersystem crossing to an excited singlet to emit fluorescence. The fluorescence in this case is light emission from the excited singlet and hence is light emission at the same wavelength as fluorescence. However, the fluorescence has a longer lifetime of light to be emitted, i.e., a longer emission lifetime than those of normal fluorescence and phosphorescence by virtue of reverse intersystem crossing from an excited triplet state to an excited singlet state, and hence is observed as fluorescence delayed as compared to the normal fluorescence and phosphorescence. This can be defined as delayed fluorescence. Through the use of such thermally activated type exciton transfer mechanism, i.e., through thermal energy absorption after carrier injection, the ratio of a compound in an excited singlet state, which has usually been generated only at a ratio of 25%, can be increased to 25% or more. The use of a compound which emits intense fluorescence and delayed fluoresce even at a low temperature of less than 100° C. results in sufficient intersystem crossing from an excited triplet state to an excited singlet state by means of heat of an device, contributing to emission of delayed fluorescence. Thus, the luminous efficiency is drastically improved.

Based on such hypothesis, Patent Literatures 1 and 2 and Non Patent Literature 1 each disclose that a specific porphyrin-based metal complex emits delayed fluorescence. However, none of the literatures discloses a relationship between the luminous efficiency and a difference between excited singlet energy and excited triplet energy and has any description suggesting the possibility of delayed fluorescence in an organic compound containing no metal atom other than the porphyrin-based metal complex. Further, the organic EL element according to each of the reports provides significantly lower luminous efficiency than a theoretical value. Thus, it is desired that an additional improvement be made in order to use the element in actual applications such as a display, a display element, a backlight, and lighting.

Patent Literatures 3 and 4 each disclose that a compound having an indolocarbazole skeleton is used in an organic EL element. However, none of the literatures discloses that delayed fluorescence is emitted in light emission of the compound itself.

CITATION LIST

Patent Literature

[PTL 1] JP 2004-241374 A
[PTL 2] JP 2006-24830 A
[PTL 3] WO 2007/063754 A1
[PTL 4] JP 11-162650 A

Non Patent Literature

[NPL 1] Adv. Funct. Mat. 21, 4802-4 806 (2009)

SUMMARY OF INVENTION

An object of the present invention is to provide a highly efficient and practically useful organic light-emitting element and an organic light-emitting material suitable for the organic light-emitting element.

The inventors of the invention have made extensive studies. As a result, the inventors have found an organic light-emitting material which emits fluorescence and delayed fluorescence and have also found that the use of the organic light-emitting material in an organic light-emitting element provides an organic PL element and a highly efficient organic EL element. Thus, the present invention has been completed.

The present invention relates to an organic light-emitting material which emits fluorescence and delayed fluorescence, the organic light-emitting material including a compound represented by the following general formula (1):

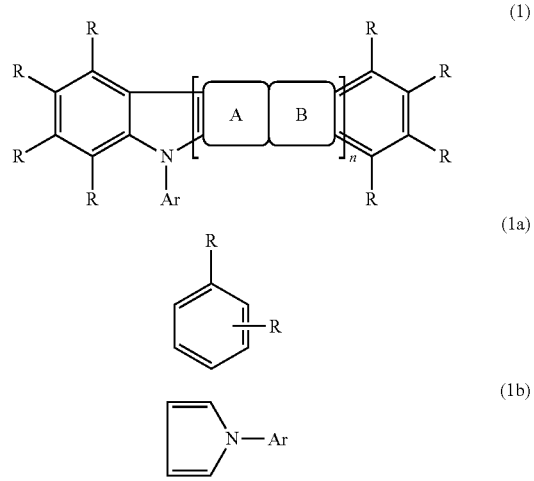

where: a ring A represents an aromatic ring represented by the formula (1a) to be fused with an adjacent ring at an arbitrary position; a ring B represents a heterocycle represented by the formula (1b) to be fused with an adjacent ring at an arbitrary position; Ar's in the formulae (1) and (1b) each independently represent an aromatic hydrocarbon group or an aromatic heterocyclic group; R's in the formulae (1) and (1a) each independently represent hydrogen or a monovalent substituent, provided that adjacent substituents may together form a ring; and n represents an integer of 1 or more and 4 or less.

The present invention also relates to an organic light-emitting material represented by the general formula (1), in which the organic light-emitting material which emits fluorescence and delayed fluorescence has a difference between excited singlet energy and excited triplet energy of 0.2 eV or less.

The present invention also relates to a fluorescence and delayed fluorescence type organic light-emitting element, including: a substrate; and at least one light-emitting layer including the organic light-emitting material, the light-emitting layer being provided on the substrate.

In the general formula (1), it is preferred to satisfy any one or more of the following requirements: n represents 1; at least one of Ar represents an aromatic heterocyclic group; and at least one of Ar represents a group represented by the following general formula (2):

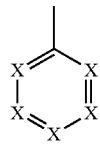

where: X's each independently represent N, C—H, or C—$Ar_1$ and at least one of X's represents N; and $Ar_1$'s each independently represent an aromatic hydrocarbon group or an aromatic heterocyclic group, provided that when X represents C—$Ar_1$, $Ar_1$ and a ring including X may have a side in common to form a fused ring.

The fluorescence and delayed fluorescence type organic light-emitting element includes an organic electroluminescence element including: a substrate; an anode; a cathode; and at least one light-emitting layer including the organic light-emitting material, the anode and the cathode being provided on the substrate and the light-emitting layer being sandwiched between the anode and the cathode.

The light-emitting layer of the fluorescence and delayed fluorescence type organic light-emitting element or the organic electroluminescence element advantageously includes: the organic light-emitting material; and a host material having at least any one of excited singlet energy and excited triplet energy higher than those of the organic light-emitting material.

Further, the organic light-emitting material formed of the compound represented by the general formula (1) is preferably a compound represented by the following general formula (11).

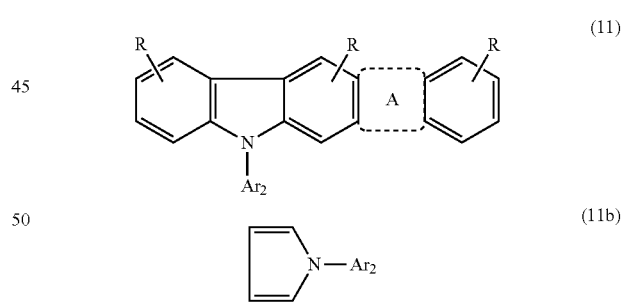

where: a ring A represents a heterocycle represented by the formula (11b) to be fused with an adjacent ring at an arbitrary position; $Ar_2$'s each independently represent an aromatic hydrocarbon group or an aromatic heterocyclic group; and R's each independently represent hydrogen or a monovalent substituent.

In the general formula (11), it is preferred that at least any one of $Ar_2$ represent an aromatic heterocyclic group or represent a group represented by the general formula (2).

BRIEF DESCRIPTION OF DRAWINGS

[FIG. 1] A schematic cross-sectional view illustrating an example of an organic EL element.

DESCRIPTION OF EMBODIMENTS

An organic light-emitting material of the present invention is a compound represented by the general formula (1) which emits fluorescence and delayed fluorescence. Further, the organic light-emitting material of the present invention is an organic light-emitting material which emits fluorescence and delayed fluorescence, the organic light-emitting material having a difference between excited singlet energy and excited triplet energy of 0.2 eV or less, preferably 0.15 ev or less.

The organic light-emitting material of the present invention is preferably a compound represented by the general formula (1) which emits fluorescence and delayed fluorescence, the compound having a difference between excited singlet energy and excited triplet energy of 0.2 eV or less. Further, the organic light-emitting material of the present invention is preferably an organic compound having no metal atom in the molecule.

The compound represented by the general formula (1) has an indolocarbazole skeleton or a skeleton in which one to three indole rings are further linked to and fused with an indolocarbazole ring. In addition, the compound has structure in which Ar is bonded to N in each of the indolocarbazole ring and the indole rings and R is bonded to each of rings free of N.

That is, in the general formula (1), a ring A is an aromatic ring represented by the formula (1a) and a ring B is a heterocycle represented by the formula (1b). Thus, a fused ring of the ring A and the ring B is an indole ring. In the fused ring of the ring A and the ring B, continuous fusion like "ring A-ring B-ring A-ring B" is possible and "n" combinations of "ring A-ring B" may exist. In the general formula (1), n represents an integer of 1 to 4.

The skeleton of the compound represented by the general formula (1) has a fused ring structure in which an indole ring, "n" fused rings of a ring A and a ring B, and a benzene ring starting from the left are linked together. For example, in the case of n=1, when a tricyclic fused ring constructed of the ring A and the indole ring on the left side of the ring A is regarded as a carbazole ring and a bicyclic fused ring constructed of the ring B and the benzene ring on the right side of the ring B is regarded as an indole ring, fusion can occur between the 1,2-position, 2,3-position, or 3,4-position of the carbazole ring and the 2,3-position or 3,2-position of the indole ring. Hence, there are isomers different in direction of N in the heterocycle represented by the formula (1b). Thus, in the case of n=1, the indolocarbazole ring, which is the skeleton of the compound represented by the general formula (1), includes five kinds of isomers represented by the following formulae (A) to (E). It should be noted that an increase in n leads town increase in the number of isomers, but the number of isomers is limited because a position at which fusion can occur is limited from the structural viewpoint.

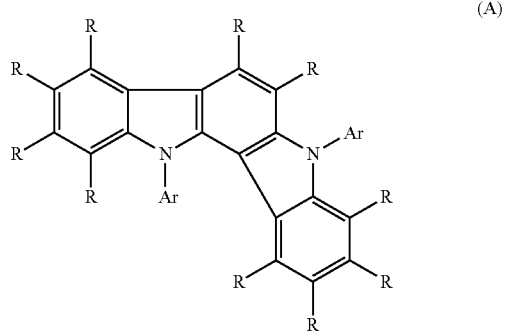
(A)

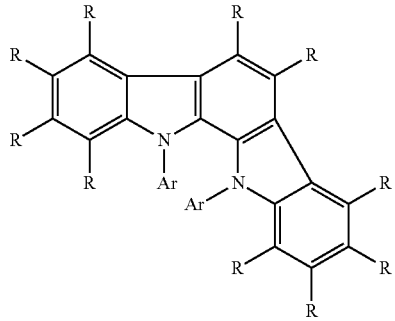
(B)

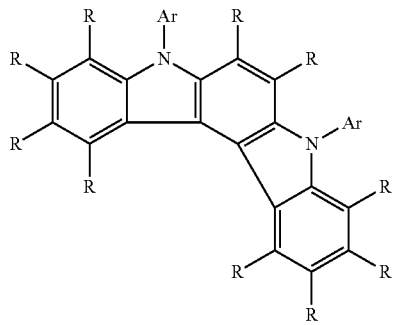
(C)

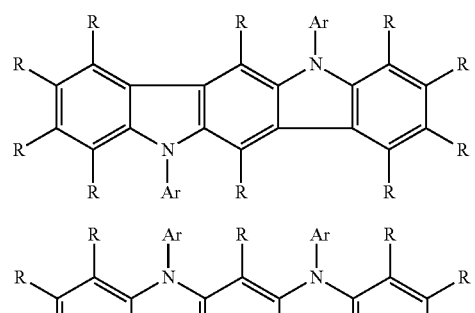
(D)

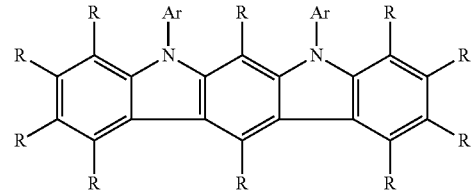
(E)

In the general formula (1) and the formula (1b), Ar's each independently represent an aromatic hydrocarbon group or an aromatic heterocyclic group, preferably an aromatic hydrocarbon group having 6 to 100 carbon atoms or an aromatic heterocyclic group having 3 to 100 carbon atoms, more preferably an aromatic hydrocarbon group having 5 to 50 carbon atoms or an aromatic heterocyclic group having 3 to 50 carbon atoms, still more preferably an aromatic hydrocarbon group having 6 to 50 carbon atoms or an aromatic heterocyclic group having 3 to 50 carbon atoms. When each of those aromatic hydrocarbon groups or aromatic heterocyclic groups has one or more substituents, the number of carbon atoms to be calculated includes the number of carbon atoms in each of those substituents.

Preferred examples of the aromatic hydrocarbon group or the aromatic heterocyclic group include groups each produced by removing one hydrogen atom from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, ovalene, corannulene, fulminene, anthanthrene, zethrene, terylene, naphthacenonaphthacene, truxene, furan, benzofuran, isobenzofuran, xanthene, oxanthrene, dibenzofuran, perixanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, indolocarbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, thebenidine, quindoline, quinindoline, acrindoline, phthaloperine, triphenodithiazine, triphenodioxazine, phenanthrazine, anthrazine, benzothiazole, benzoimidazole, benzooxazole, benzisooxazole, benzisothiazole, or an aromatic compound having a plurality of these aromatic rings linked together. More preferred examples thereof include groups each produced by removing one hydrogen atom from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, carbazole, indolocarbazole, or an aromatic compound having a plurality of these aromatic rings linked together. It should be noted that in the case of the group produced from each of the aromatic compounds having a plurality of aromatic rings linked together, the number of the aromatic rings to be linked together is preferably 2 to 10, more preferably 2 to 7 and the aromatic rings to be linked together may be identical to or different from each other. In that case, a bonding position at which Ar is bonded to N is not limited and may be a ring at the end portion or a ring at the central portion of the aromatic rings linked together. Further, in the case where Ar represents a group produced by removing one hydrogen atom from each of the aromatic compounds having a plurality of aromatic rings linked together, when an aromatic ring to be first bonded to N in the general formulae (1) and (1b) is an aromatic hydrocarbon ring, the group is included in an aromatic hydrocarbon group, and when an aromatic ring to be first bonded to N is an aromatic heterocycle, the group is included in an aromatic heterocyclic group. Herein, the aromatic ring is a collective term for an aromatic hydrocarbon ring and an aromatic heterocycle.

Herein, the group produced from a plurality of aromatic rings linked together is, for example, represented by each of the following formulae.

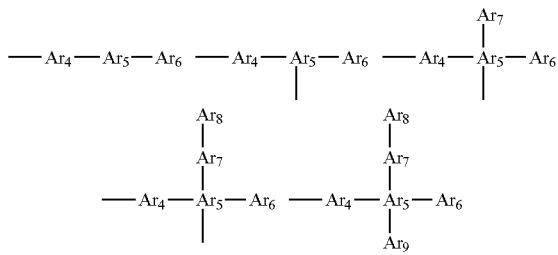

($Ar_4$ to $Ar_9$ each represent a substituted or unsubstituted aromatic ring.)

Specific examples of the group produced from a plurality of aromatic rings linked together include groups each produced by removing one hydrogen atom from biphenyl, terphenyl, bipyridine, bipyrimidine, bitriazine, terpyridine, bistriazylbenzene, dicarbazolylbenzene, carbazolylbiphenyl, dicarbazolylbiphenyl, indolocarbazolyltriazine, phenylterphenyl, carbazolylterphenyl, binaphthalene, phenylpyridine, phenylcarbazole, diphenylcarbazole, diphenylpyridine, phenylpyrimidine, diphenylpyrimidine, phenyltriazine, diphenyltriazine, phenylnaphthalene, diphenylnaphthalene, indolocarbazolylbenzene, indolocarbazolylpyridine, or indolocarbazolyltriazine.

The aromatic hydrocarbon group or the aromatic heterocyclic group may have a substituent and the total number of substituents is 1 to 10, preferably 1 to 6, more preferably 1 to 4. It should be noted that the group produced from an aromatic compound having a plurality of aromatic rings linked together may also have a substituent. Preferred examples of the substituent include an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, a diarylamino group having 12 to 24 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, a trialkylsilylalkynyl group having 5 to 20 carbon atoms, a cyano group, a nitro group, and a hydroxy group. More preferred examples of the substituent include a methyl group, an ethyl group, an n-propyl group, an i-propyl group, an n-butyl group, a t-butyl group, a methoxy group, an ethoxy group, an n-propoxy group, an i-propoxy group, and a diphenylamino group. When two or more substituents exist, the substituents may be identical to or different from each other.

At least one of Ar's in the general formulae (1) and (1b) represents preferably an aromatic heterocyclic group, more preferably a group represented by the general formula (2). Although details of the reasons why the groups are preferred are not clear, possible reasons are that when at least one aromatic heterocyclic group is bonded to N in the indolocarbazole skeleton represented by the general formula (1), an electronic state in the molecule becomes preferred for delayed fluorescence emission and an appropriate positional relationship is formed for the intermolecular conformation as well. As a result, it is estimated that the organic light-emitting material of the present invention efficiently emits delayed fluorescence and an element using the organic light-emitting material of the present invention can serve as a highly efficient organic light-emitting element.

In the general formula (2), X's each independently represent N, C—H, or C—$Ar_1$ and at least one of X's represents N. One to three N atoms are preferred, two or three N atoms are more preferred, and three N atoms are still more preferred.

Herein, when X's in the general formula (2) each represent C—$Ar_1$, $Ar_1$'s each independently represent an aromatic hydrocarbon group or an aromatic heterocyclic group, provided that $Ar_1$ and a ring including X may have a side in common to form a fused ring. Preferred specific examples of $Ar_1$ are the same as those of the aromatic hydrocarbon group or the aromatic heterocyclic group described for Ar. Preferred examples of the substituent are also the same as those of the substituent described for Ar.

Specific examples of the group represented by the general formula (2) include groups each produced from pyridine, pyrazine, pyrimidine, pyridazine, or triazine. Specific examples of the group in the case where $Ar_1$ and a ring including X have a side in common to form a fused ring in the general formula (2) include groups each produced by removing one hydrogen atom from indolizine, purine, quinolizine, isoquinoline, naphthyridine, phthalazine, quinazoline, quinoxaline, cinnoline, quinoline, pteridine, phenanthridine, acridine, perimidine, phenanthroline, phenazine, carboline, anthyridine, thebenidine, quindoline, quinindoline, acrindoline, or phthaloperine. Of those, groups each produced by removing one hydrogen atom from pyridine, pyrazine, pyrimidine, pyridazine, triazine, purine, quinolizine, naphthyridine, phthalazine, quinazoline, quinoxaline, cinnoline, pteridine, or anthyridine are preferred.

R's in the general formulae (1) and (1a) each independently represent hydrogen or a monovalent substituent. R may be exemplified by hydrogen or an alkyl group having 1 to 20 carbon atoms, an aralkyl group having 7 to 20 carbon atoms, an alkenyl group having 2 to 20 carbon atoms, an alkynyl group having 2 to 20 carbon atoms, a cyano group, a dialkylamino group having 2 to 20 carbon atoms, a diarylamino group having 12 to 20 carbon atoms, a diaralkylamino group having 12 to 20 carbon atoms, an amino group, a nitro group, an acyl group having 2 to 20 carbon atoms, an alkoxycarbonyl group having 2 to 20 carbon atoms, an alkoxy group having 1 to 20 carbon atoms, an alkylsulfonyl group having 1 to 20 carbon atoms, a hydroxy group, an amide group, a substituted or unsubstituted aromatic hydrocarbon group having 6 to 30 carbon atoms, a substituted or unsubstituted aromatic heterocyclic group having 3 to 30 carbon atoms, a haloalkyl group having 1 to 10 carbon atoms, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, or a trialkylsilylalkynyl group having 5 to 20 carbon atoms. R may be preferably exemplified by hydrogen, an alkyl group having 1 to 10 carbon atoms, an alkoxy group having 1 to 10 carbon atoms, an alkylthio group having 1 to 10 carbon atoms, an alkylamino group having 1 to 10 carbon atoms, an acyl group having 2 to 10 carbon atoms, an aralkyl group having 7 to 20 carbon atoms, a substituted or unsubstituted aromatic hydrocarbon group having 6 to 30 carbon atoms, or a substituted or unsubstituted aromatic six-membered heterocyclic group having 3 to 30 carbon atoms. R more preferably represents hydrogen or an alkyl group having 1 to 3 carbon atoms, an alkoxy group having 1 to 3 carbon atoms, an acyl group having 2 to 4 carbon atoms, a phenyl group, or a pyridyl group.

Of the compounds each represented by the general formula (1), a compound represented by the general formula (11) is given as a preferred compound. In the general formula (11), a ring A is a heterocycle represented by the formula (11b), which corresponds to the formula (1b) of the general formula (1), and $Ar_2$ corresponds to Ar of the general formula (1). Thus, from the descriptions thereof in the general formula (1), the general formula (11) and the formula (11b) are understood.

Of the compounds each represented by the general formula (1), compounds represented by the following general formulae (3) to (8) are given as preferred compounds.

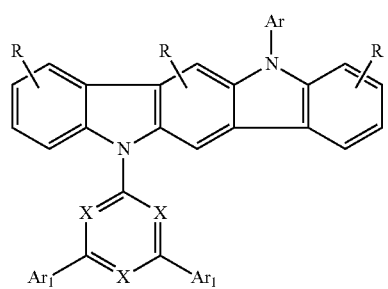

(3)

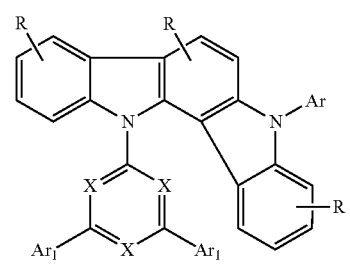

(4)

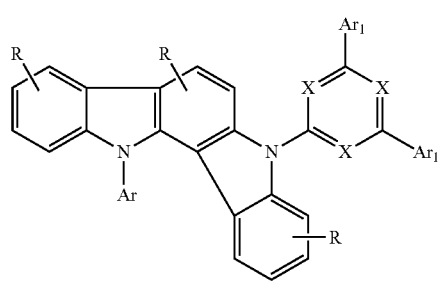

(5)

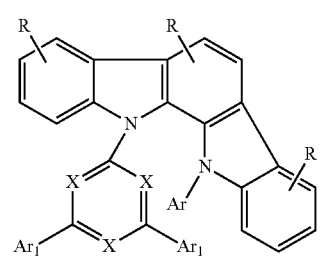

(6)

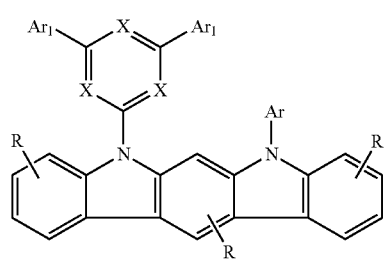

(7)

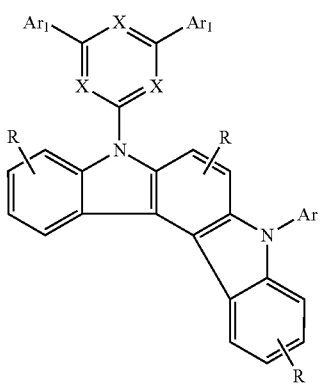

(8)

In the general formulae (3) to (8), X's and $Ar_1$'s have the same meanings as those in the general formula (2). Further, Ar's have the same meanings as that in the general formula (1). Of the compounds represented by the general formulae (3) to (8), a case where all X's each represent N is given as a more preferred compound.

Ar's and R's in the general formulae (3) to (8) have the same meanings as Ar's and R's in the general formula (1) and the formulae (1a) and (1b). Further, $Ar_1$'s have the same meanings as $Ar_1$ in the case where X's in the general formula (2) each represent C—$Ar_1$. Preferred examples of Ar, $Ar_1$, and R are also the same as described above. It should be noted that the phrase "have the same meanings" means that definitions of those symbols are identical to each other, and when a plurality of those symbols exist, the meaning of each of the symbols may vary in the range of the definitions.

The compound represented by the general formula (1) of the present invention may be easily manufactured by a known method. For example, a compound represented by the general formula (6) where Ar represents a phenyl group and all X's each represent N may be manufactured in accordance with the following reaction formula with reference to the synthesis example shown in Synlett, 2005(1), 42.

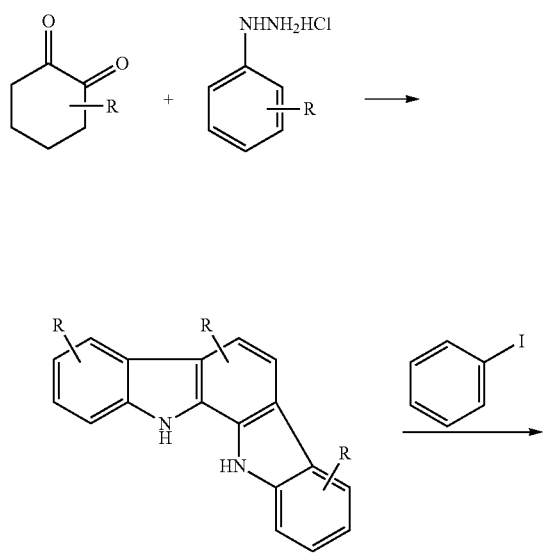

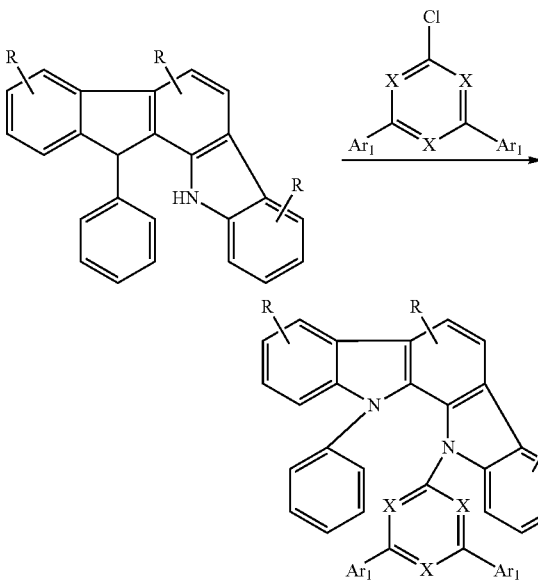

Further, a compound represented by the general formula (3) where X's each represent N may be produced in accordance with the following reaction formula with reference to synthesis examples disclosed in Archiv der Pharmazie (Weinheim, Germany), 1987, 320(3), 280.

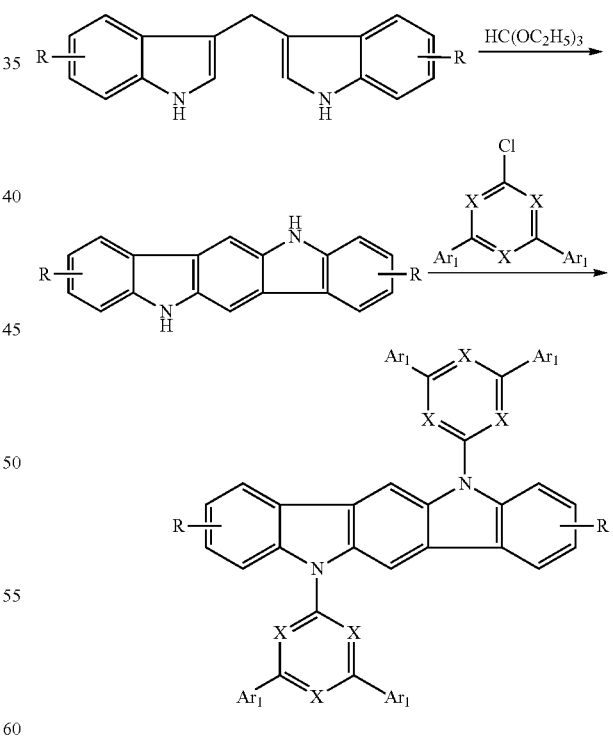

Further, a compound represented by the general formula (5) where Ar represents a phenyl group and all X's each represent N may be synthesized in accordance with the following reaction formula with reference to synthesis examples disclosed in The Journal of Organic Chemistry, 2007, 72(15) 5886 and Tetrahedron, 1999, 55, 2371.

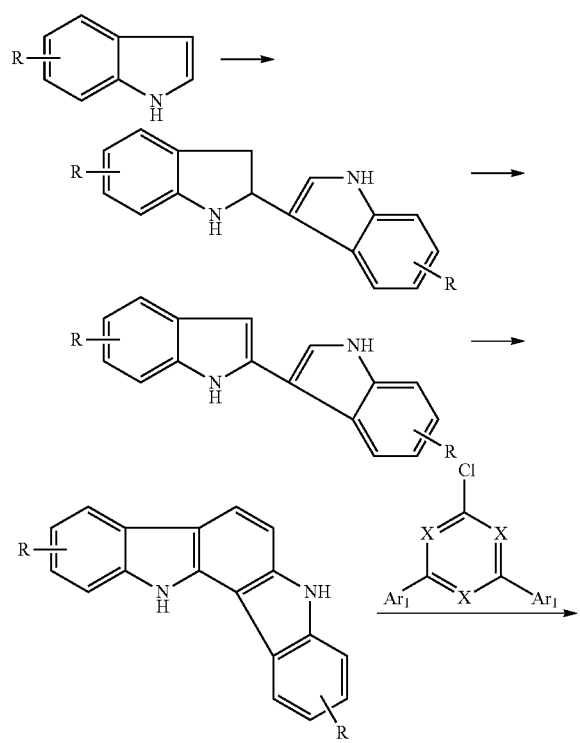
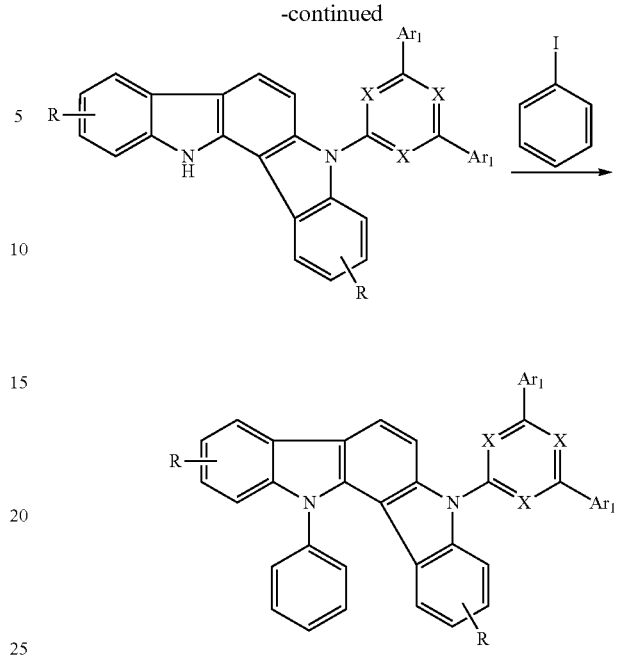
Hereinafter, there are given preferred specific examples of the compound represented by the general formula (1). However, the compound is not limited thereto.
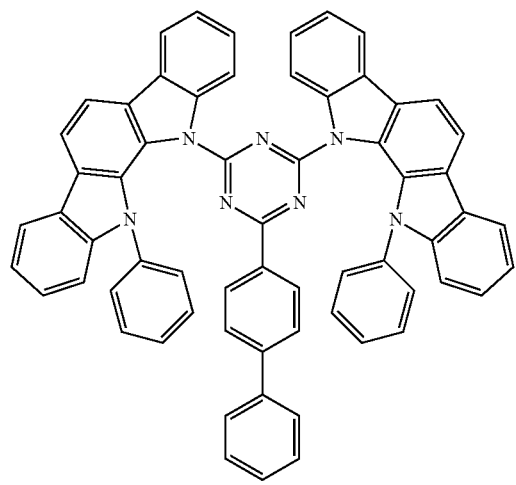
(11)
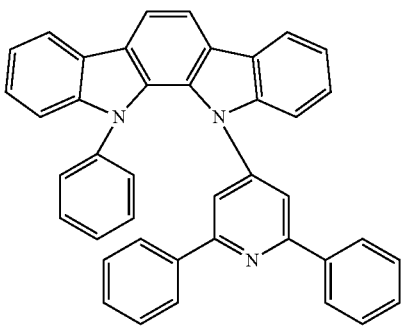
(12)
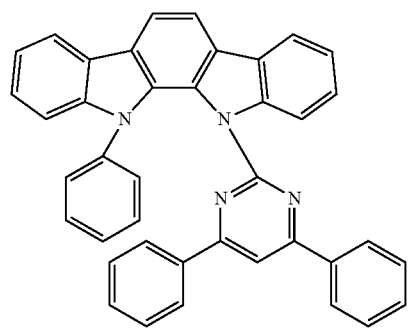
(13)
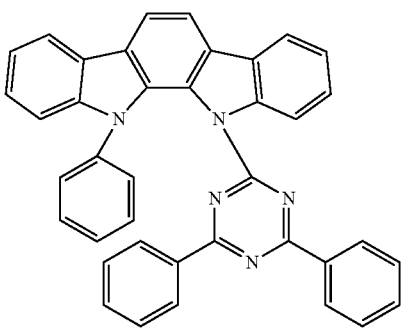
(14)

-continued
(15)
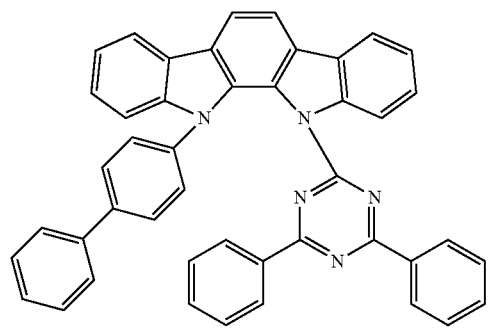
(16)
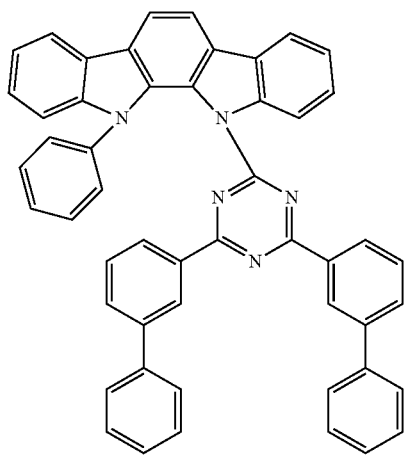
(17)
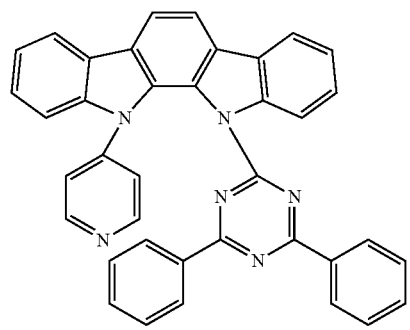
(18)
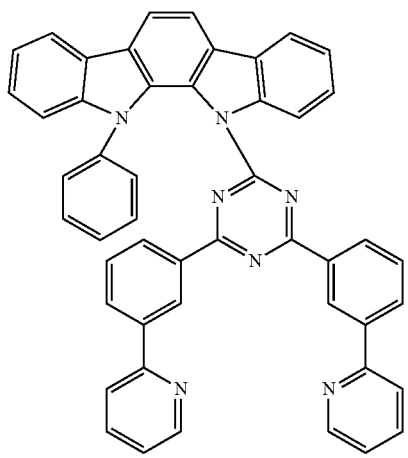
(19)
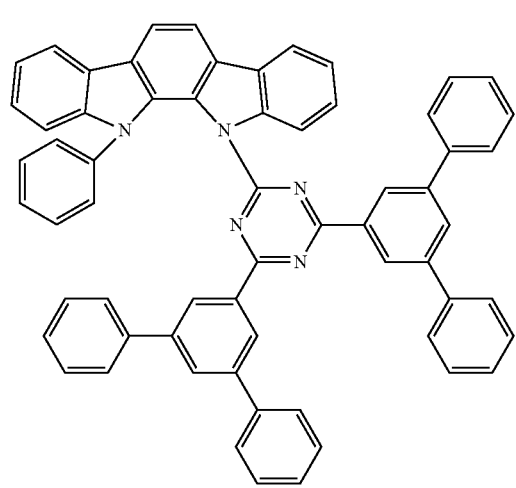
(20)
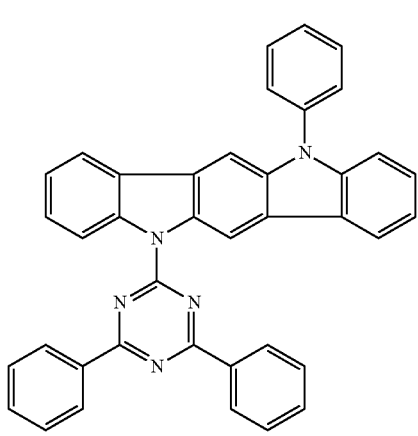

-continued
(21)
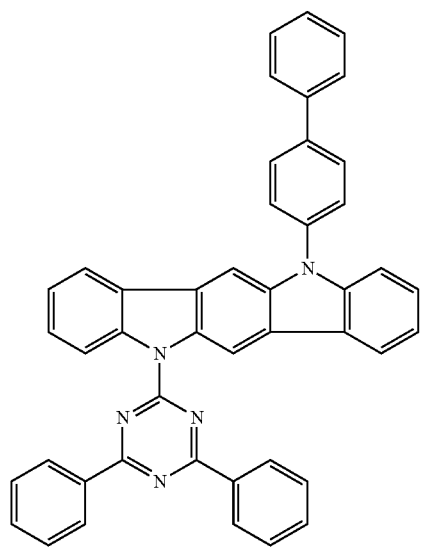
(22)
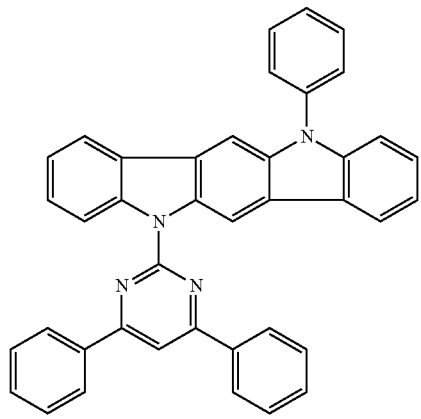
(23)
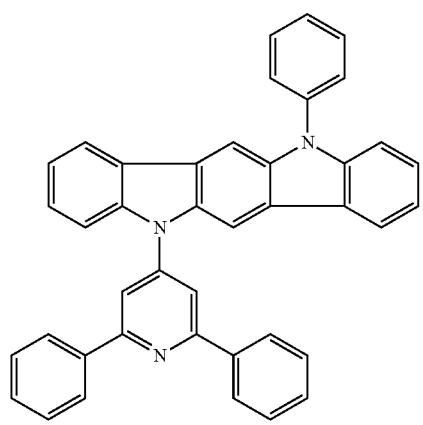
(24)
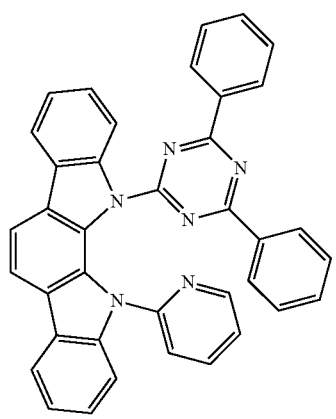
(25)
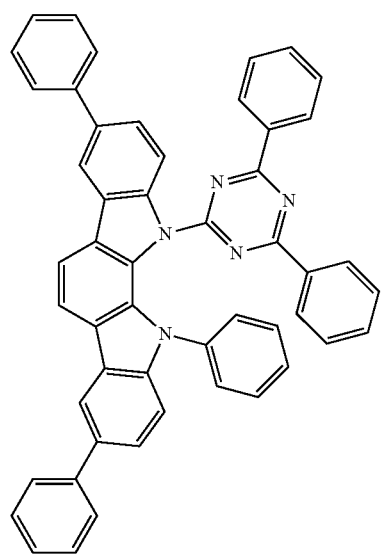
(26)
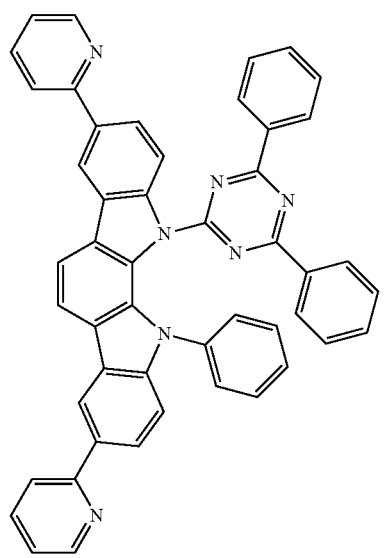

-continued
(27)
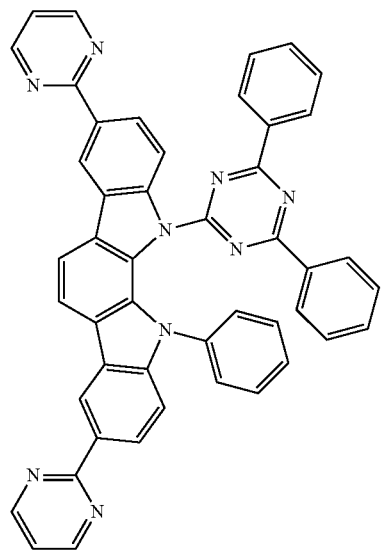
(28)
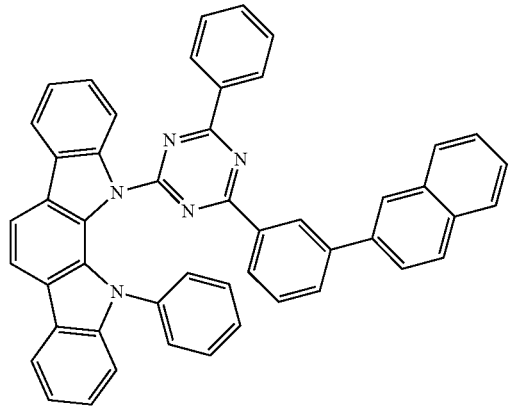
(29)
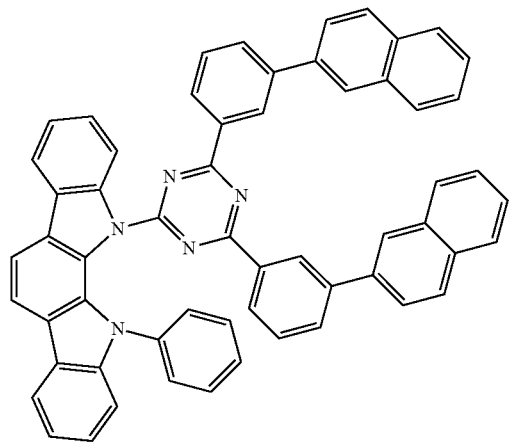
(30)
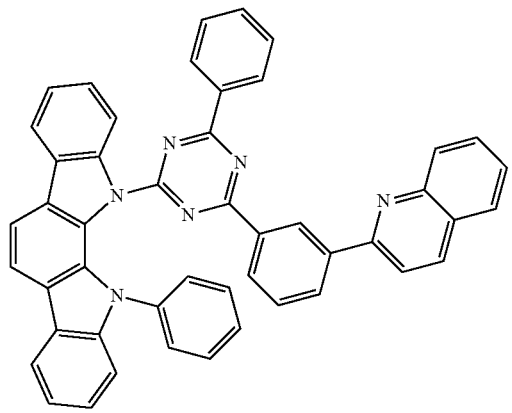
(31)
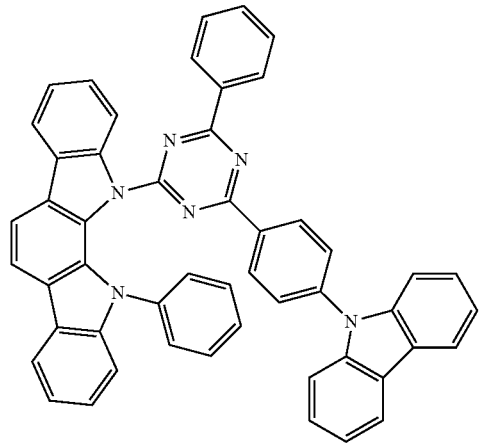
(32)
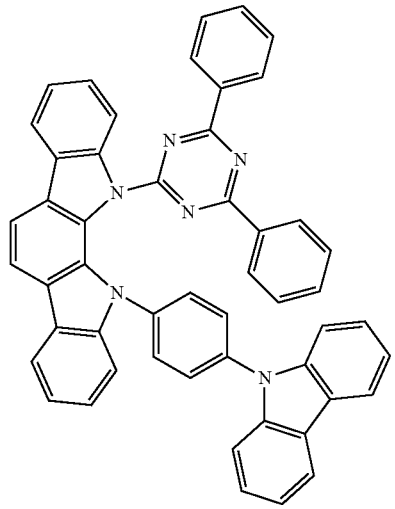

-continued
(33)
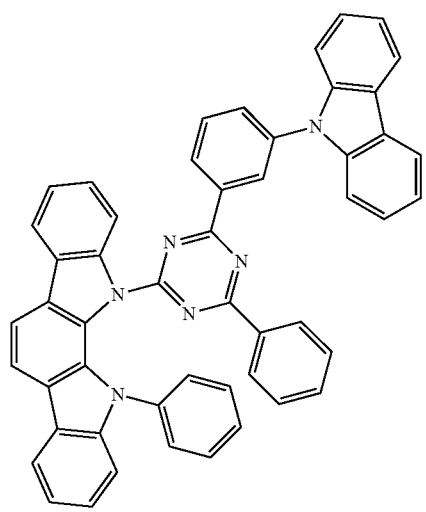
(34)
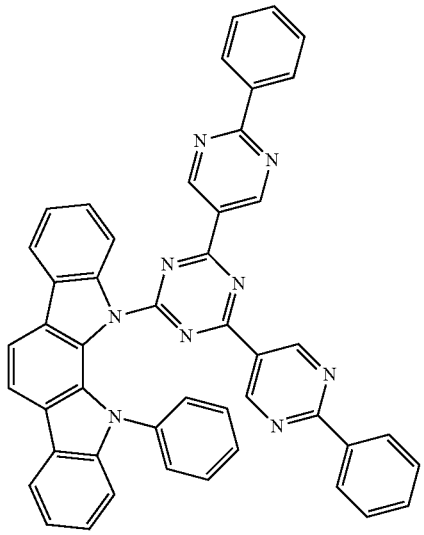
(35)
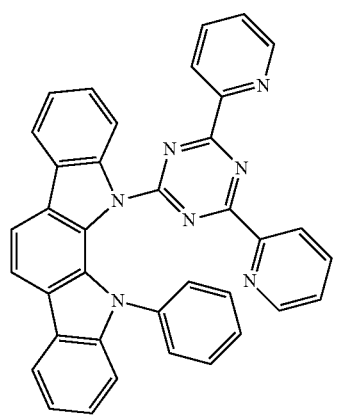
(36)
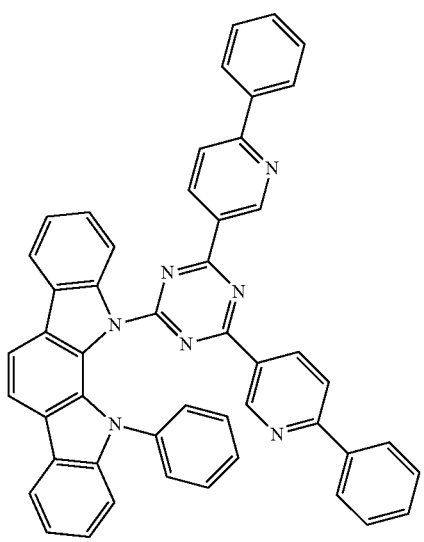
(37)
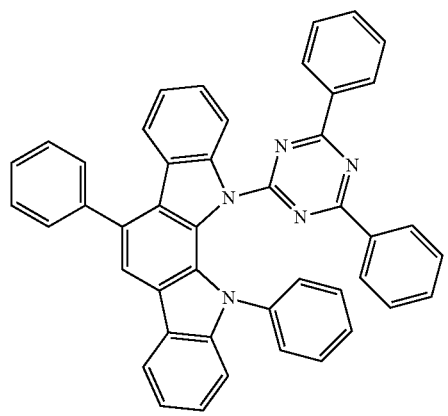
(38)
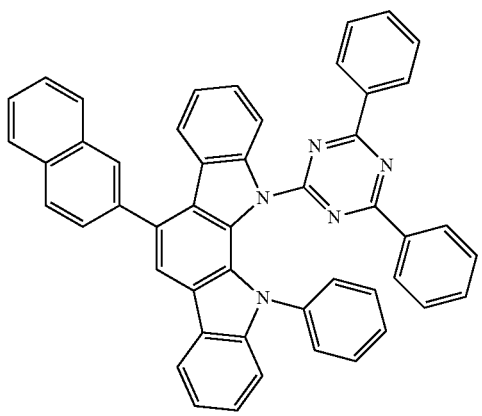

-continued
(39)
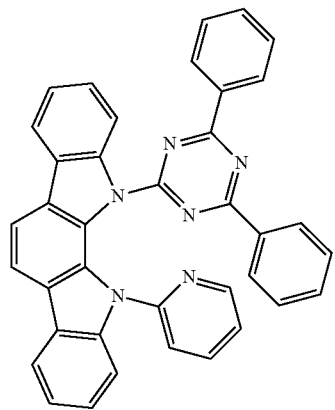
(40)
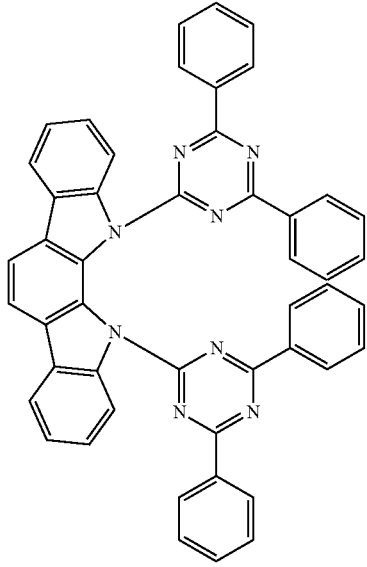
(41)
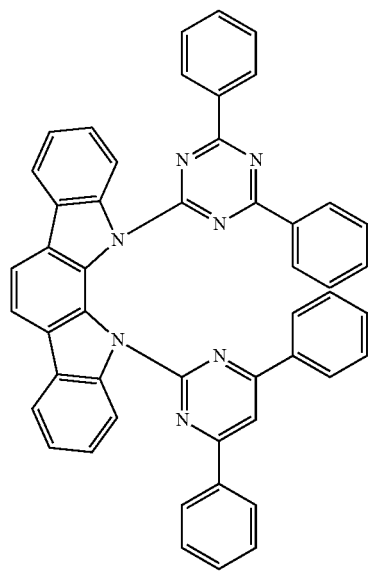
(42)
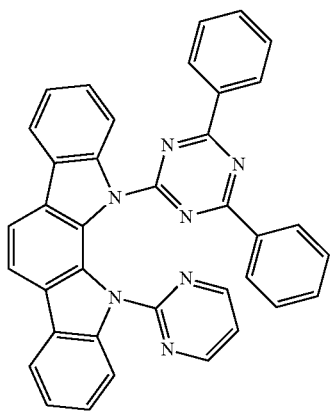
(43)
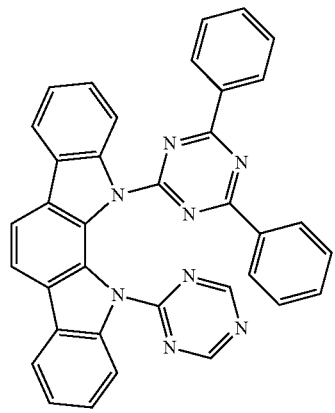
(44)
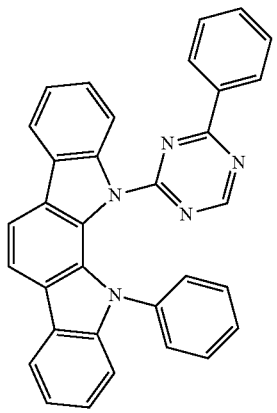

-continued
(45)
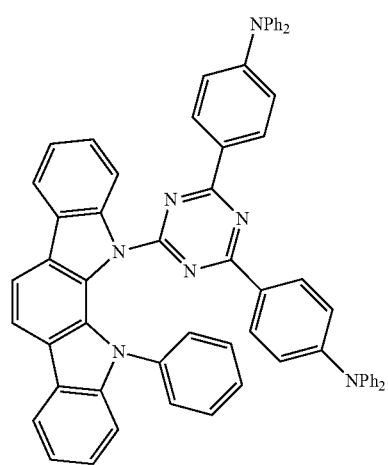
(46)
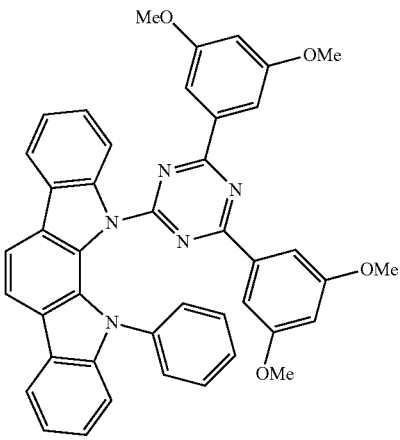
(47)
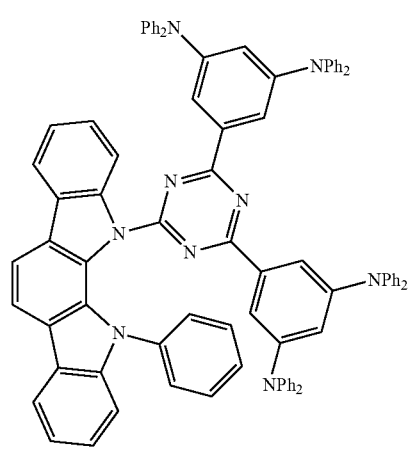
(48)
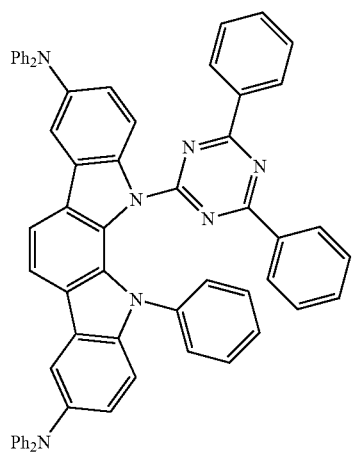
(49)
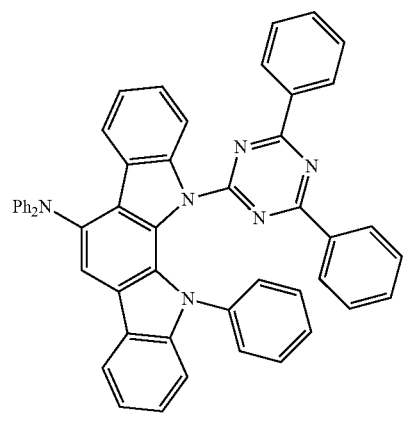
(50)
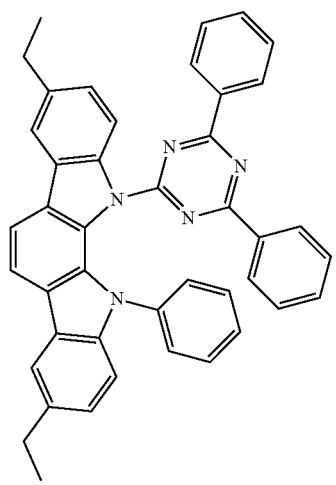

-continued
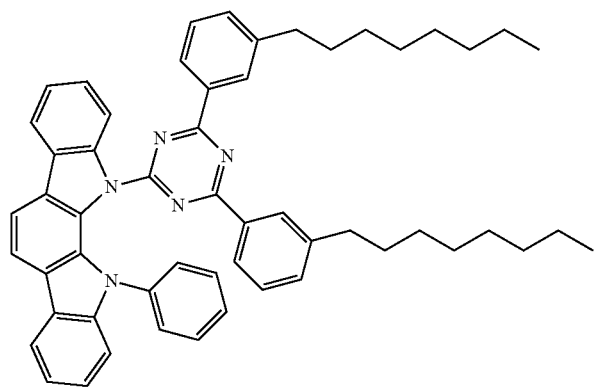
(51)
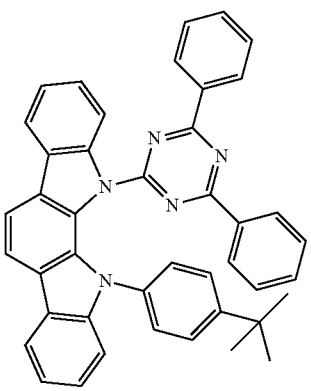
(52)
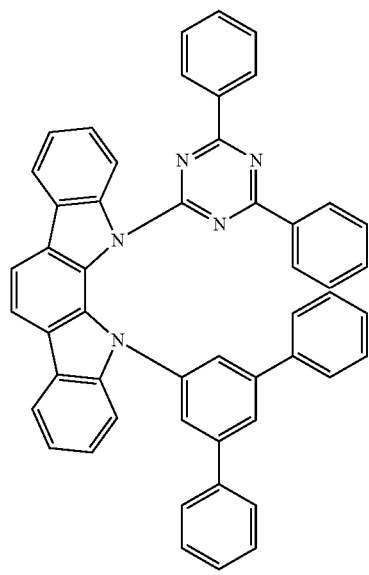
(53)
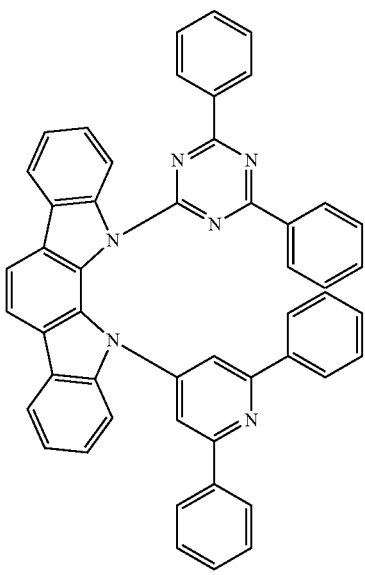
(54)
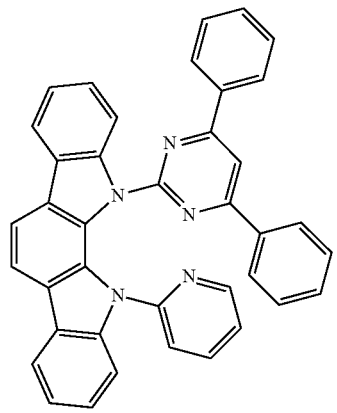
(55)
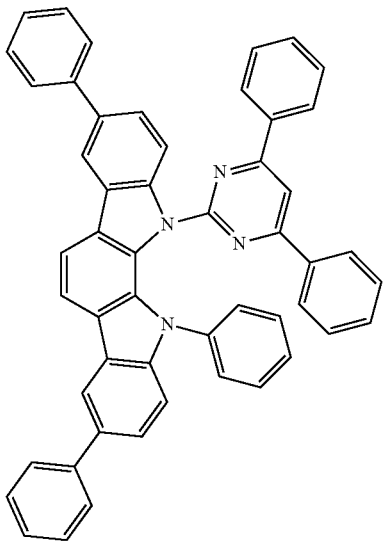
(56)

(57)
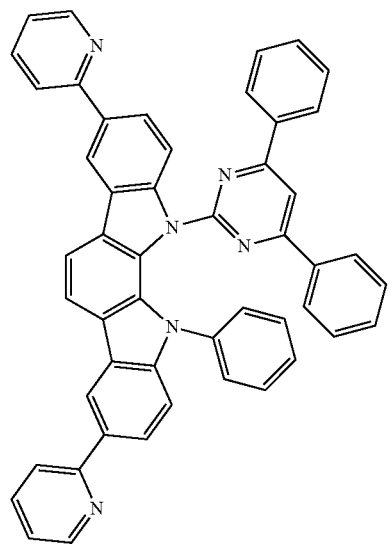
(58)
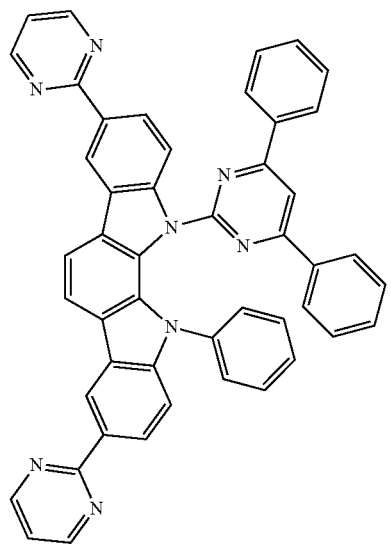
(59)
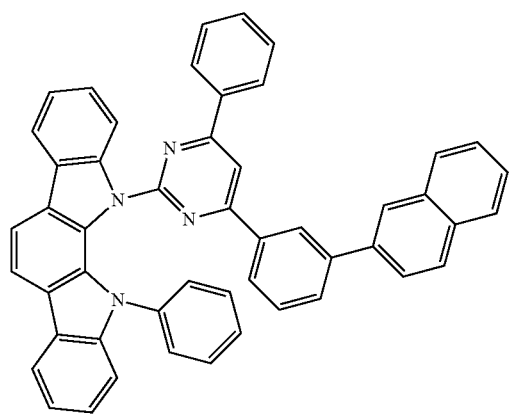
(60)
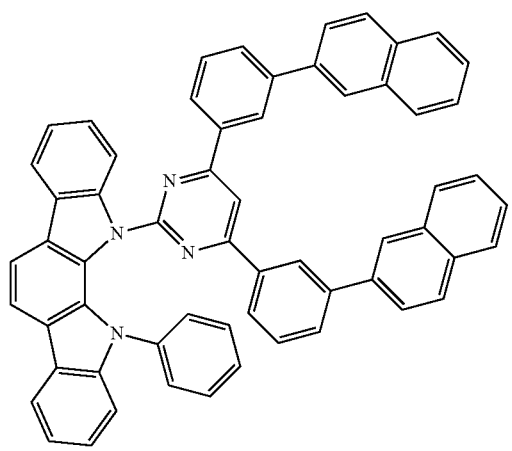
(61)
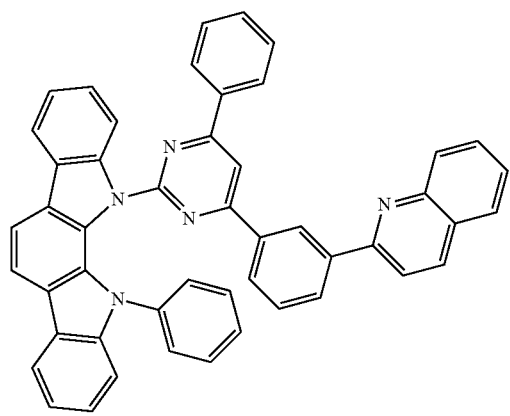
(62)
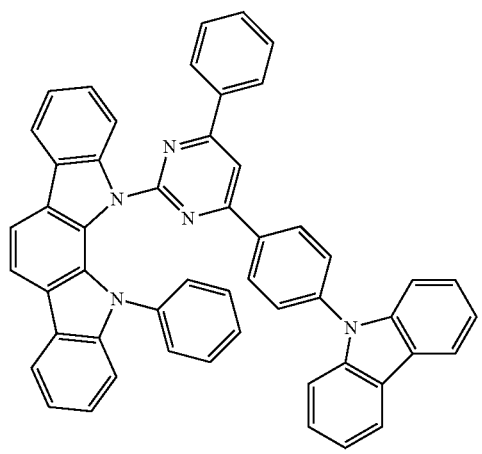

-continued
(63) 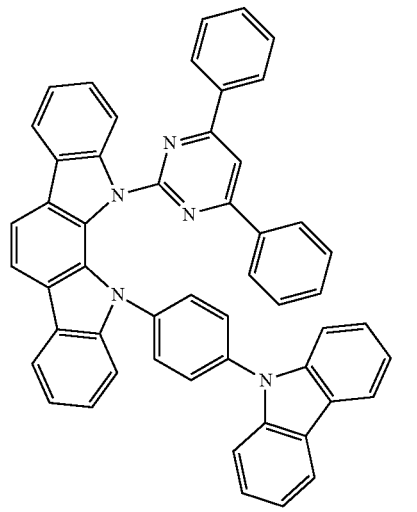
(64) 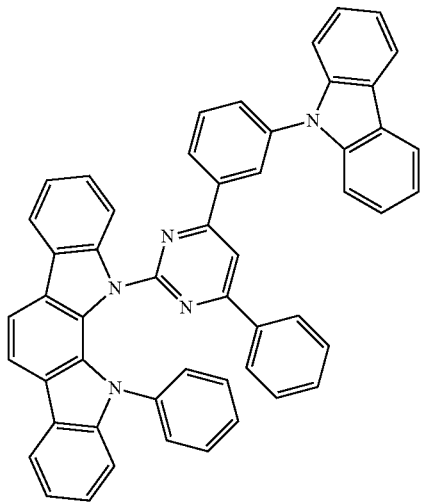
(65) 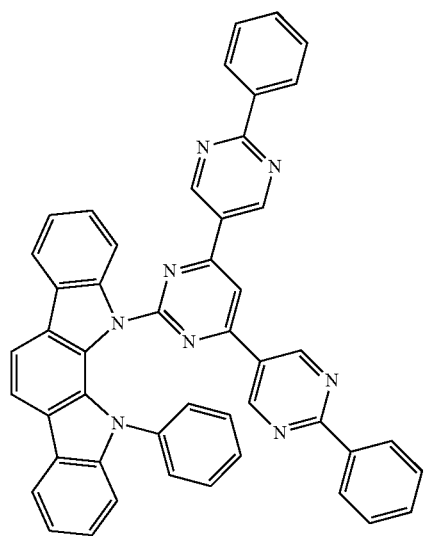
(66) 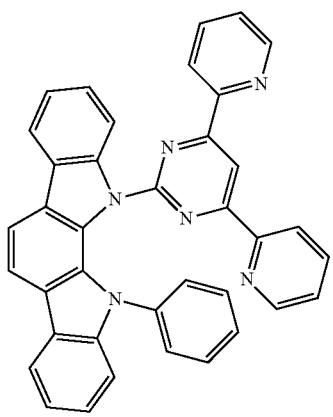
(67) 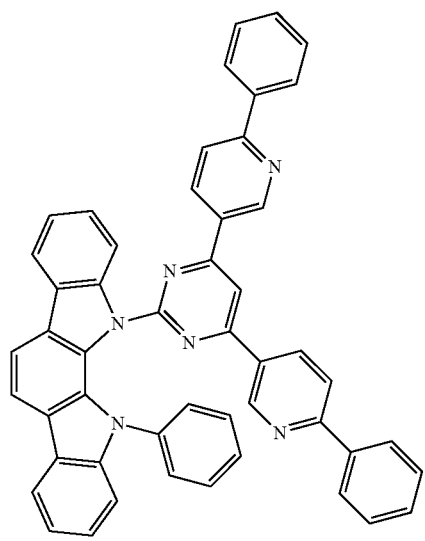
(68) 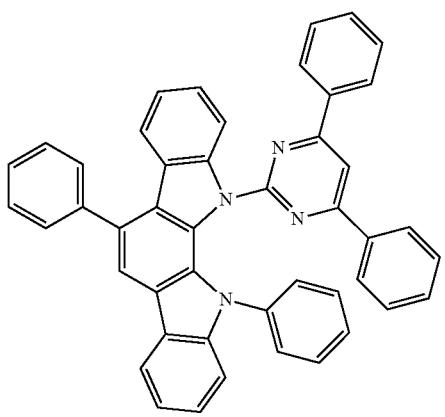

-continued
(69)
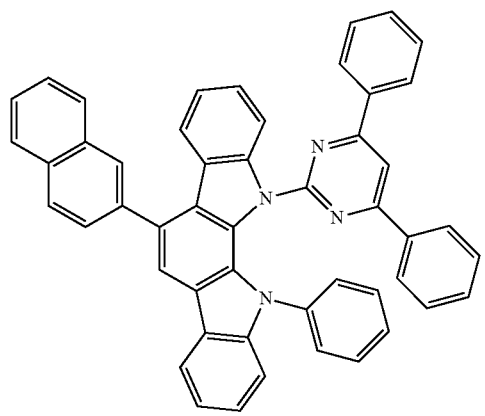
(70)
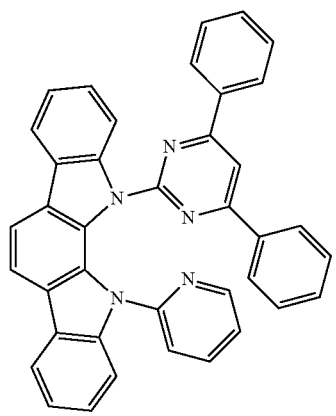
(71)
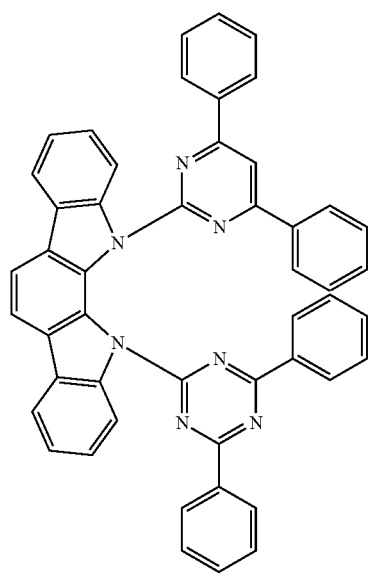
(72)
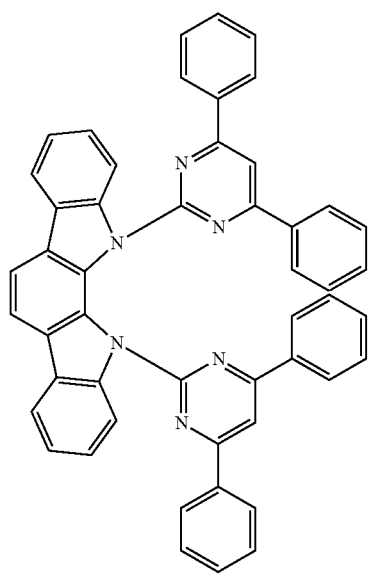
(73)
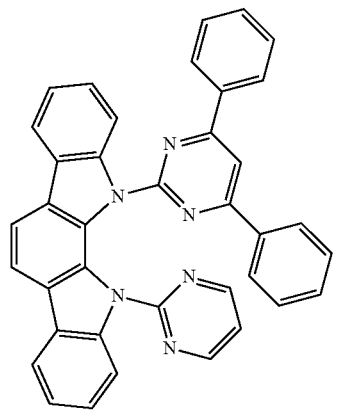
(74)
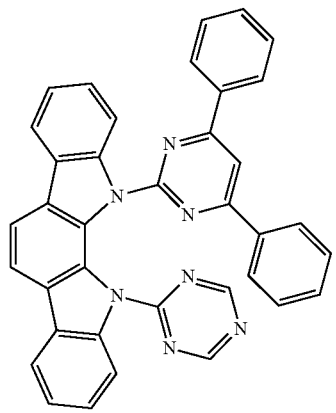

(75)
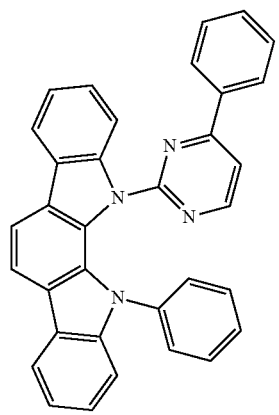
(76)
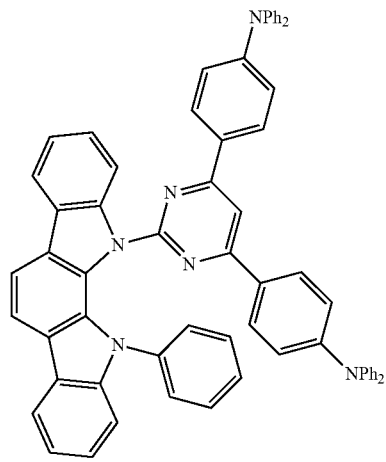
(77)
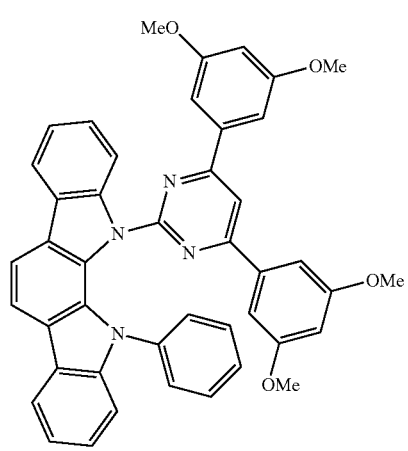
(78)
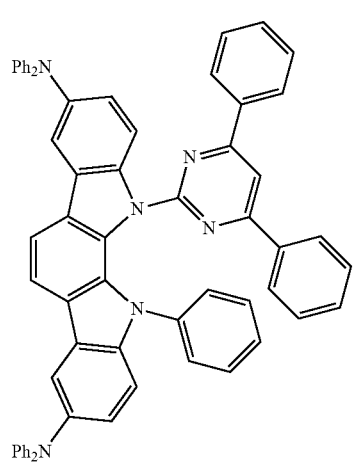
(79)
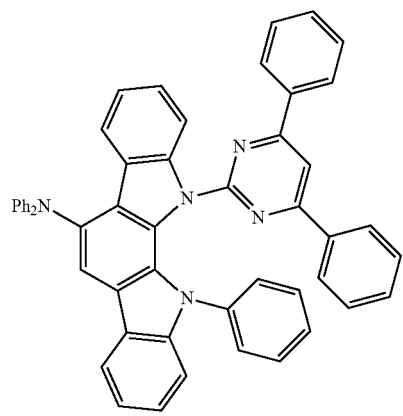
(80)
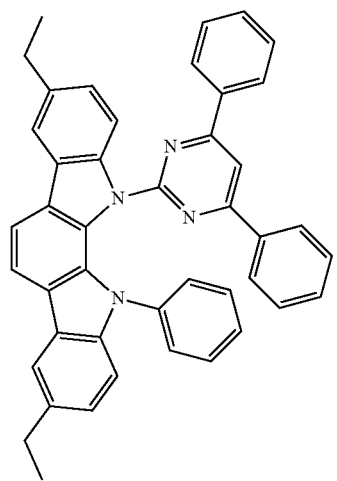

-continued
(81)
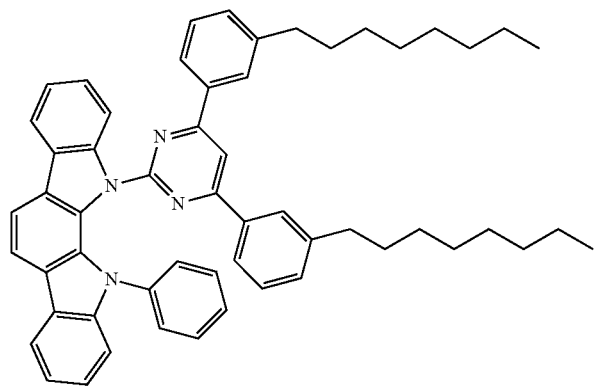
(82)
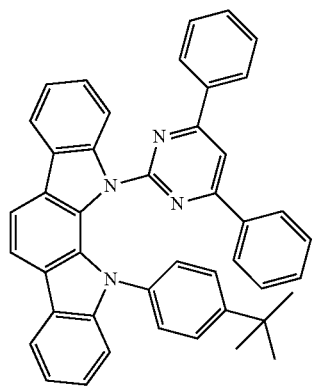
(83)
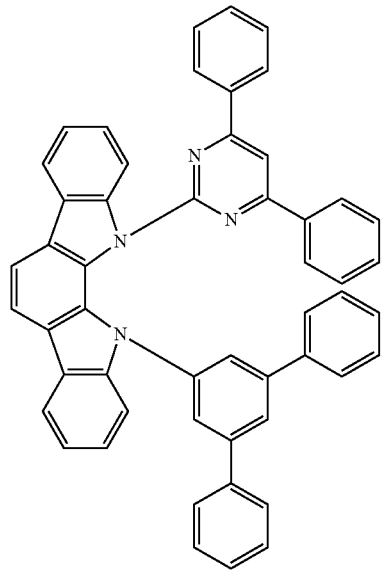
(84)
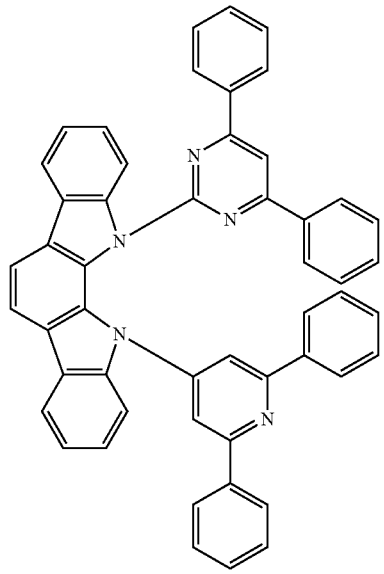
(85)
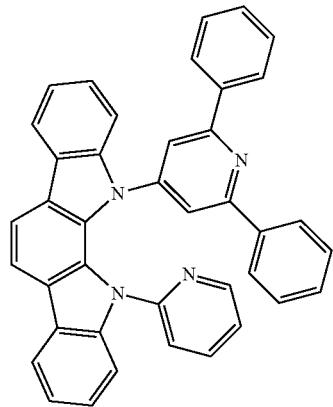
(86)
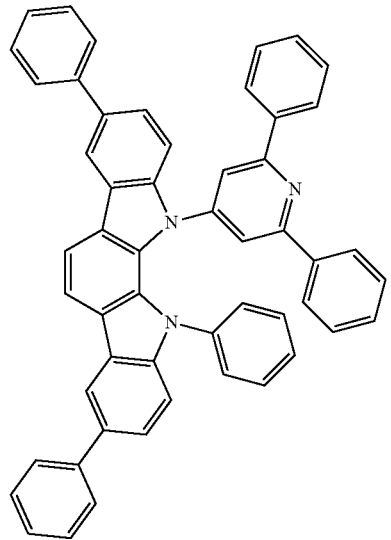

-continued
(87)
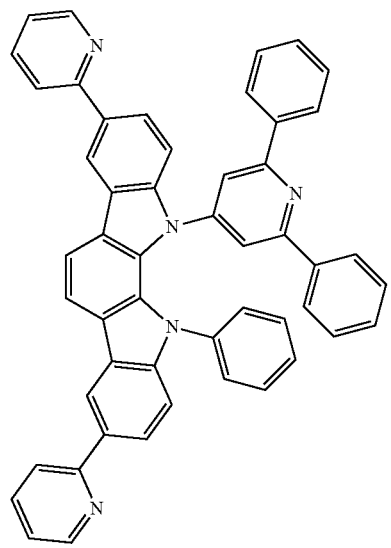
(88)
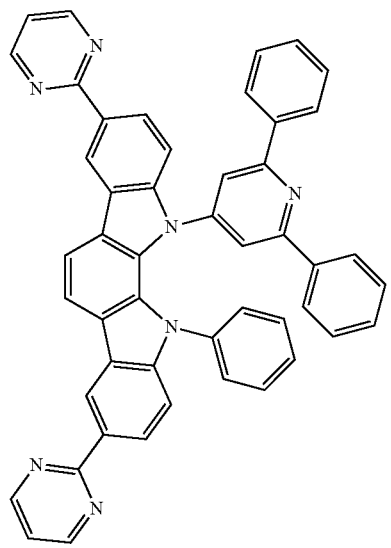
(89)
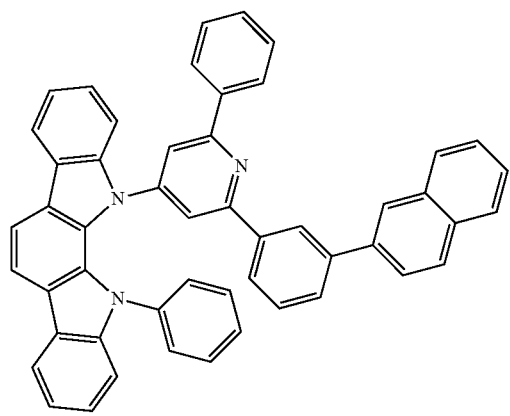
(90)
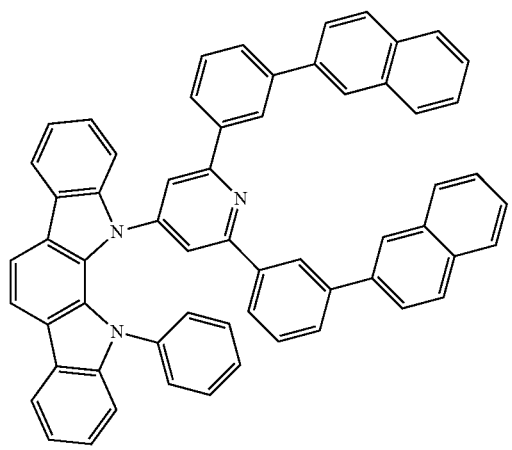
(91)
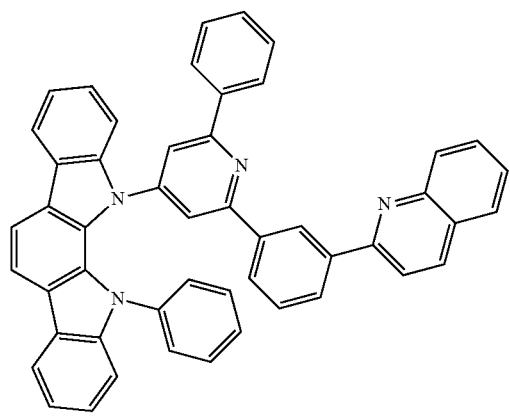
(92)
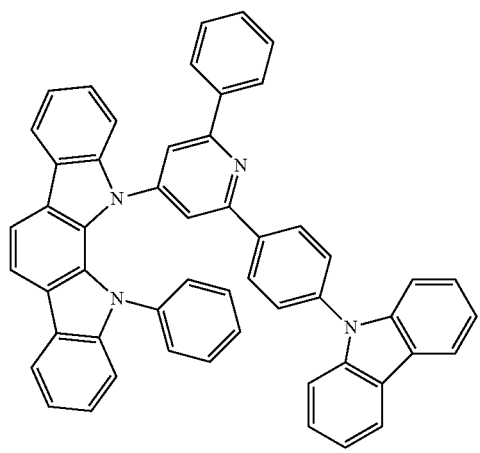

-continued
(93)
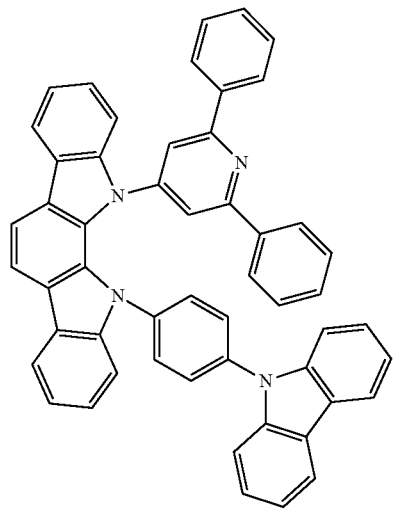
(94)
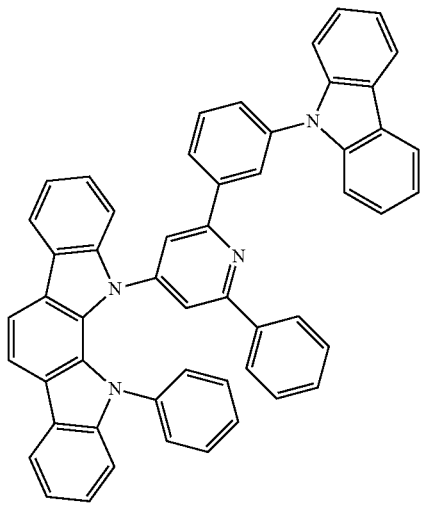
(95)
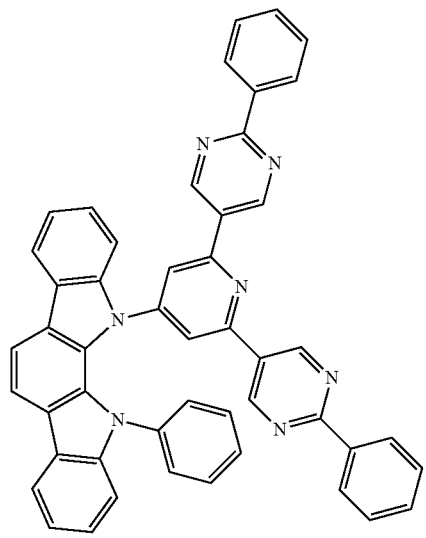
(96)
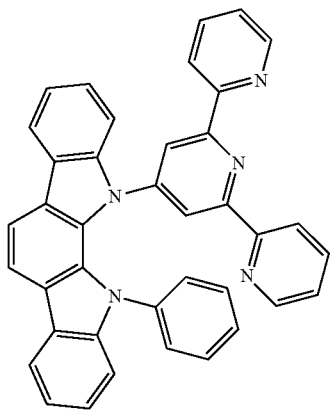
(97)
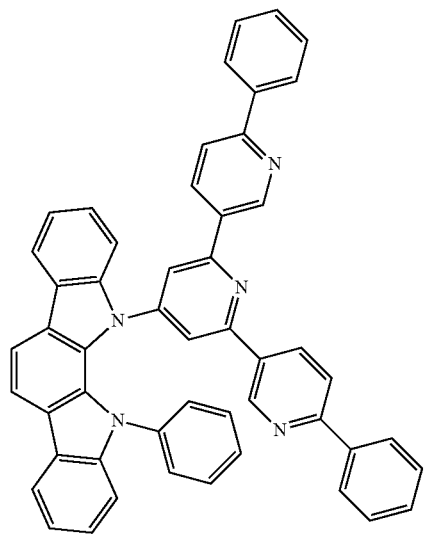
(98)
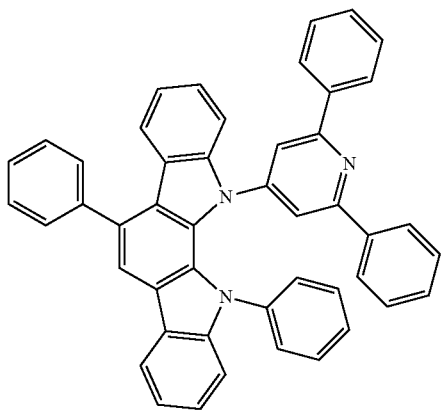

(99)
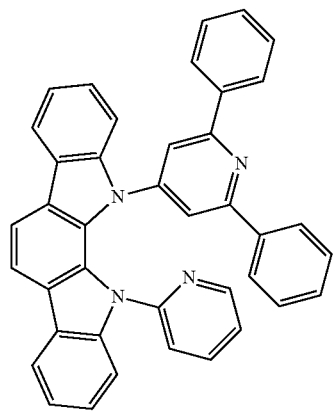
(100)
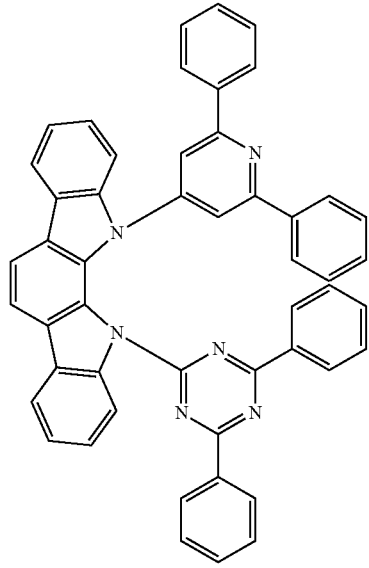
(101)
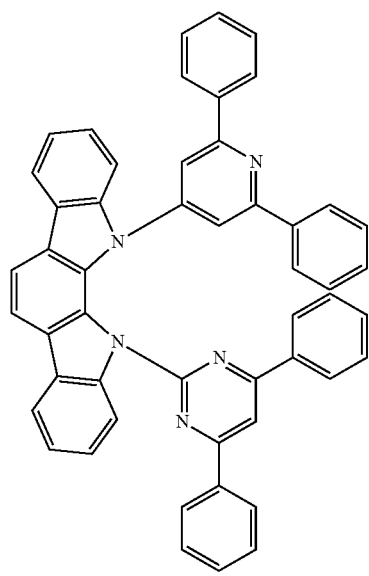
(102)
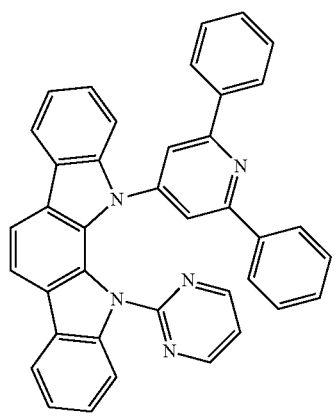
(103)
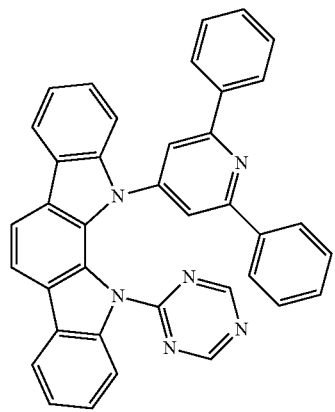
(104)
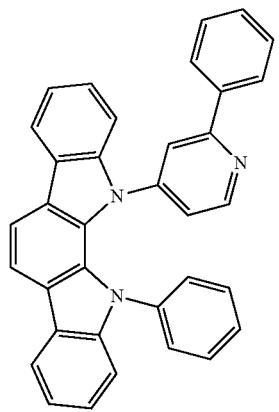

-continued
(105)
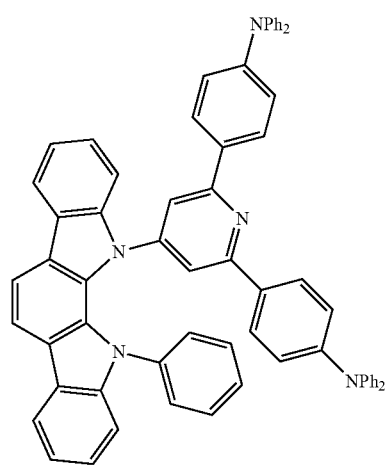
(106)
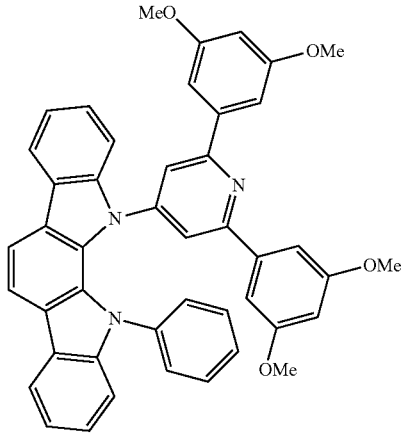
(107)
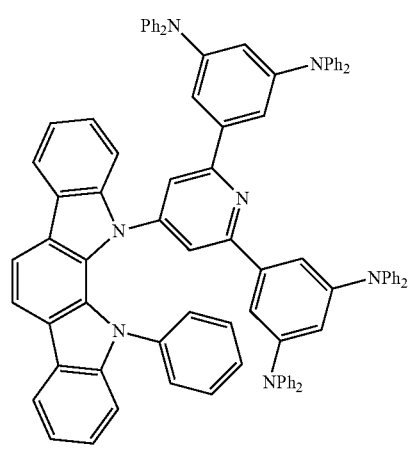
(108)
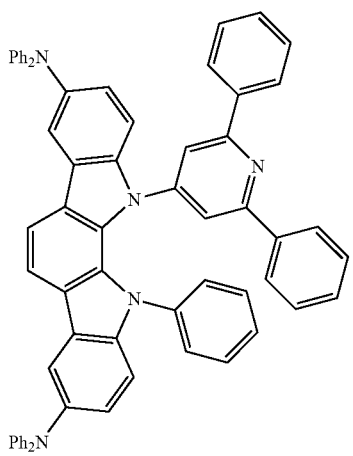
(109)
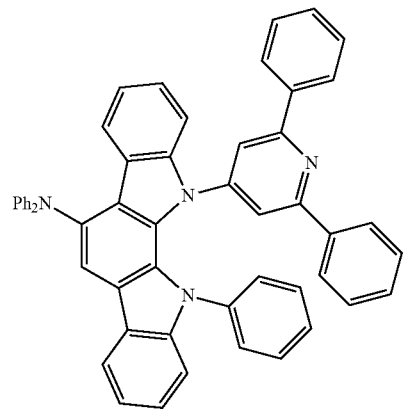
(110)
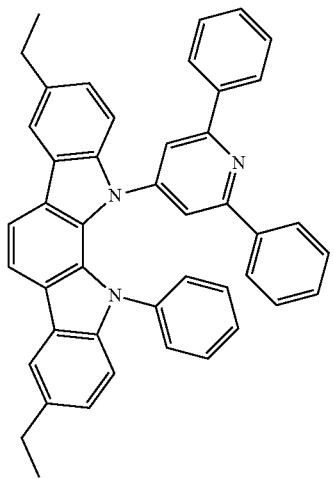

-continued
(111)
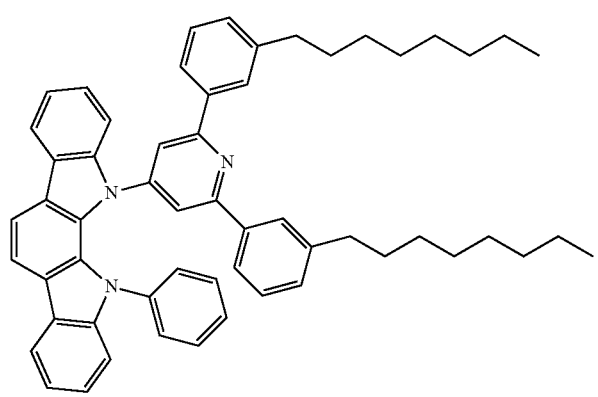
(112)
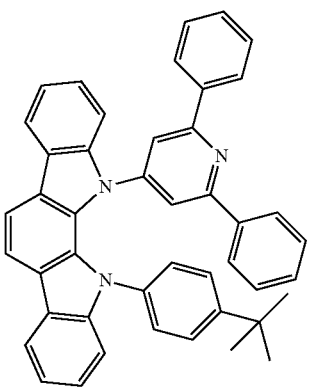
(113)
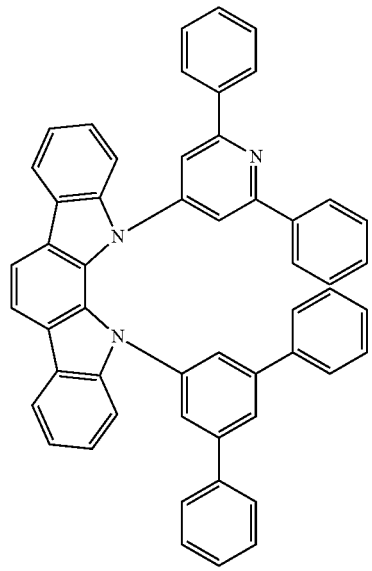
(114)
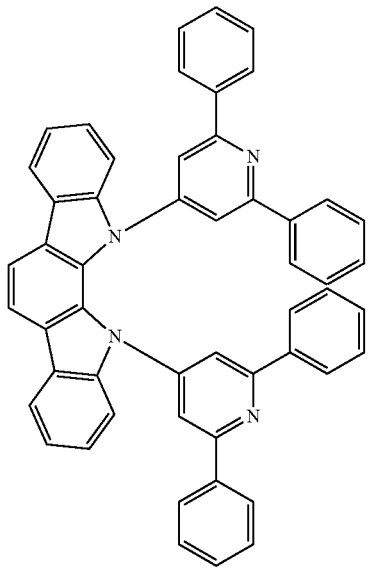
(115)
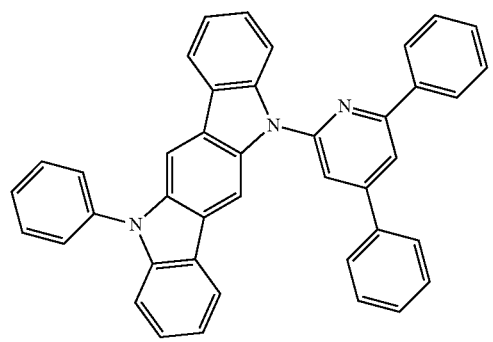
(116)
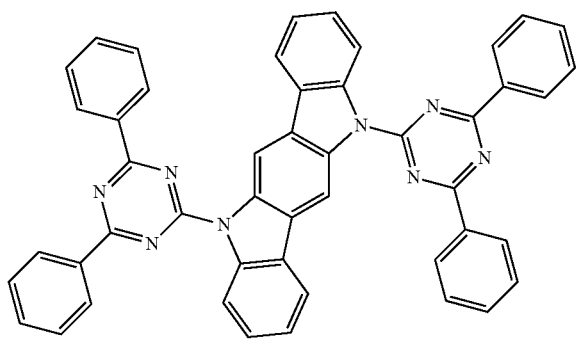

-continued
(117)
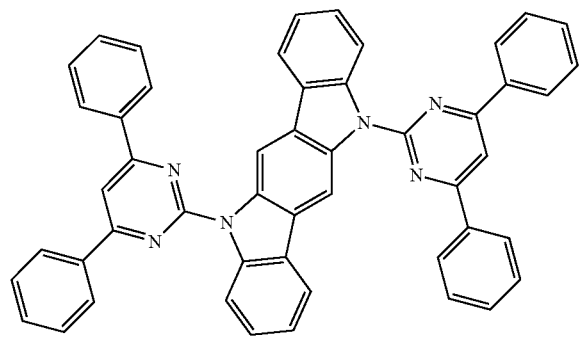
(118)
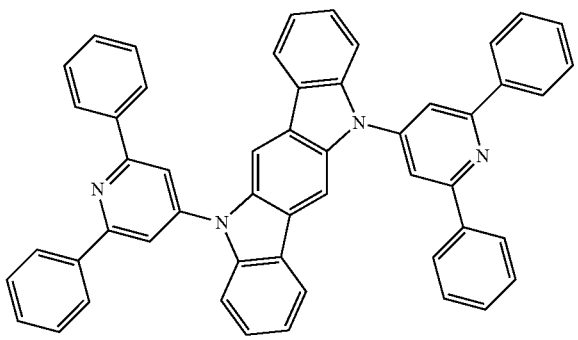
(119)
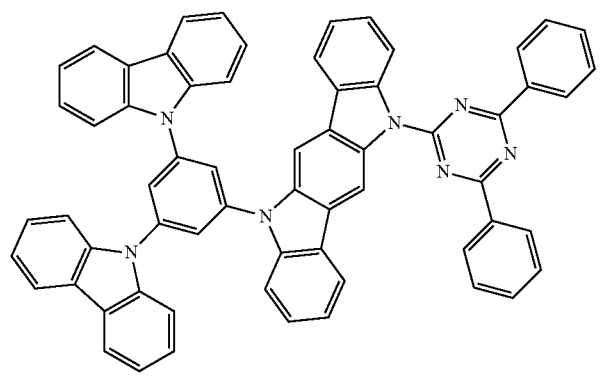
(120)
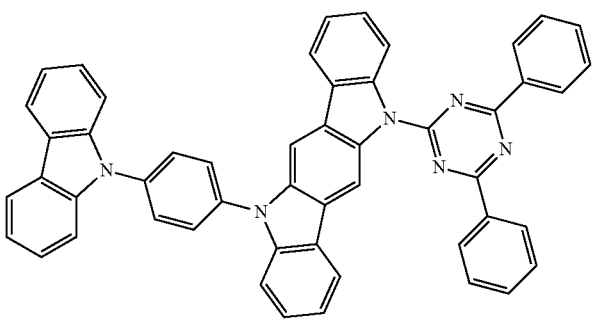
(130)
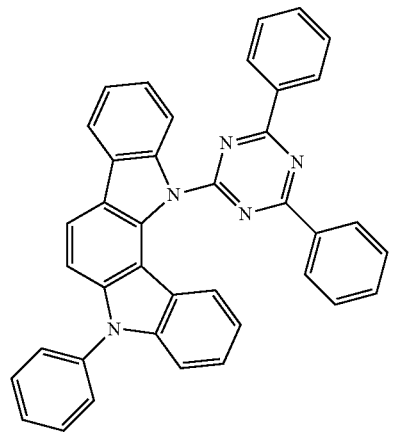
(131)
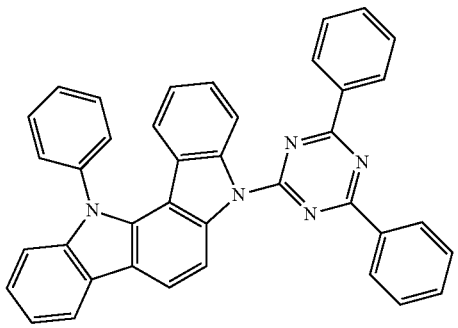
(132)
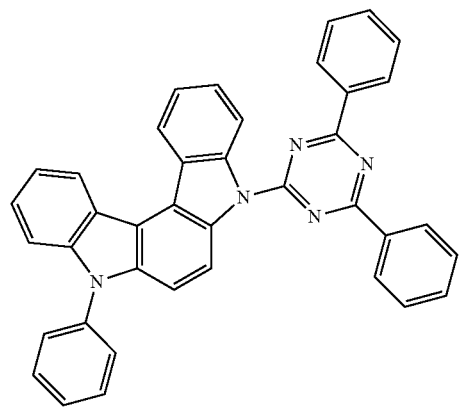
(133)
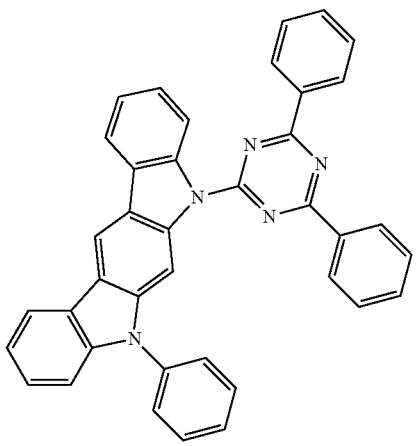

-continued
(134)
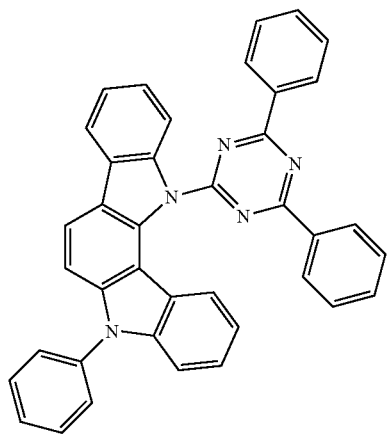
(135)
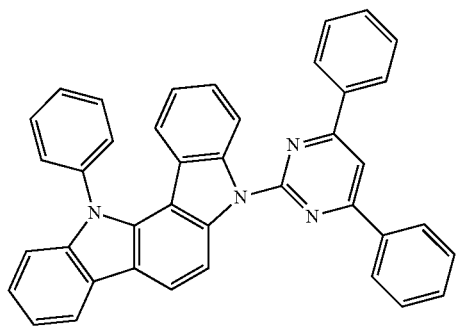
(136)
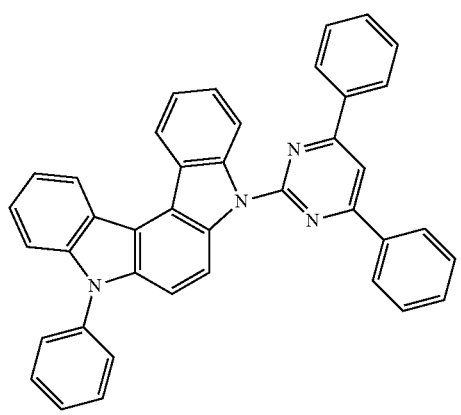
(137)
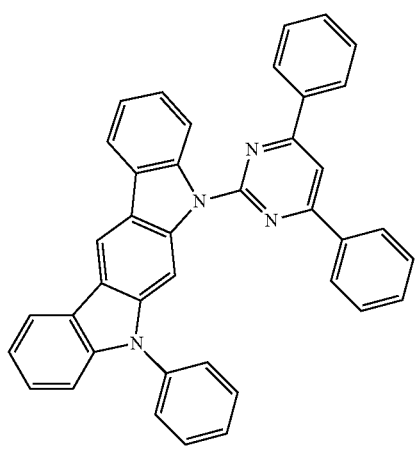
(138)
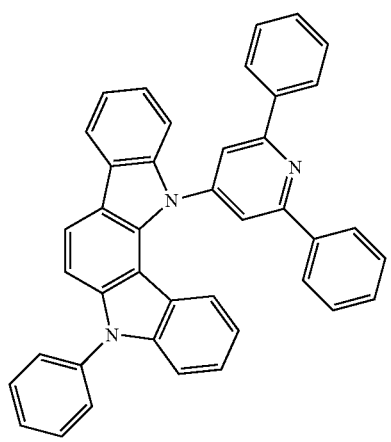
(139)
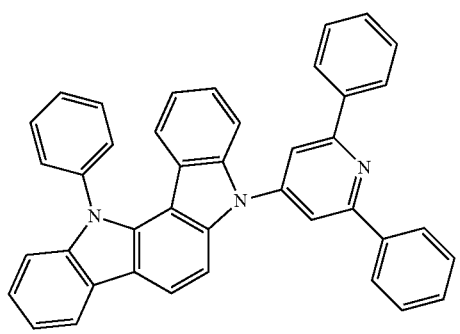

-continued
(140)
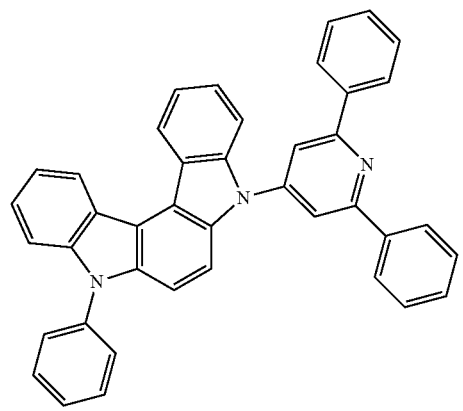
(141)
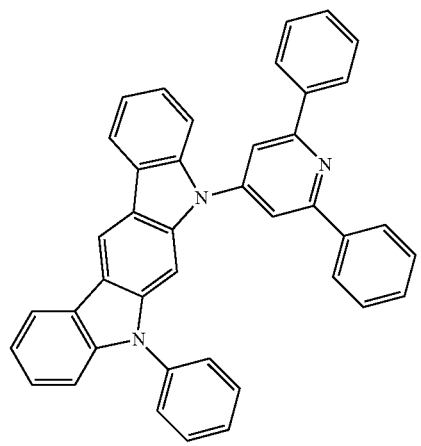
(142)
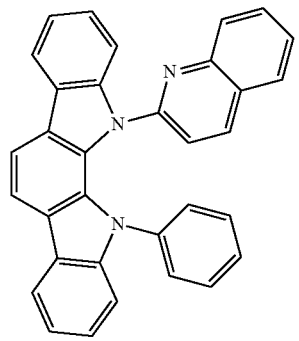
(143)
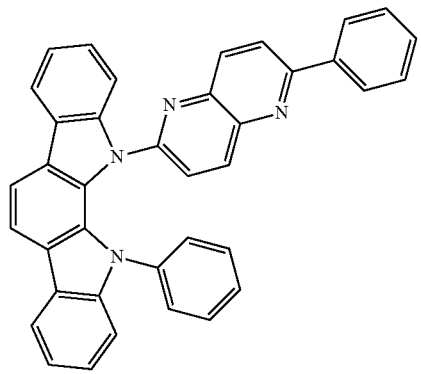
(144)
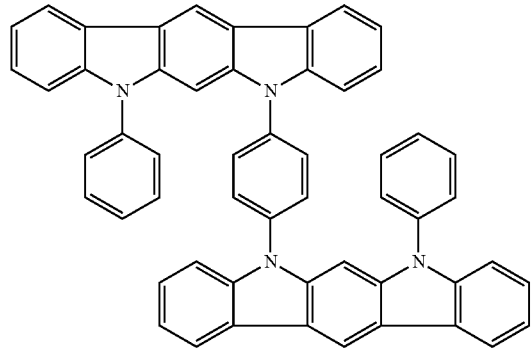
(145)
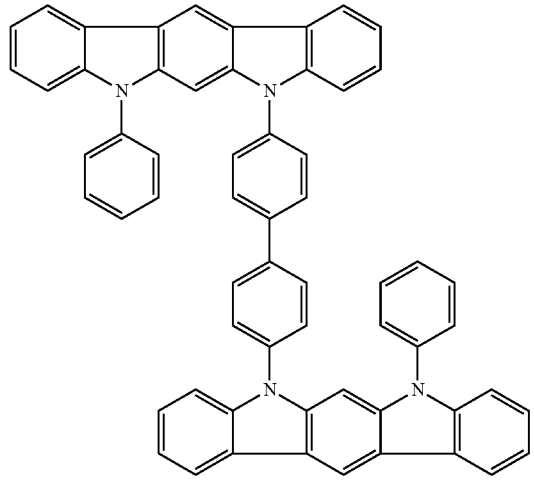

-continued
(146)
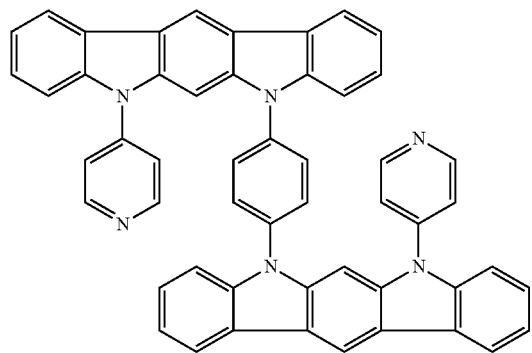
(147)
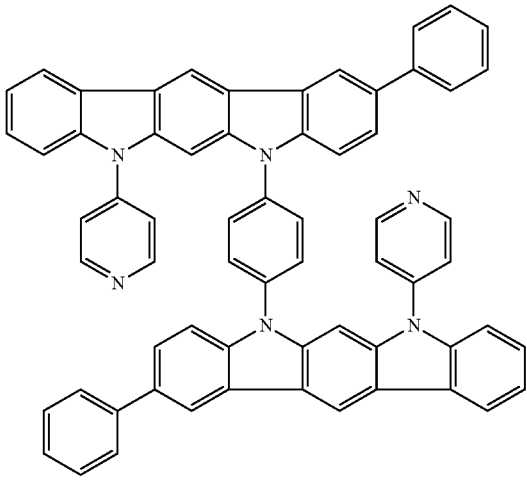
(148)
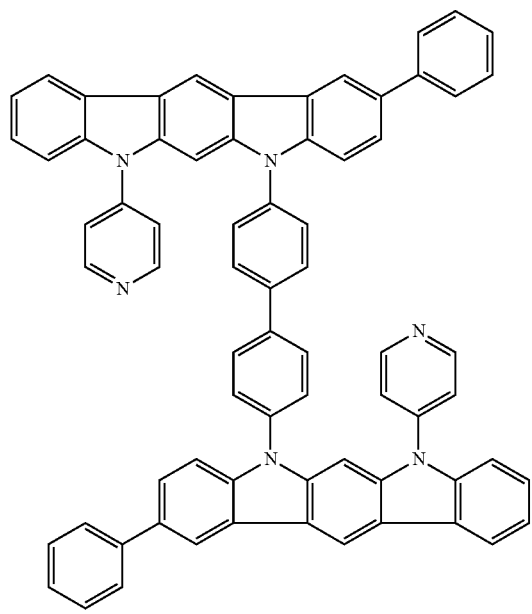
(149)
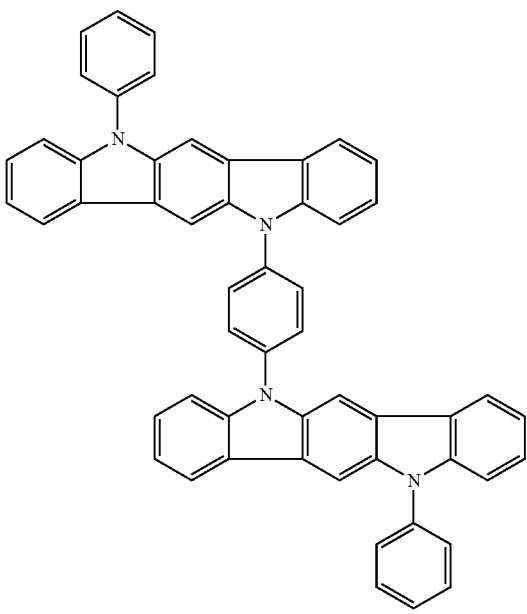

-continued
(150)
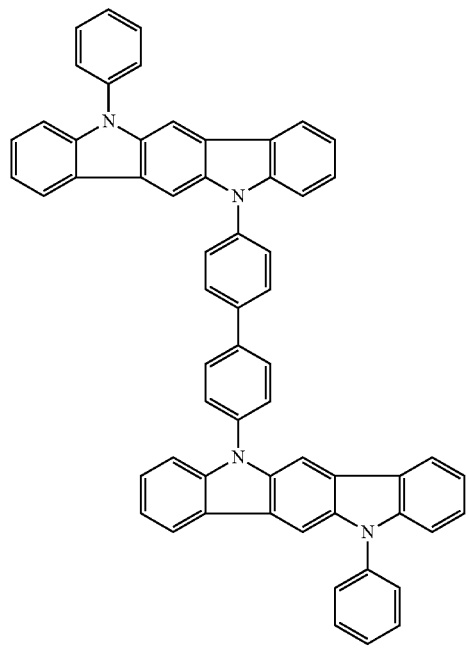
(151)
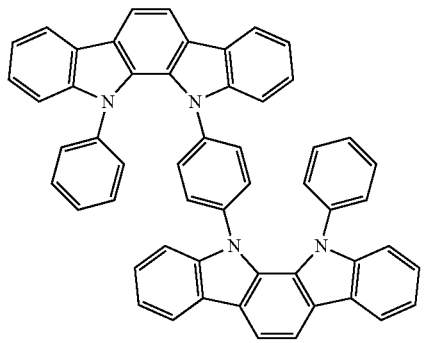
(152)
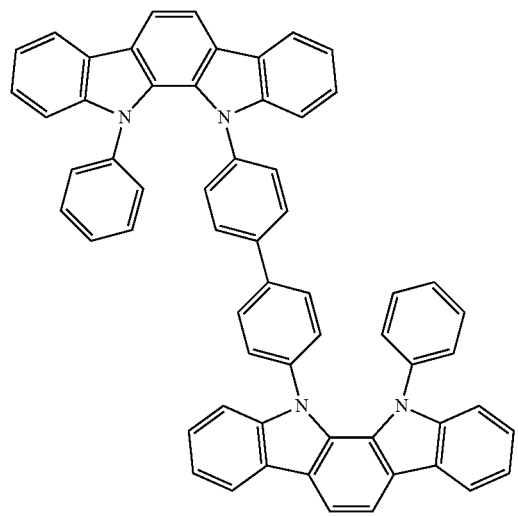
(153)
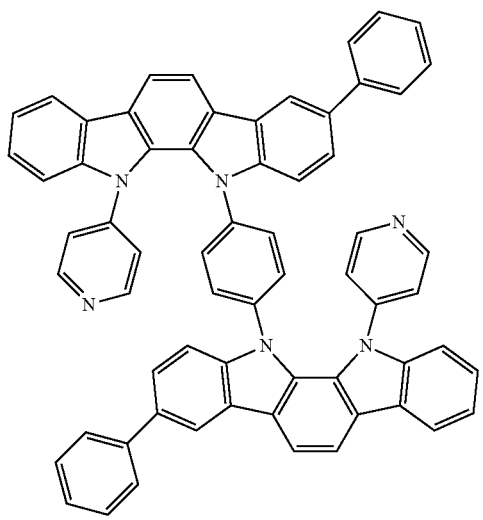

-continued
(154)
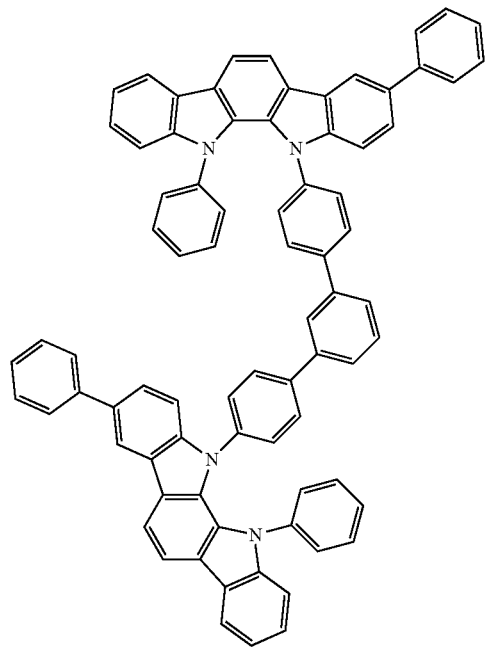
(155)
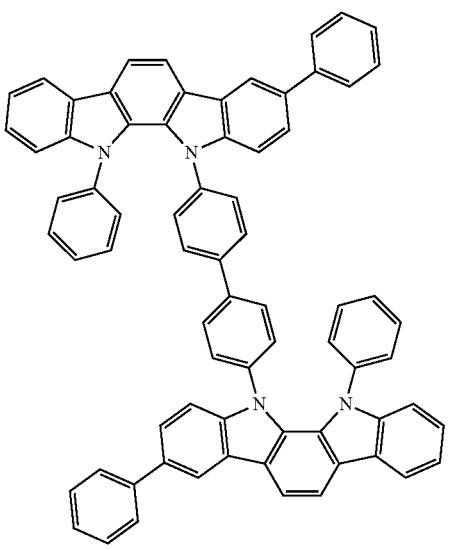
(156)
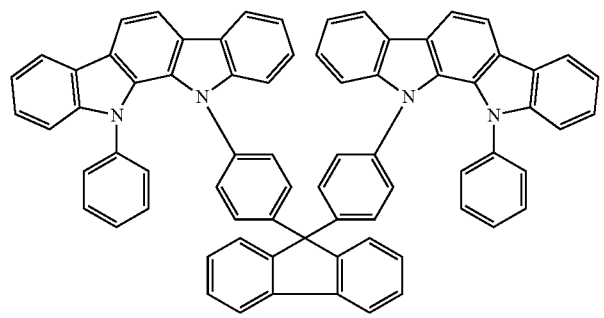
(157)
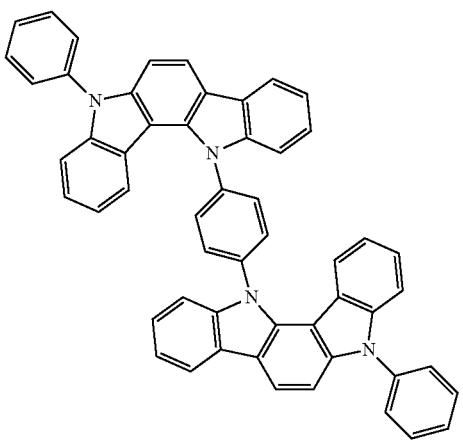

-continued
(158)
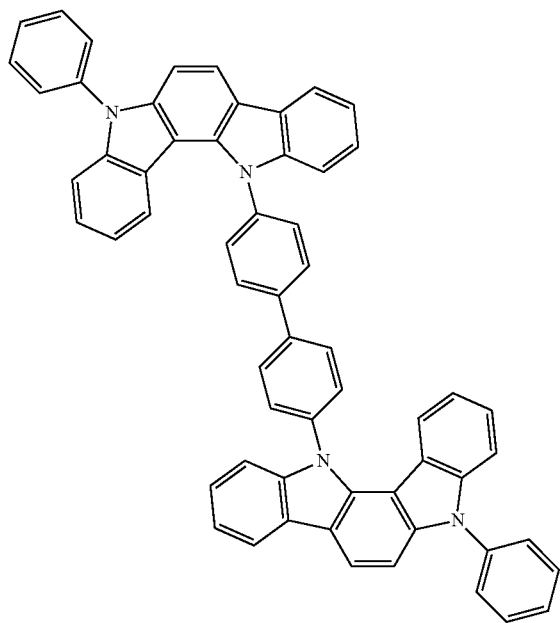
(159)
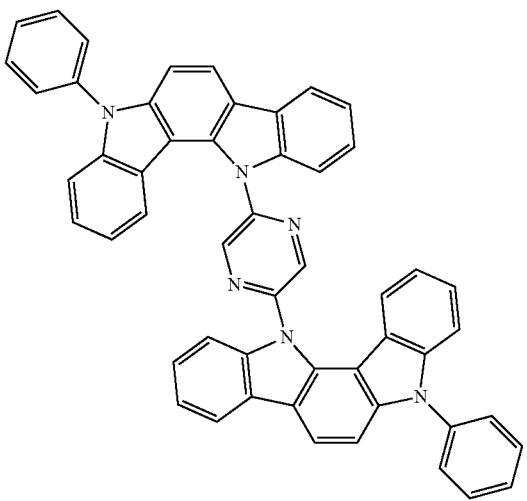
(160)
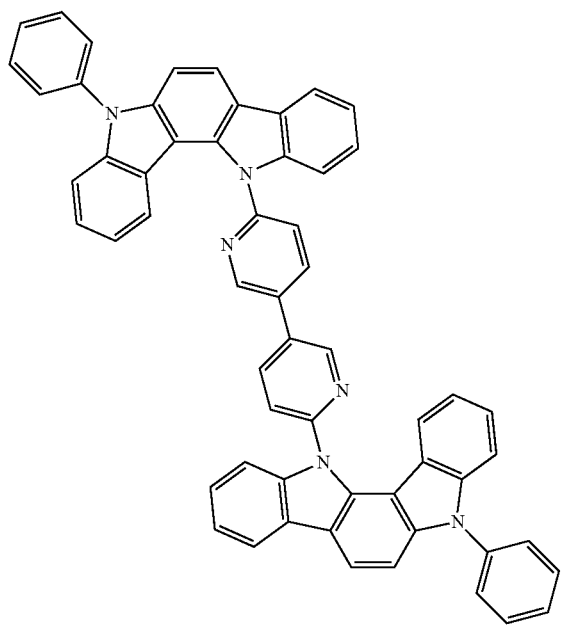
(161)
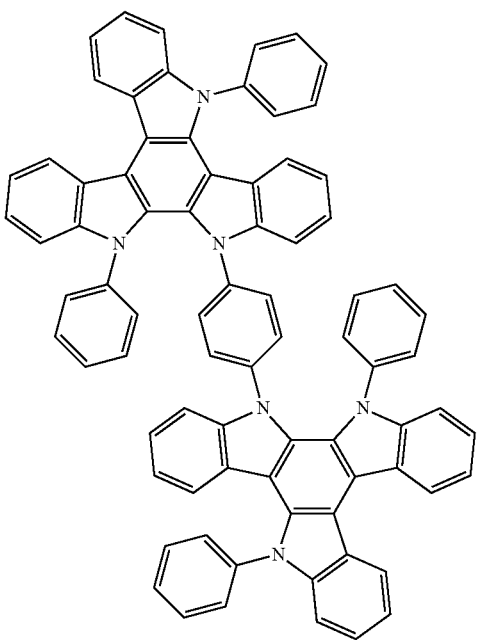

-continued
(162)
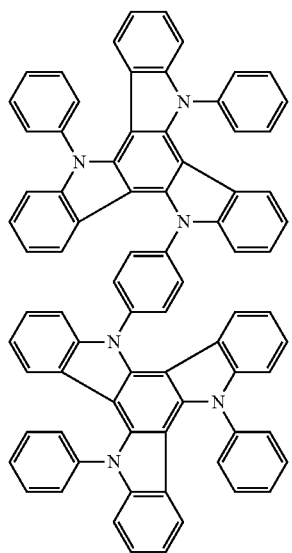
(163)
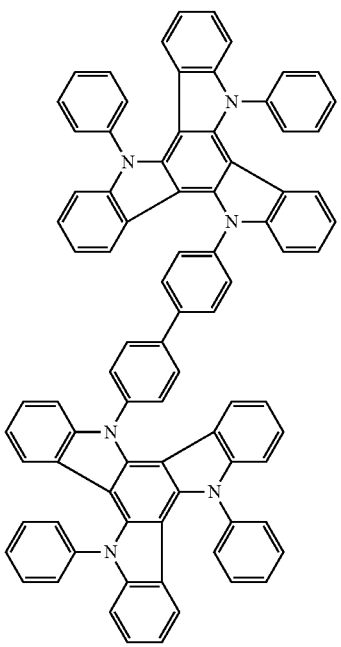
(164)
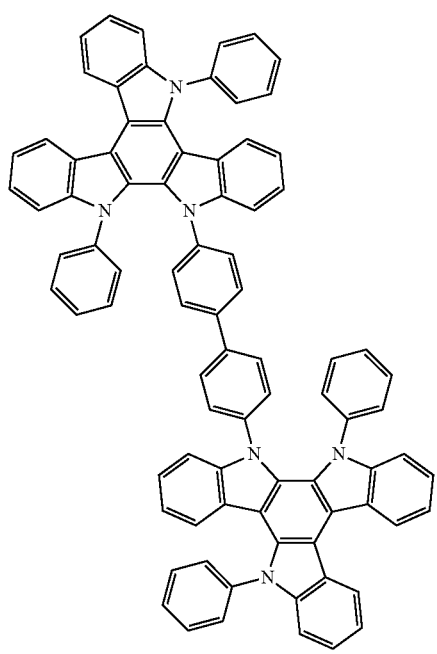
(165)
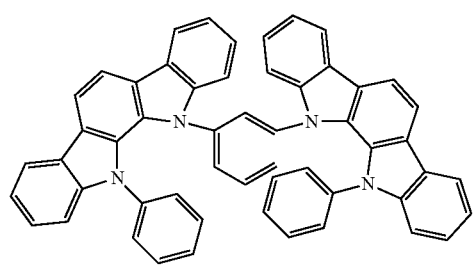
(166)
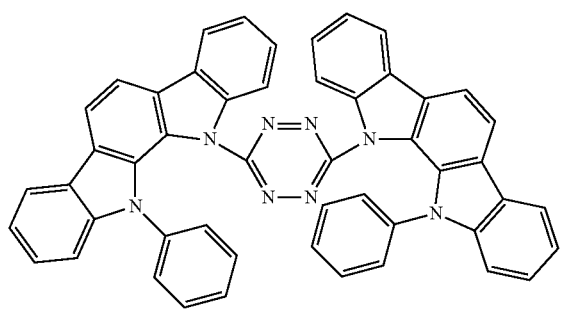
(167)
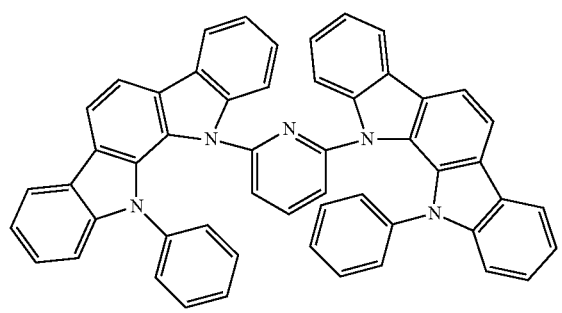

-continued
(168)
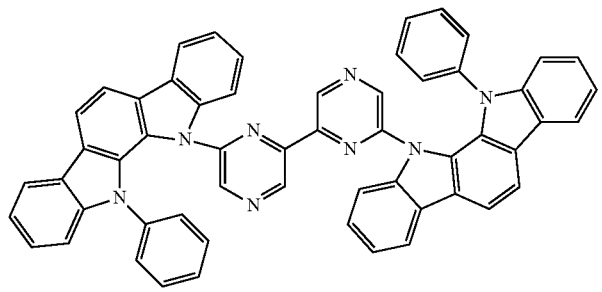
(169)
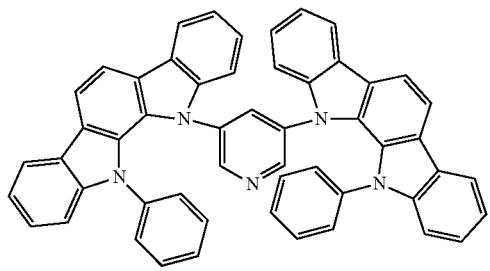
(170)
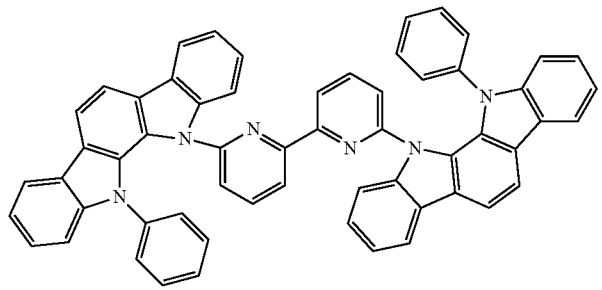
(171)
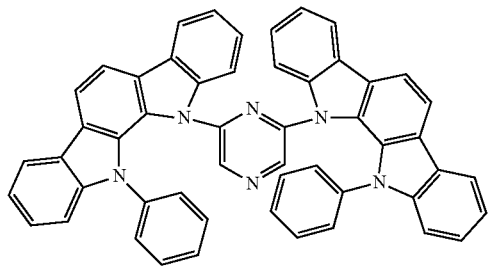
(172)
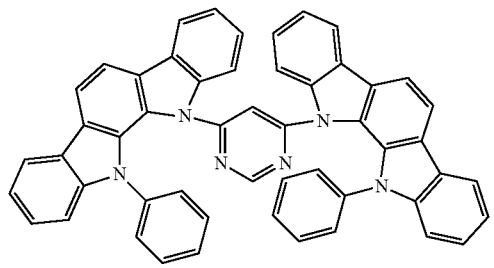
(173)
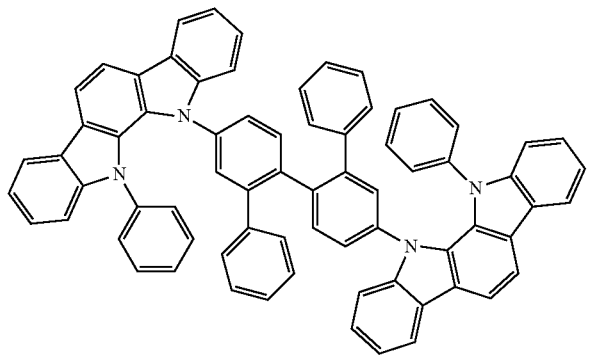
(174)
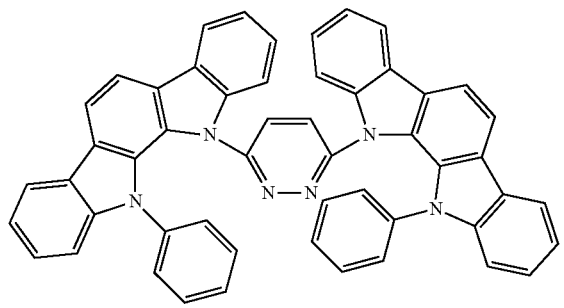
(175)
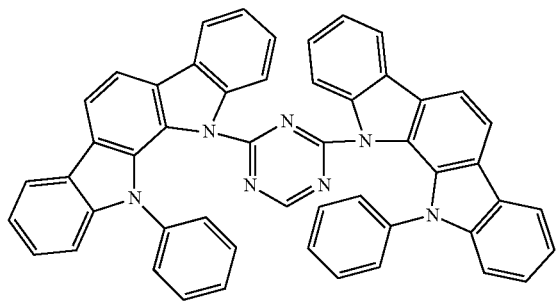

-continued
(176)
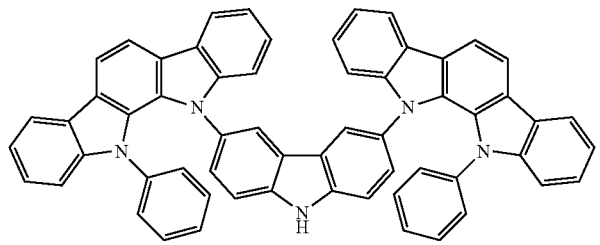
(177)
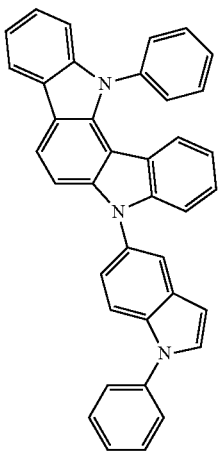
(178)
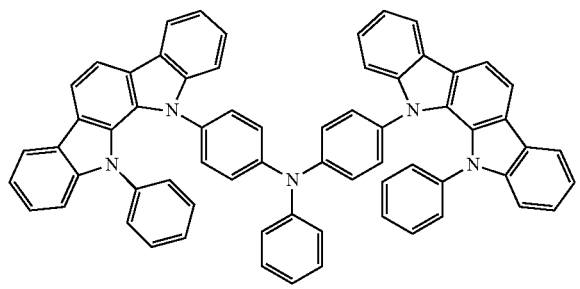
(179)
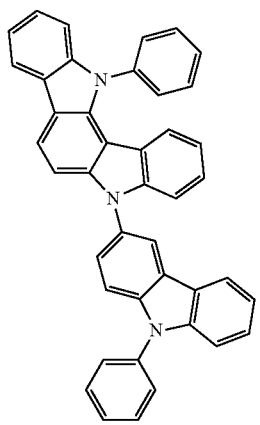
(180)
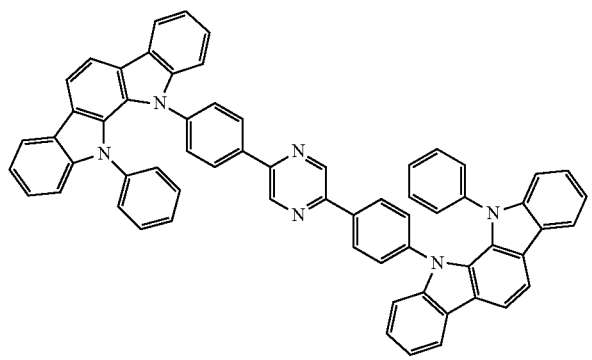
(181)
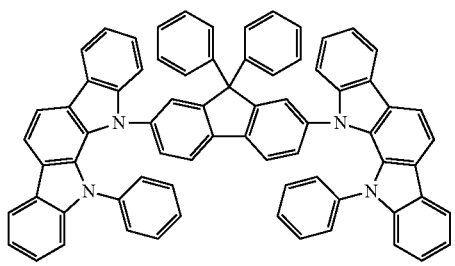
(182)
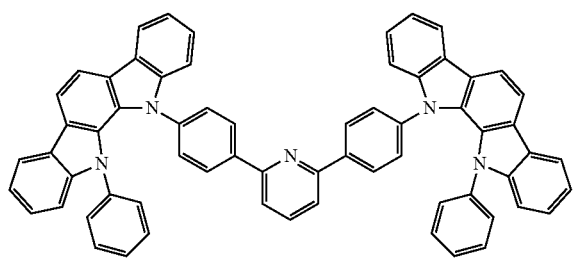
(183)
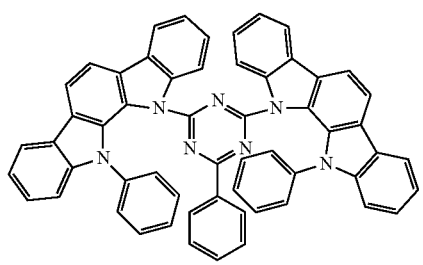

-continued
(184)
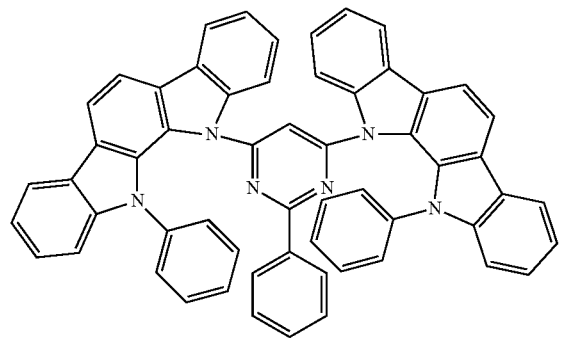
(185)
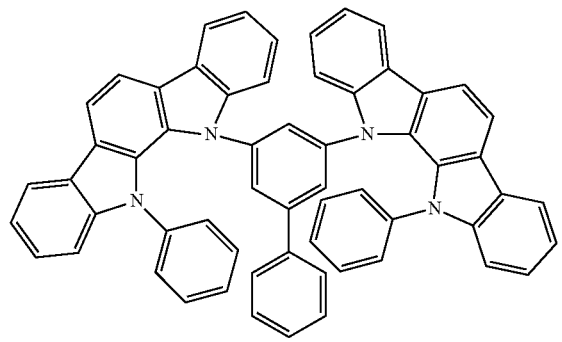
(186)
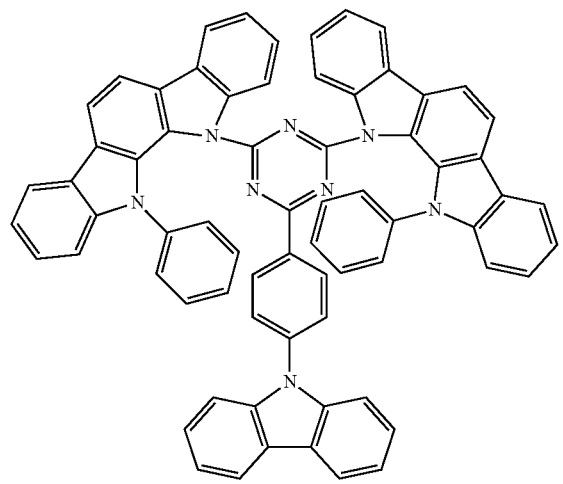
(187)
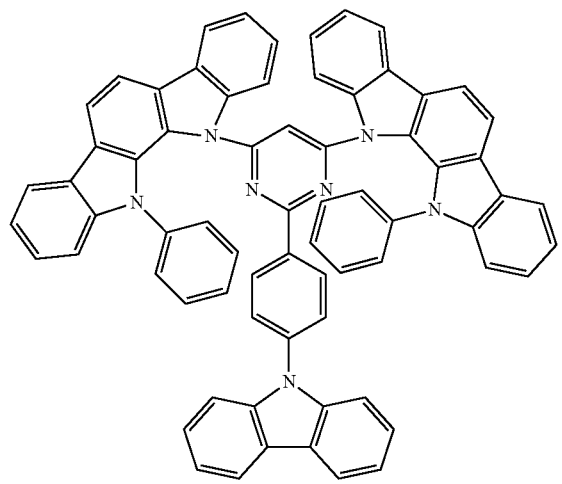
(188)
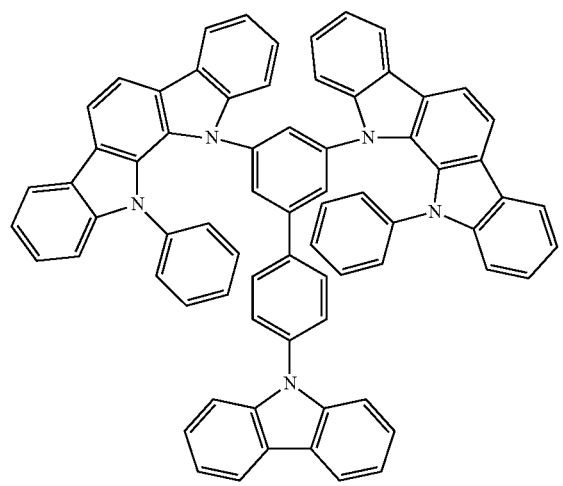
(189)
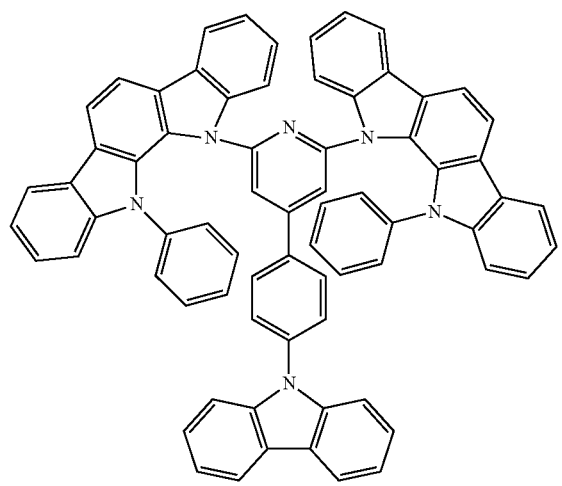

-continued
(190)
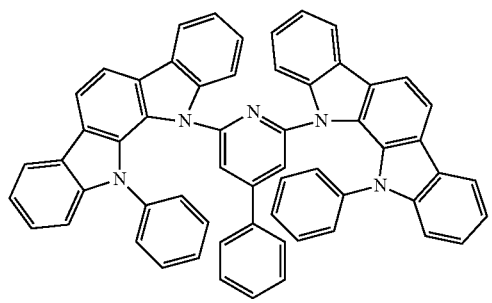
(191)
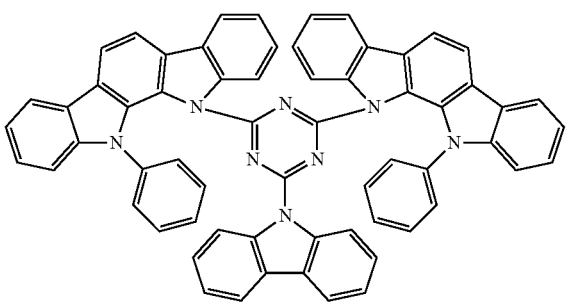
(192)
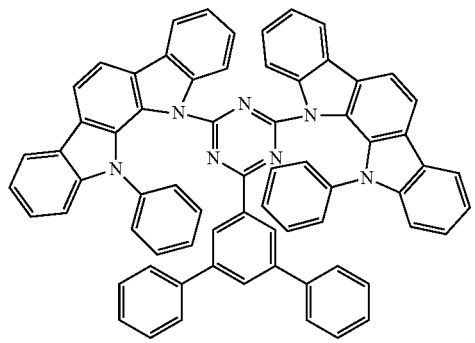
(193)
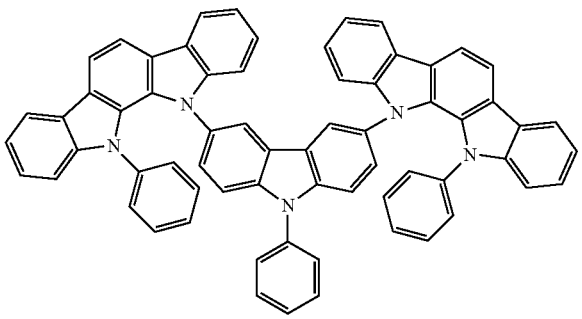
(194)
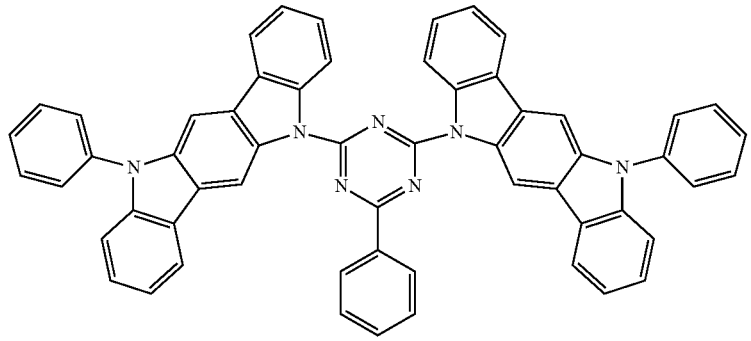
(195)
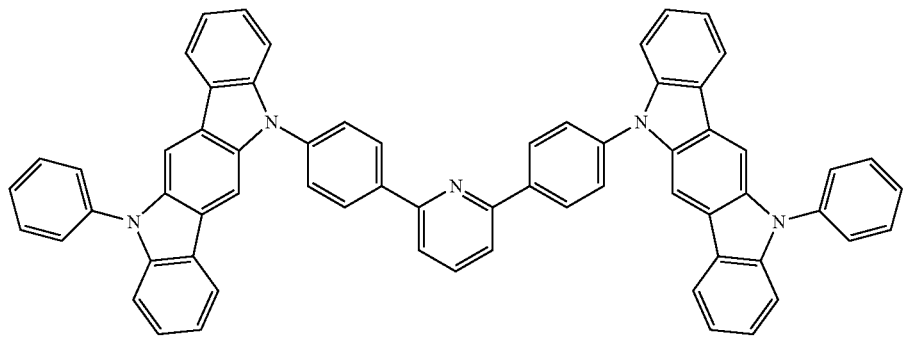

-continued
(196)
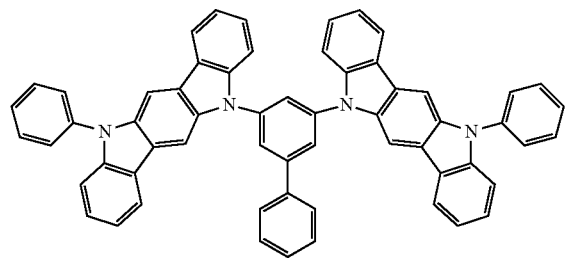
(197)
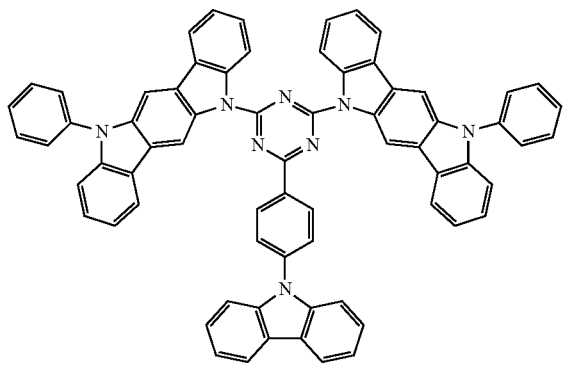
(198)
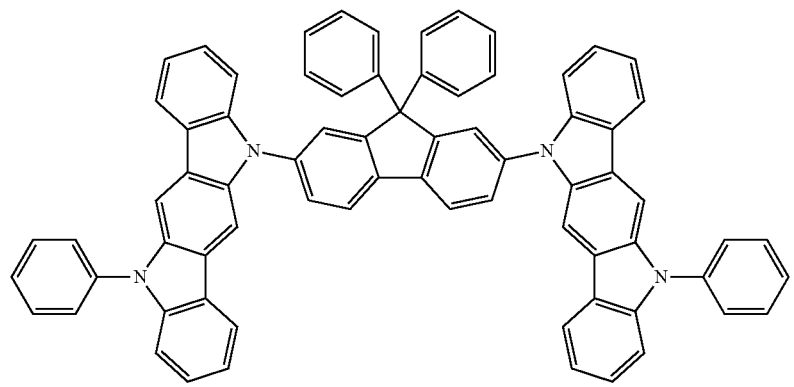
(199)
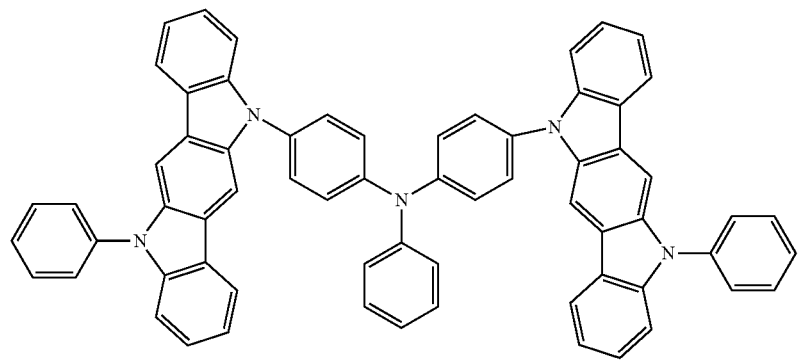
(200)
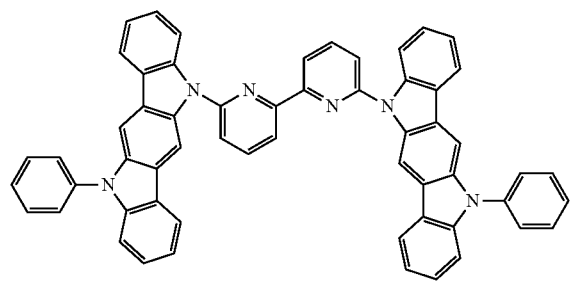
(201)
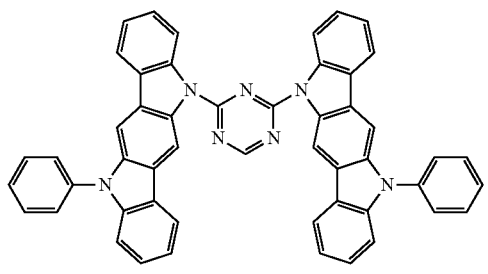

-continued
(202)
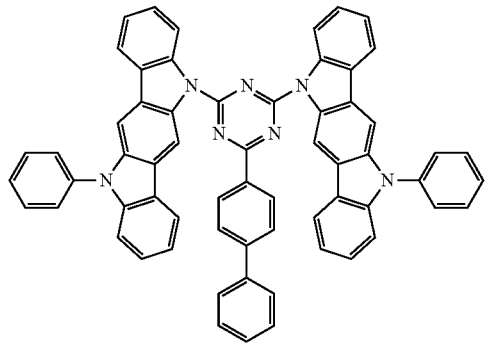
(203)
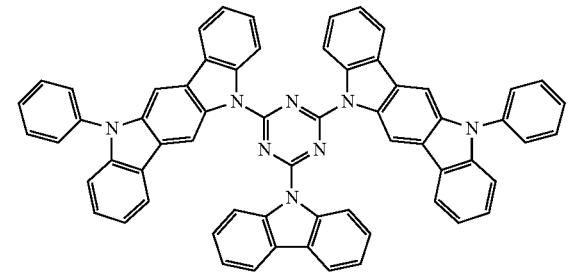
(204)
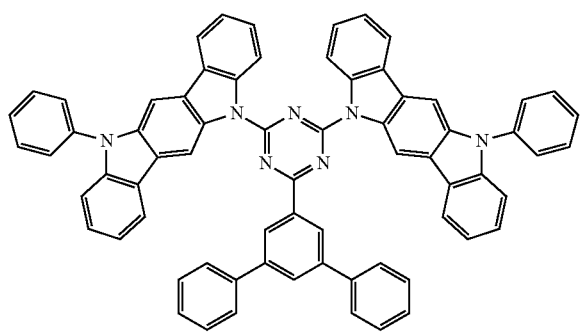
(205)
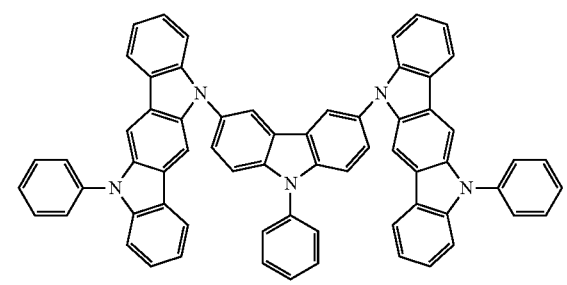
(206)
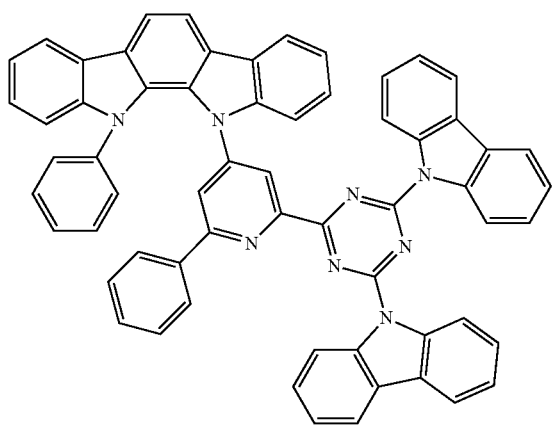
(207)
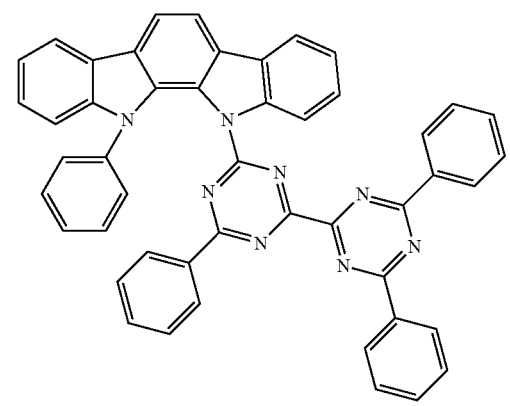
(208)
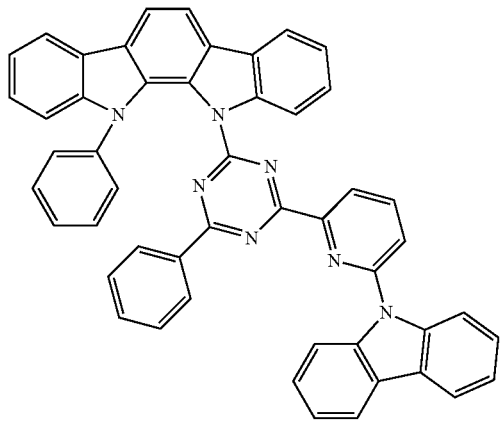
(209)
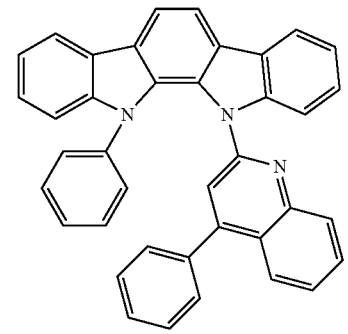

-continued
(210)
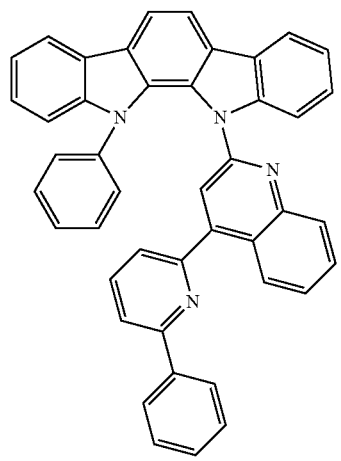
(211)
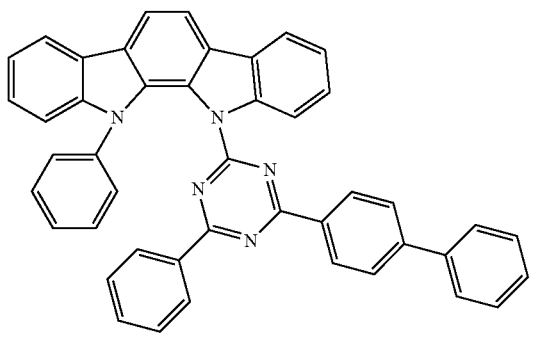
(211)
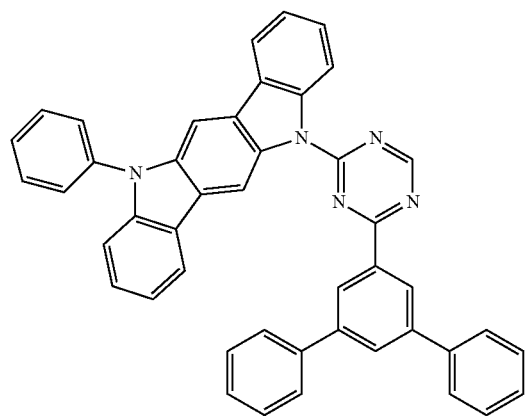
(212)
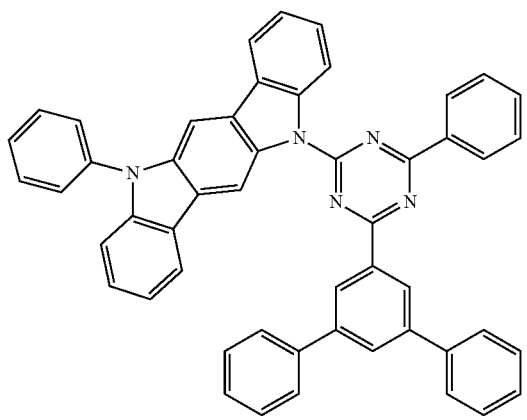
(213)
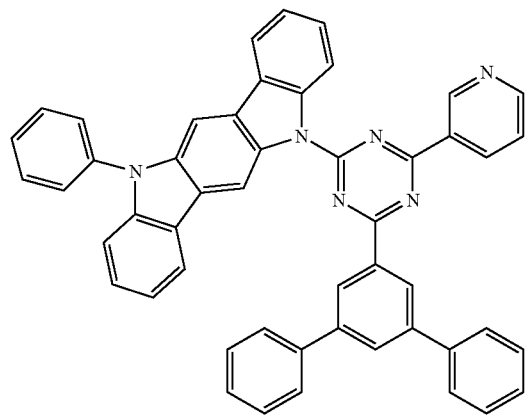
(214)
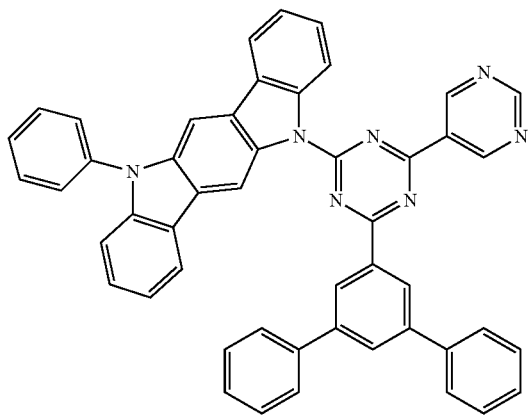

-continued
(215)
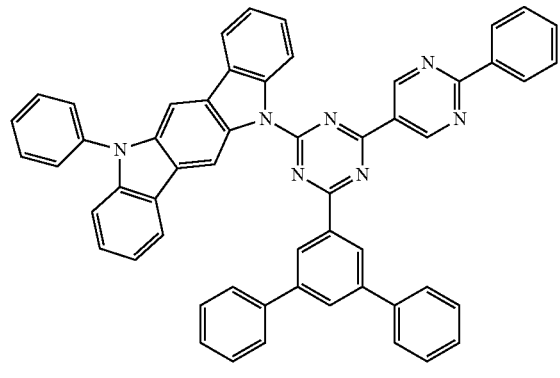
(216)
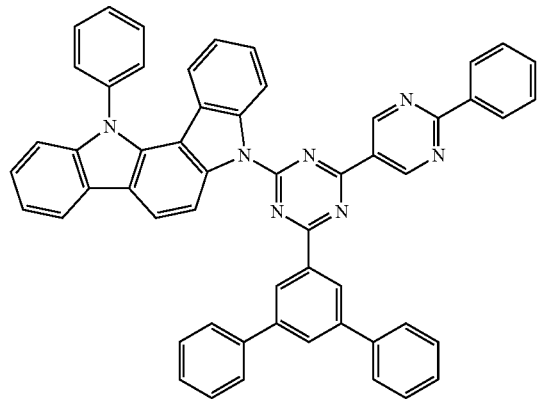
(217)
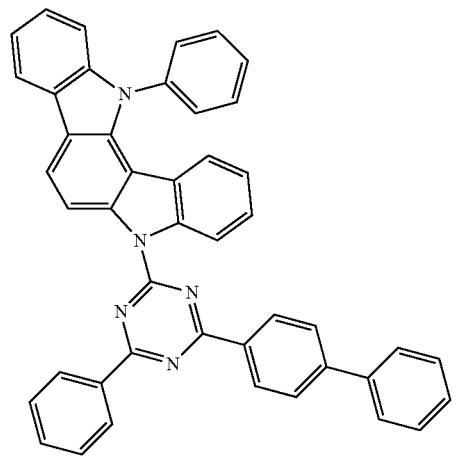
(218)
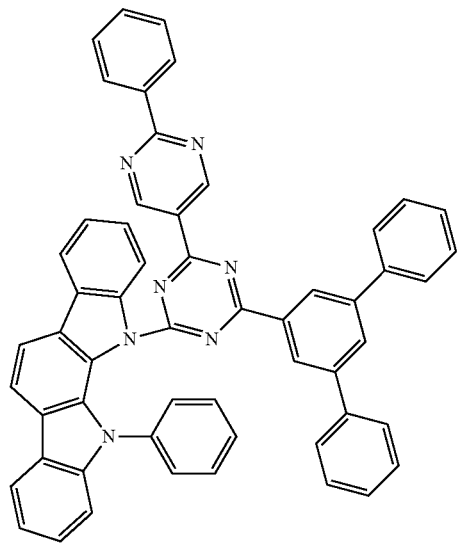
(219)
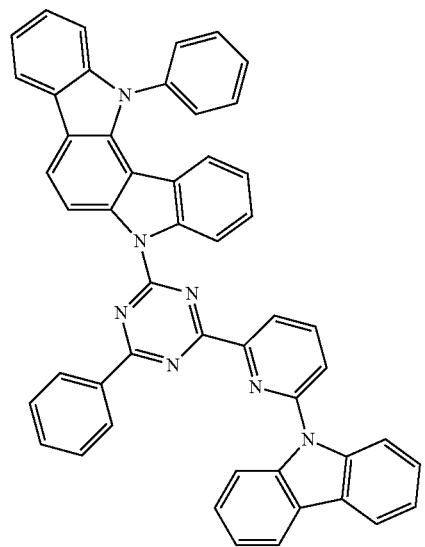
(220)
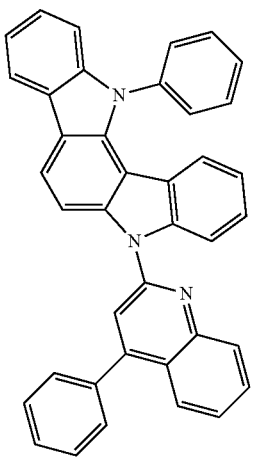

(221)
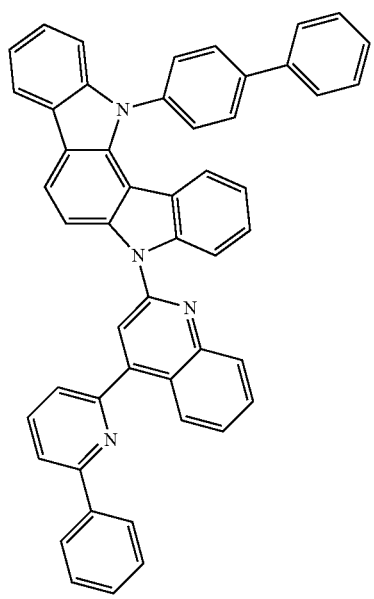
(222)
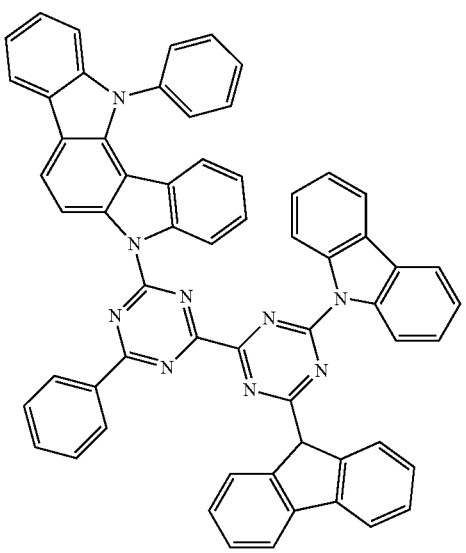
(223)
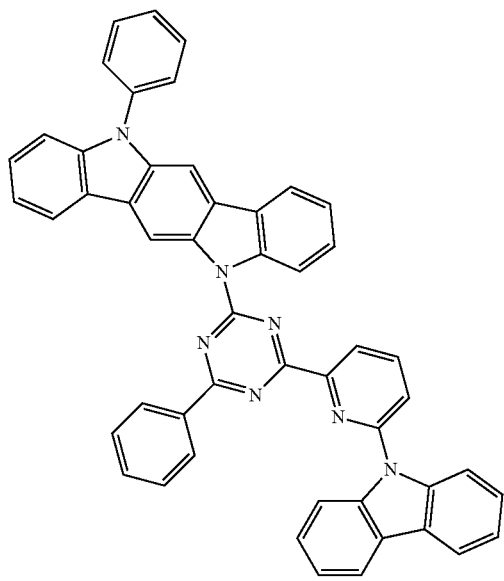
(224)
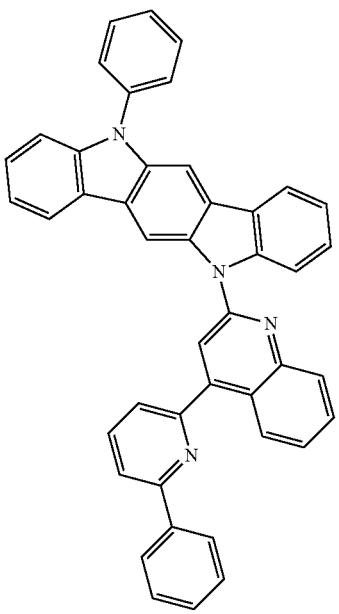

-continued
(225)
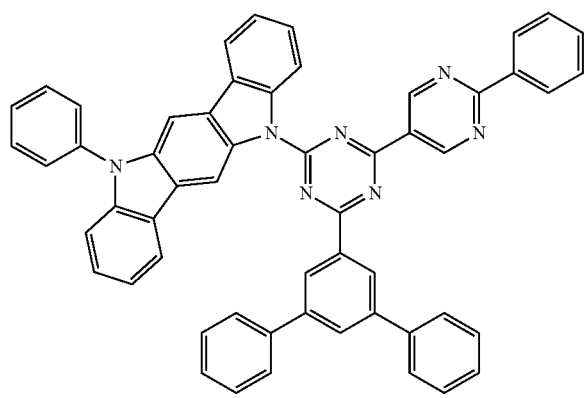
(226)
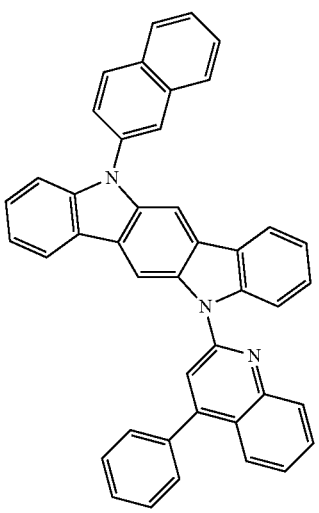
(227)
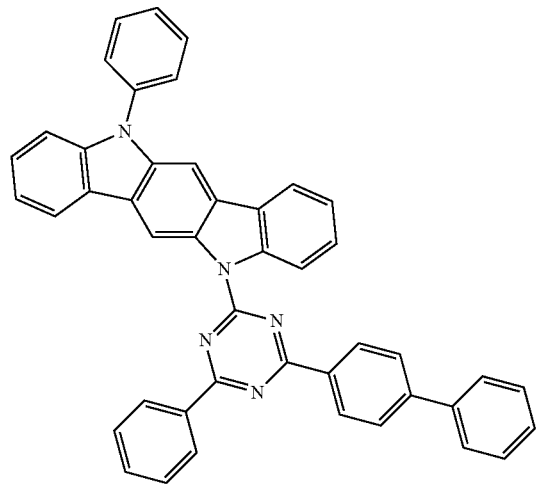
(228)
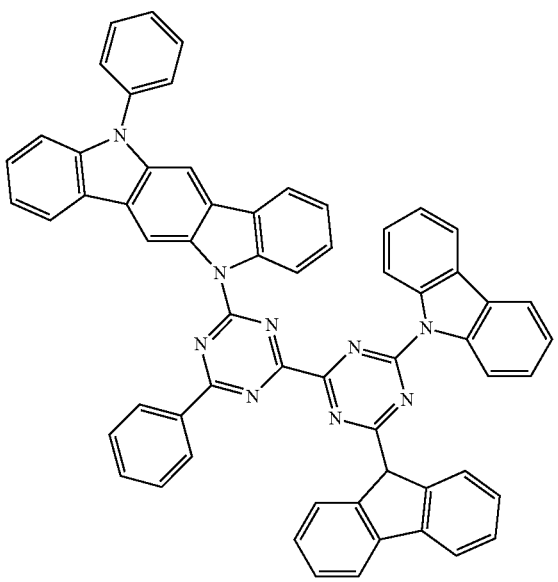

-continued
(229)
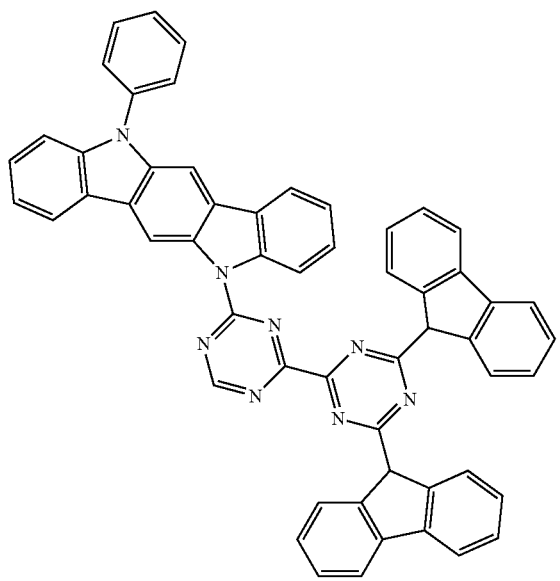
(230)
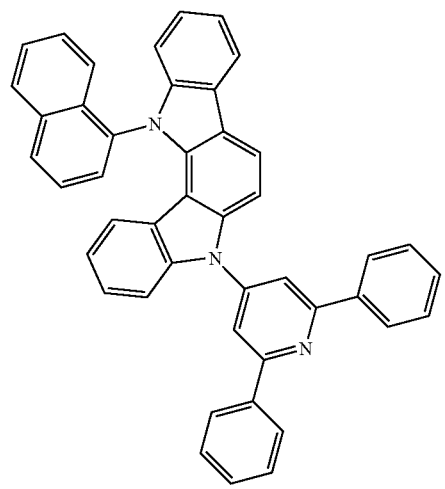
(231)
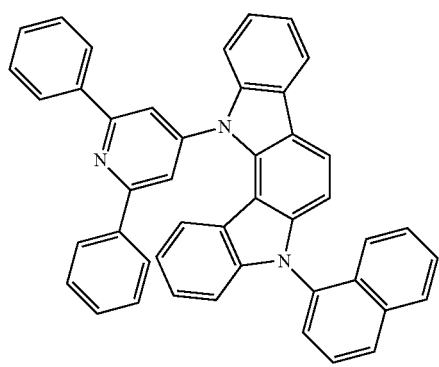
(232)
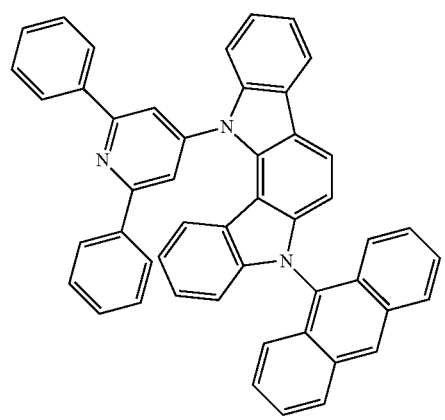
(233)
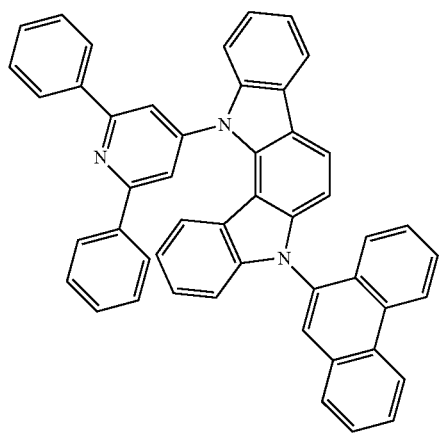
(234)
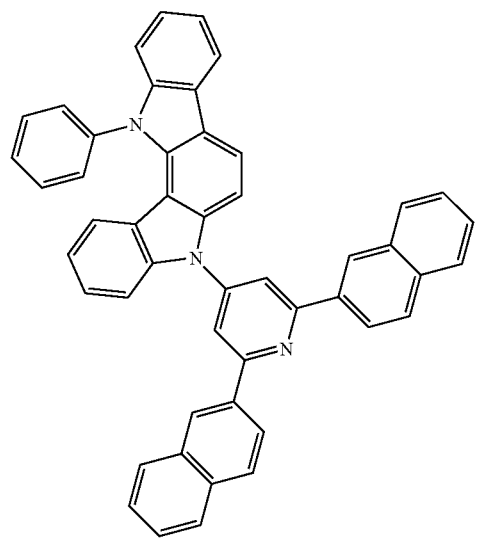

-continued
(235)
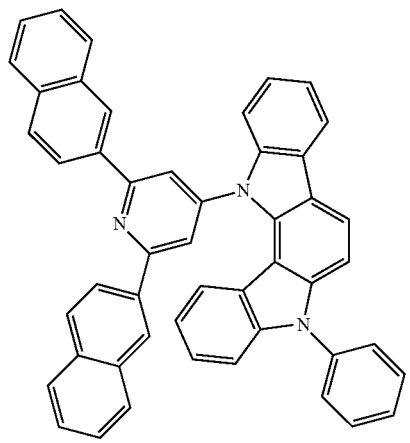
(236)
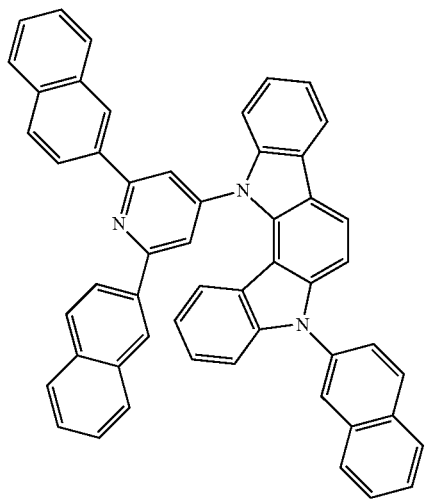
(237)
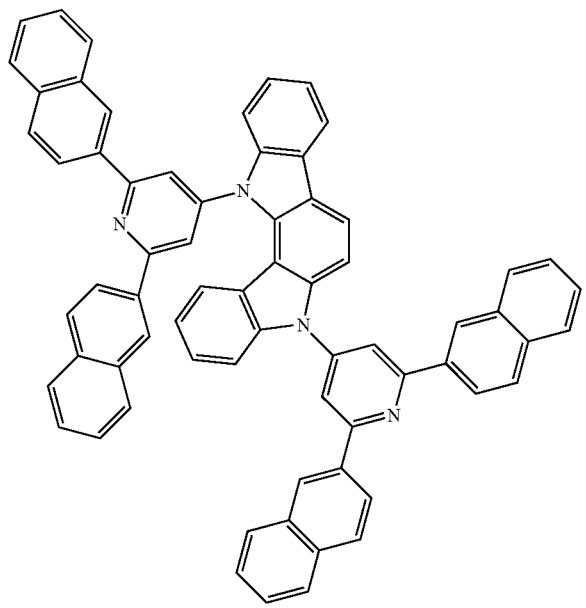
(238)
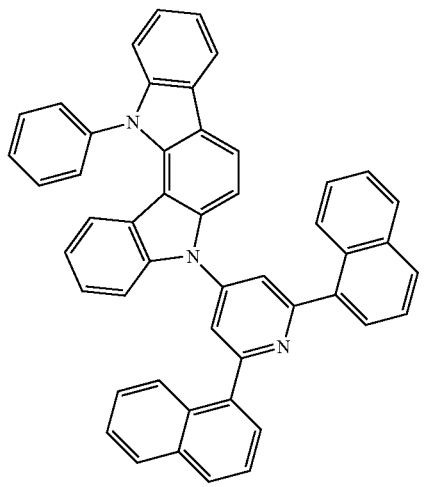
(239)
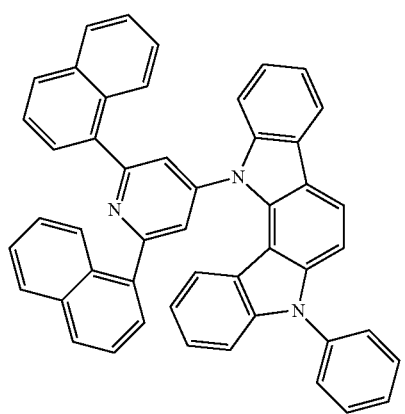
(240)
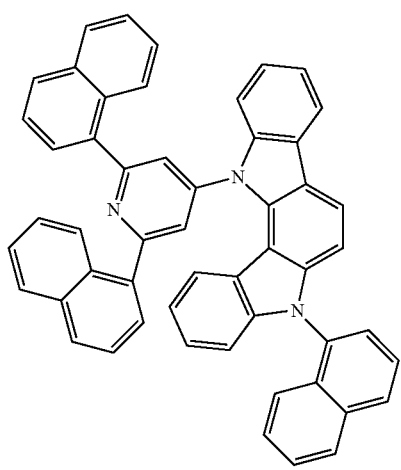

(241)
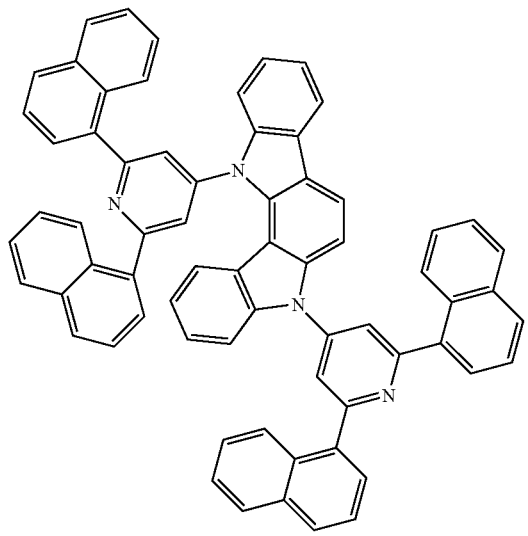
(242)
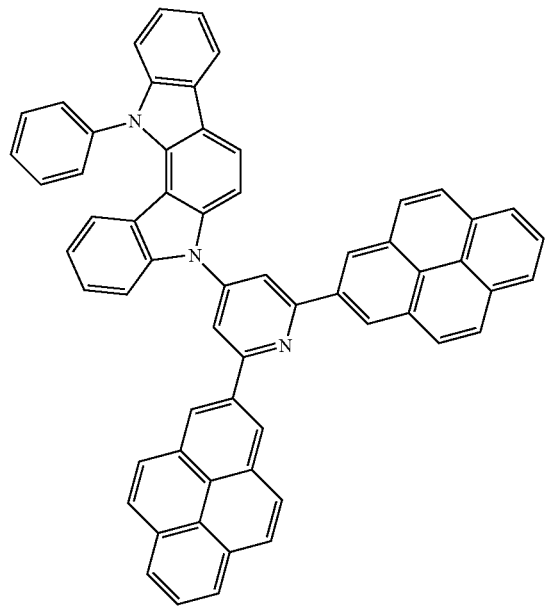
(243)
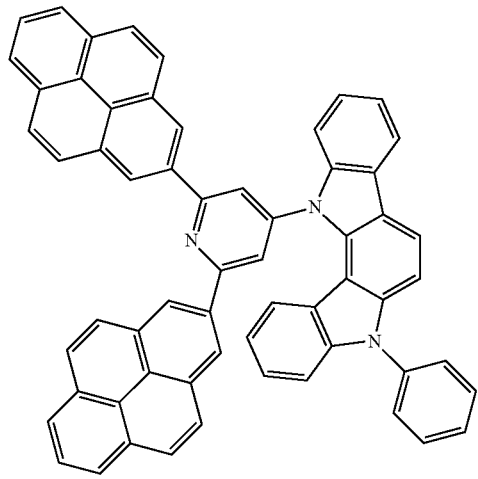
(244)
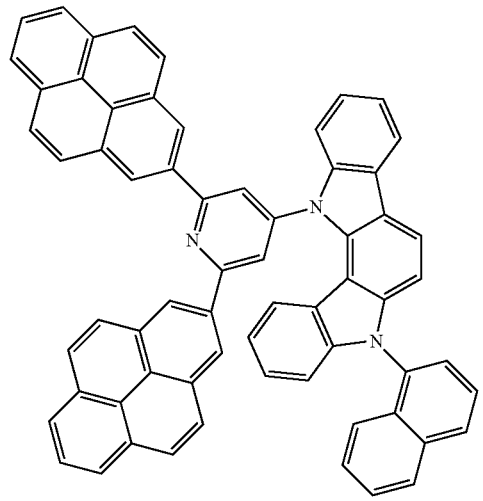

-continued
(245)
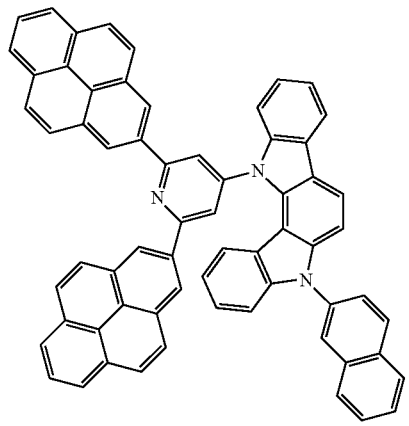
(246)
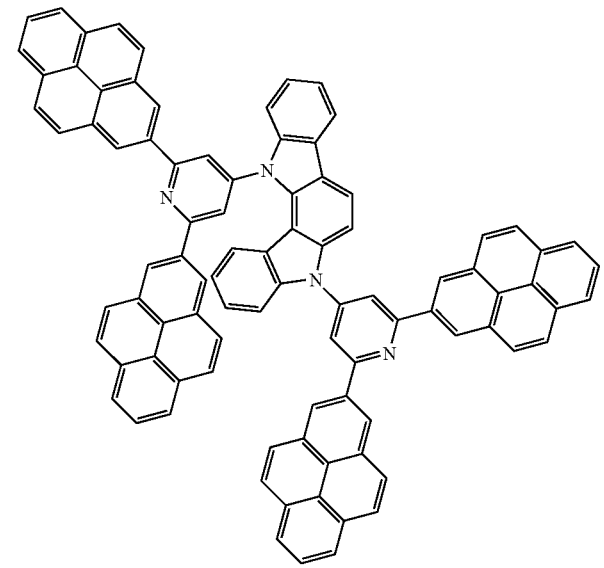
(247)
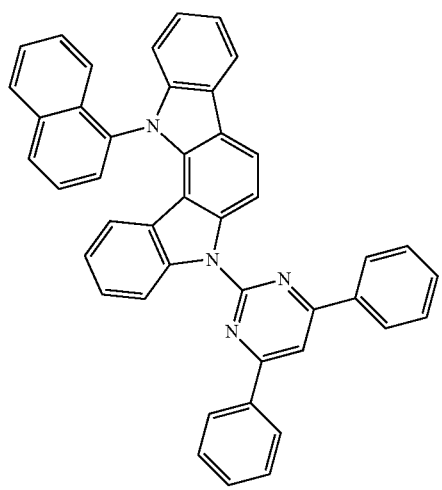
(248)
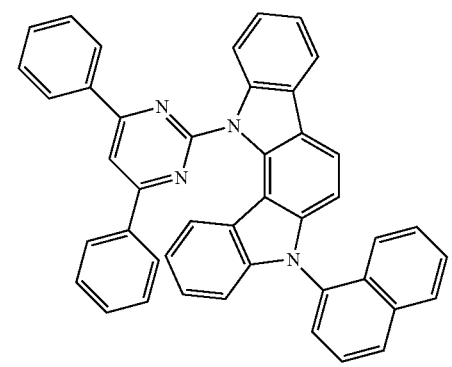
(249)
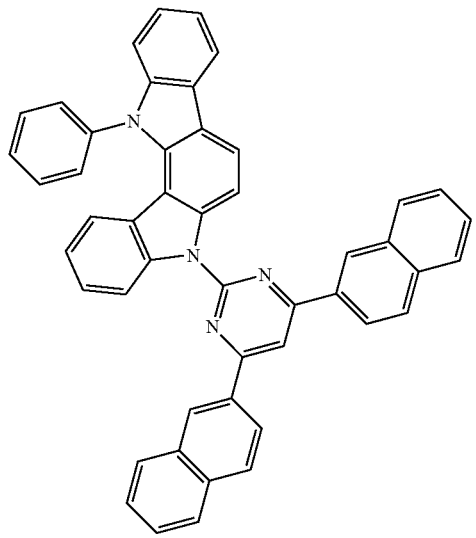
(250)
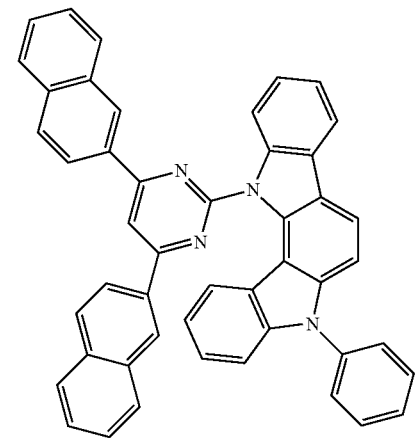

-continued
(251)
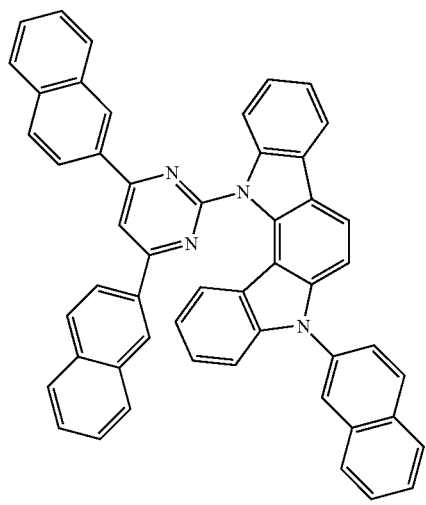
(252)
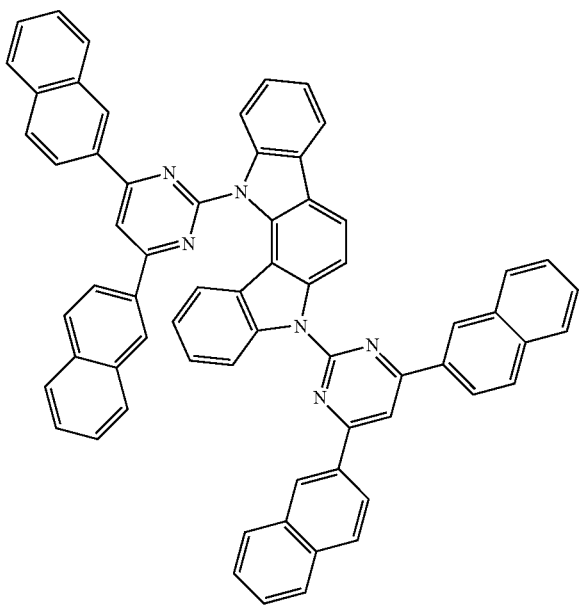
(253)
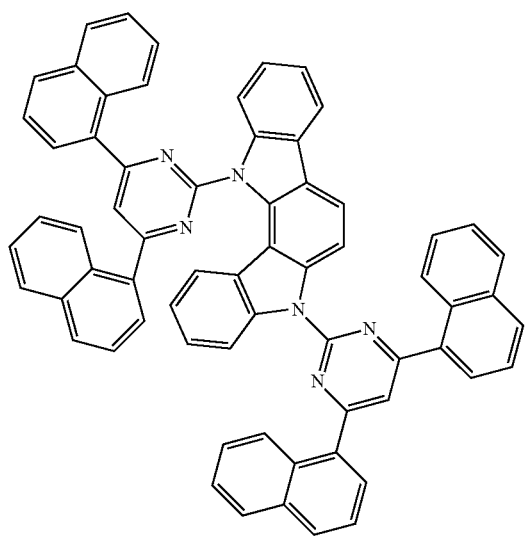
(254)
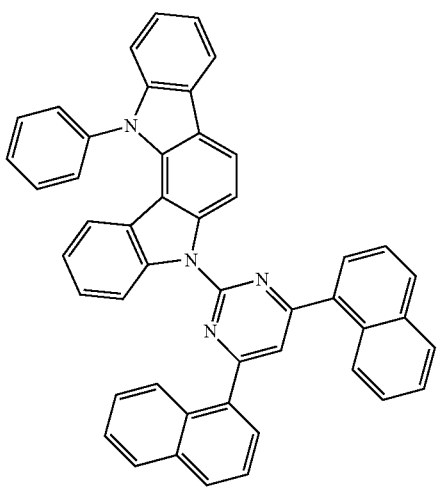
(255)
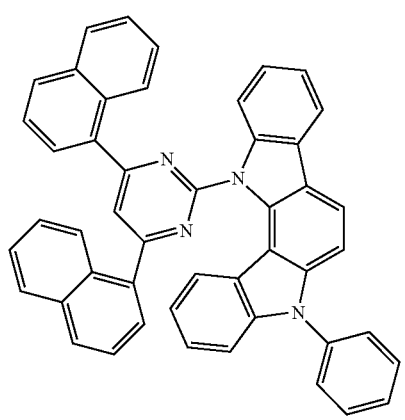
(256)
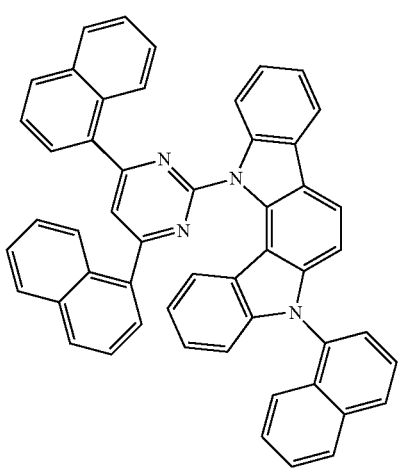

-continued
(257)
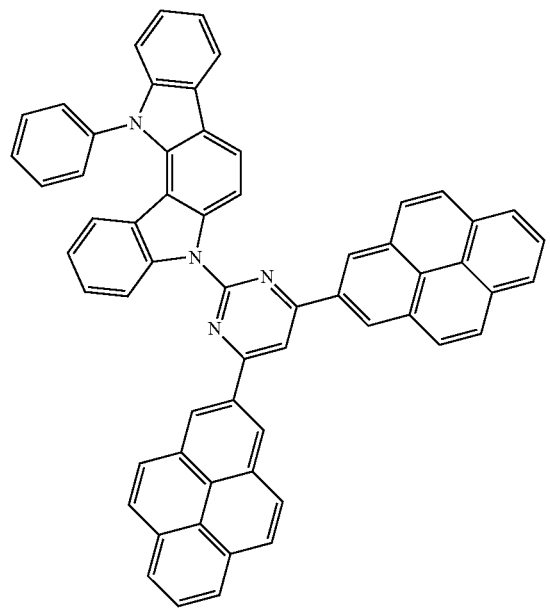
(258)
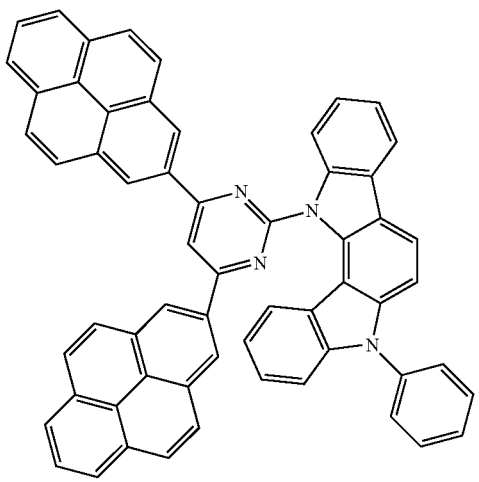
(259)
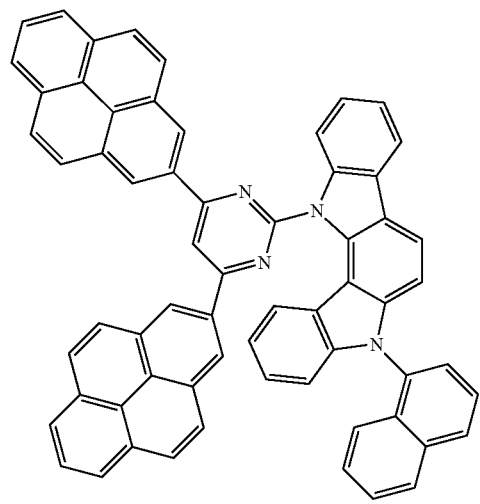
(260)
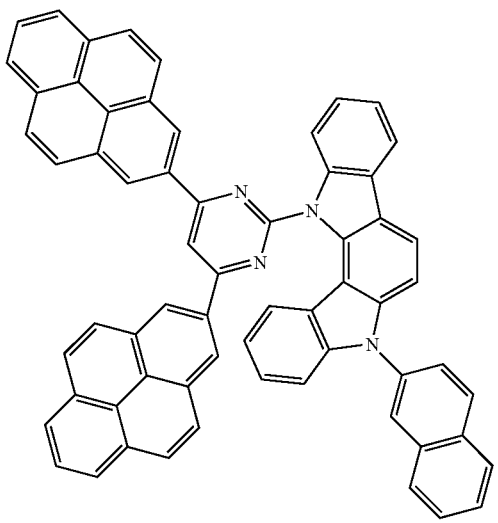
(261)
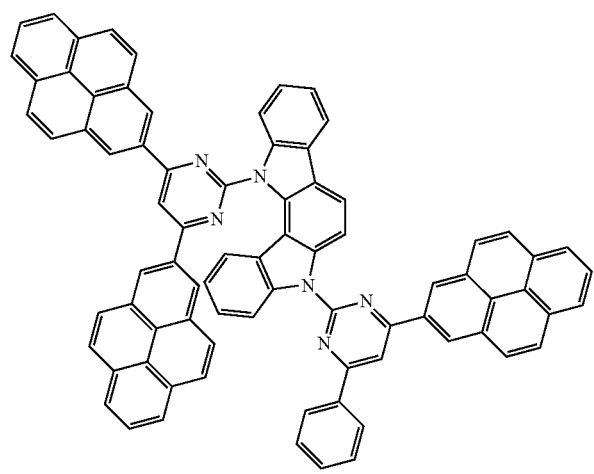
(262)
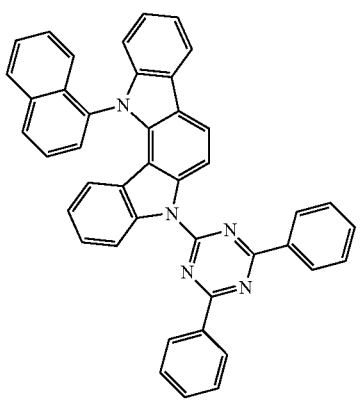

-continued
(263)
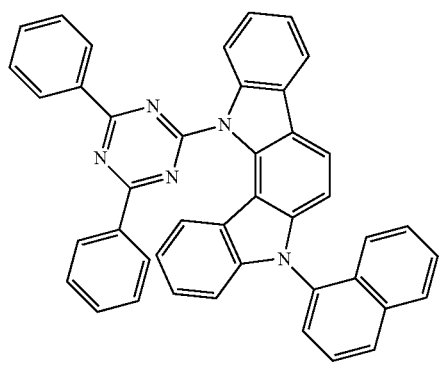
(264)
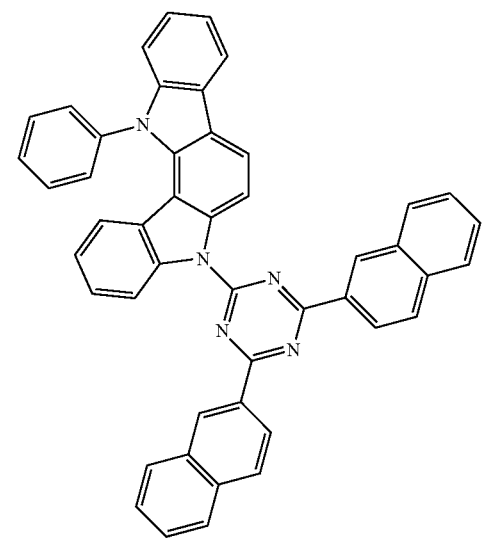
(265)
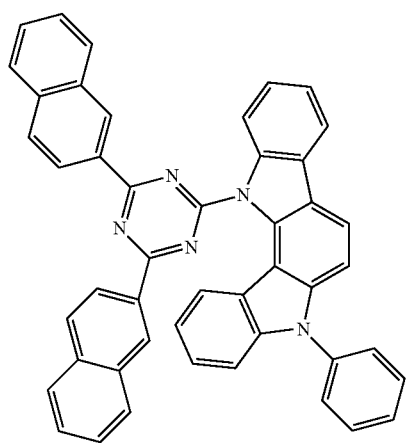
(266)
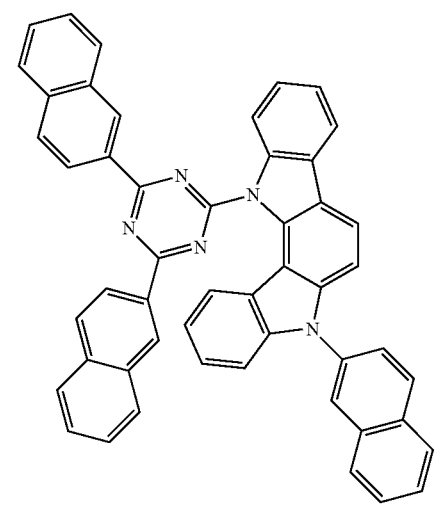
(267)
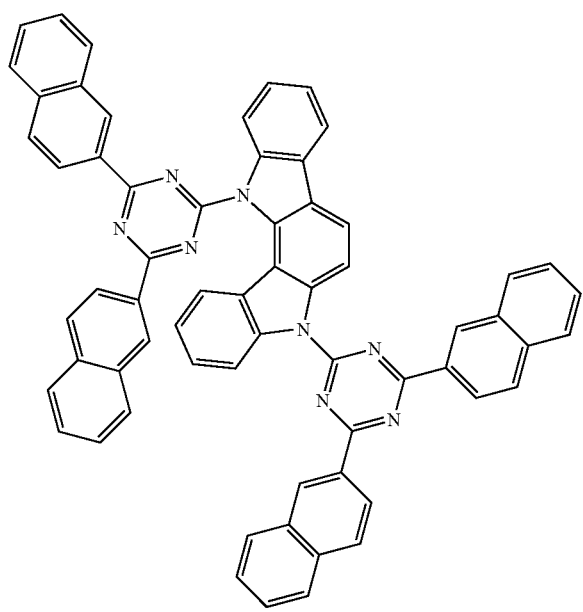
(268)
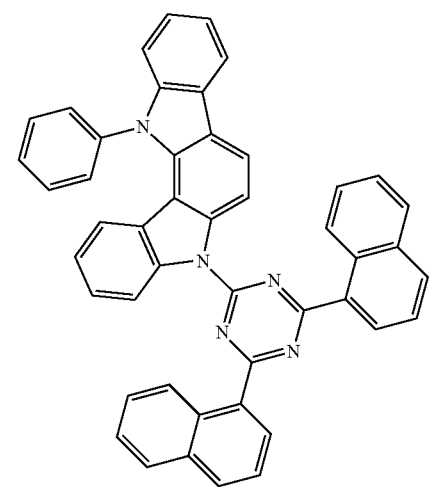

-continued
(269)
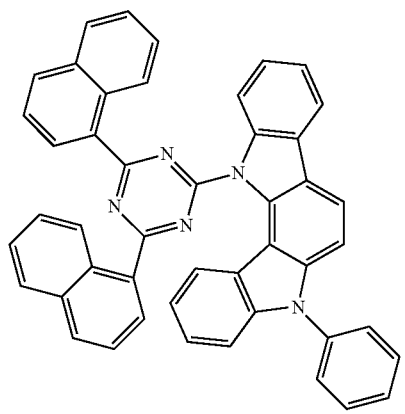
(270)
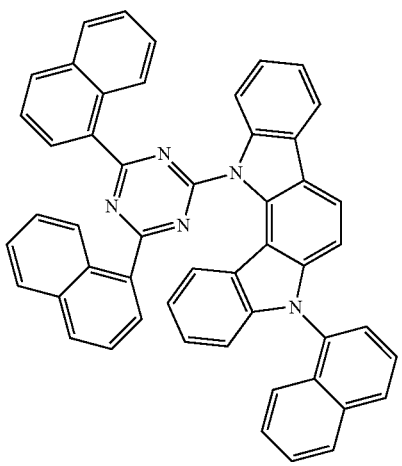
(271)
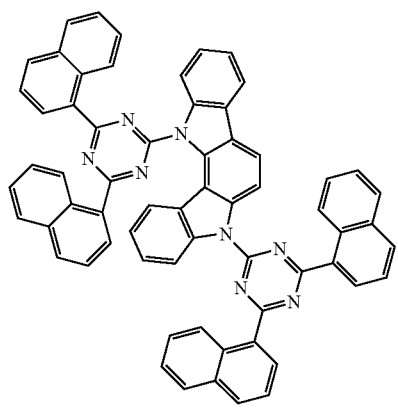
(272)
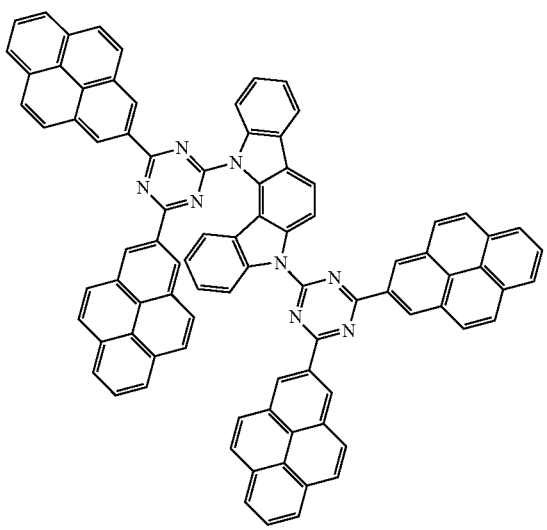
(273)
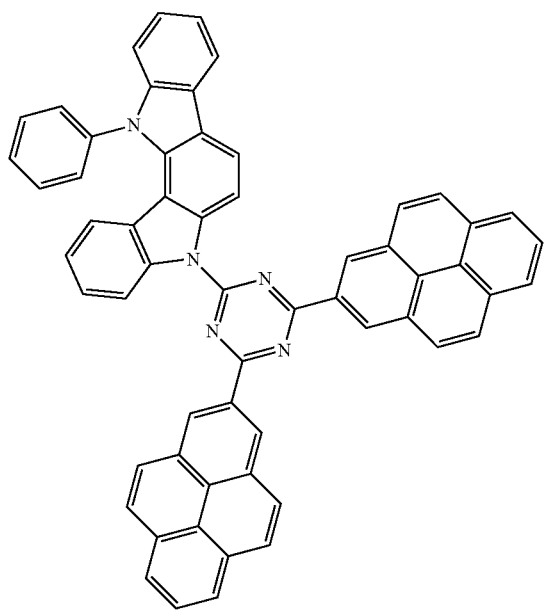
(274)
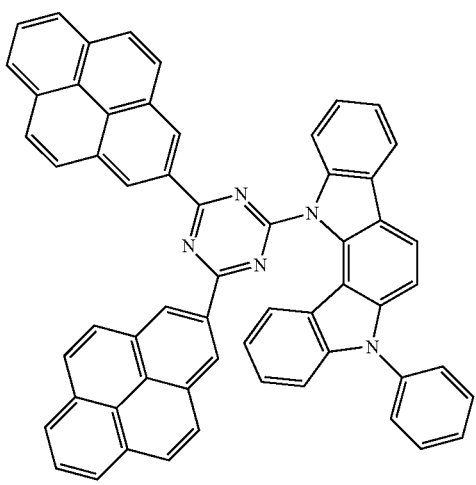

-continued
(275)
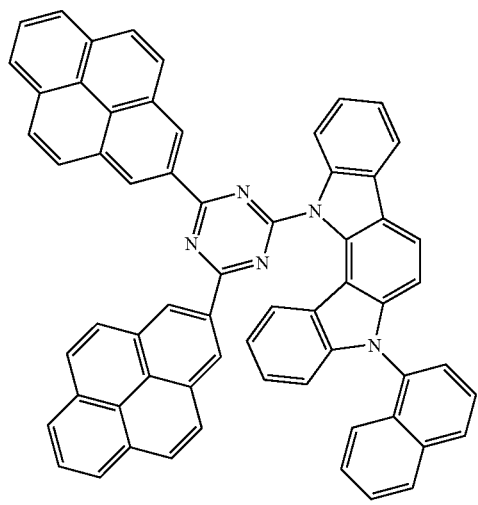
(276)
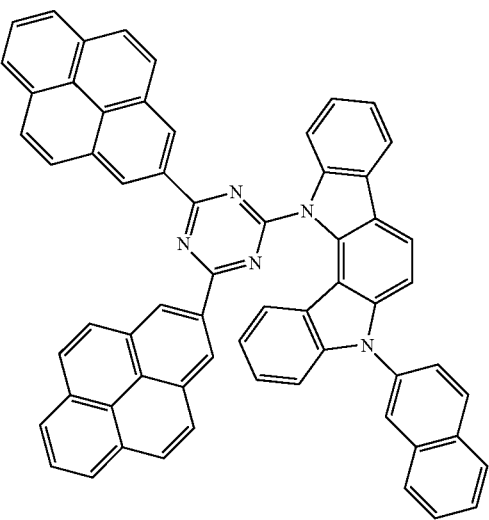
(277)
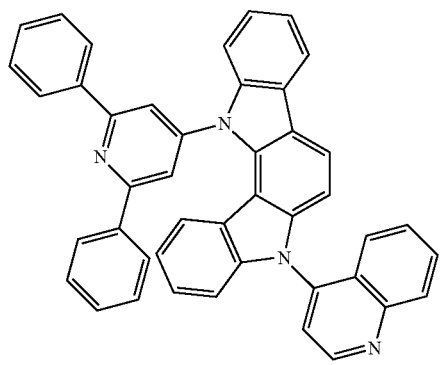
(278)
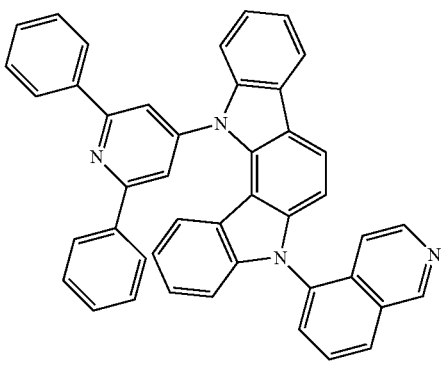
(279)
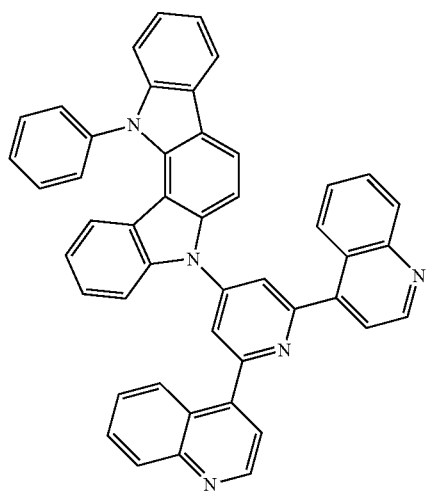
(280)
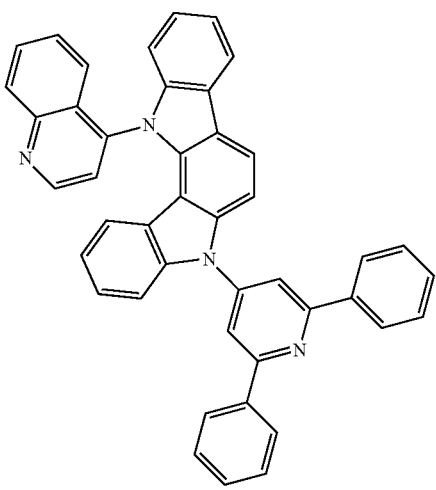

-continued
(281)
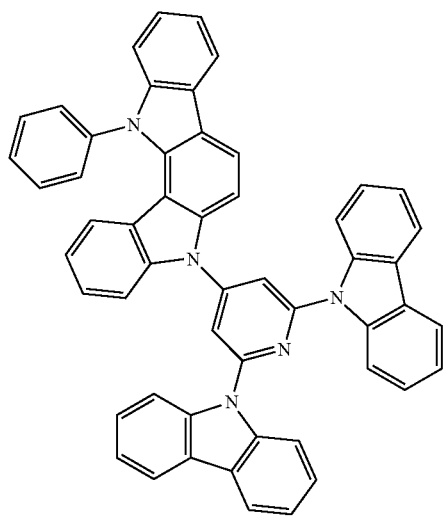
(282)
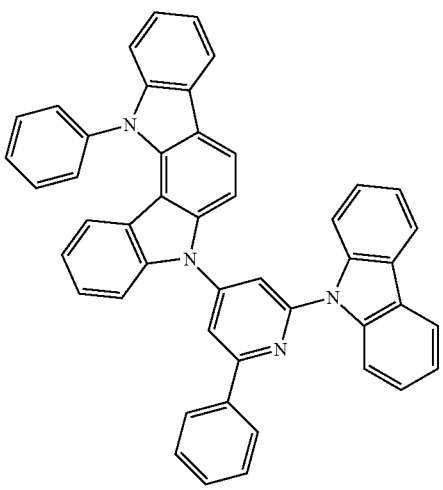
(283)
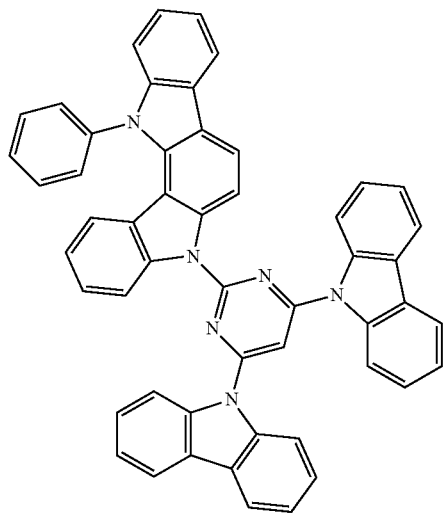
(284)
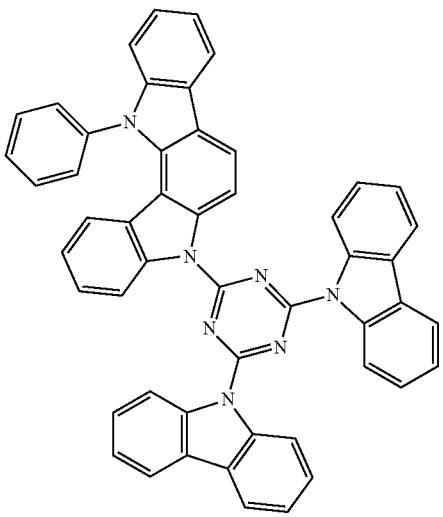
(285)
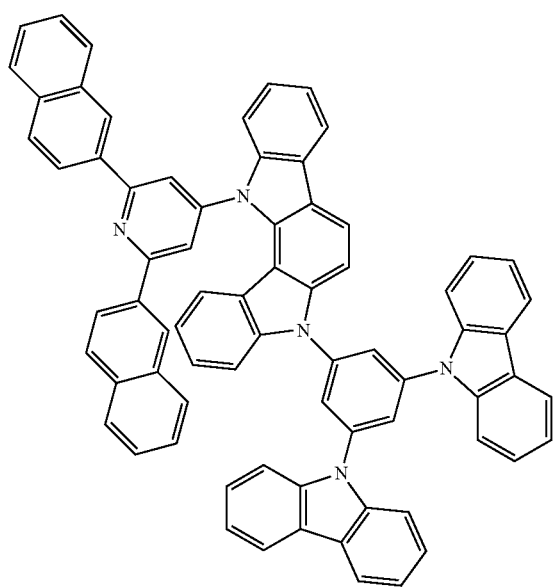
(286)
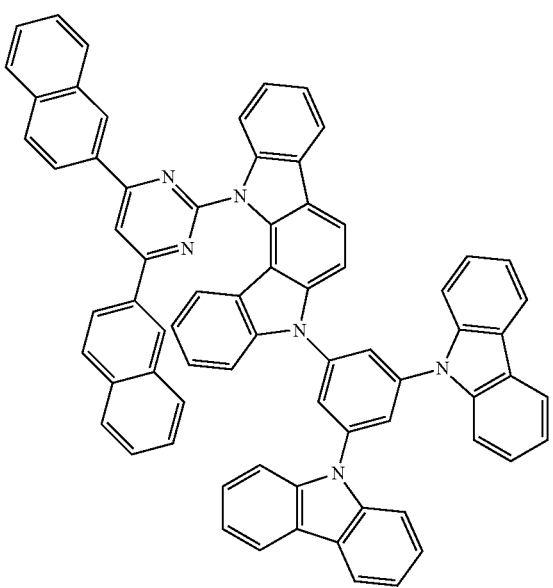

(287)
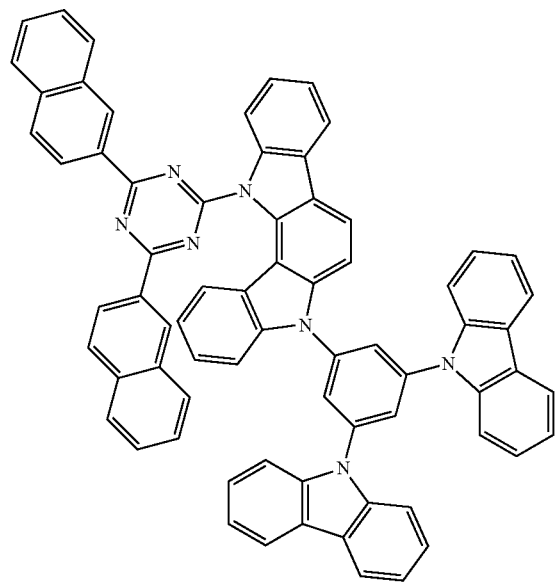
(288)
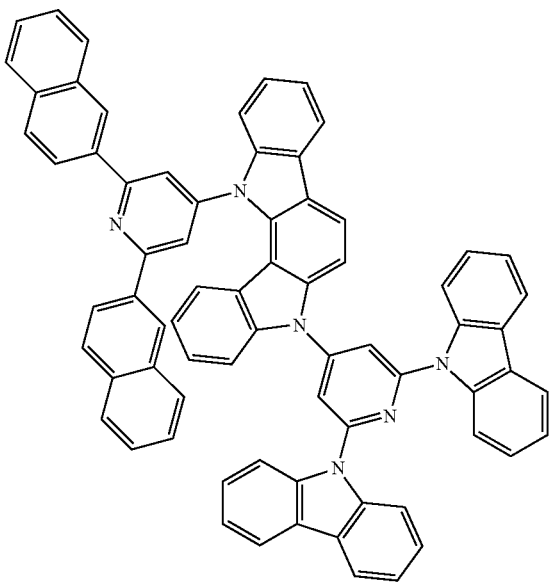
(289)
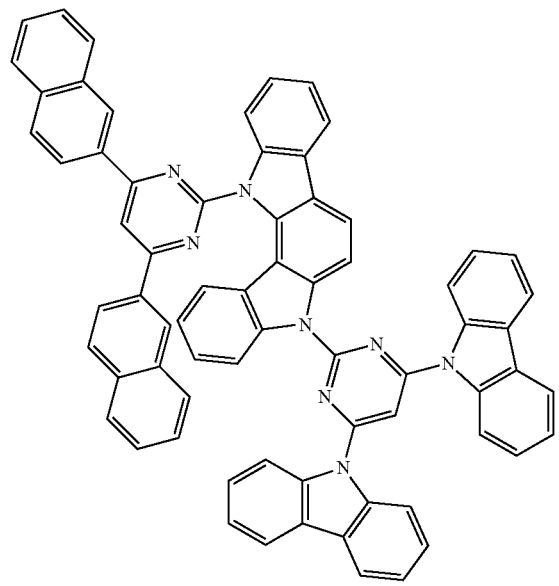
(290)
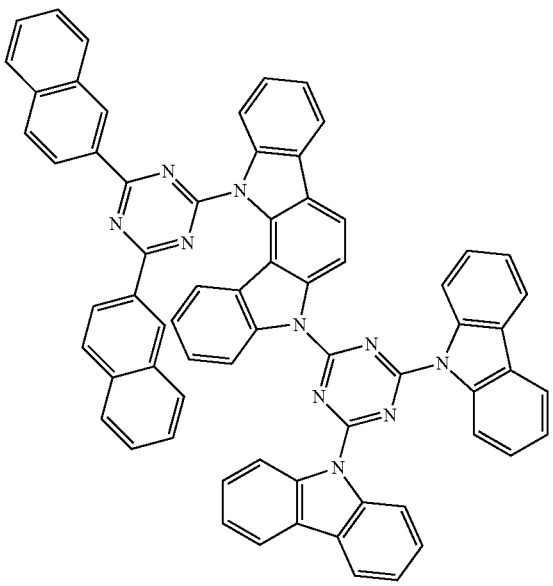

(291)
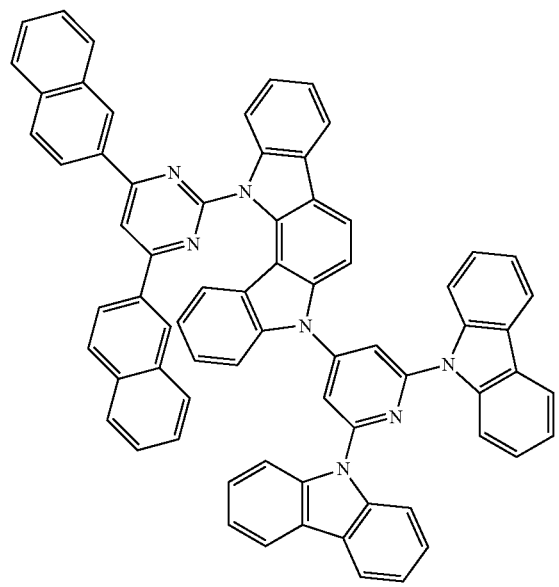
(292)
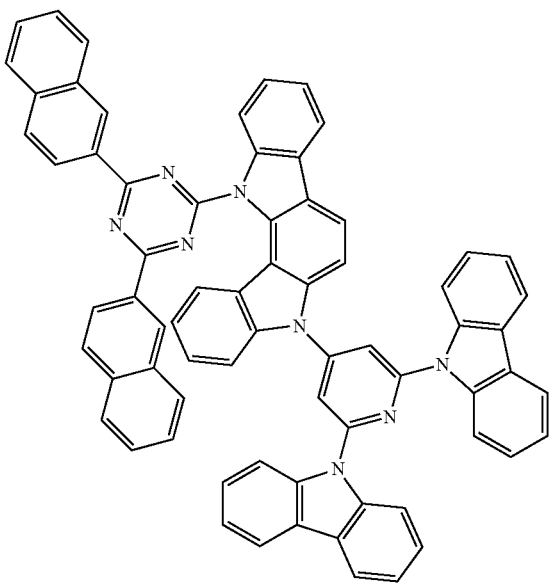
(293)
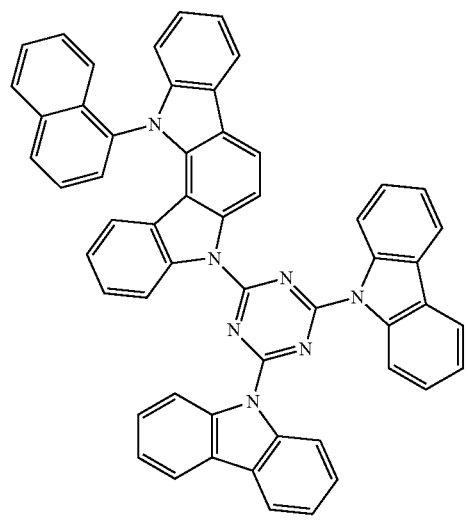
(294)
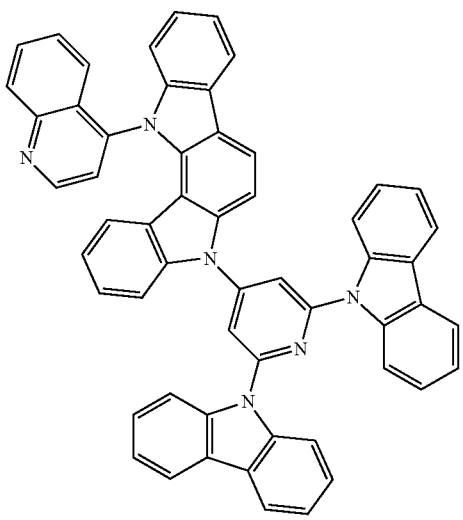

(295)
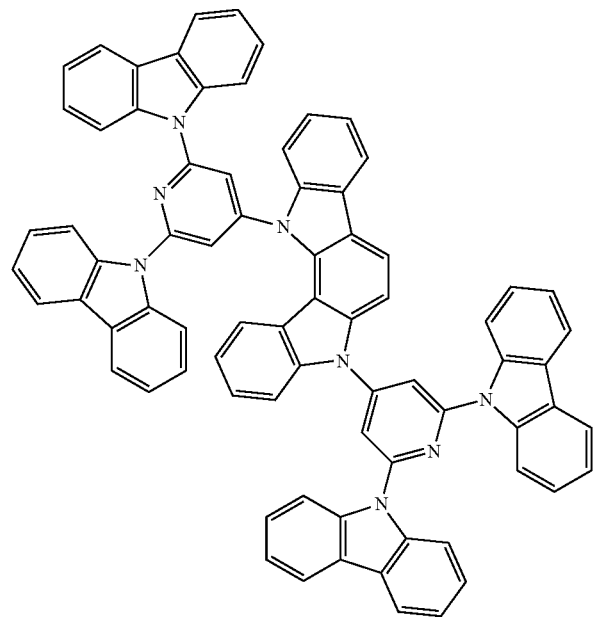
(296)
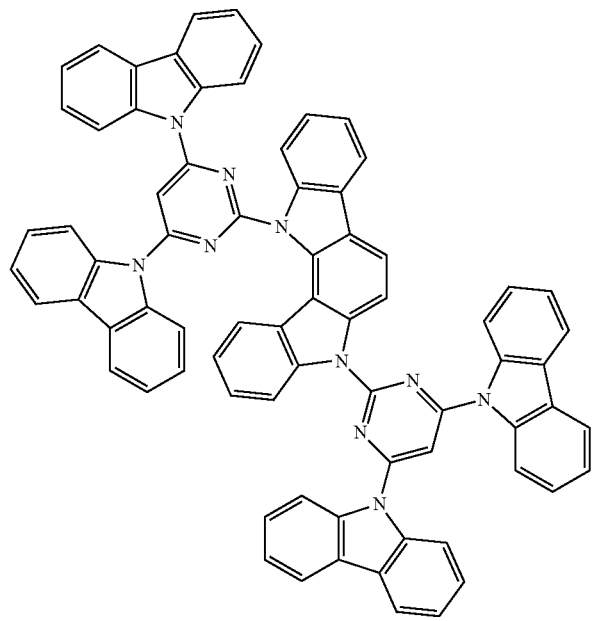
(297)
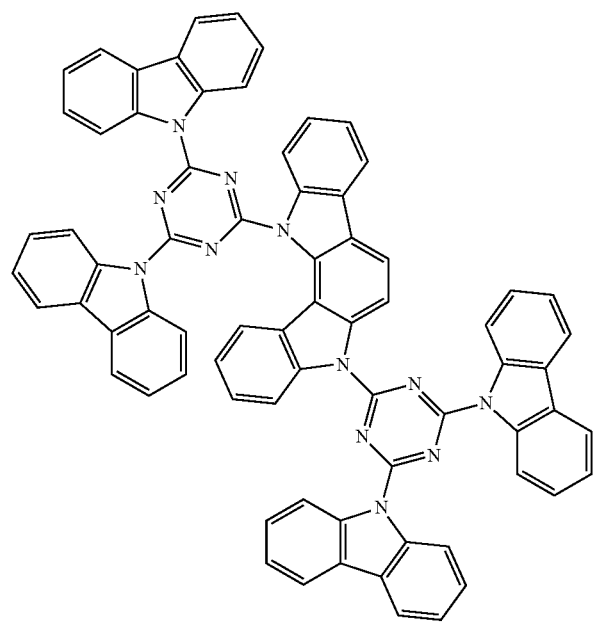
(298)
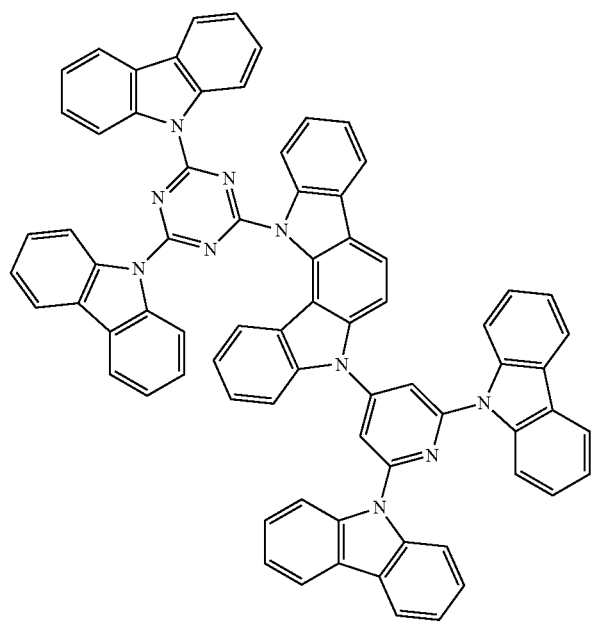

-continued
(299)
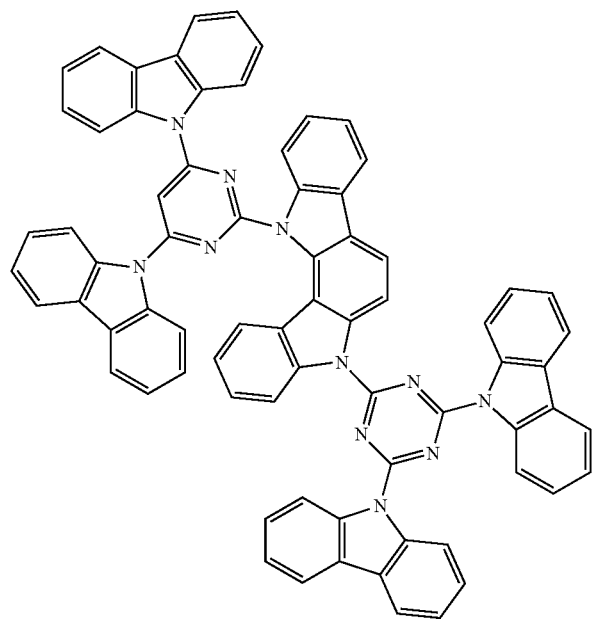
(300)
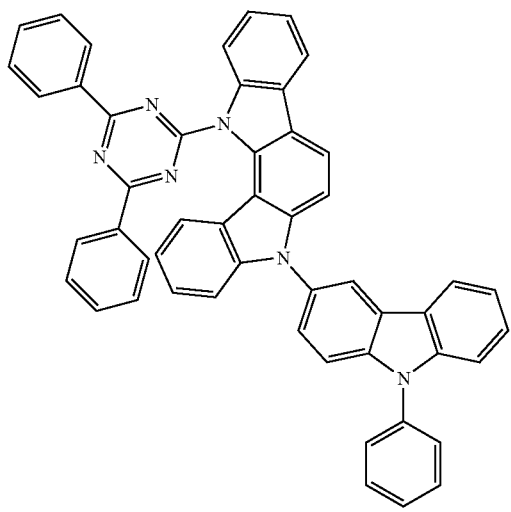
(301)
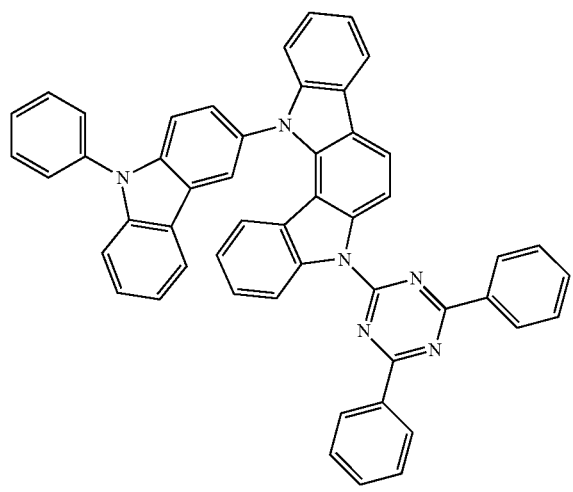
(302)
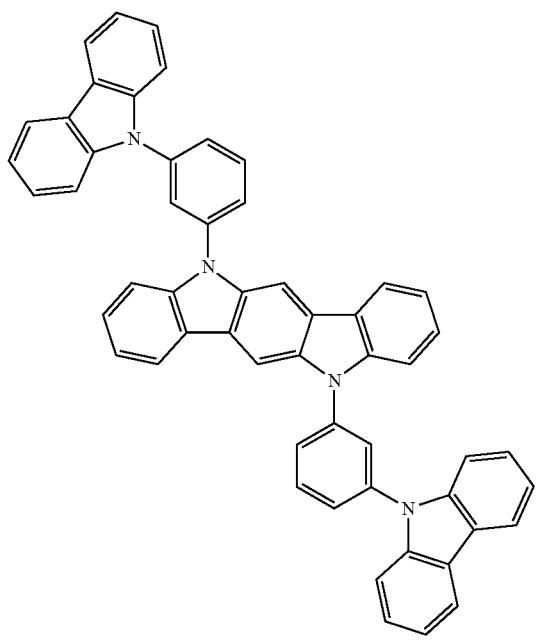

(303)
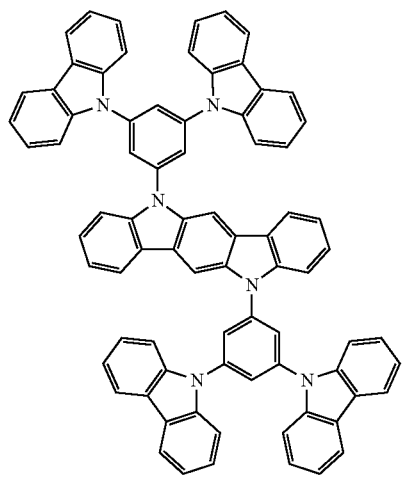
(304)
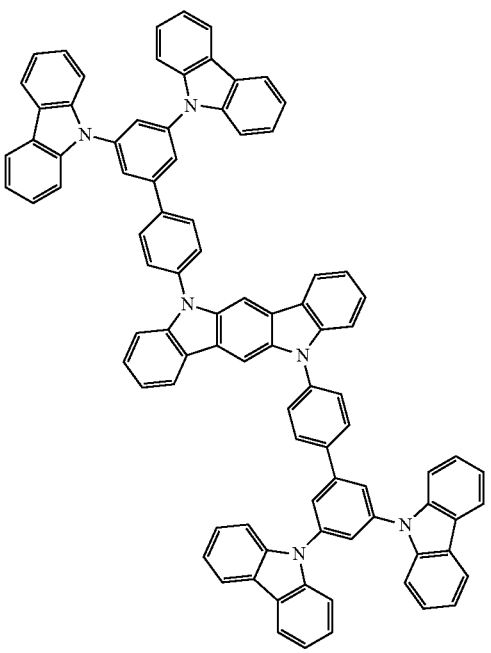
(305)
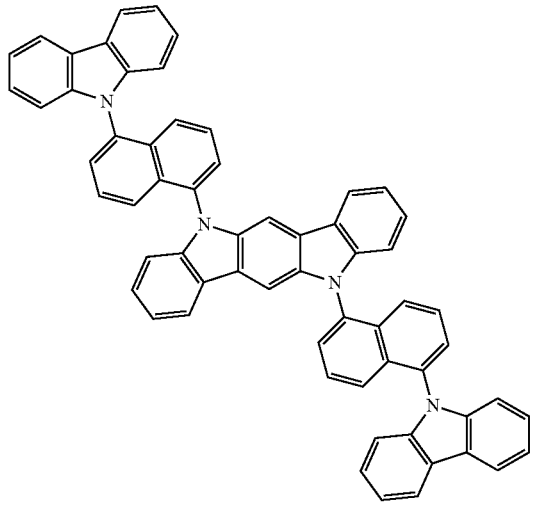
(306)
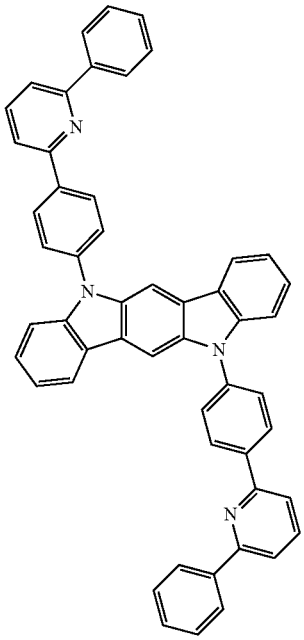

-continued
(307)
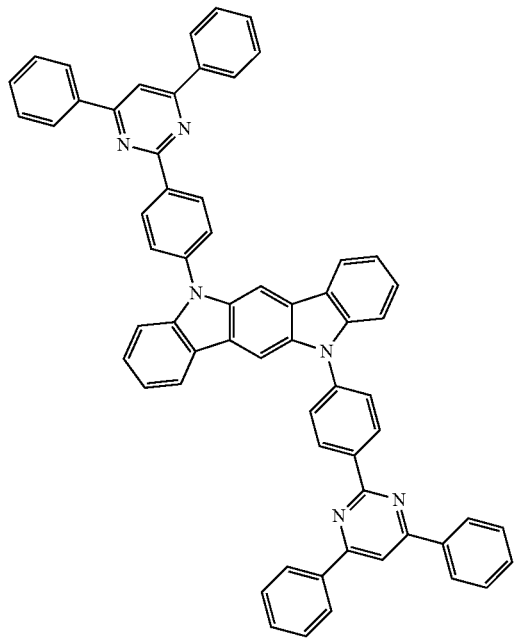
(308)
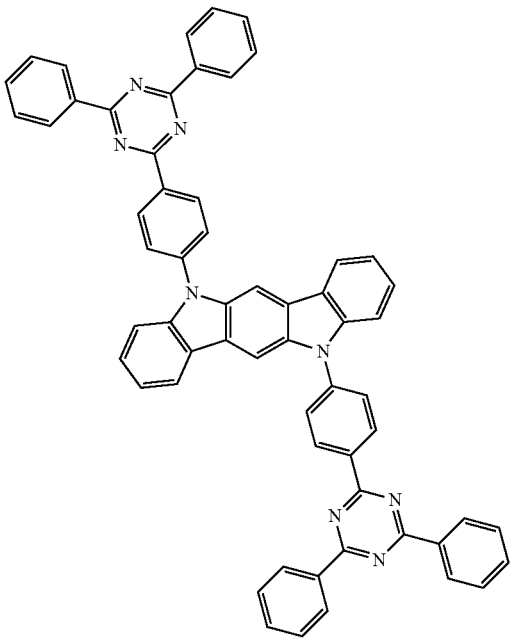
(309)
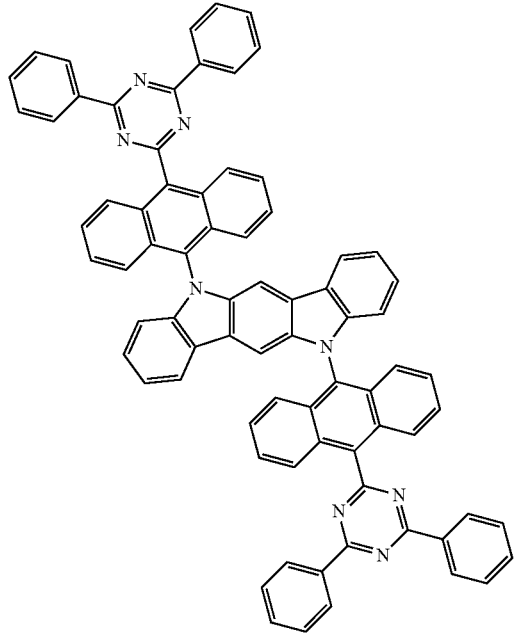
(310)
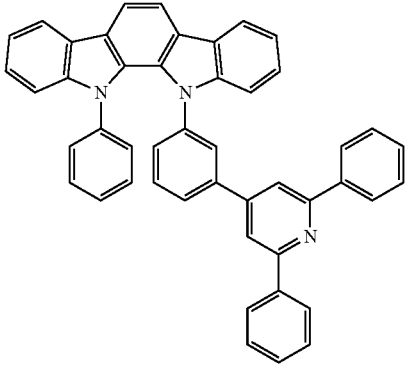

-continued
(311)
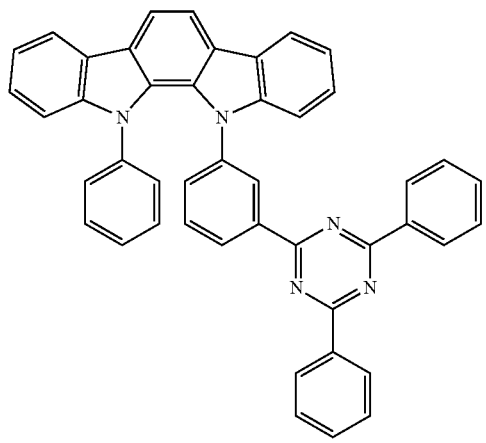
(312)
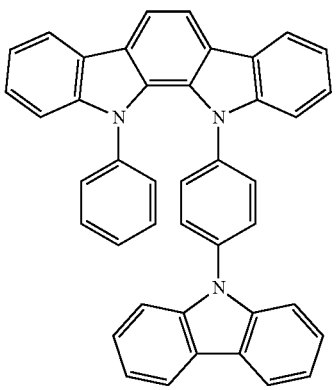
(313)
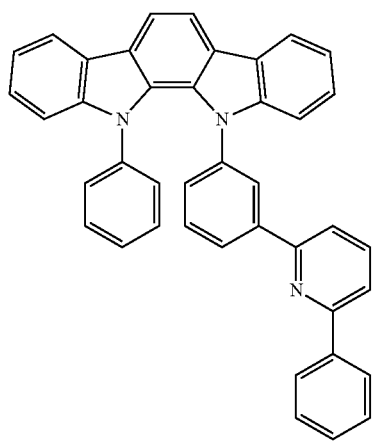
(314)
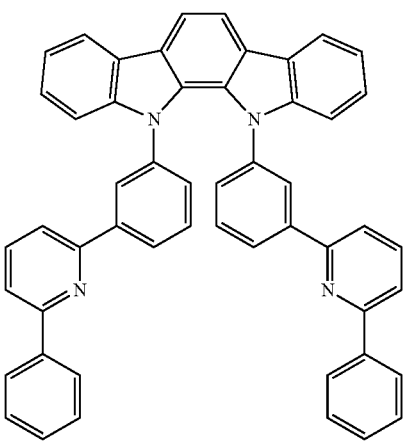
(315)
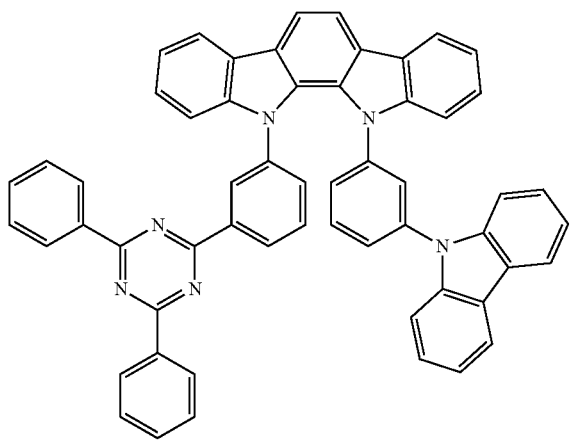
(316)
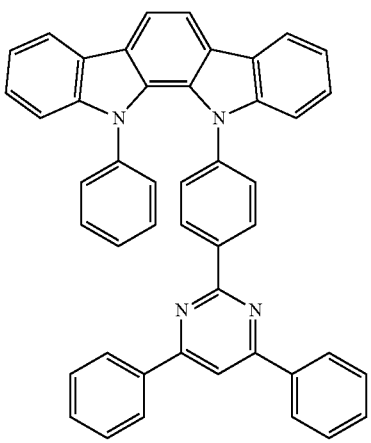

-continued
(317)
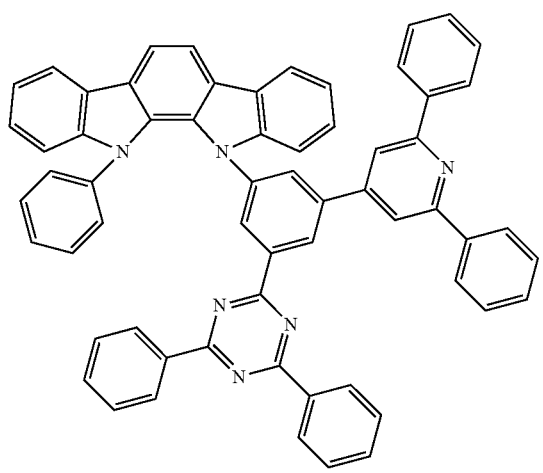
(318)
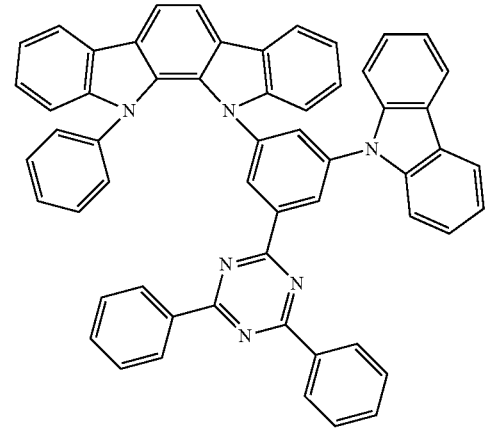
(319)
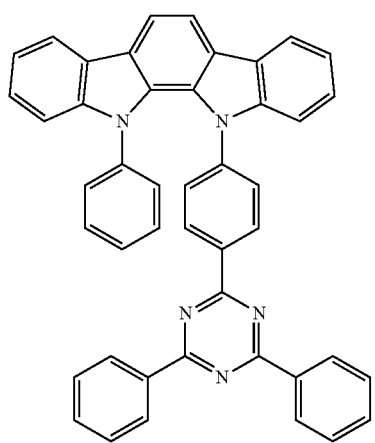
(320)
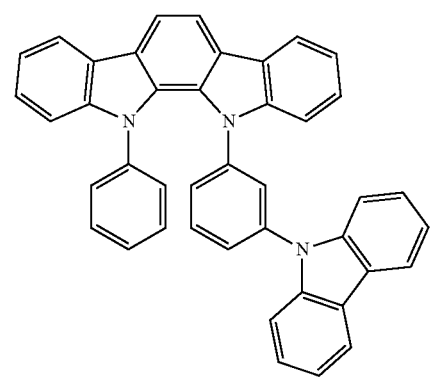
(321)
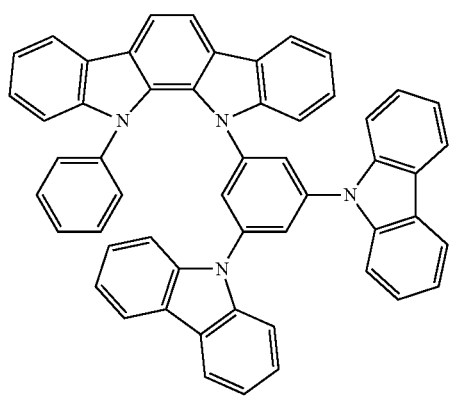
(322)
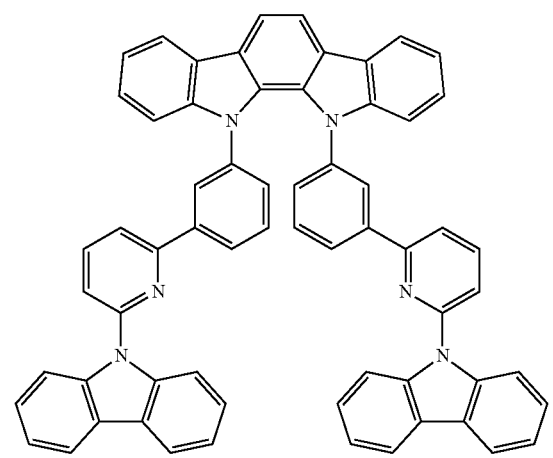

121
(323)
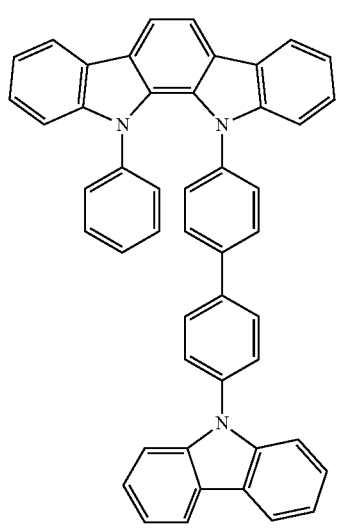
122
-continued
(324)
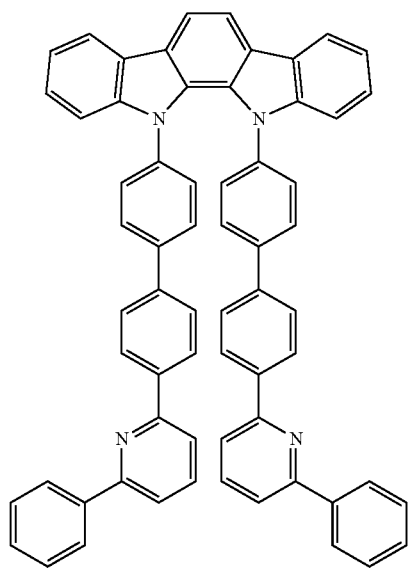
(325)
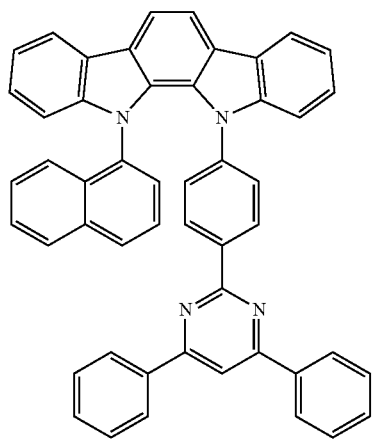
(326)
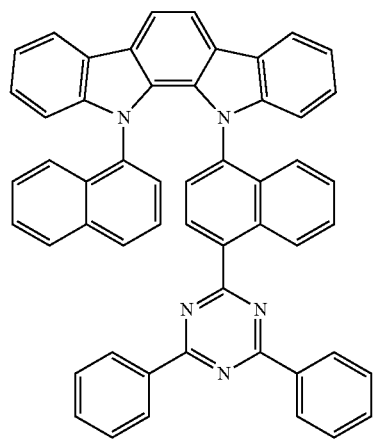
(327)
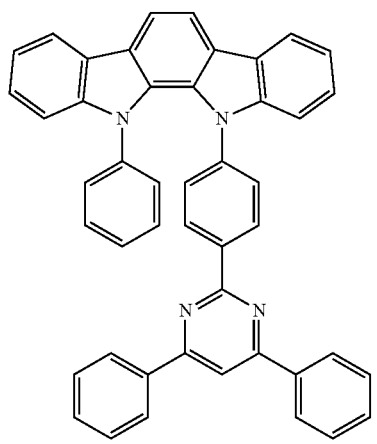
(328)
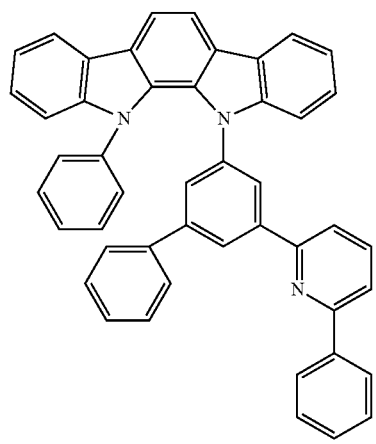

-continued
(329)
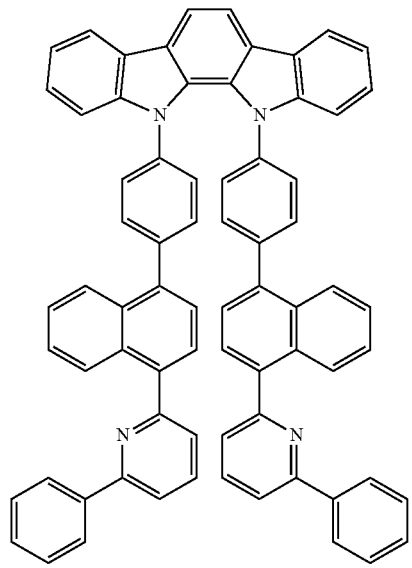
(330)
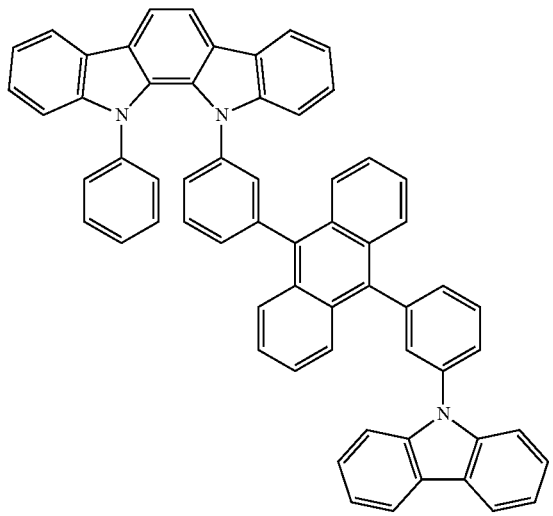
(331)
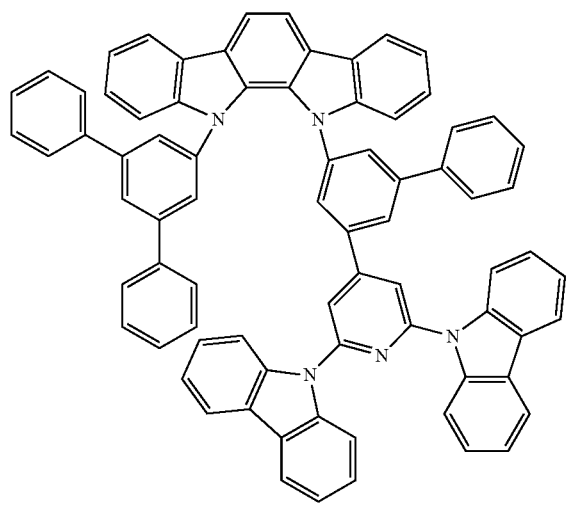
(332)
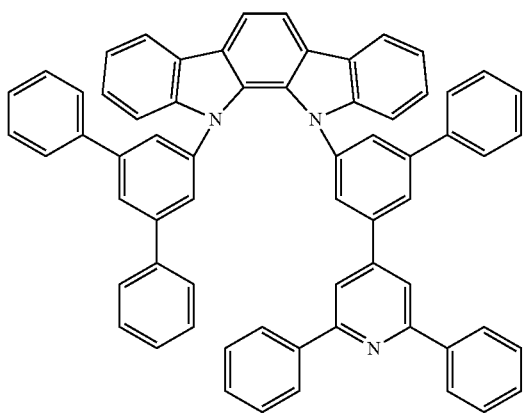
(333)
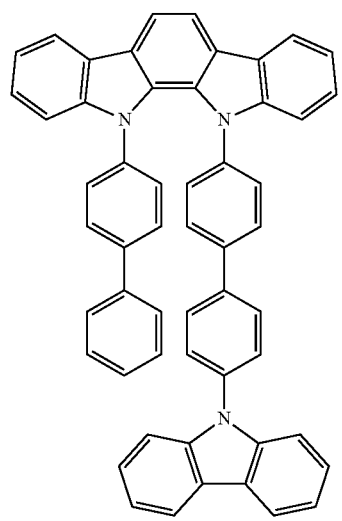
(334)
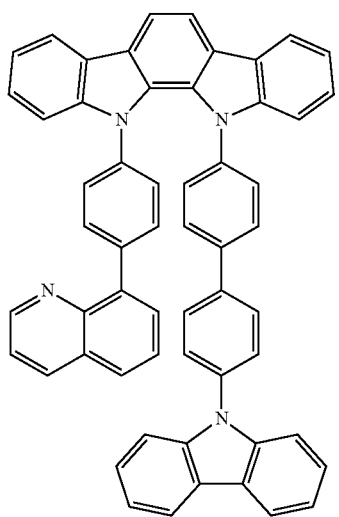

-continued
(335)
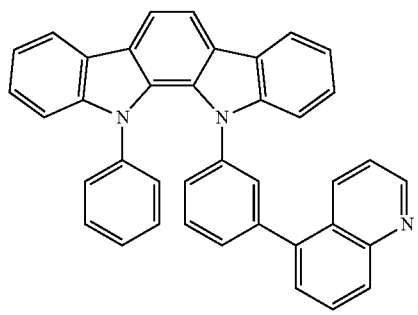
(336)
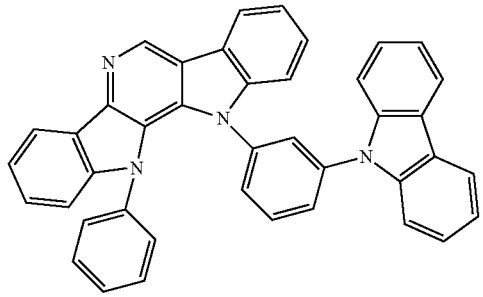
(337)
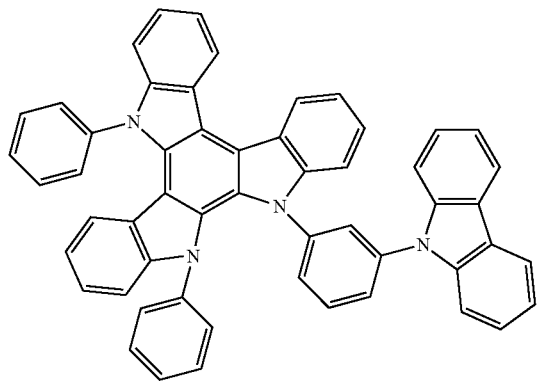
(338)
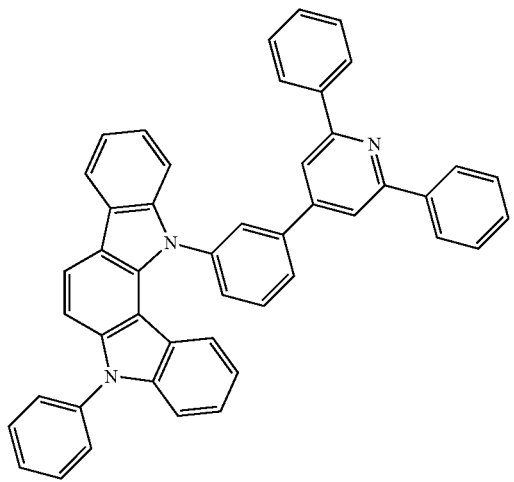
(339)
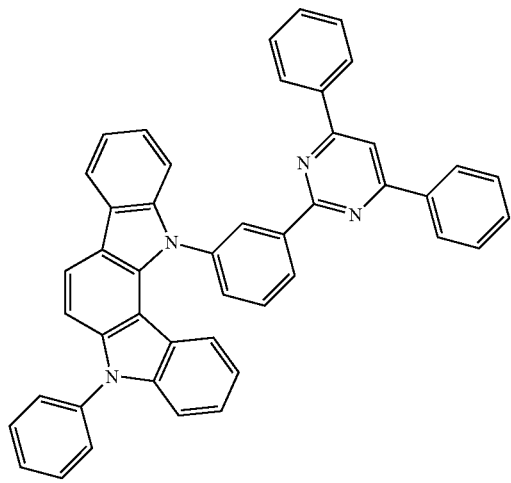
(340)
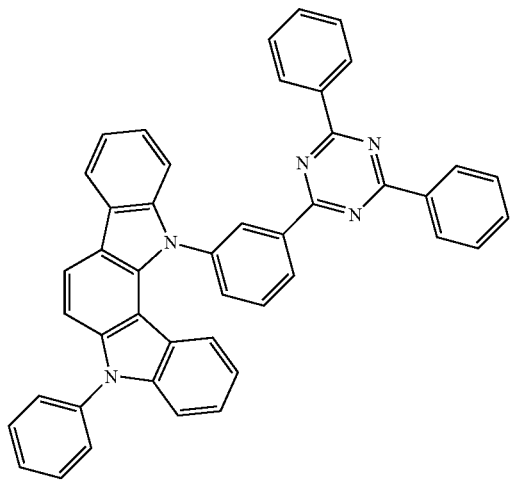

-continued
(341)
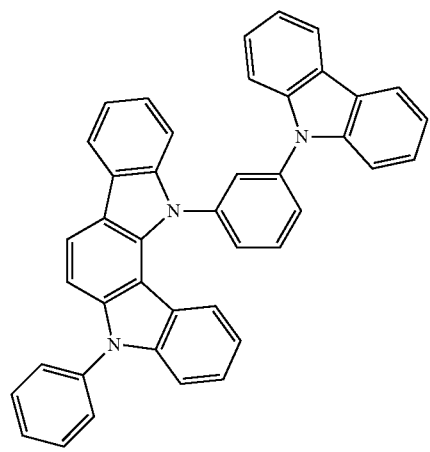
(342)
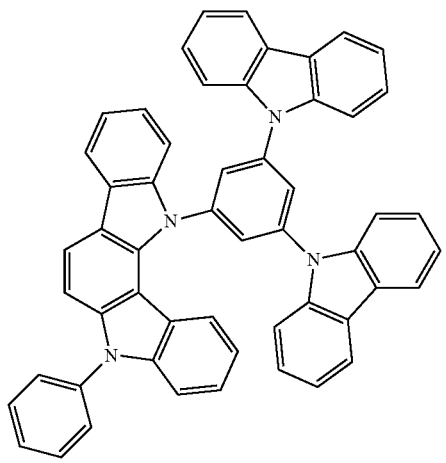
(343)
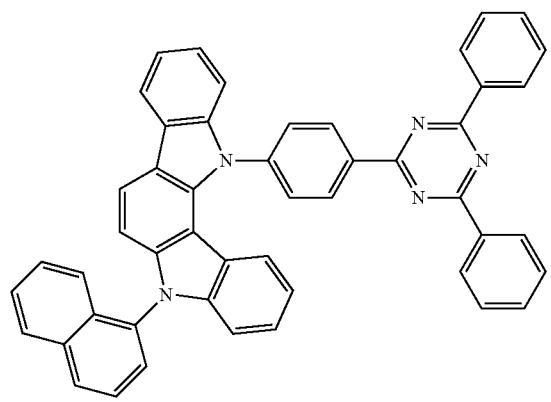
(344)
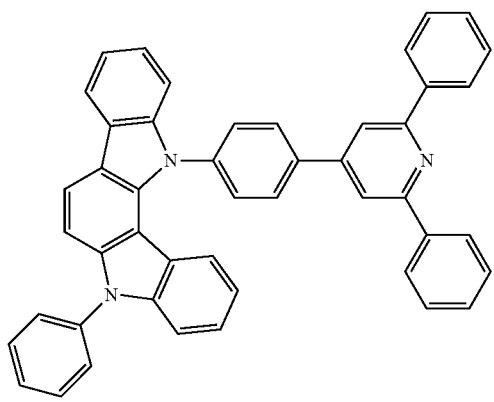
(345)
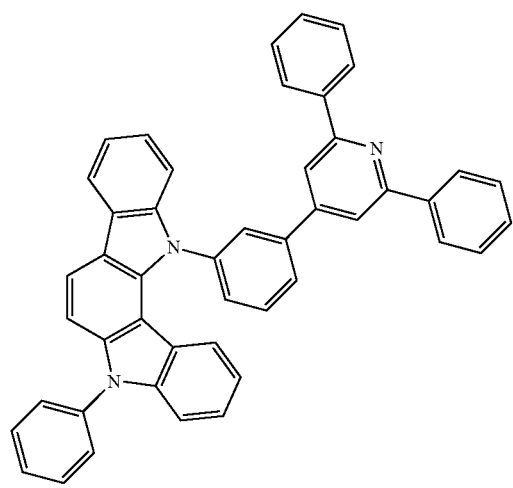
(346)
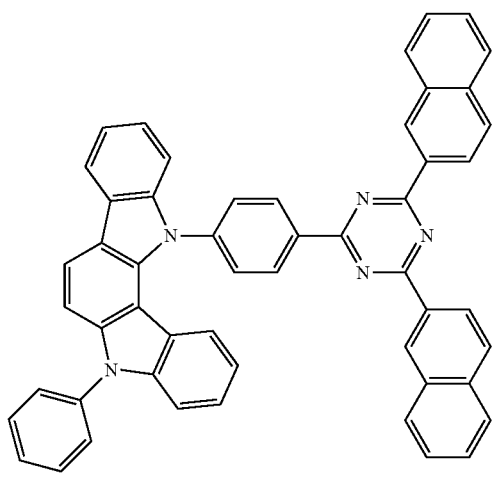

-continued
(347)
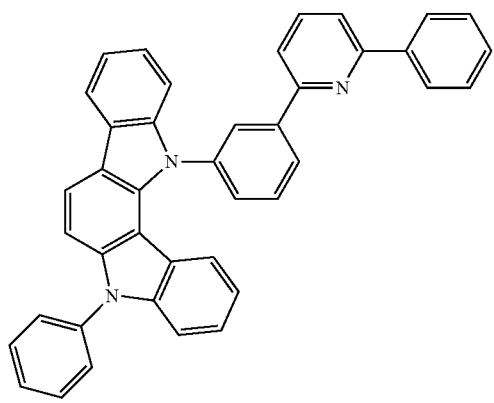
(348)
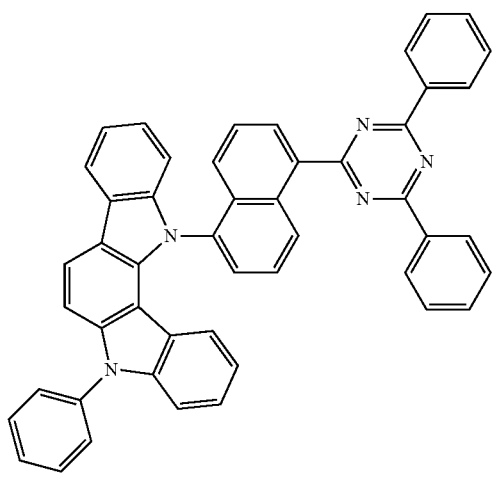
(349)
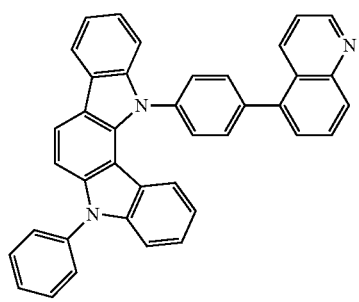
(350)
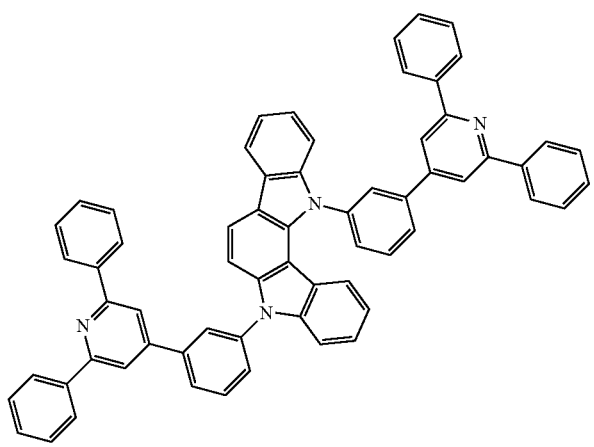
(351)
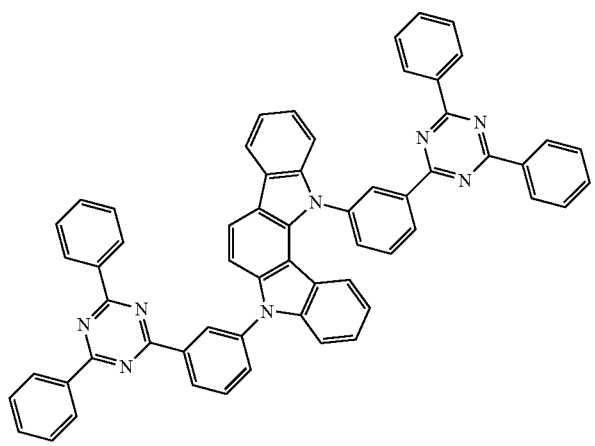
(352)
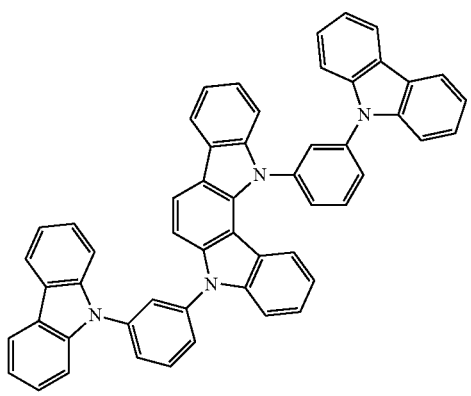

-continued
(353)
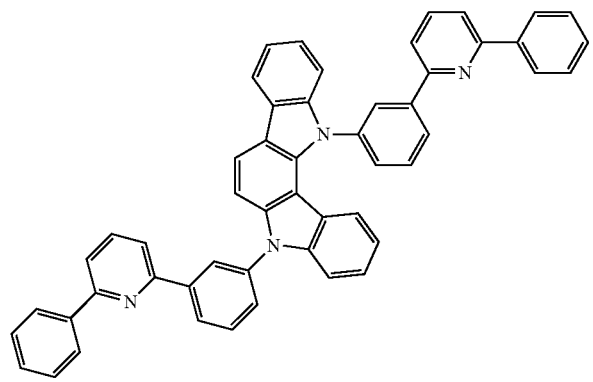
(354)
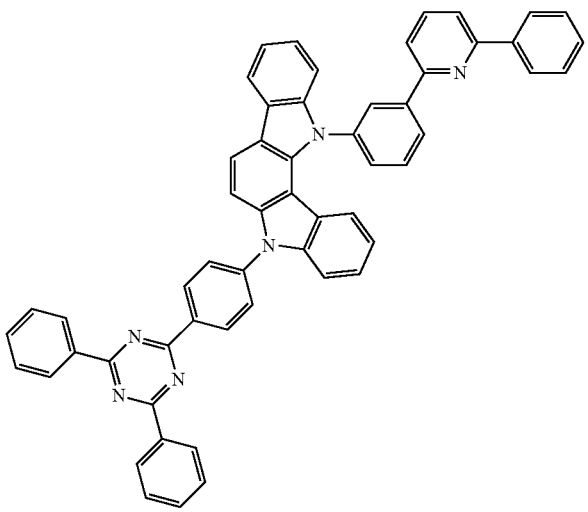
(355)
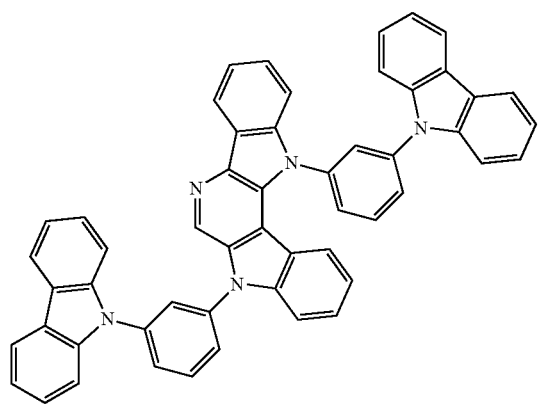
(356)
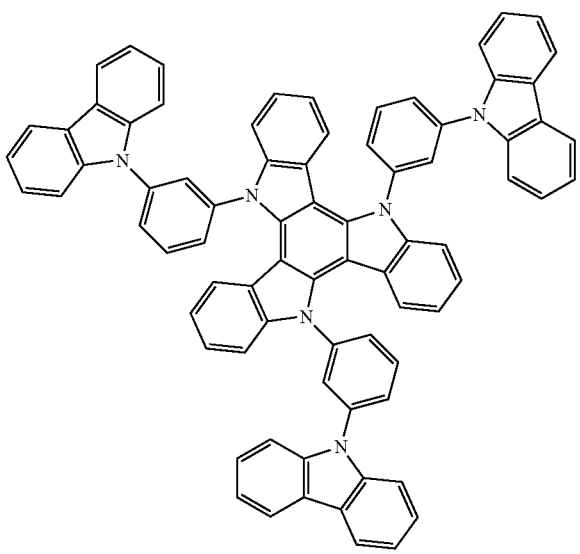
(357)
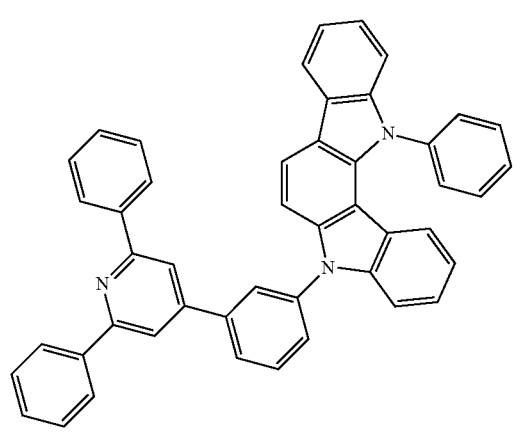
(358)
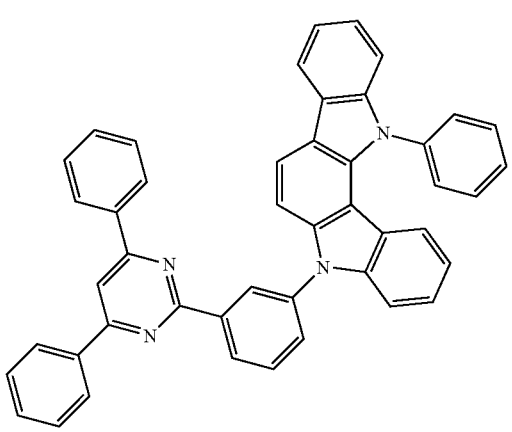

-continued
(359)
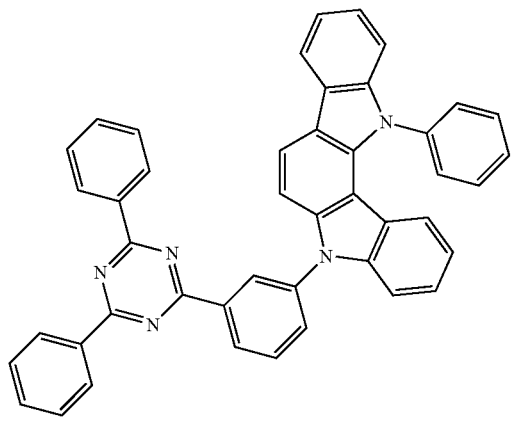
(360)
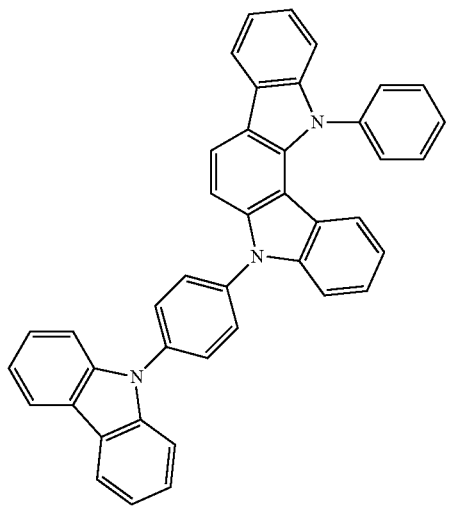
(361)
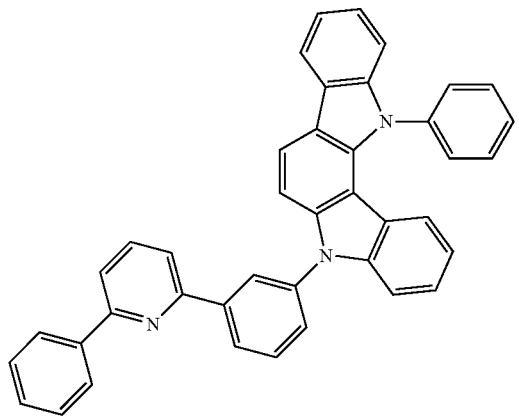
(362)
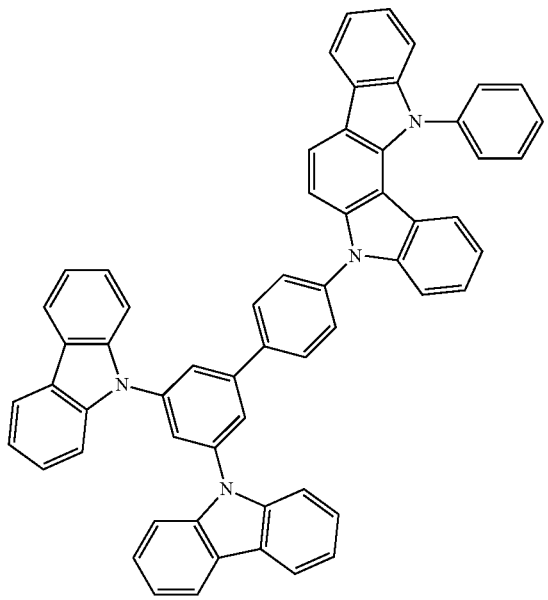
(363)
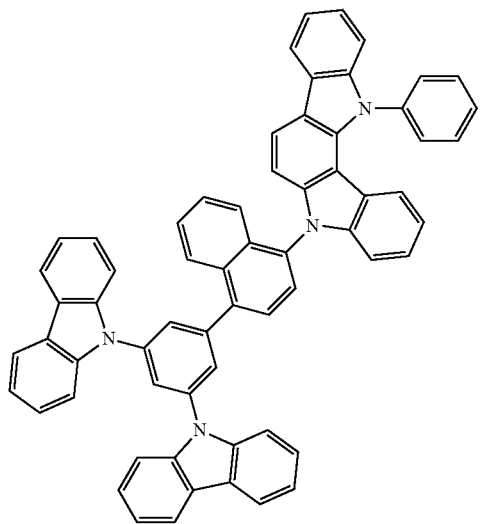
(364)
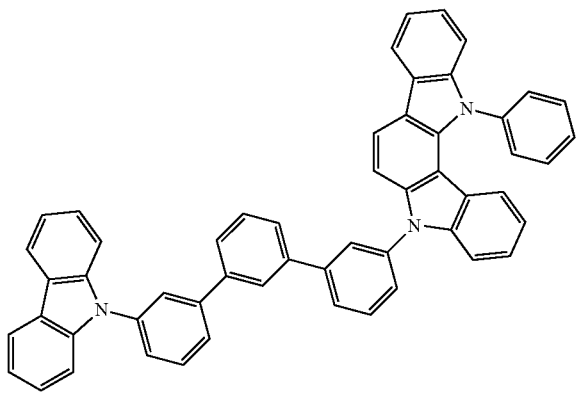

-continued
(365)
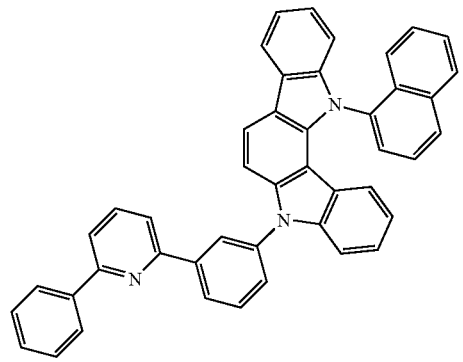
(366)
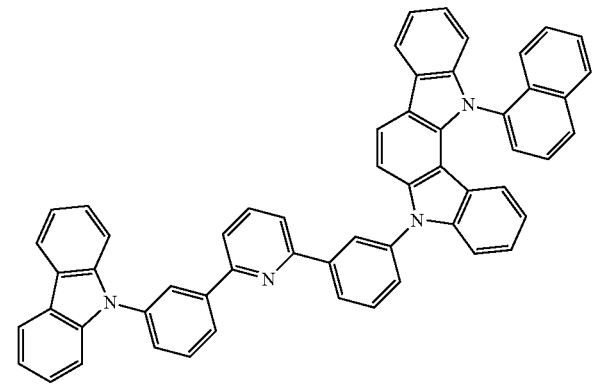
(367)
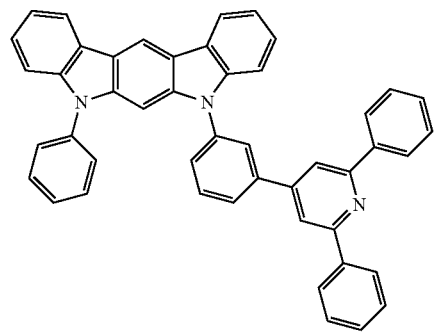
(368)
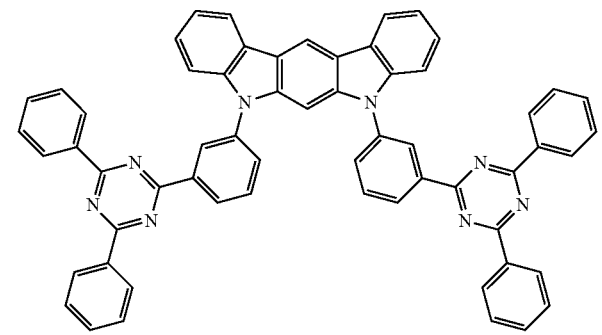
(369)
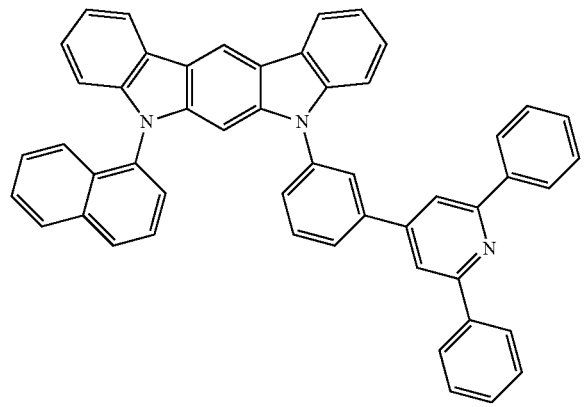
(370)
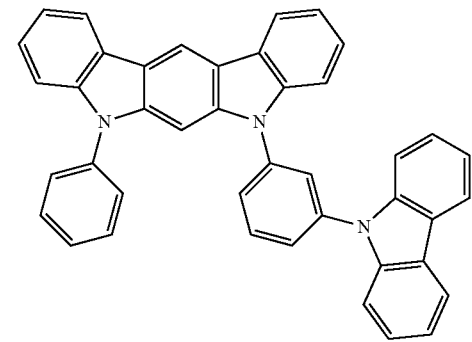
(371)
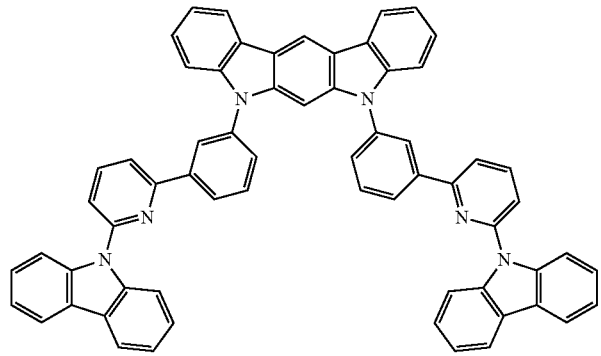
(372)
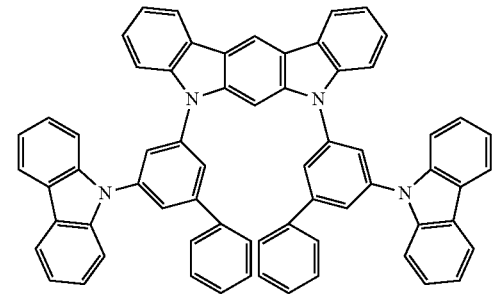

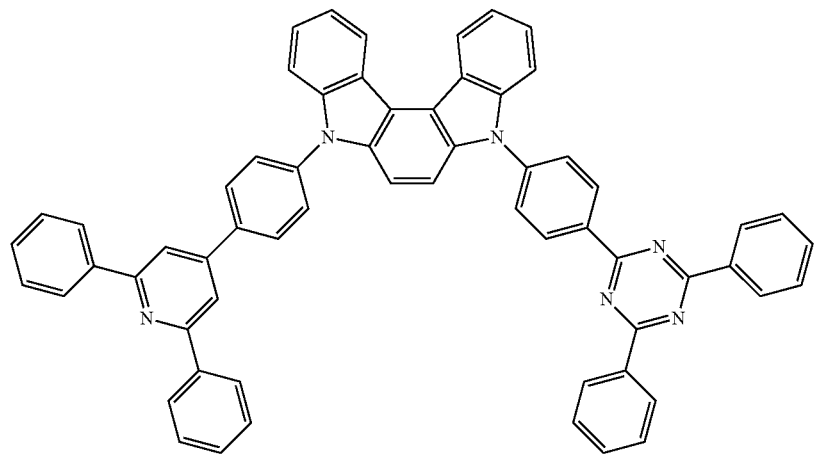
(373)
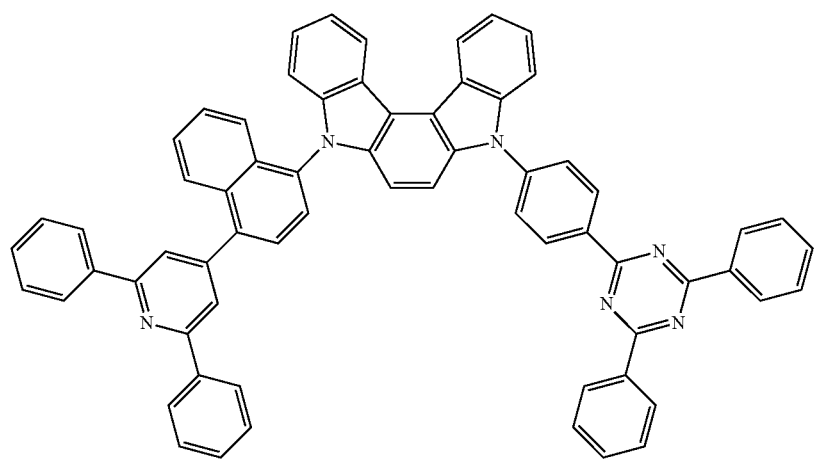
(374)
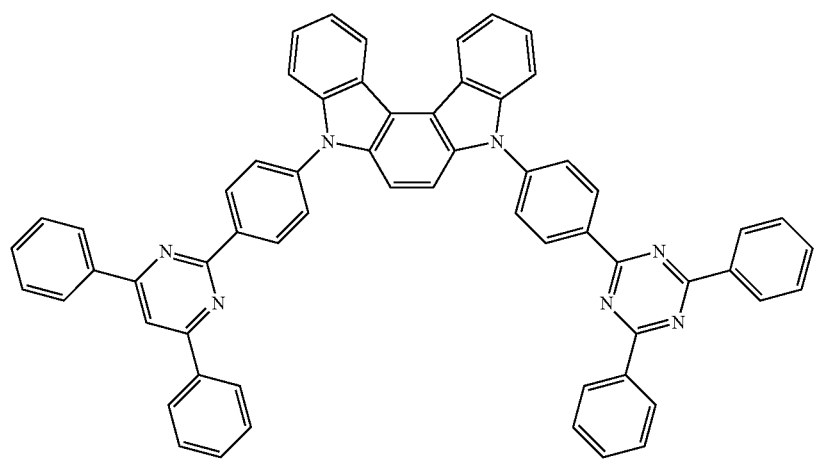
(375)

-continued
(376)
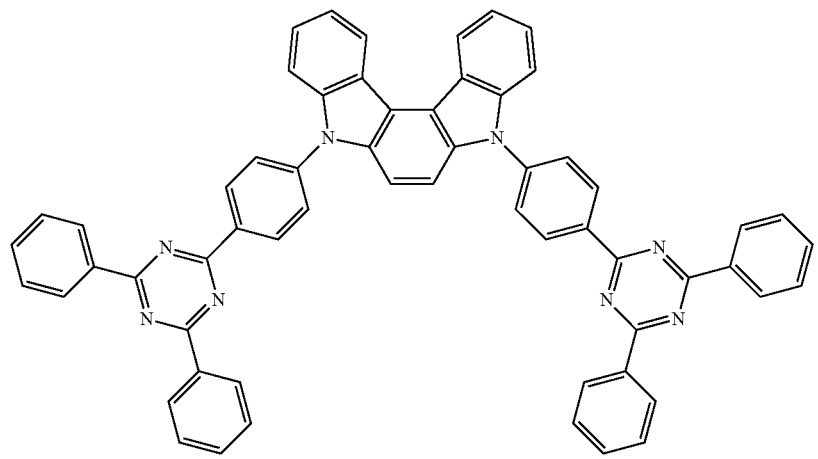
(377)
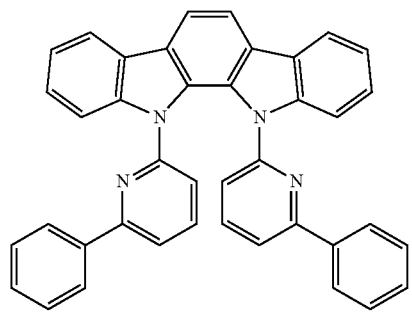
(378)
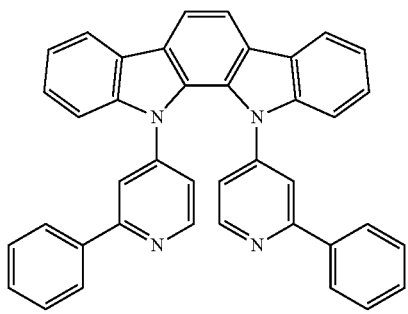
(379)
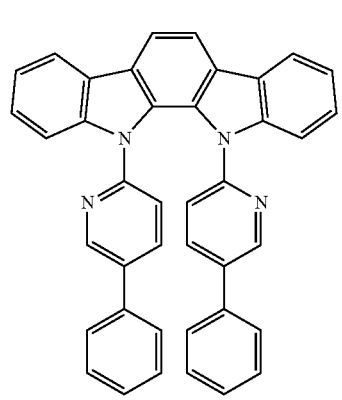
(380)
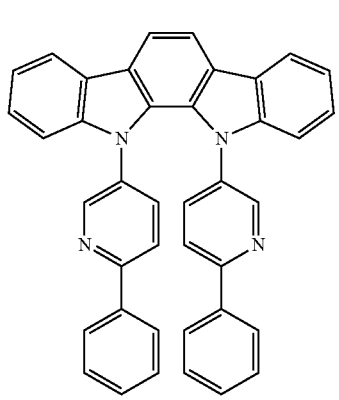
(381)
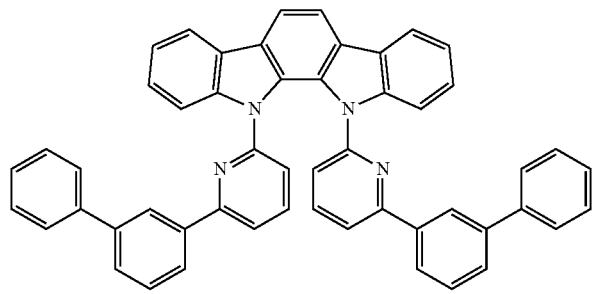
(382)
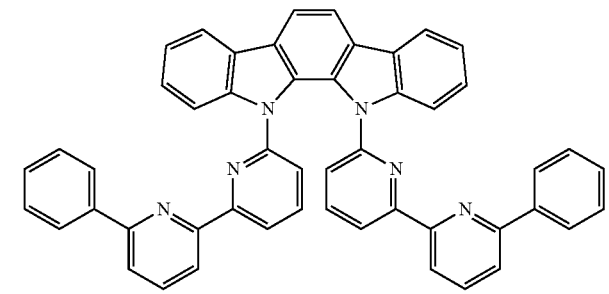

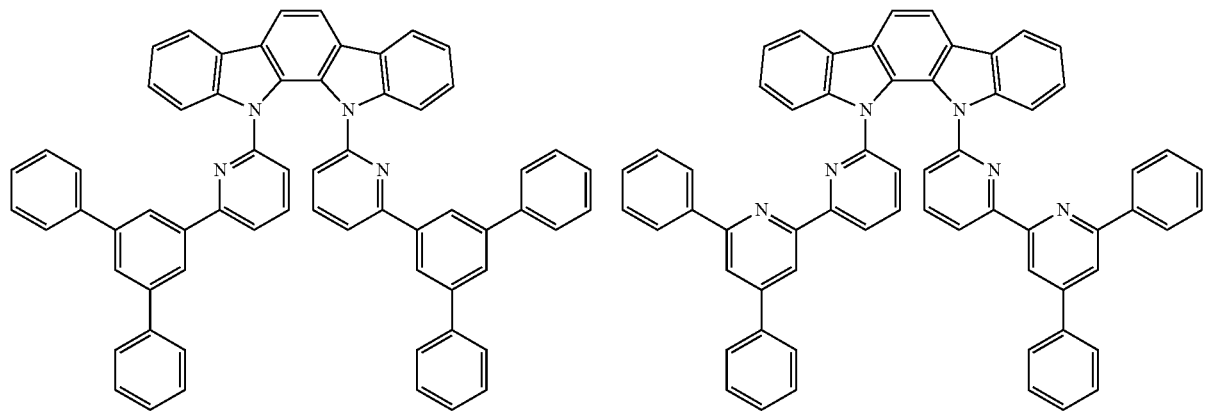
(383) (384)
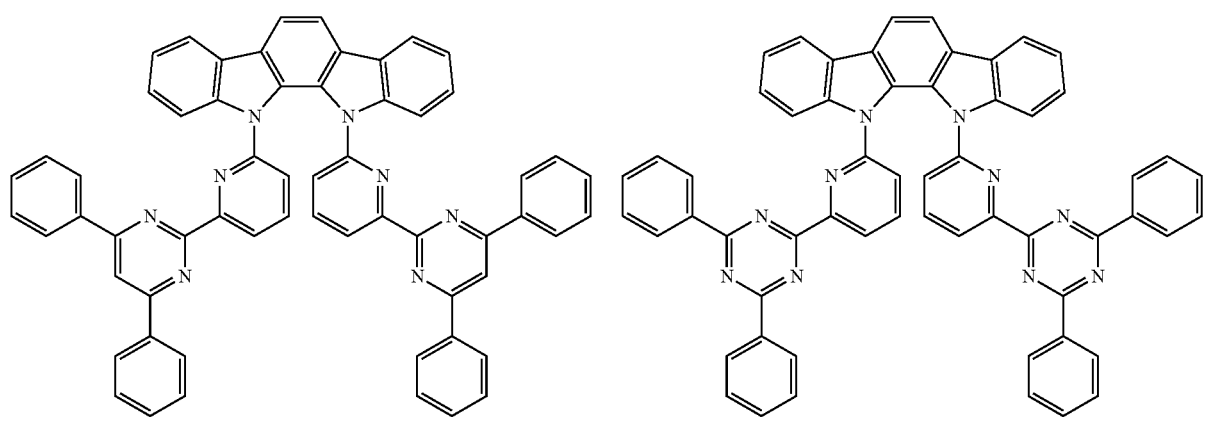
(385) (386)
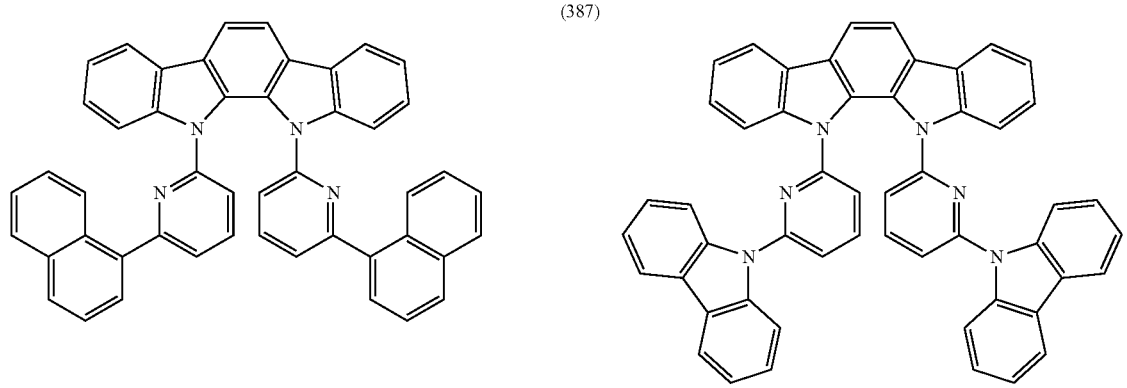
(387) (388)

-continued
(389)
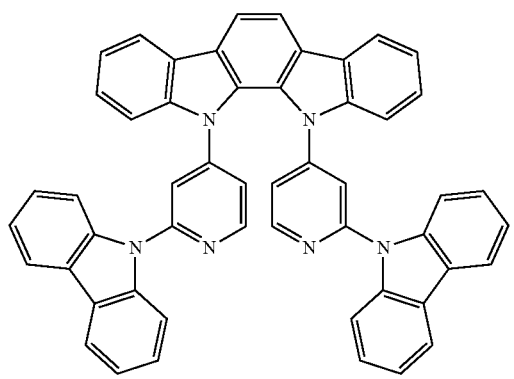
(390)
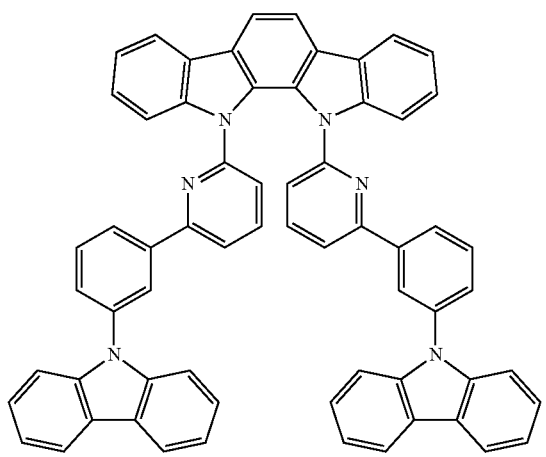
(391)
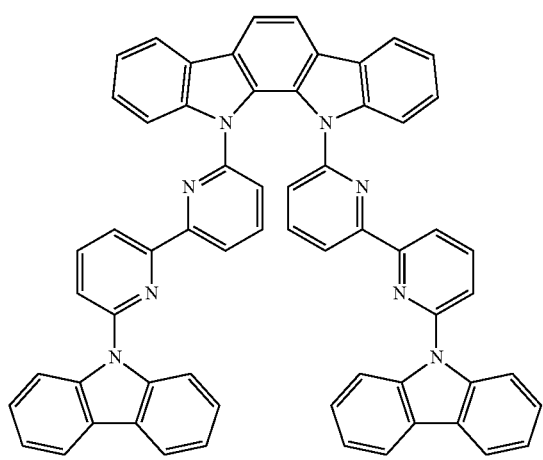
(392)
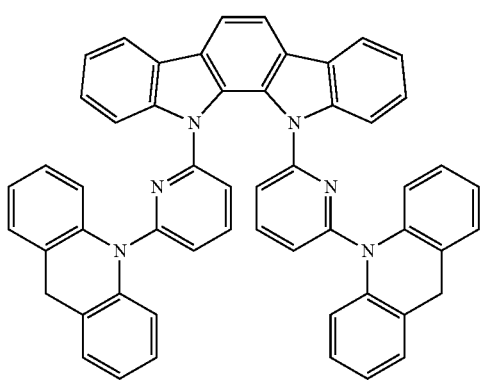
(393)
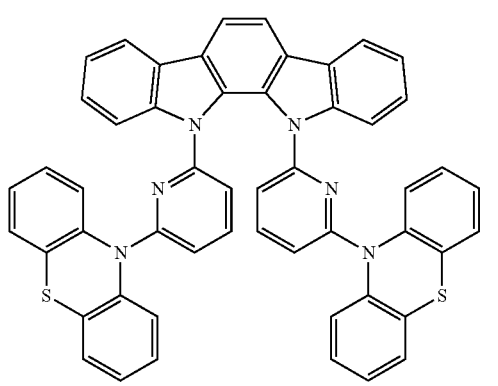
(394)
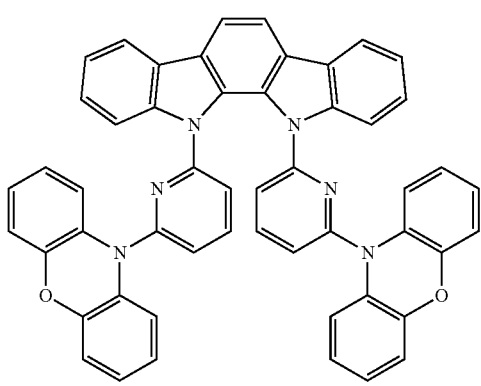
(395)
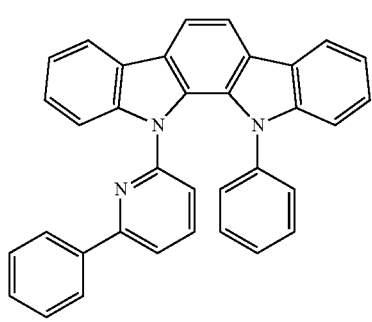
(396)
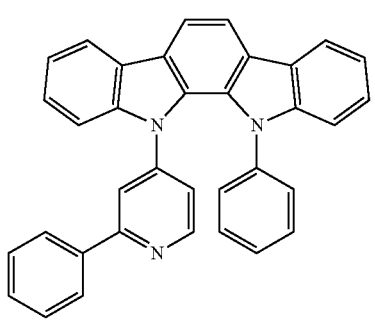

-continued
(397)
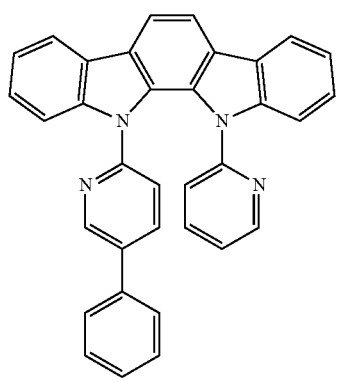
(398)
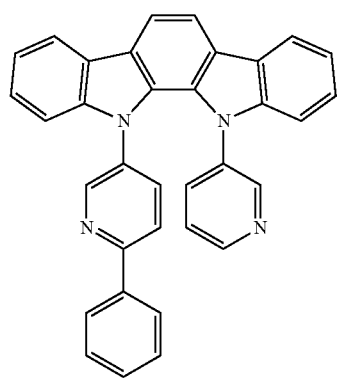
(399)
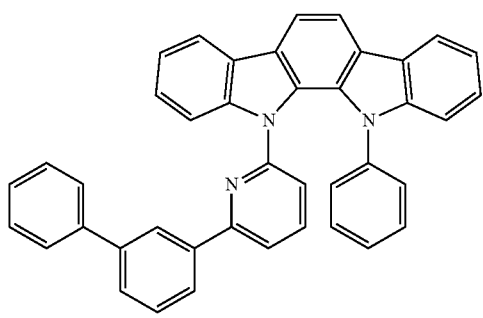
(400)
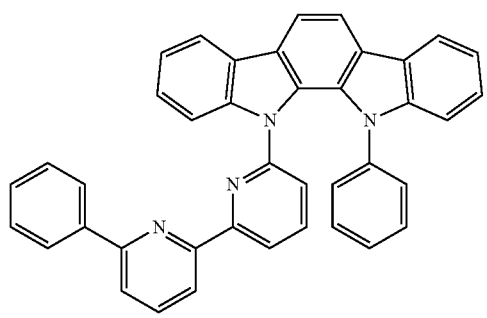
(401)
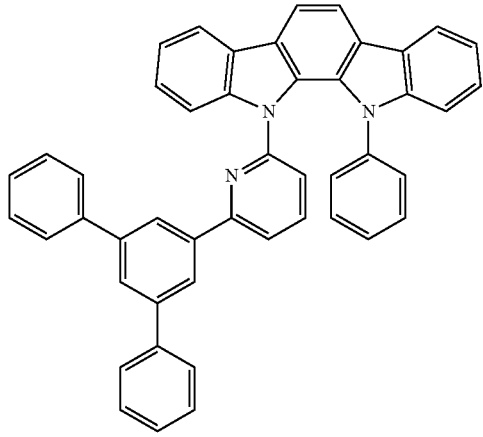
(402)
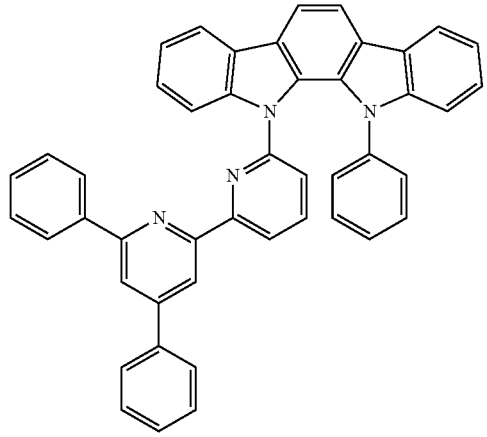
(403)
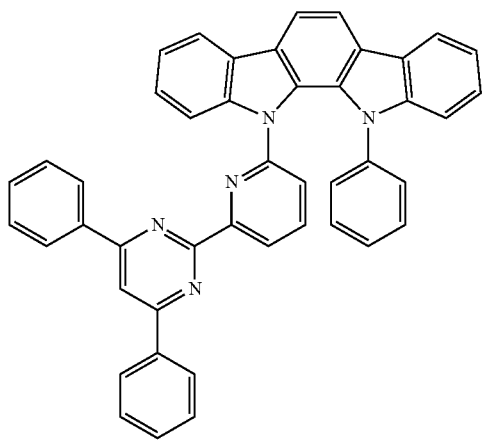
(404)
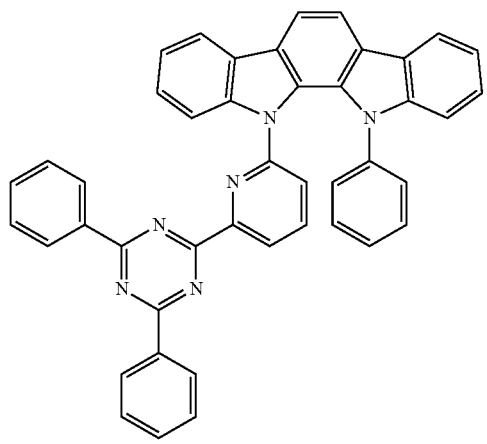

-continued
(405)
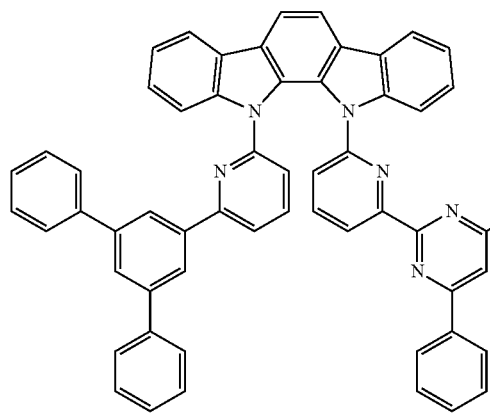
(406)
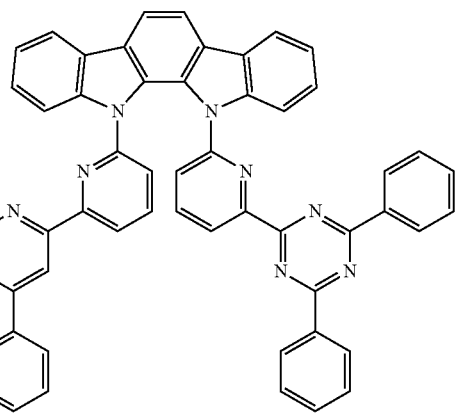
(407)
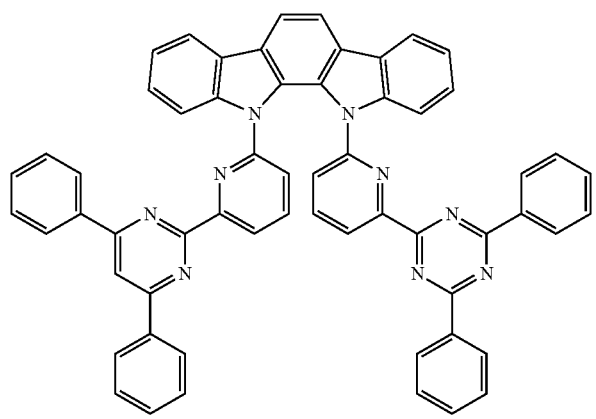
(408)
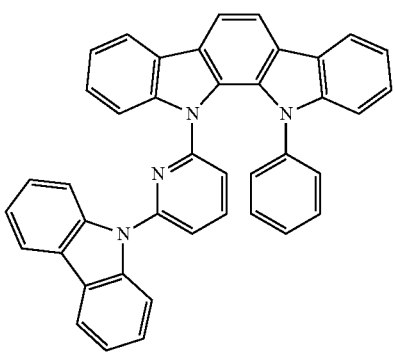
(409)
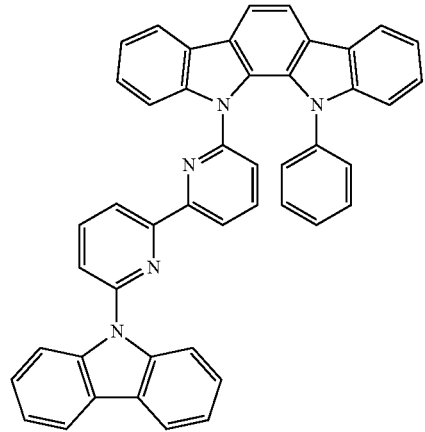
(410)
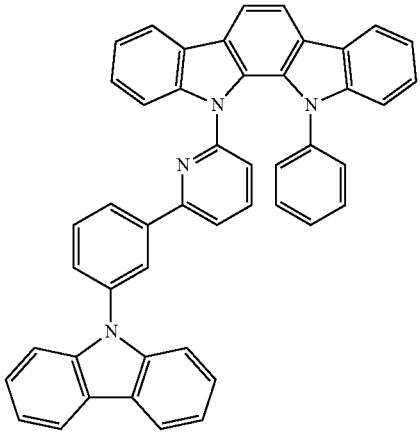

-continued
(411)
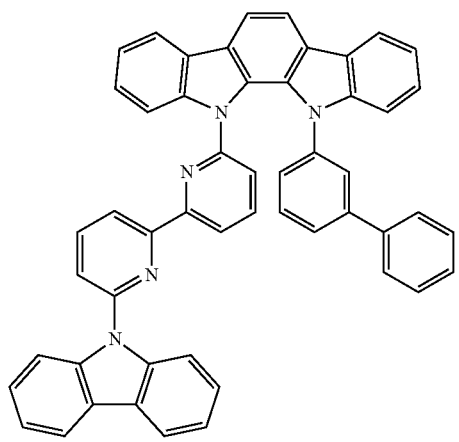
(412)
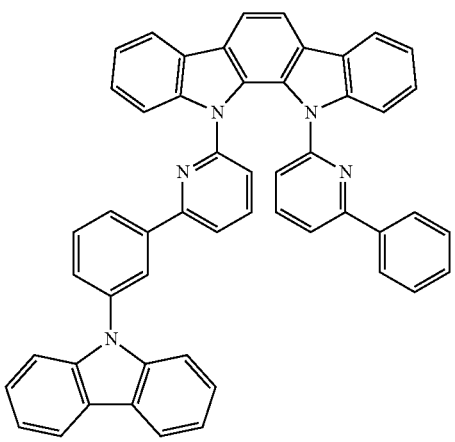
(413)
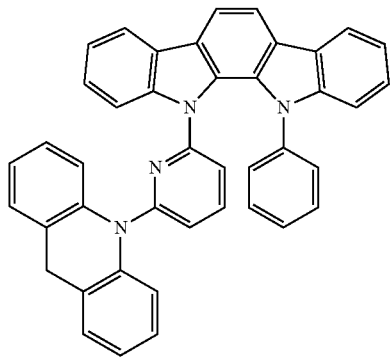
(414)
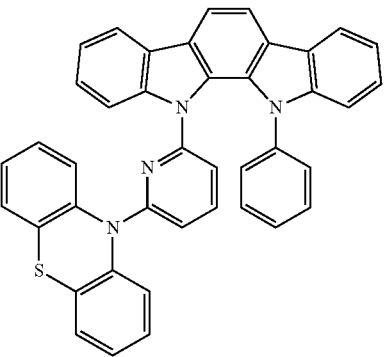
(415)
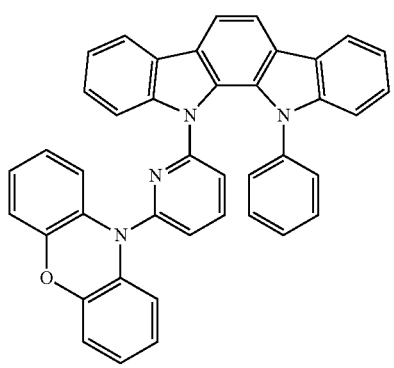
(416)
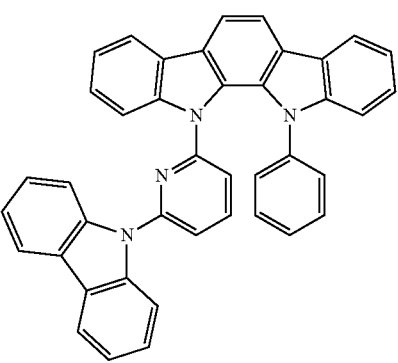
(417)
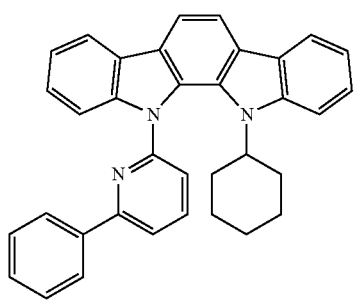
(418)
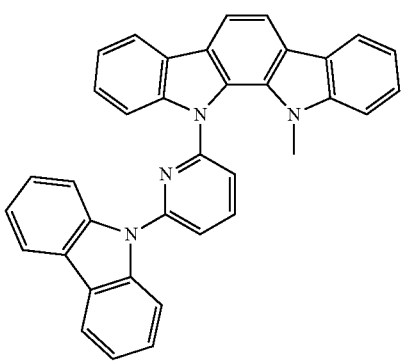

151
-continued
(419)
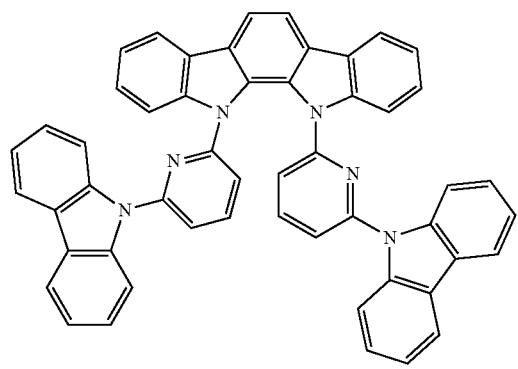
152
(420)
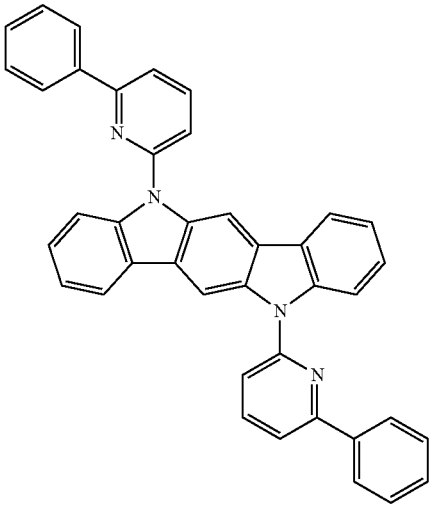
(421)
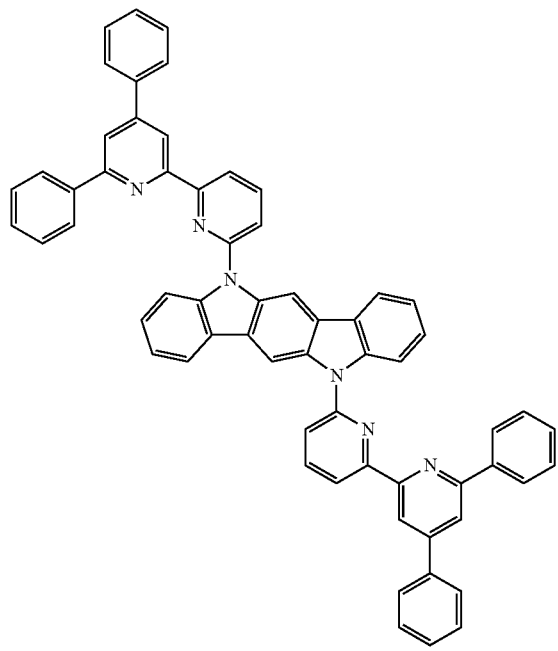
(422)
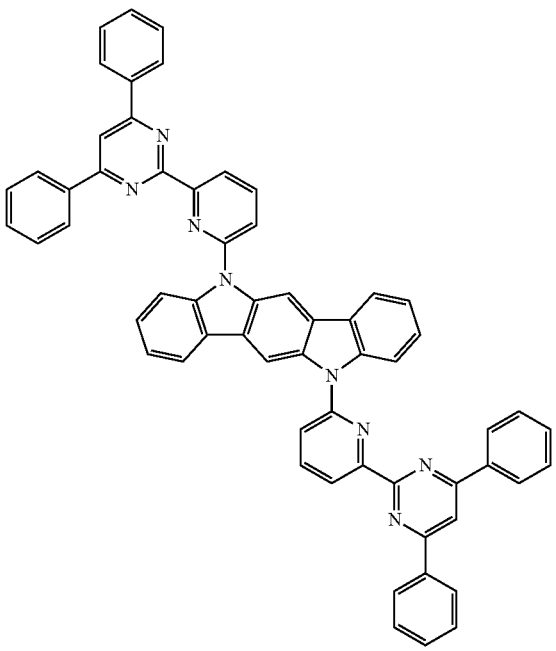

(423)
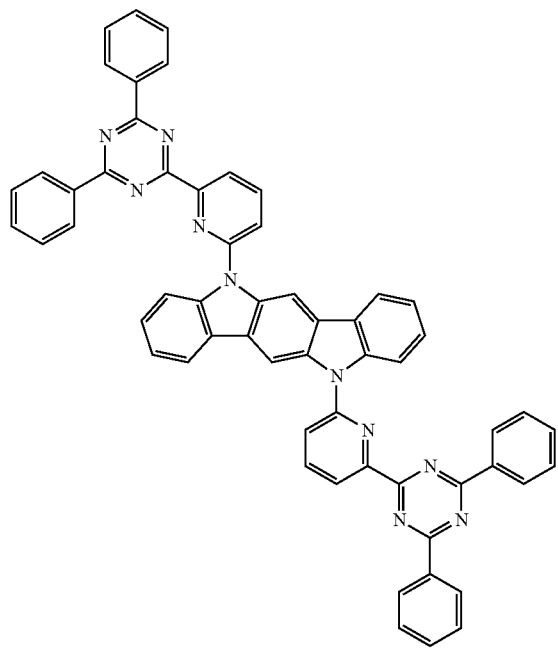
(424)
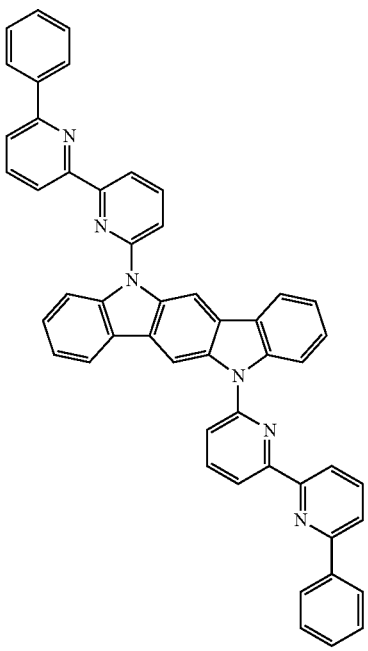
(425)
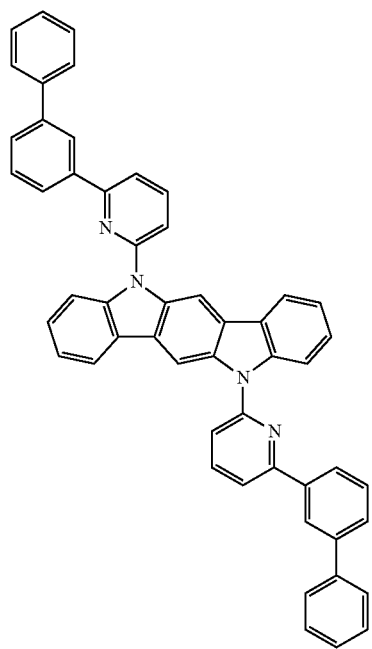
(426)
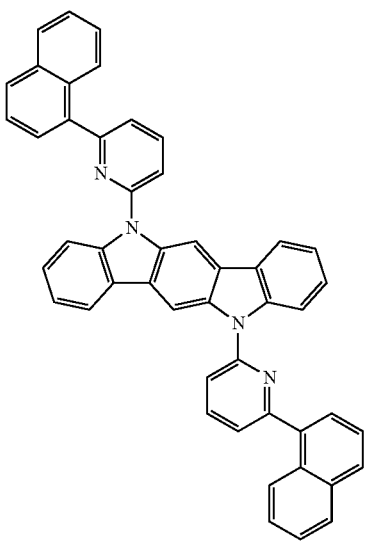

(427)
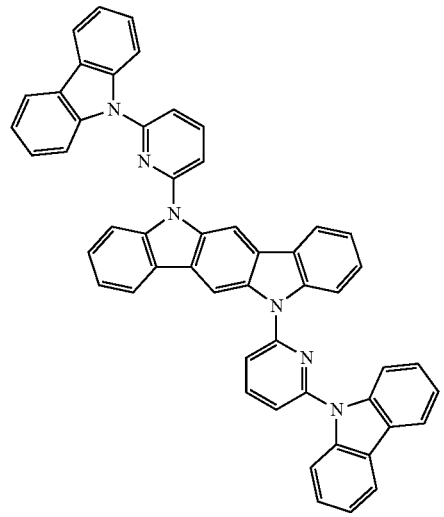
(428)
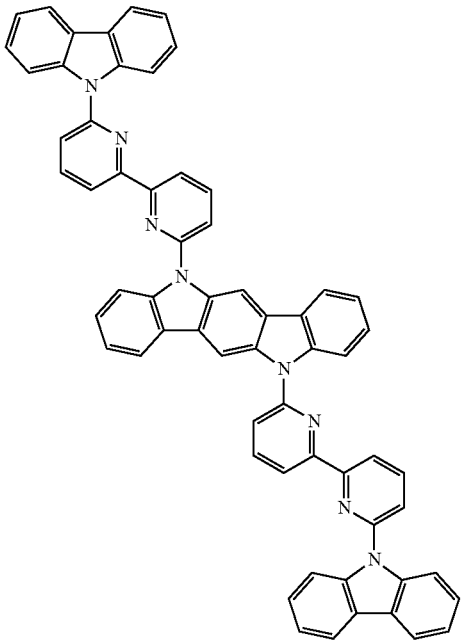
(429)
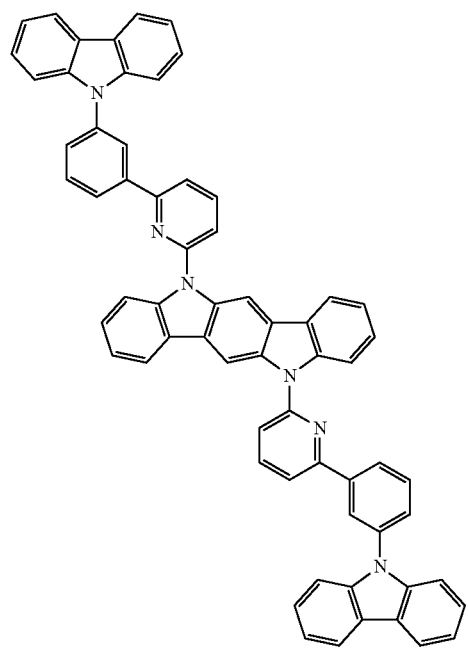
(430)
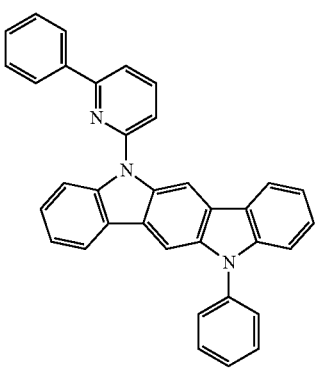

-continued
(431)
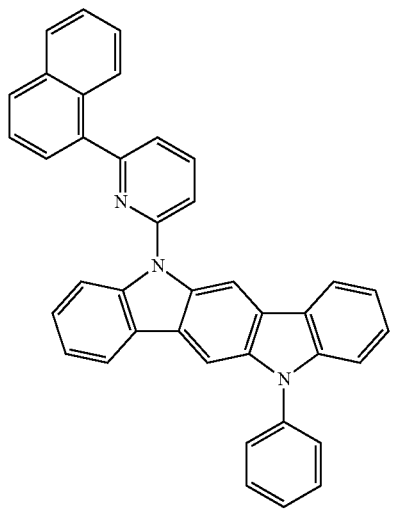
(432)
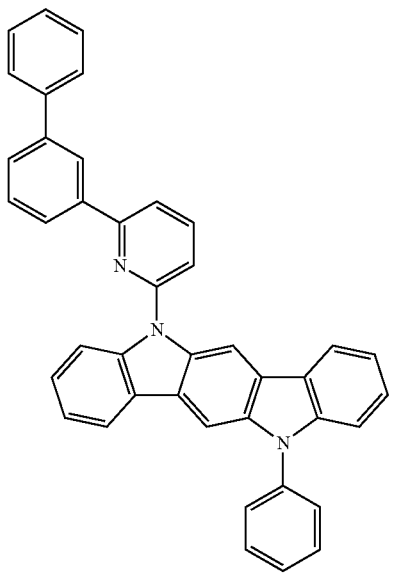
(433)
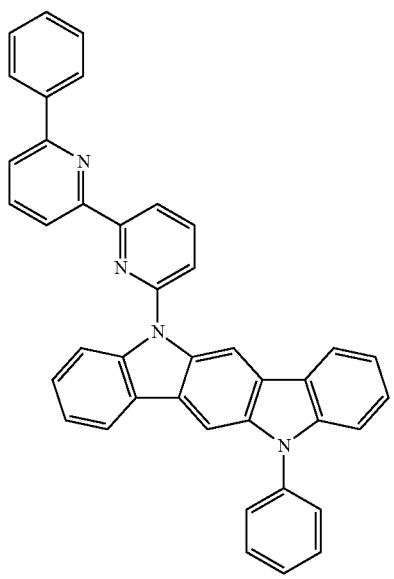
(434)
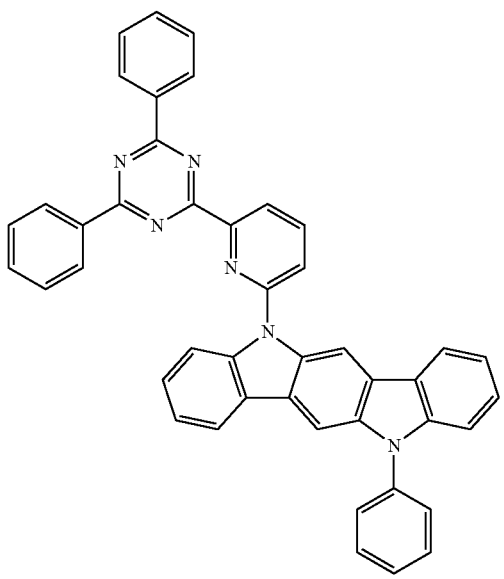

-continued
(435)
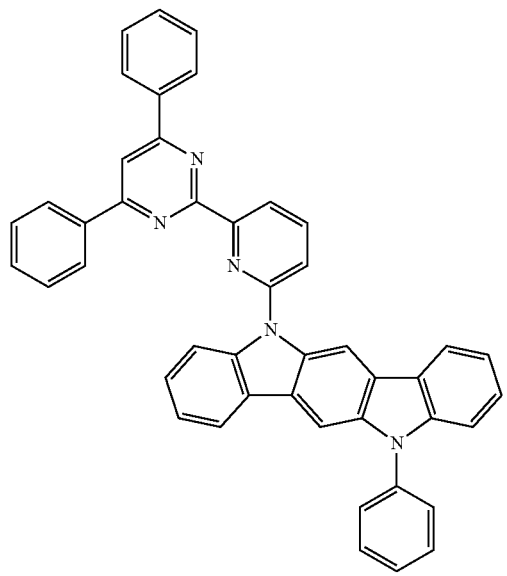
(436)
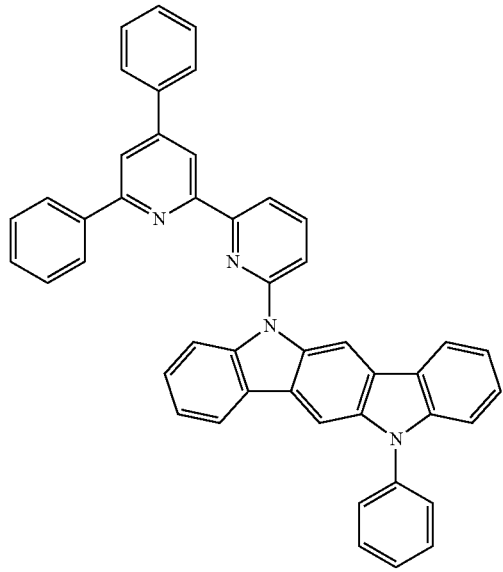
(437)
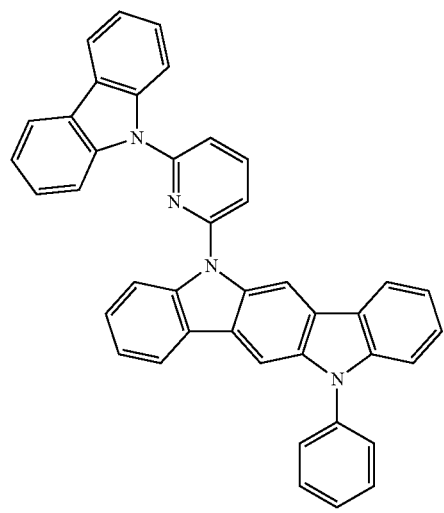
(438)
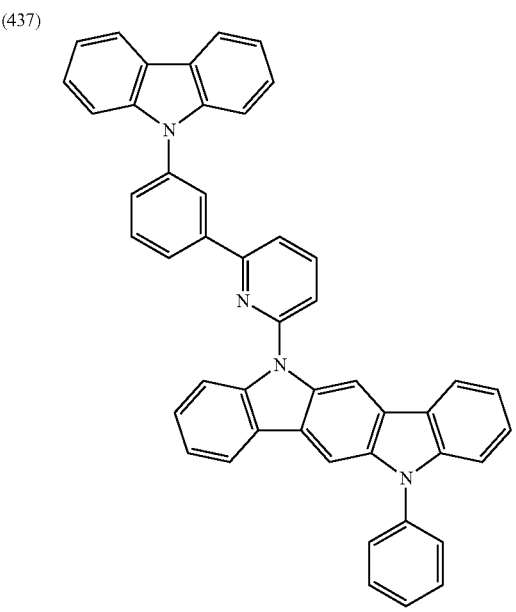

-continued
(439)
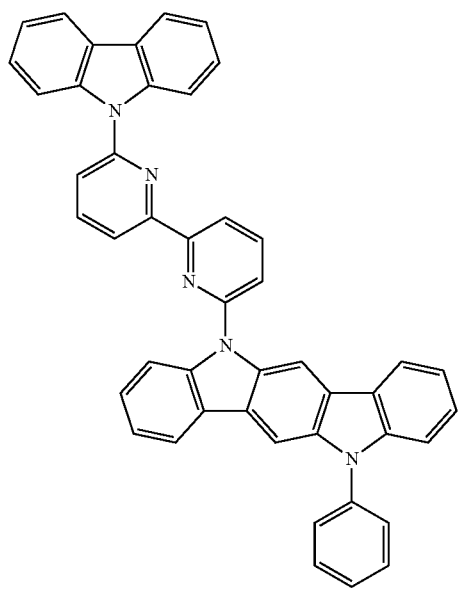
(440)
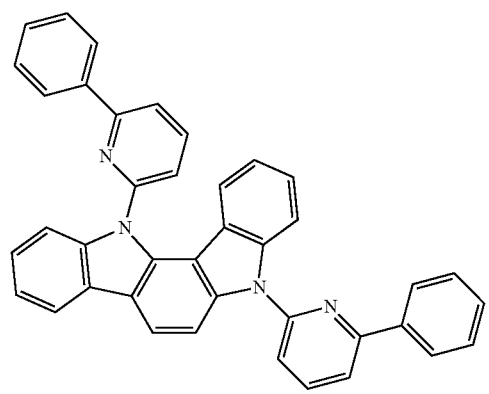
(441)
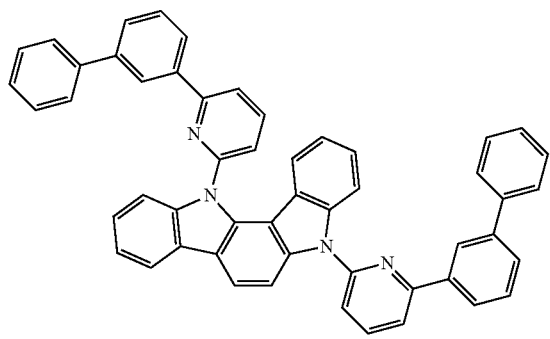
(442)
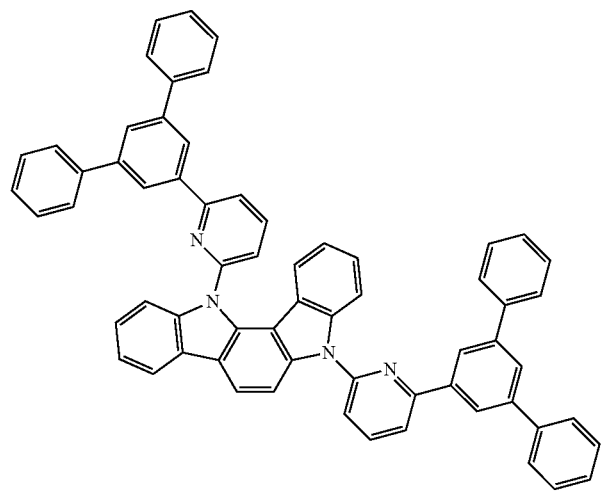
(443)
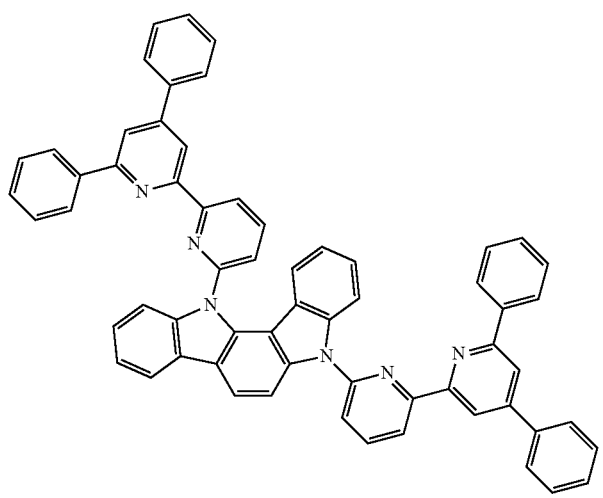
(444)
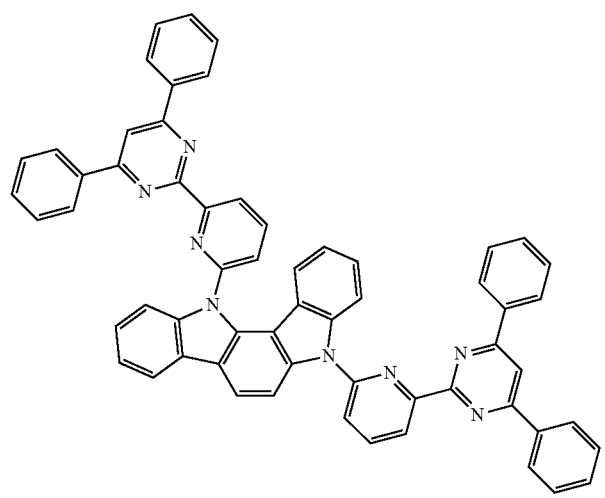

(445)
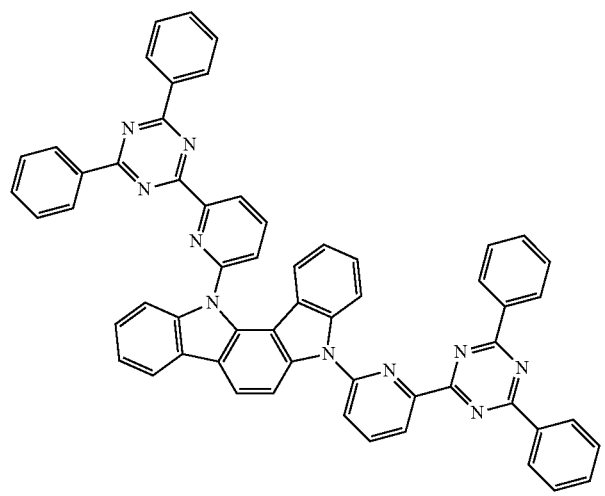
(446)
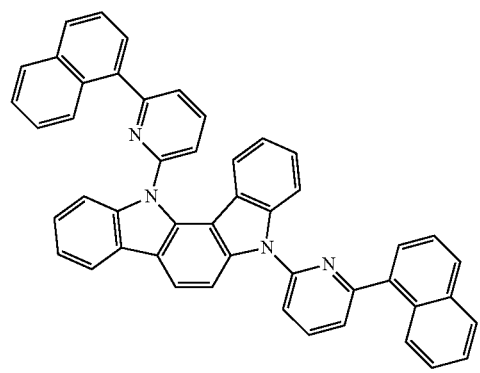
(447)
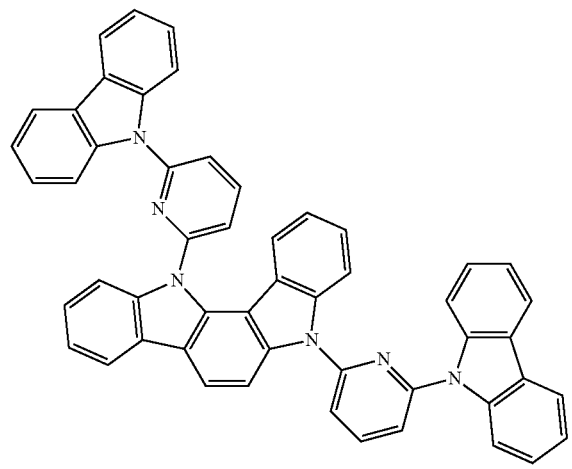
(448)
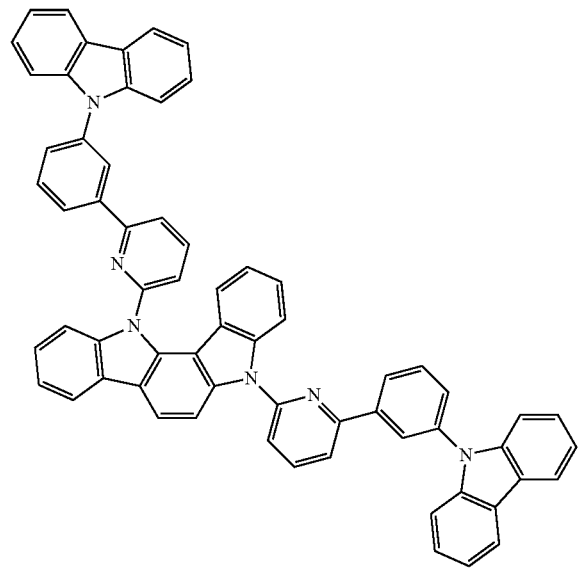

-continued
(449)
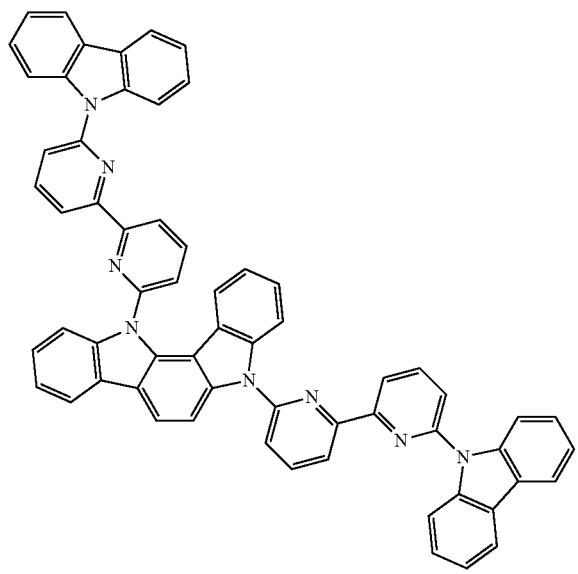
(450)
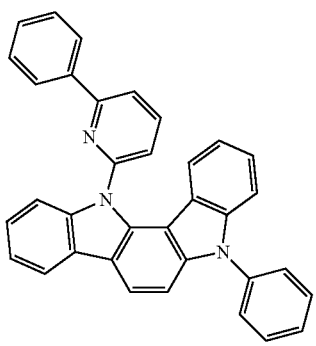
(451)
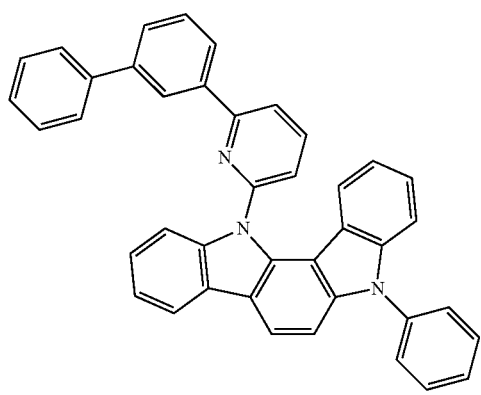
(452)
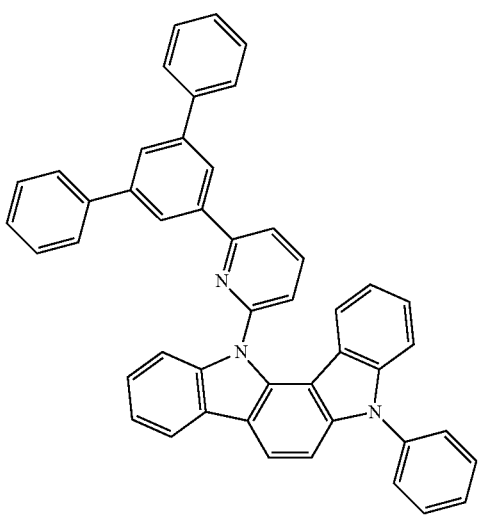
(453)
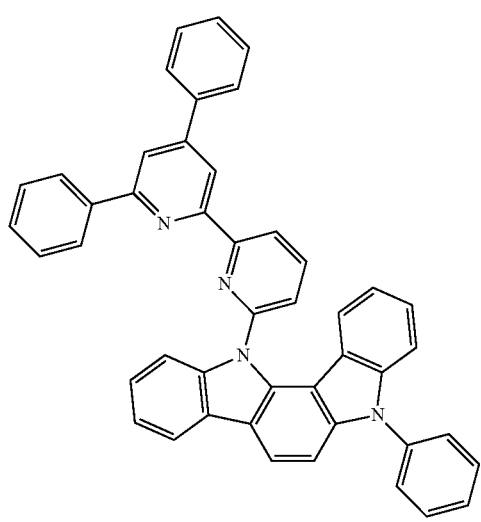
(454)
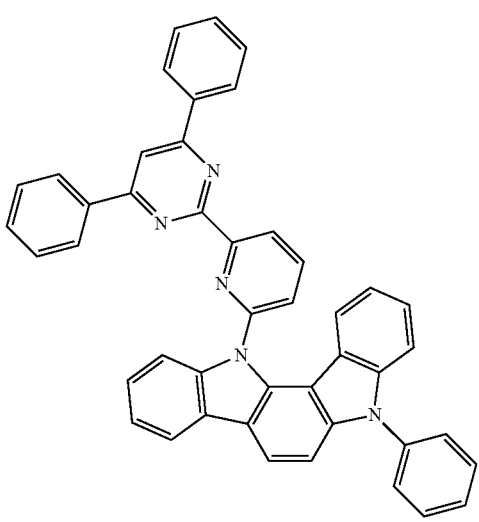

-continued
(455)
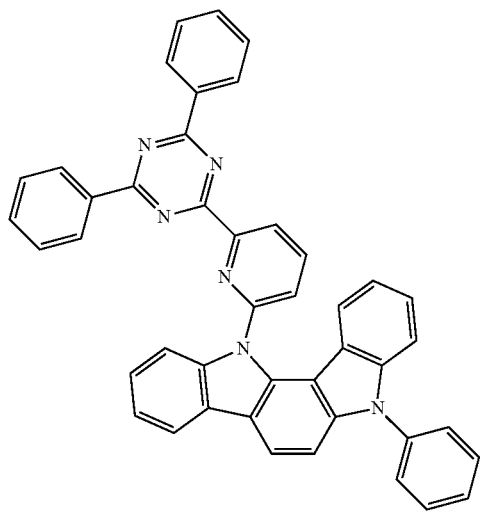
(456)
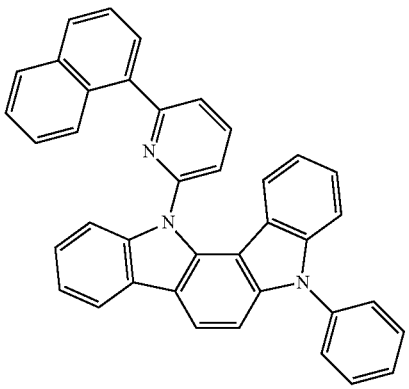
(457)
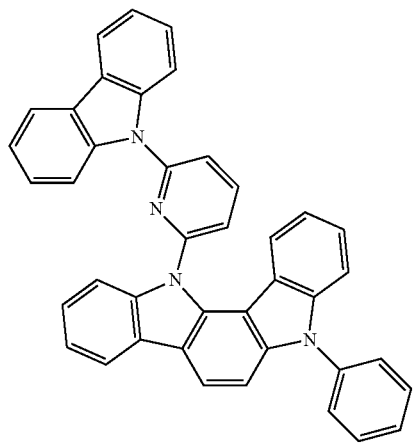
(458)
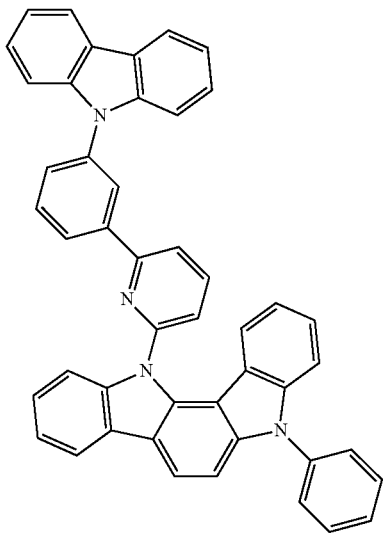
(459)
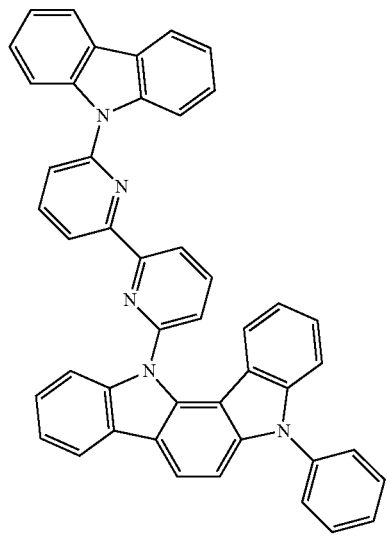
(460)
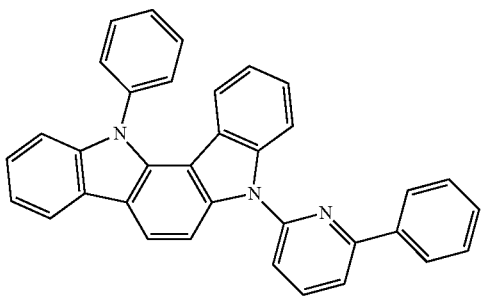

-continued
(461)
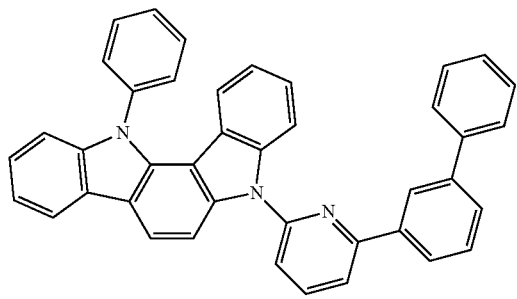
(462)
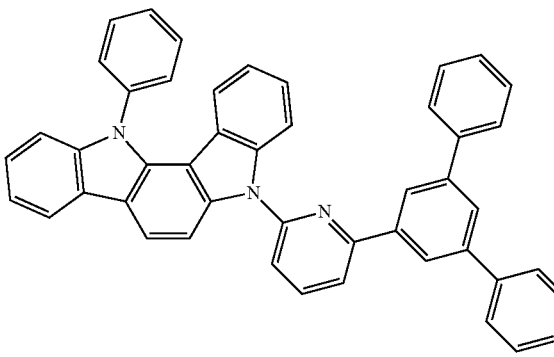
(463)
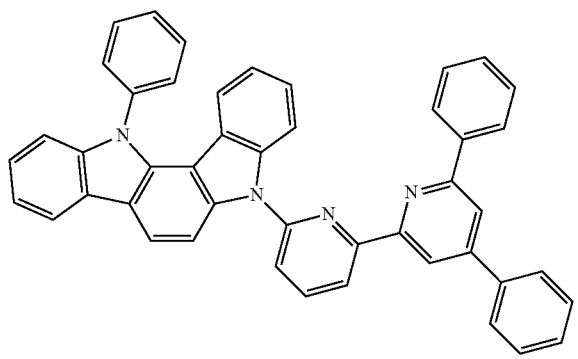
(464)
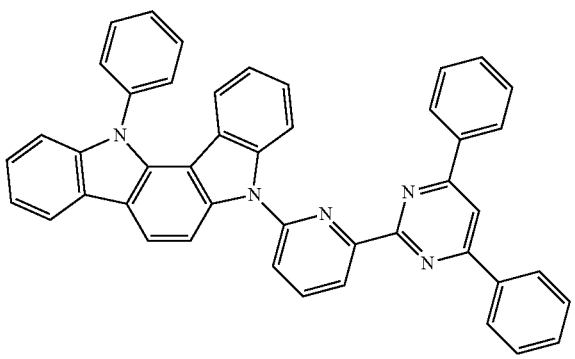
(465)
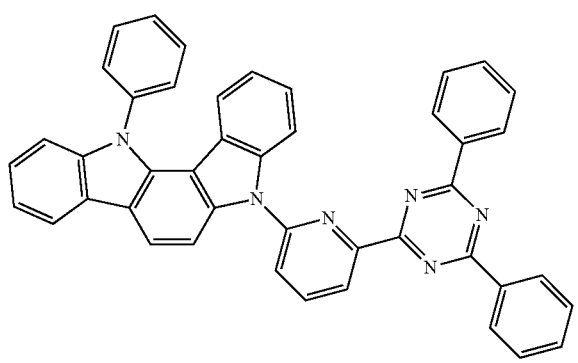
(466)
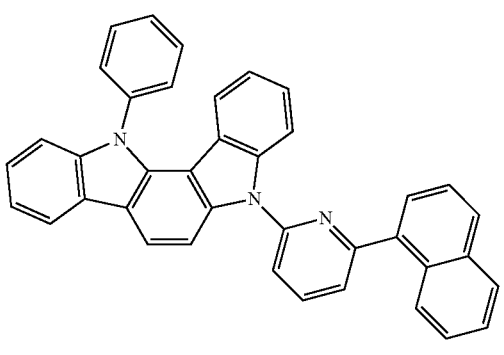
(467)
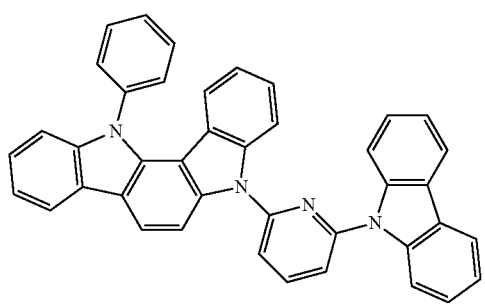
(468)
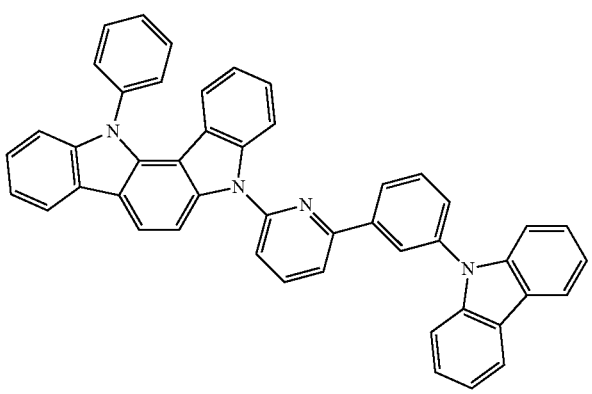

-continued
(469)
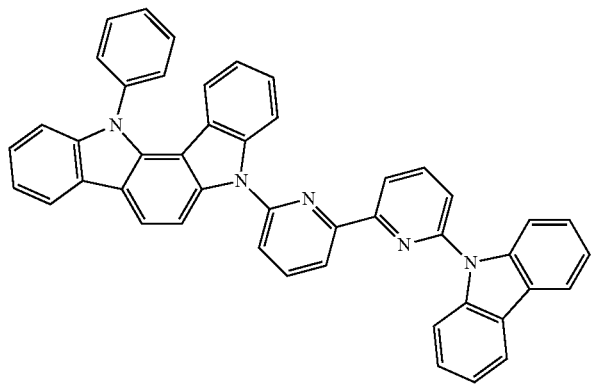
(470)
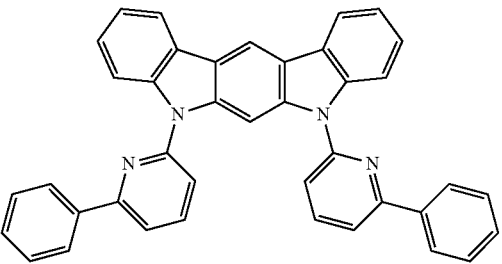
(471)
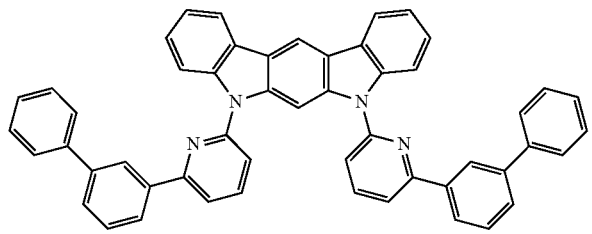
(472)
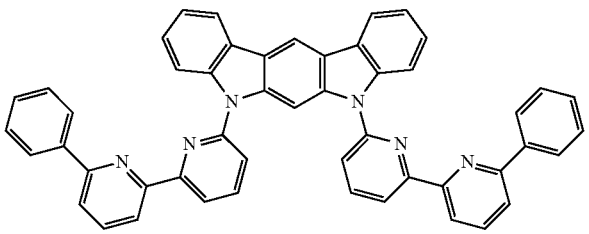
(473)
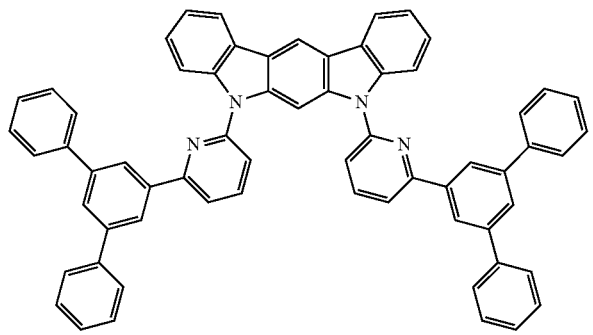
(474)
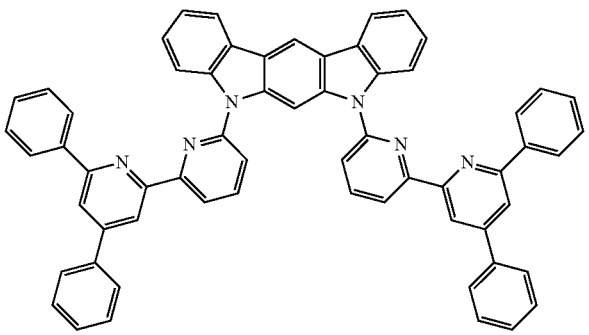
(475)
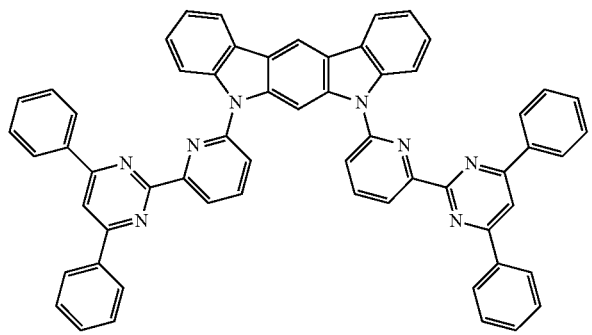
(476)
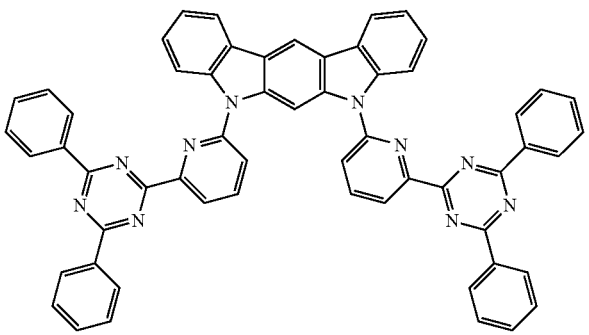

-continued
(477)
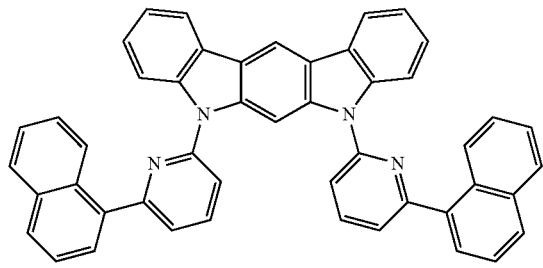
(478)
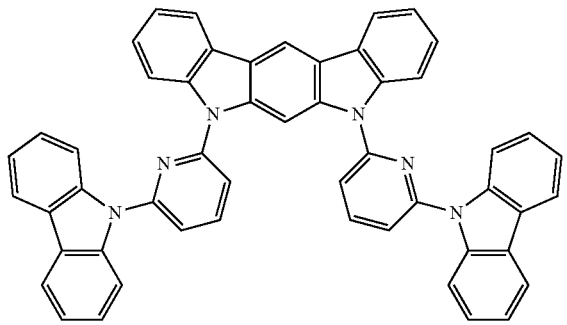
(479)
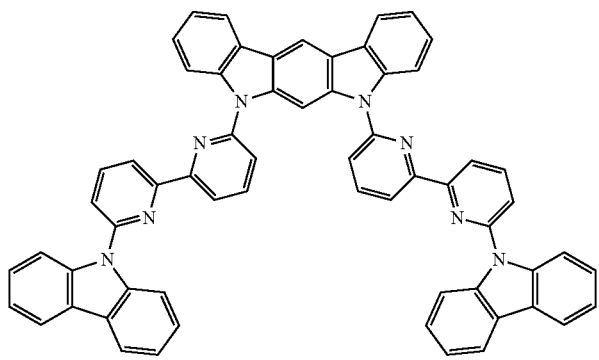
(480)
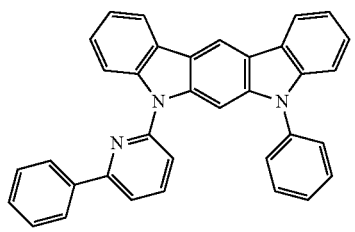
(481)
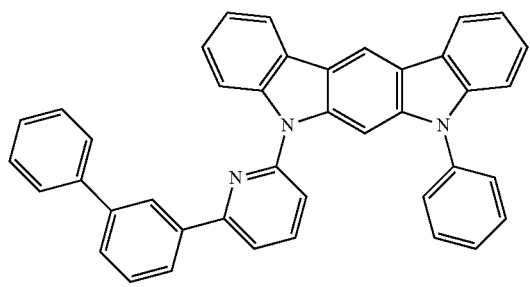
(482)
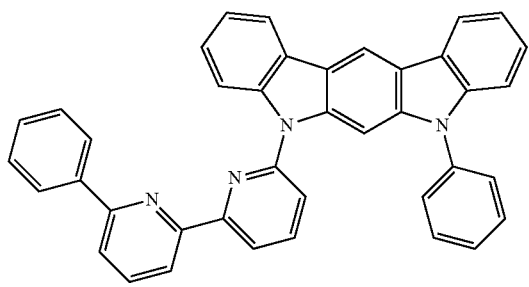
(483)
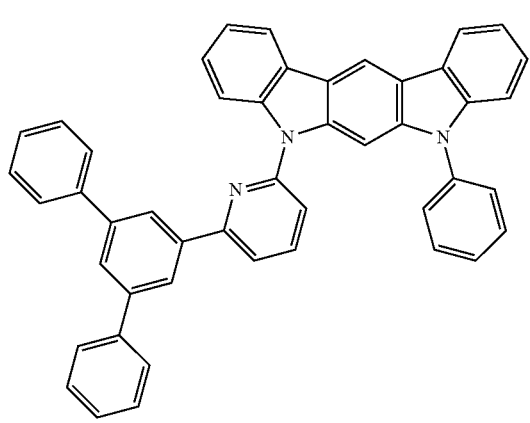
(484)
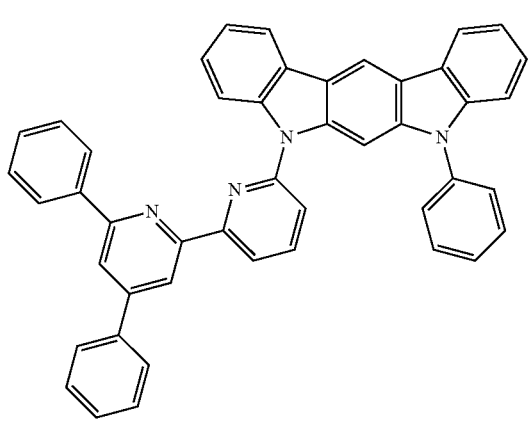

-continued
(485)
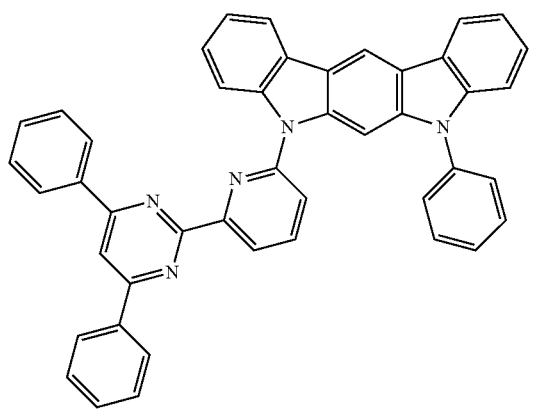
(486)
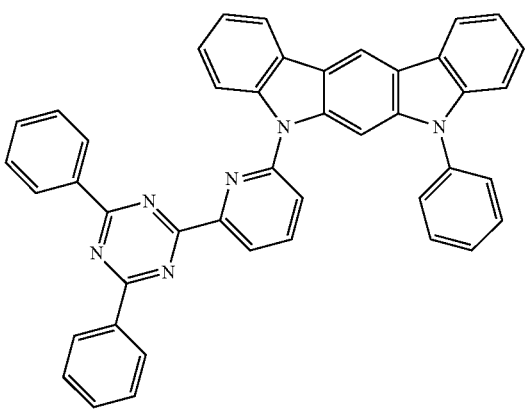
(487)
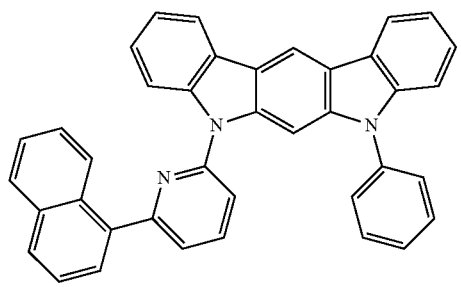
(488)
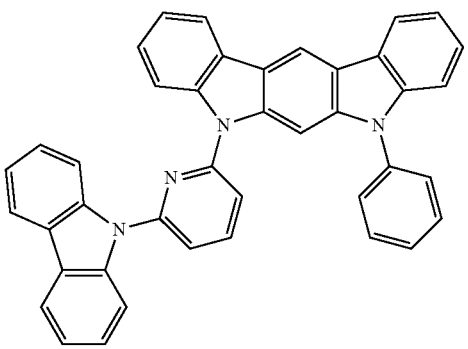
(489)
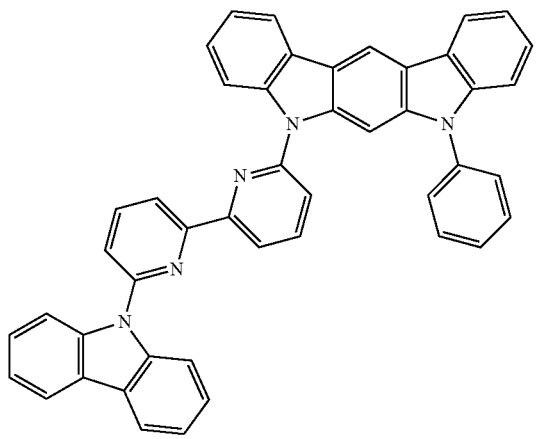
(490)
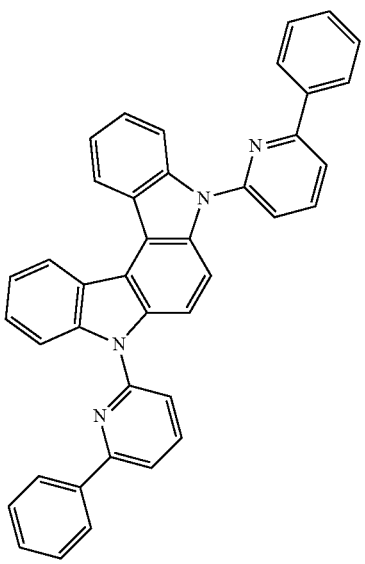

-continued
(491)
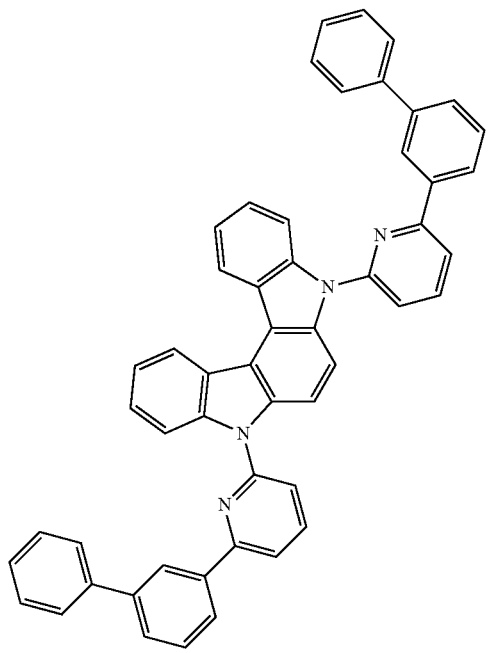
(492)
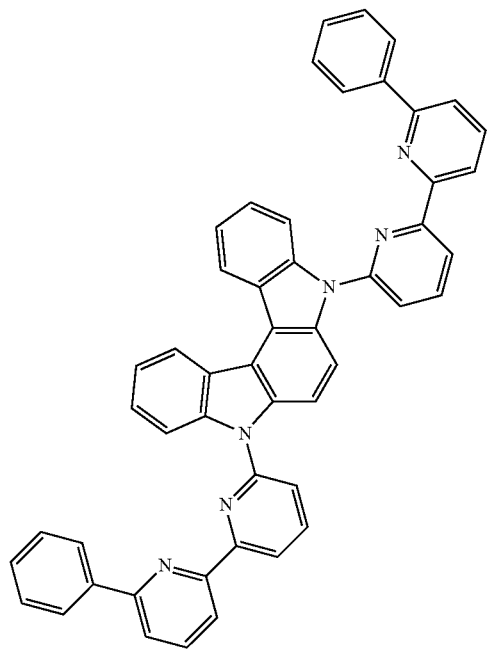
(493)
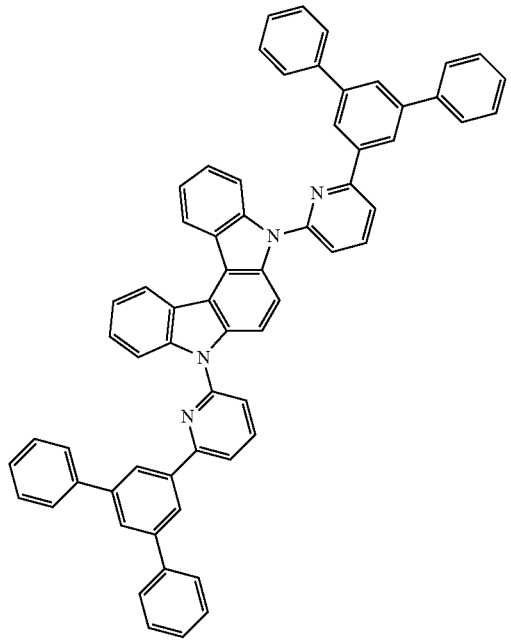
(494)
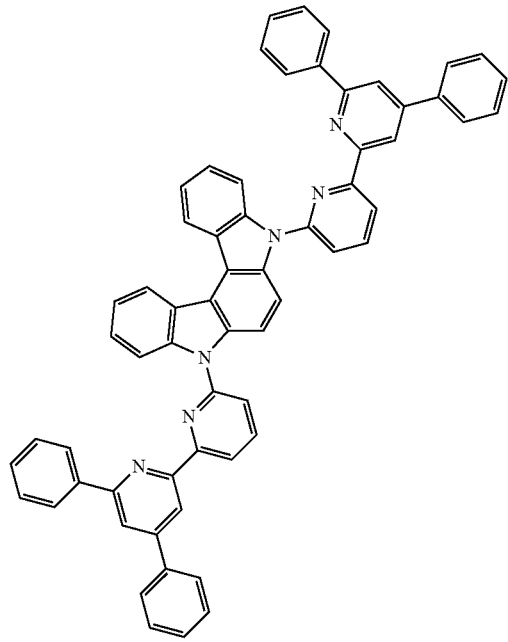

-continued
179
(495)
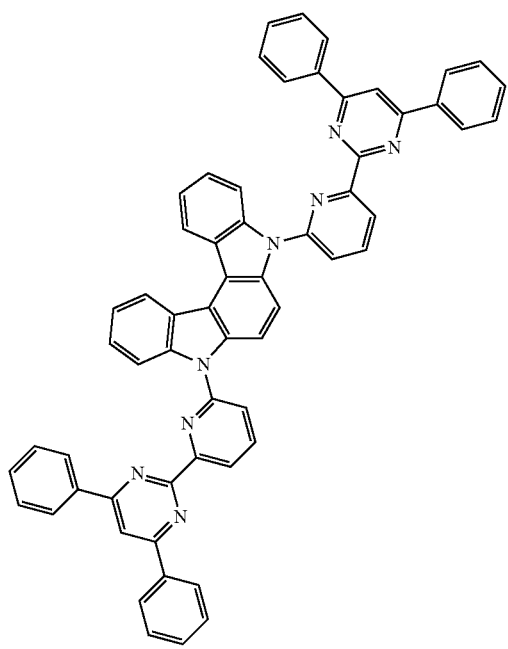
180
(496)
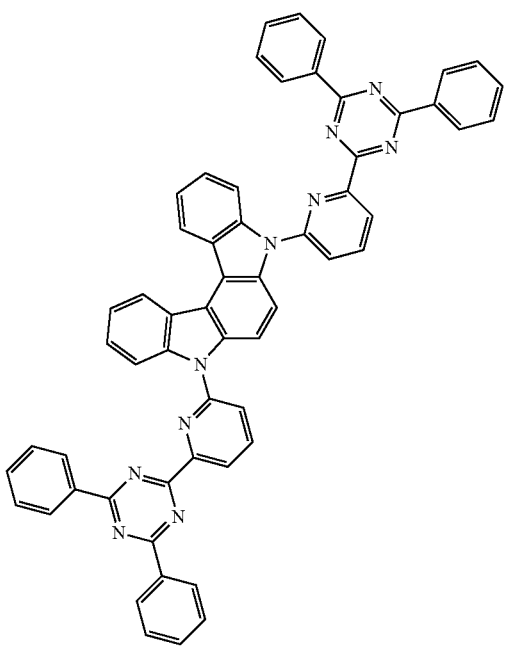
(497)
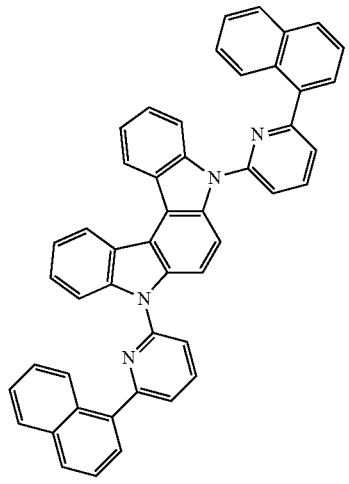
(498)
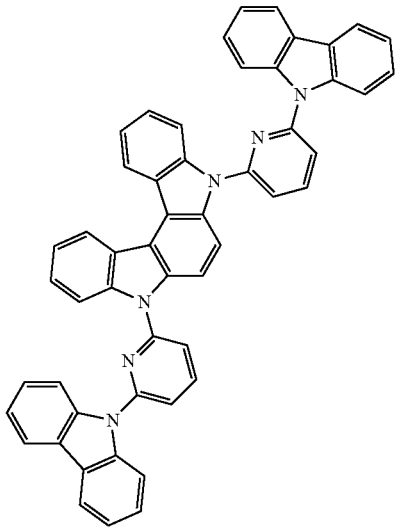

-continued
(499)
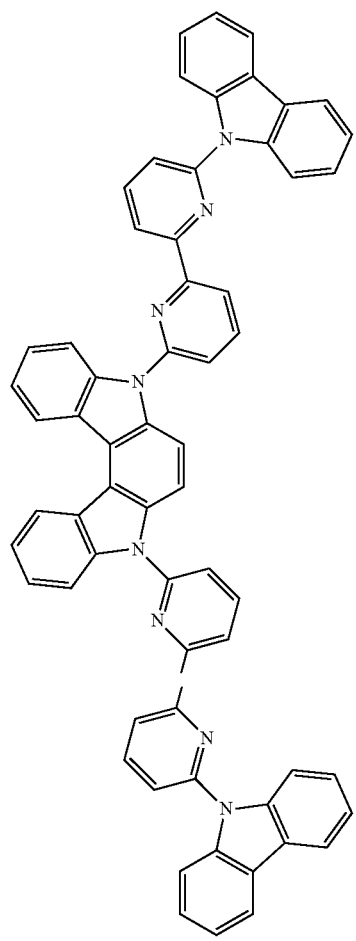
(500)
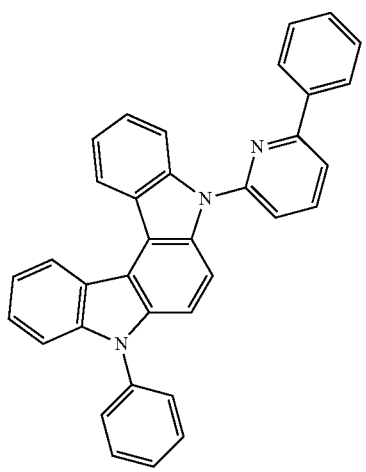
(501)
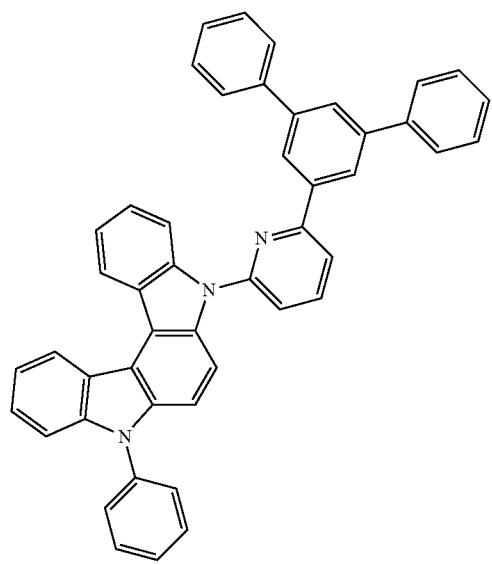
(502)
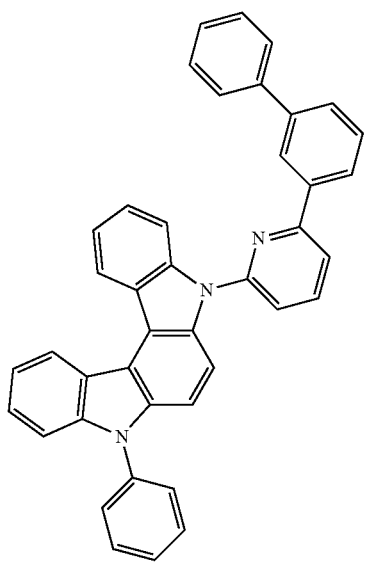

-continued
(503)
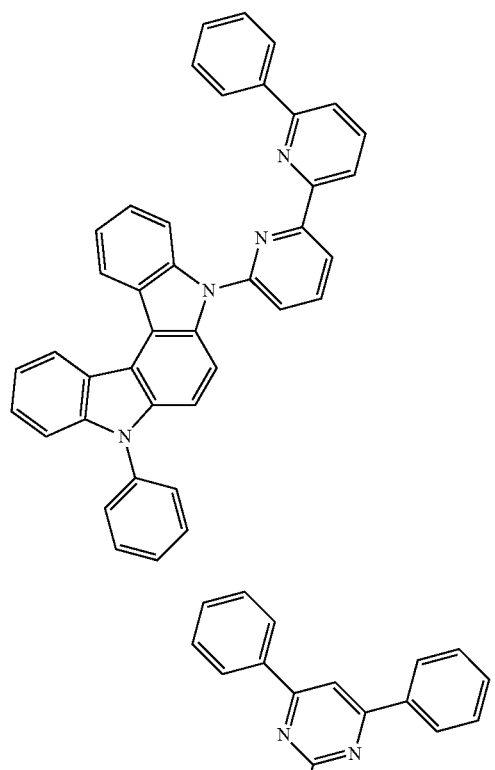
(504)
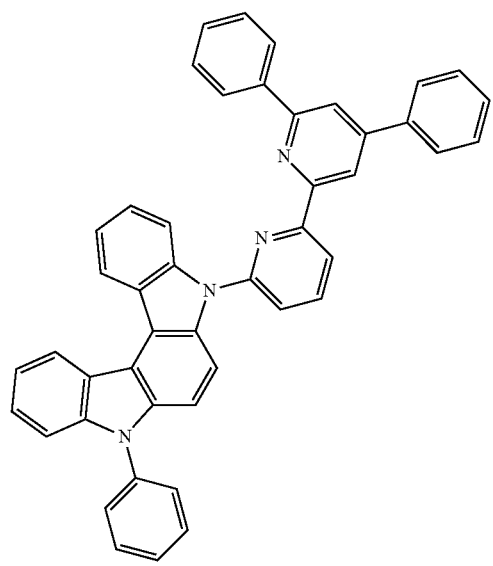
(505)
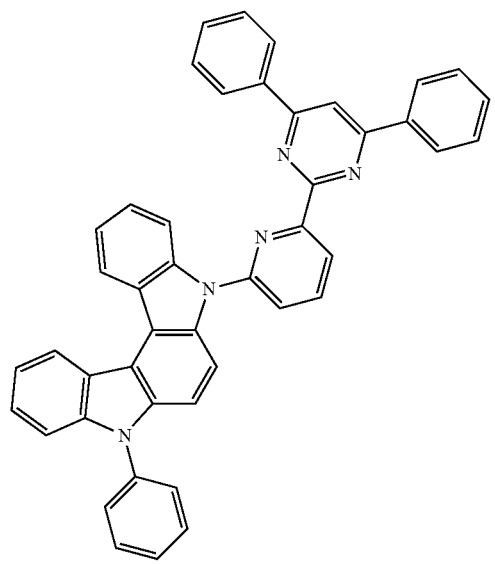
(506)
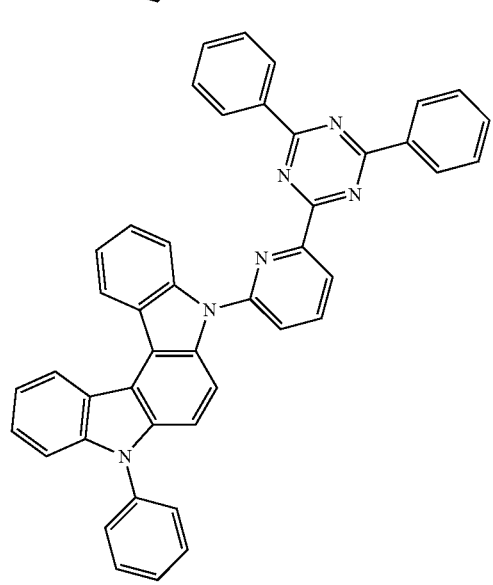
(507)
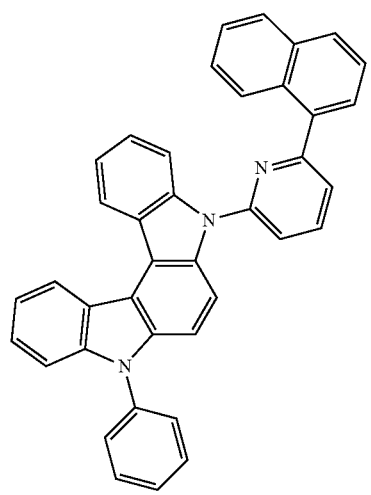
(508)
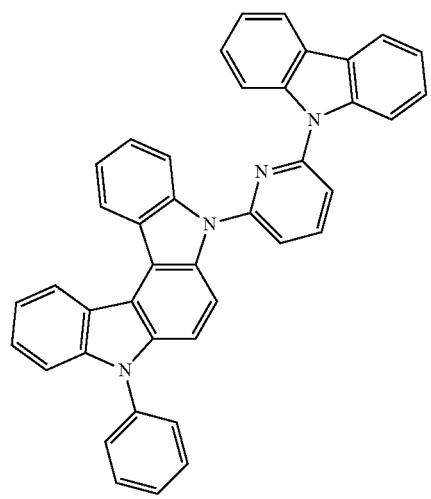

(509)
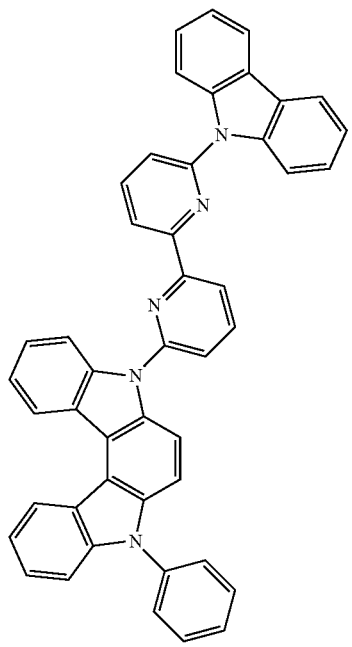
(510)
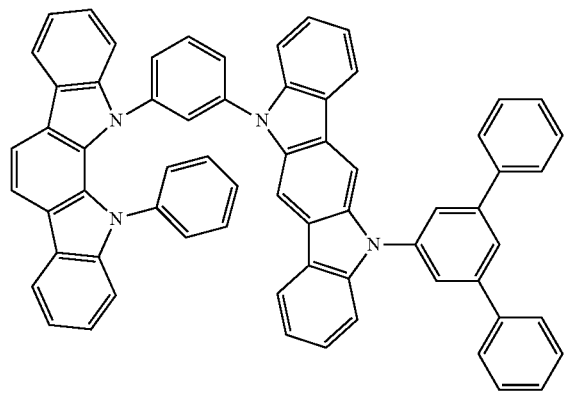
(511)
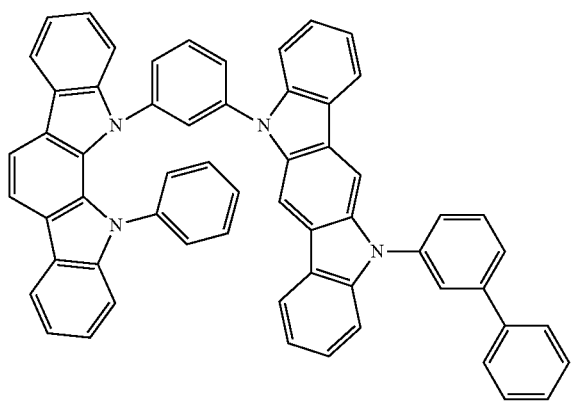
(512)
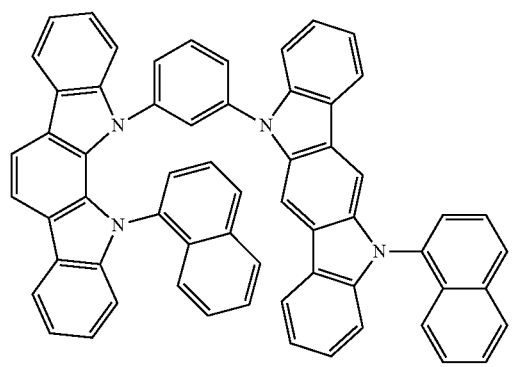
(513)
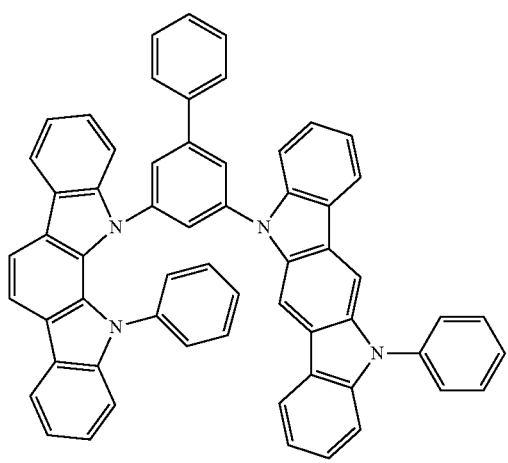
(514)
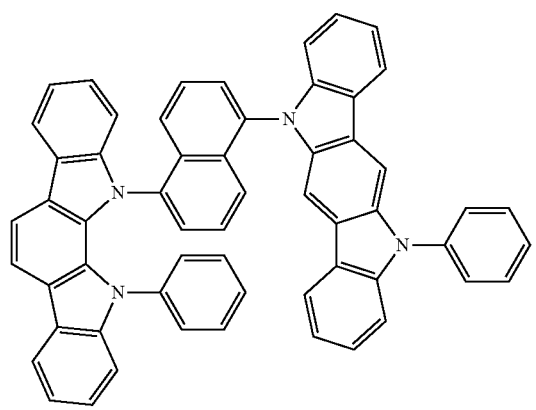

-continued
(515)
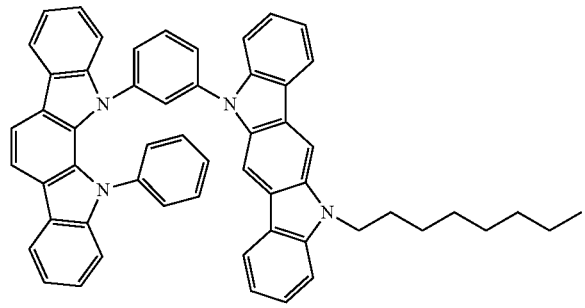
(516)
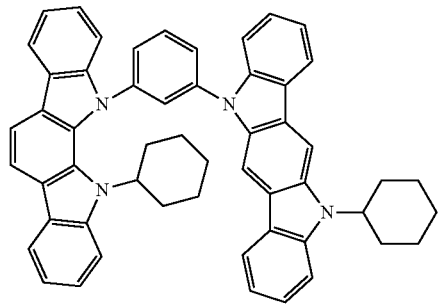
(517)
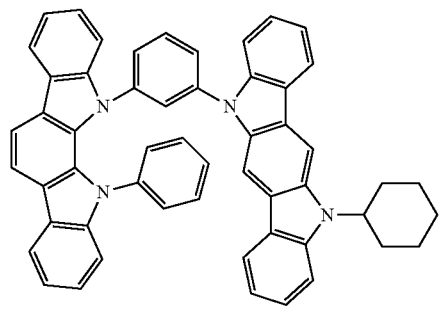
(518)
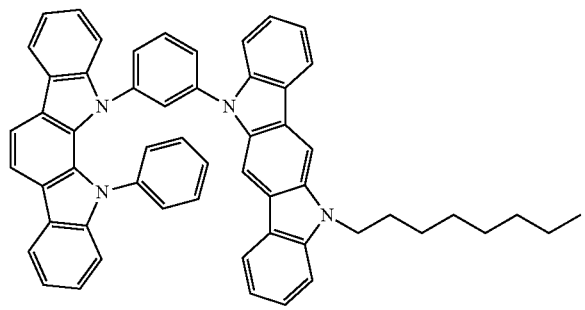
(519)
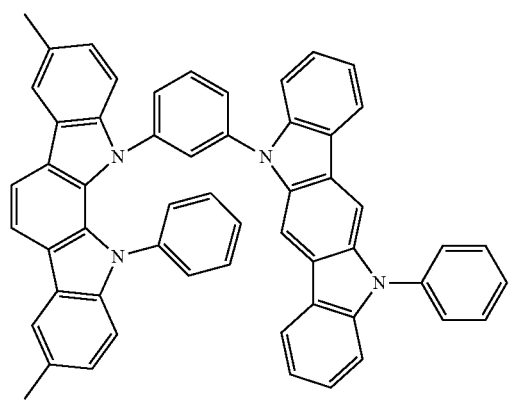
(520)
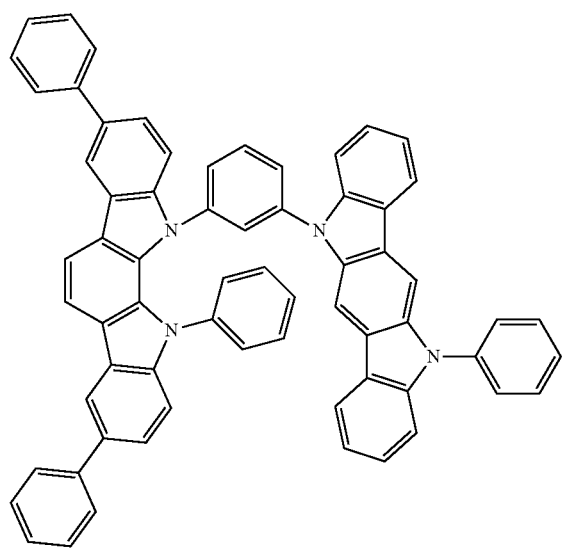
(521)
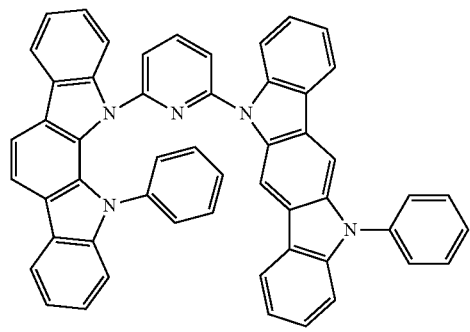
(522)
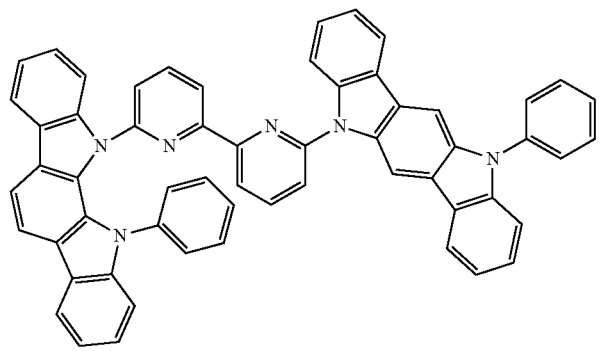

-continued
(523)
(524)
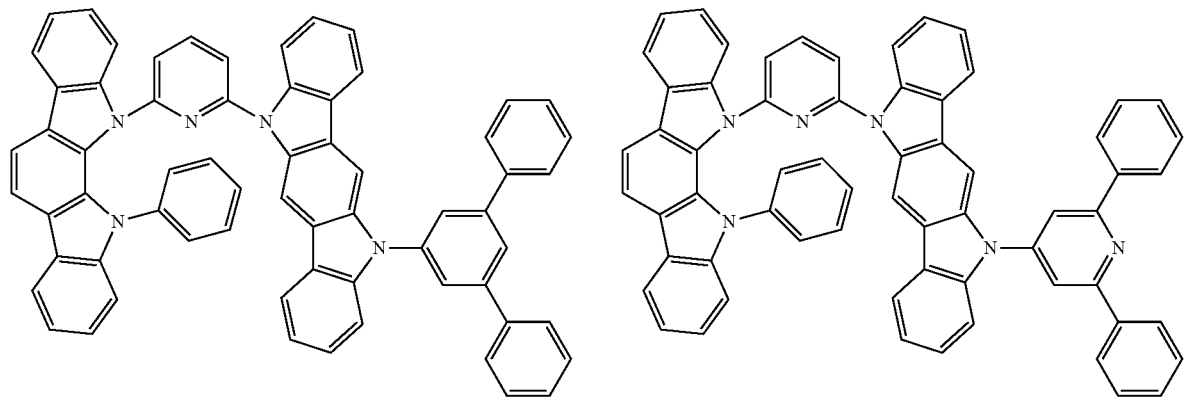
(525)
(526)
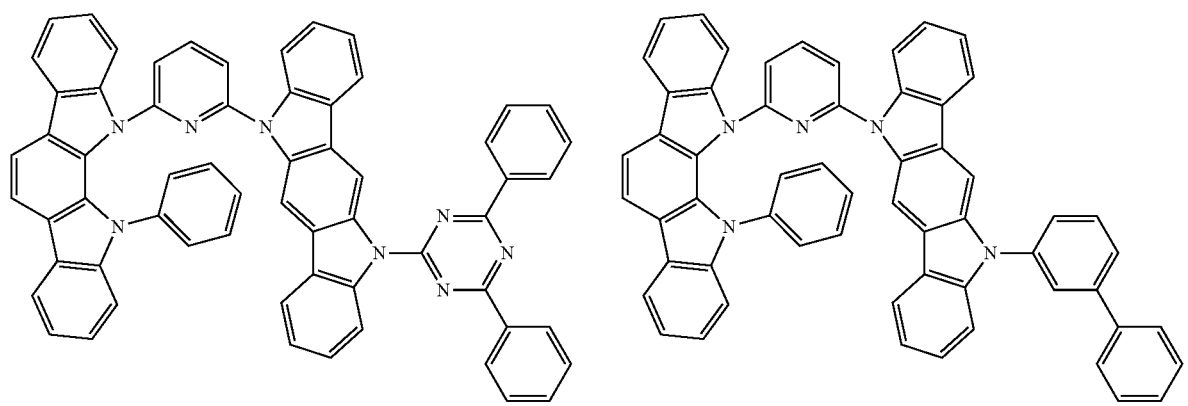
(527)
(528)
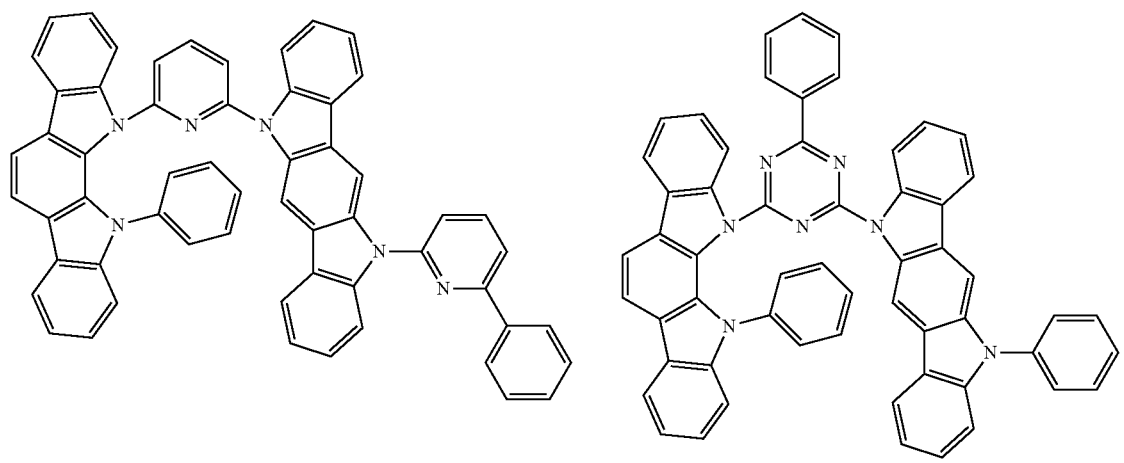

-continued
(529)
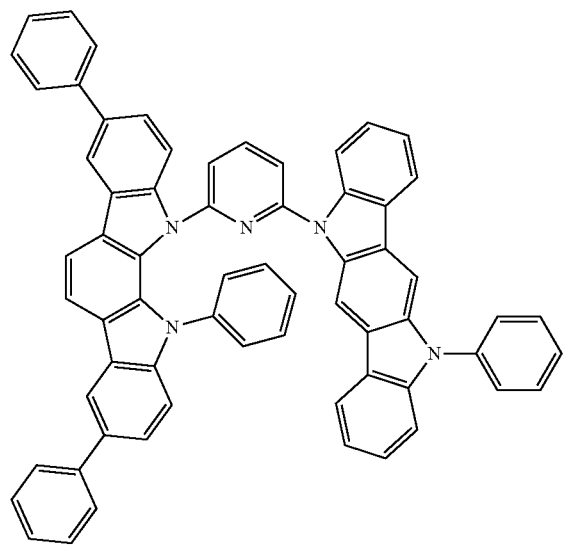
(530)
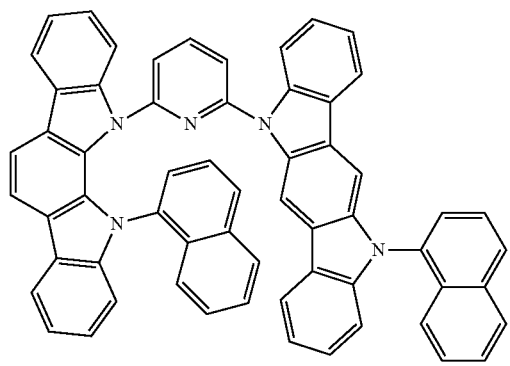
(531)
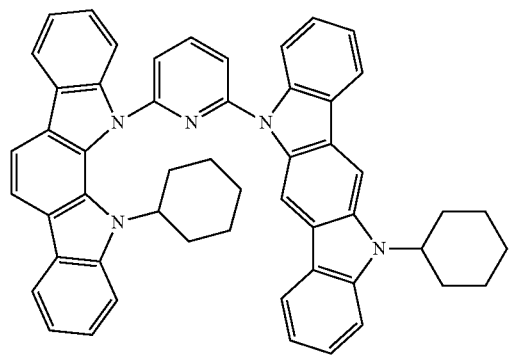
(532)
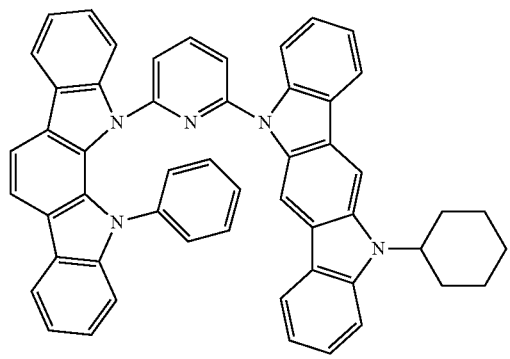
(533)
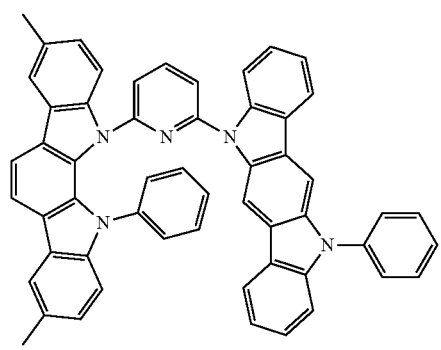
(534)
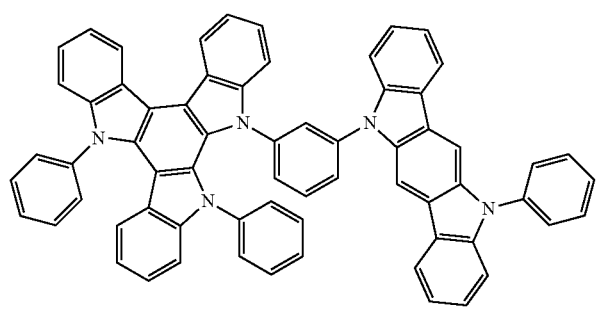

-continued
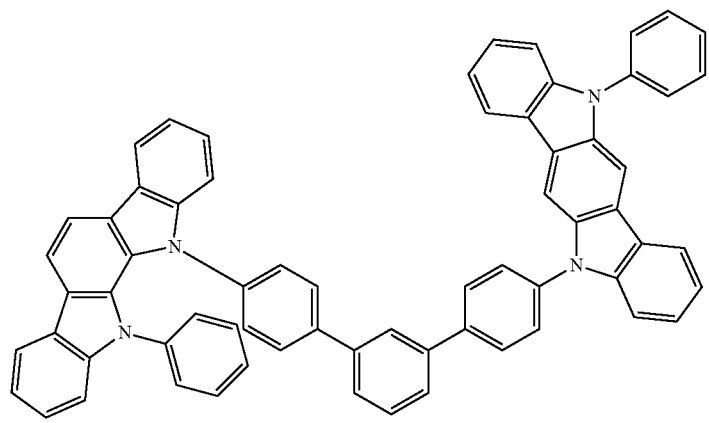
(535)
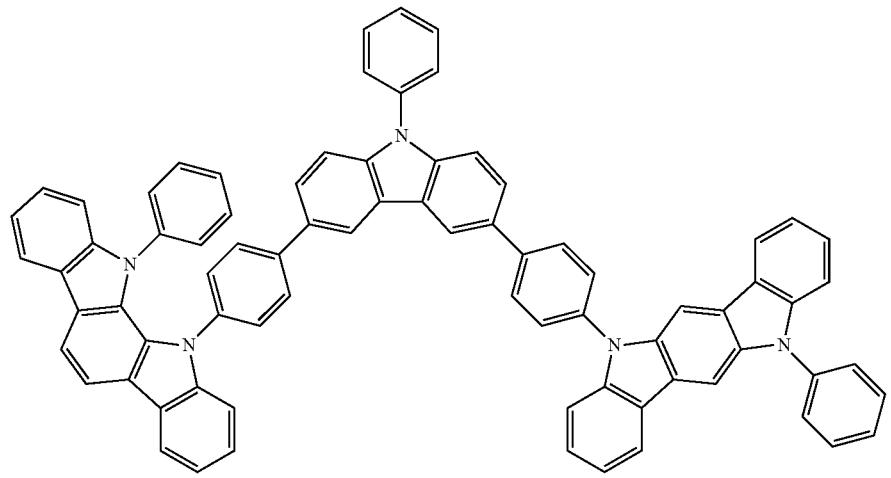
(536)
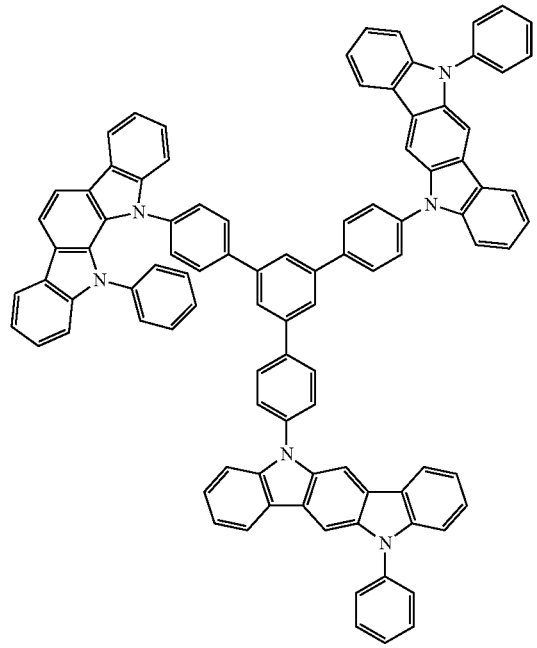
(537)
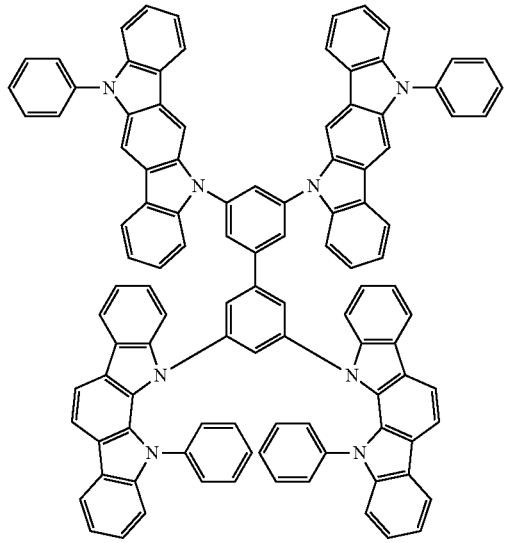
(538)

-continued
(539)
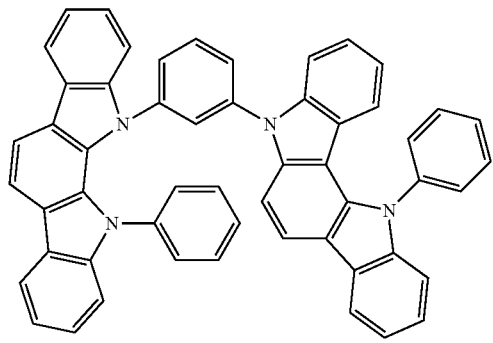
(540)
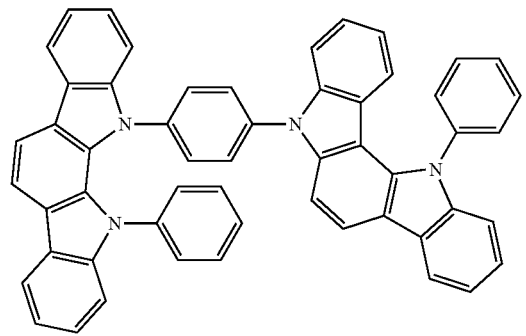
(541)
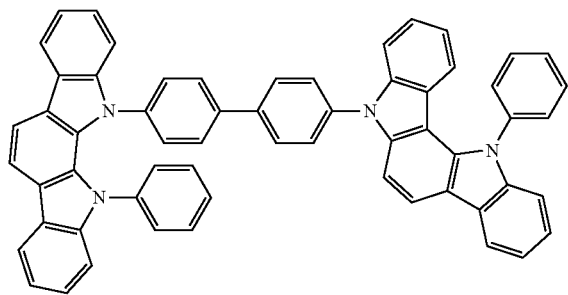
(542)
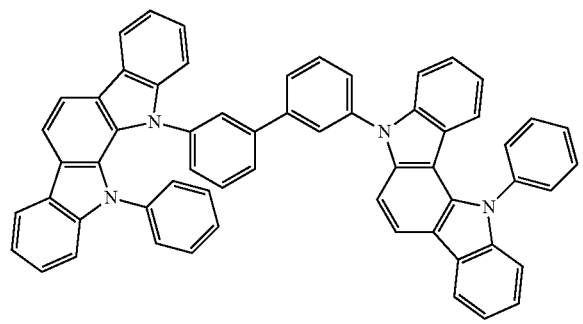
(543)
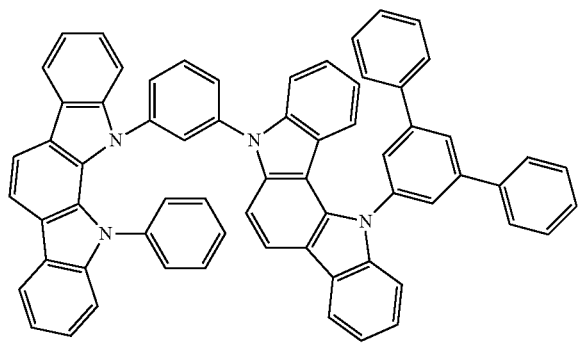
(544)
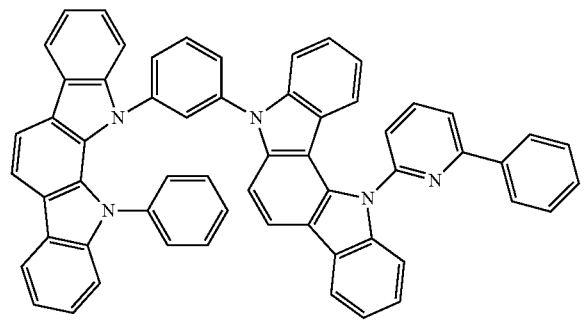
(545)
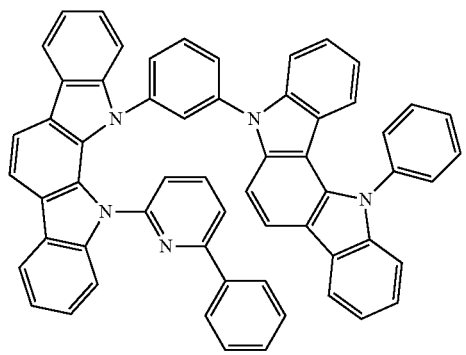
(546)
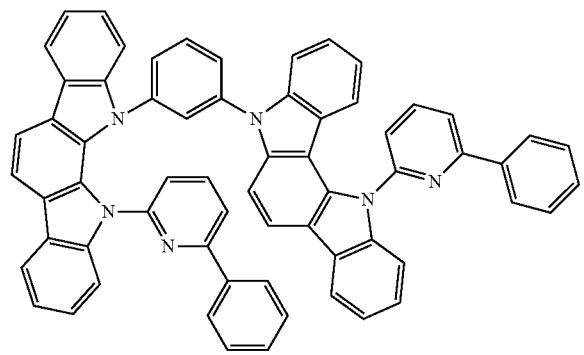

-continued
(547)
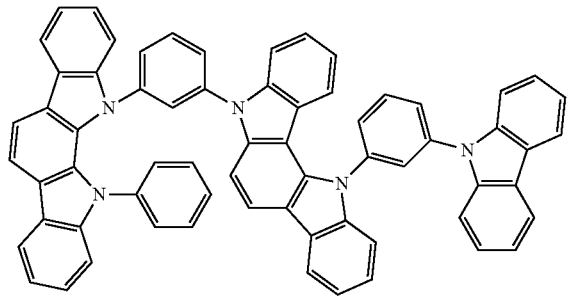
(548)
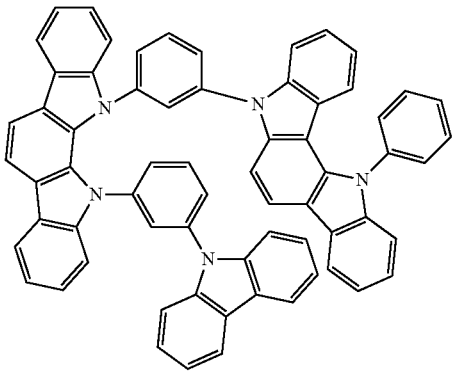
(549)
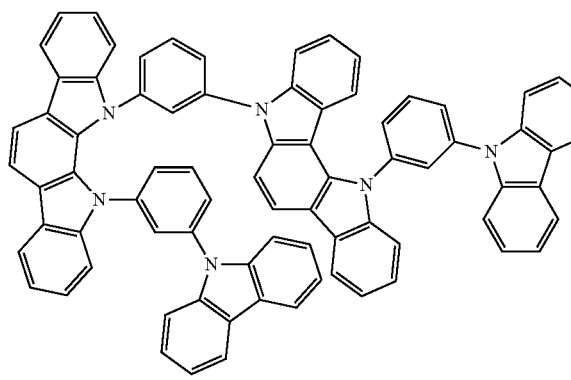
(550)
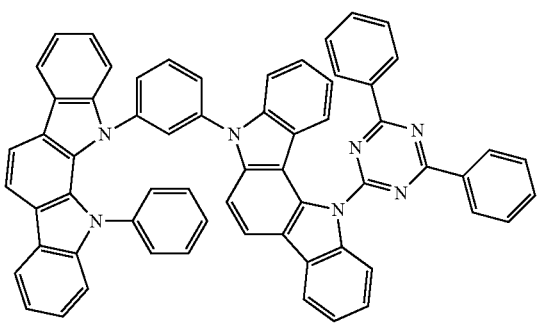
(551)
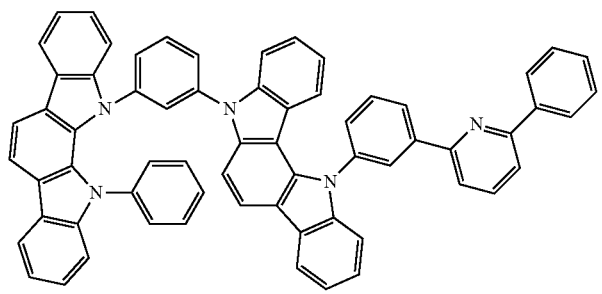
(552)
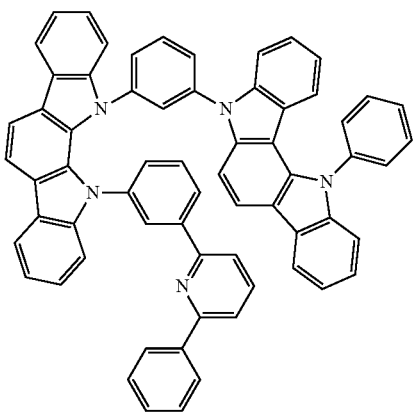
(553)
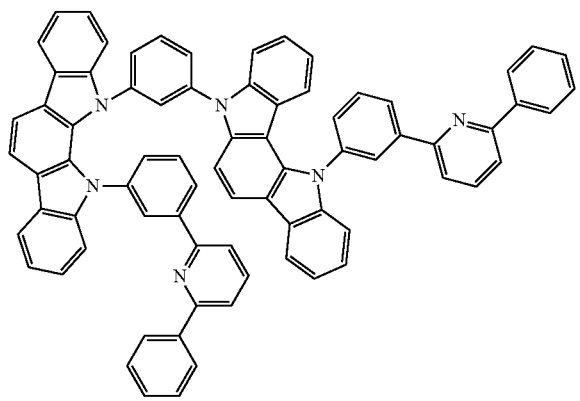
(554)
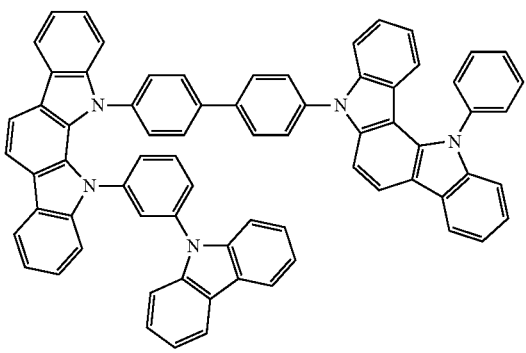

-continued
(555)
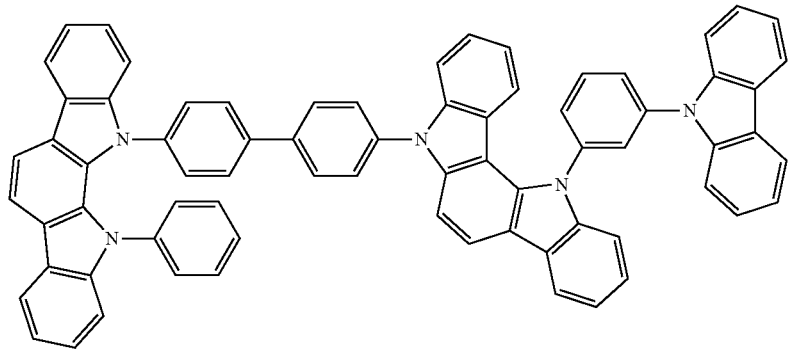
(556)
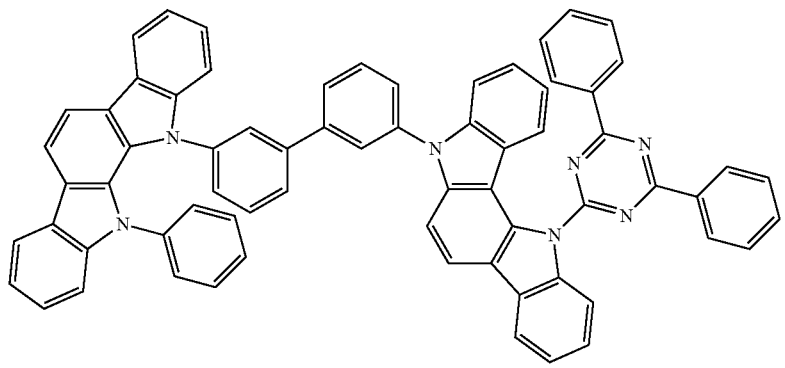
(557)
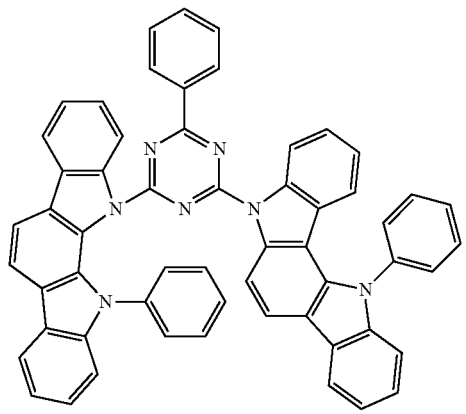
(558)
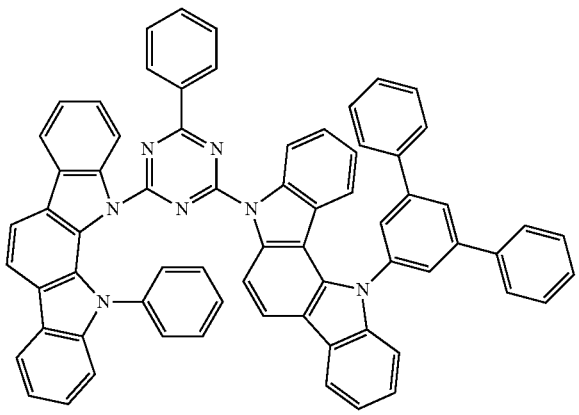
(559)
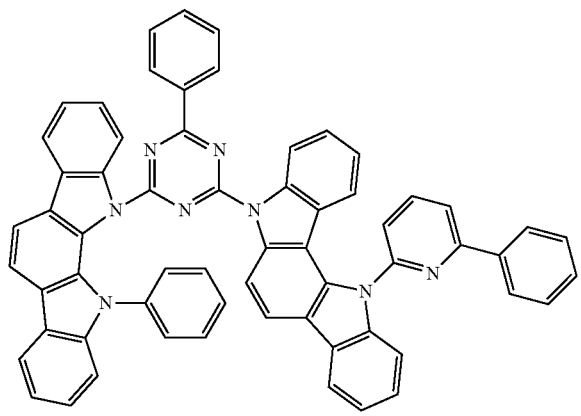
(560)
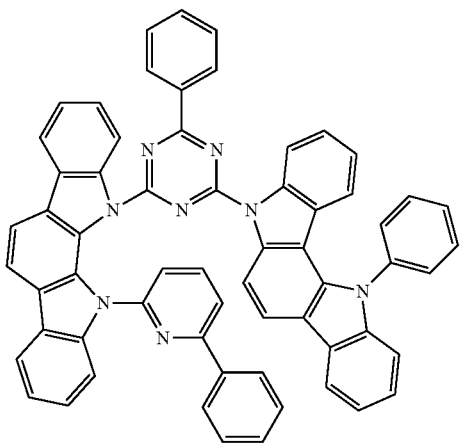

-continued
(561)
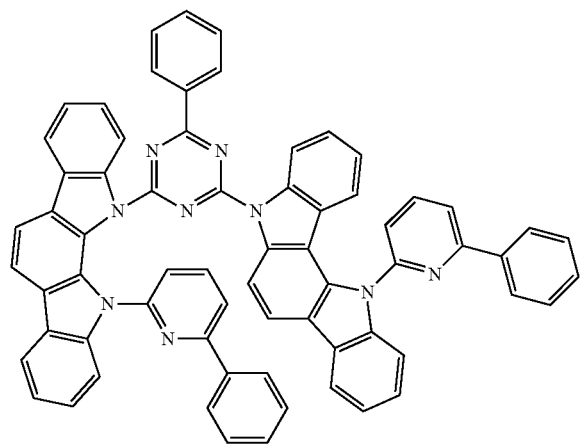
(562)
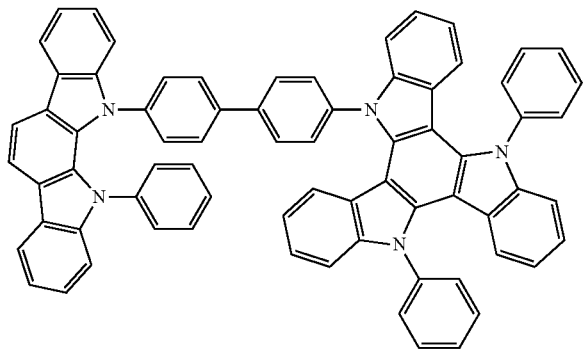
(563)
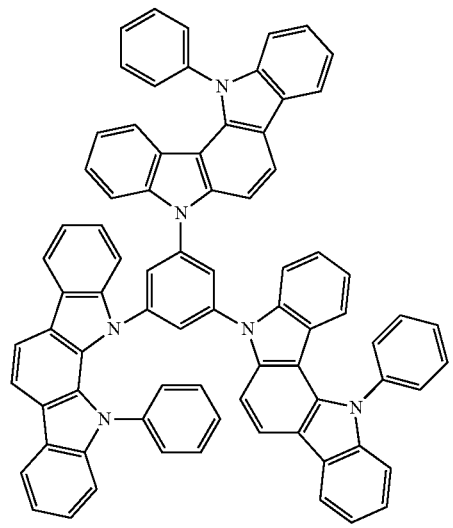
(564)
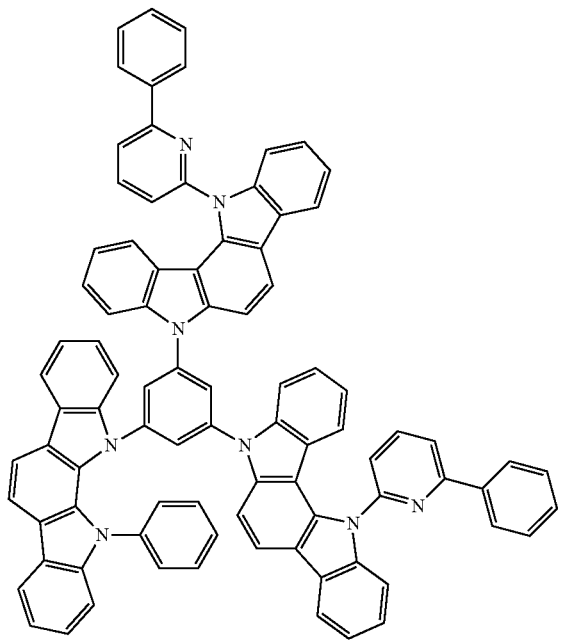

(565)
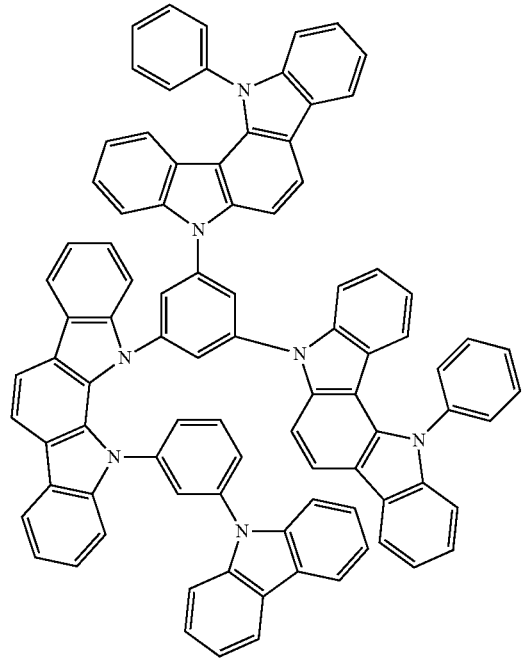
(566)
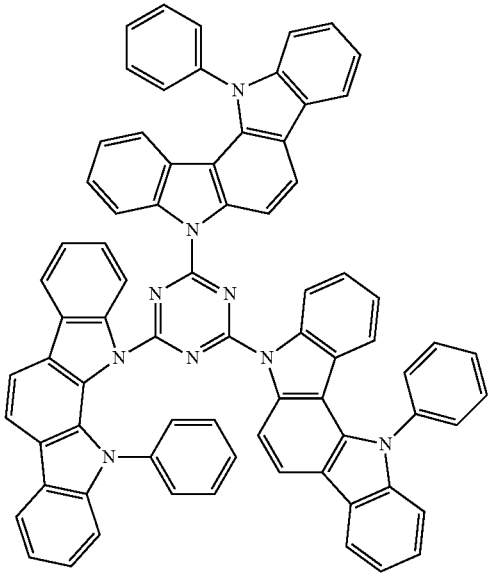
(567)
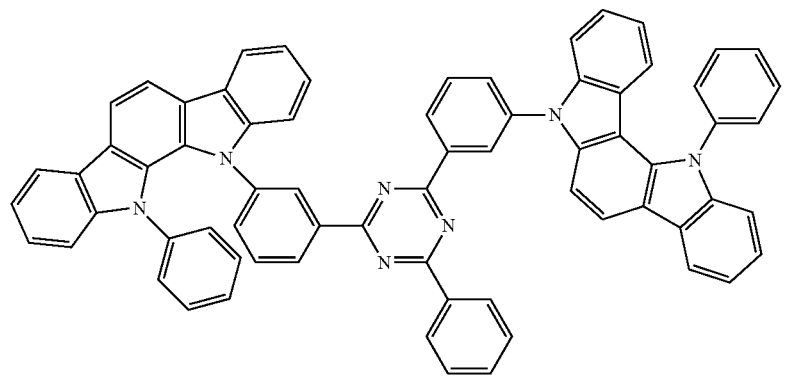
(568)
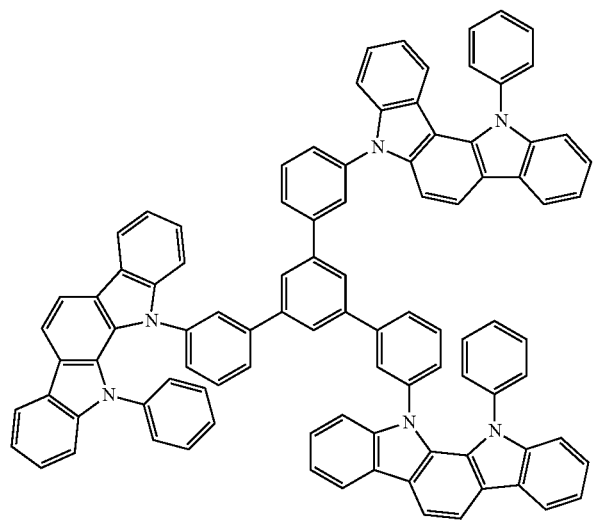
(569)
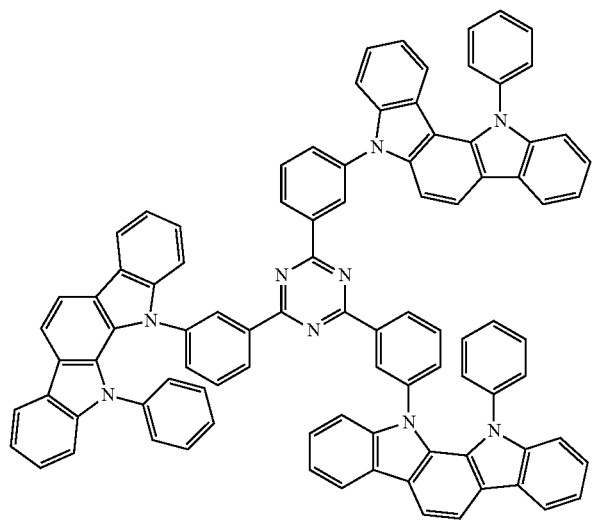

-continued
(570)
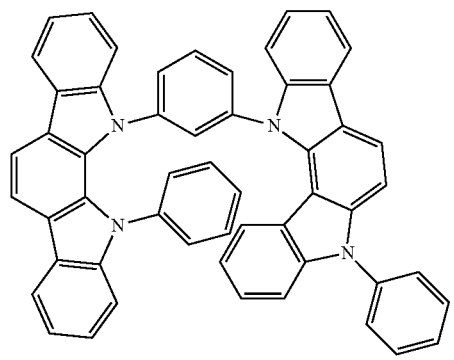
(571)
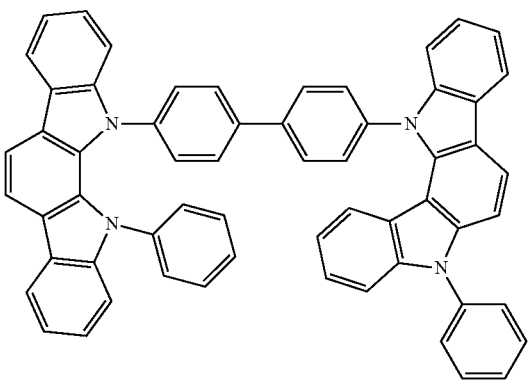
(572)
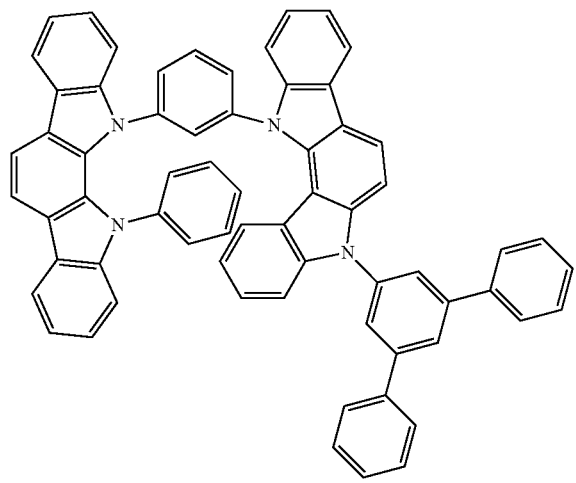
(573)
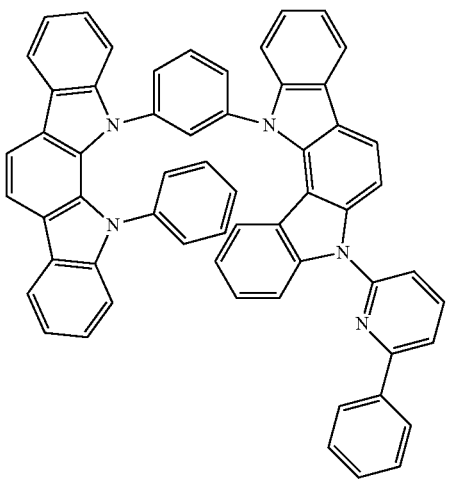
(574)
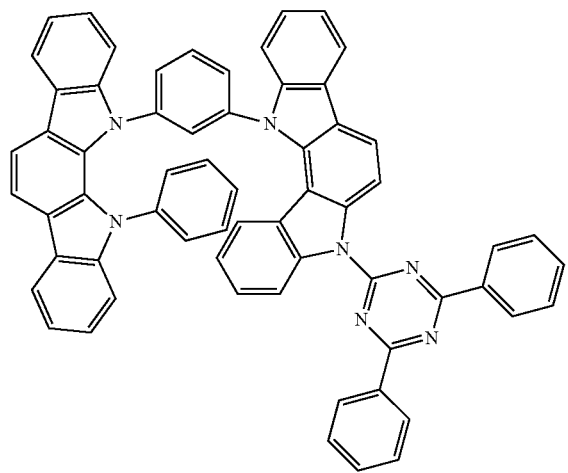
(575)
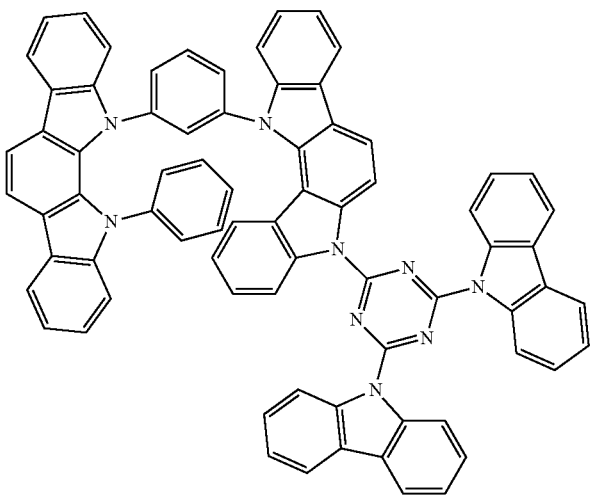

-continued
(576)
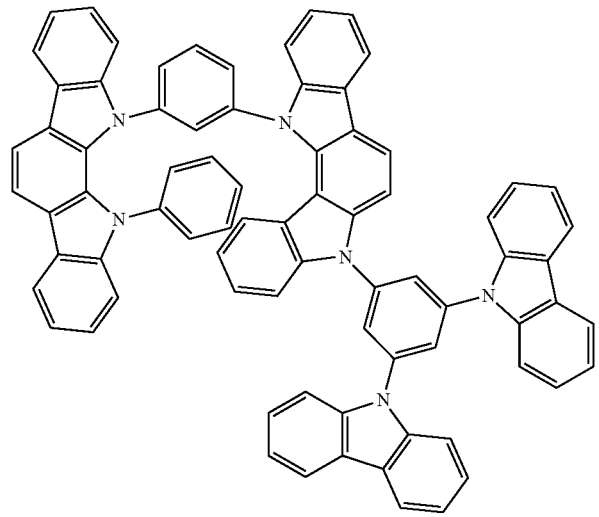
(577)
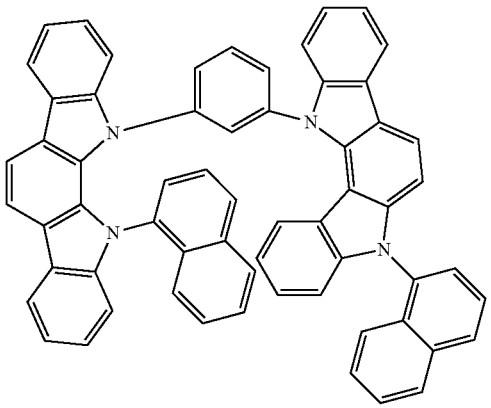
(578)
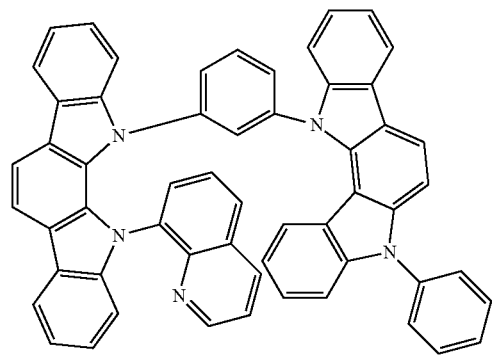
(579)
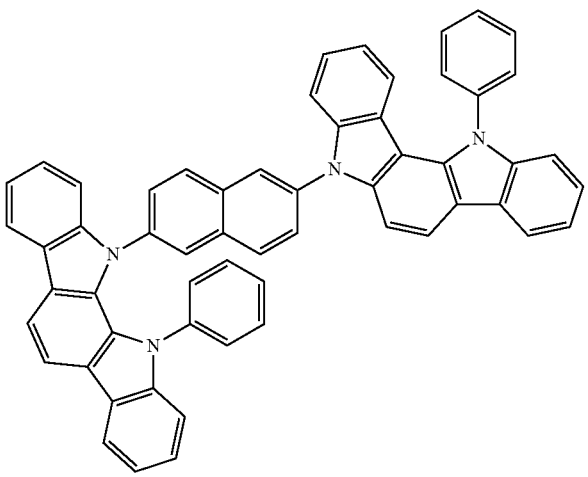
(580)
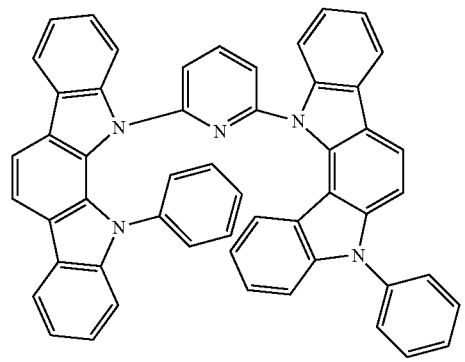
(581)
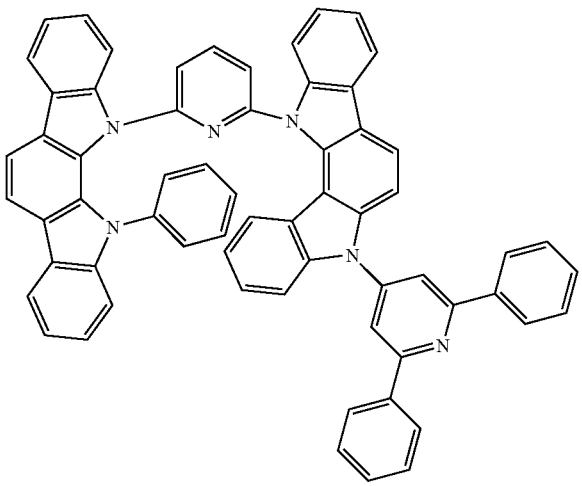

-continued
(582)
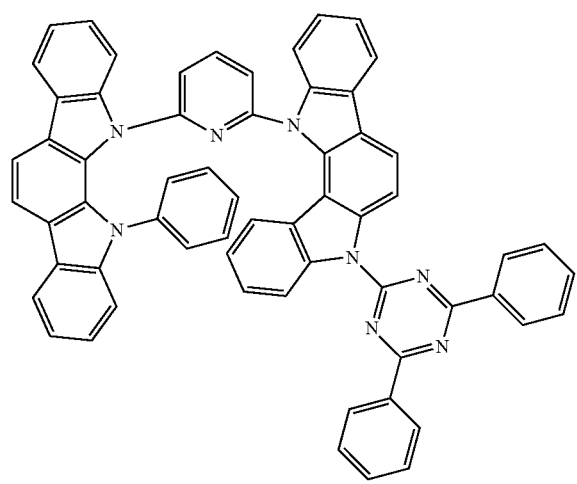
(583)
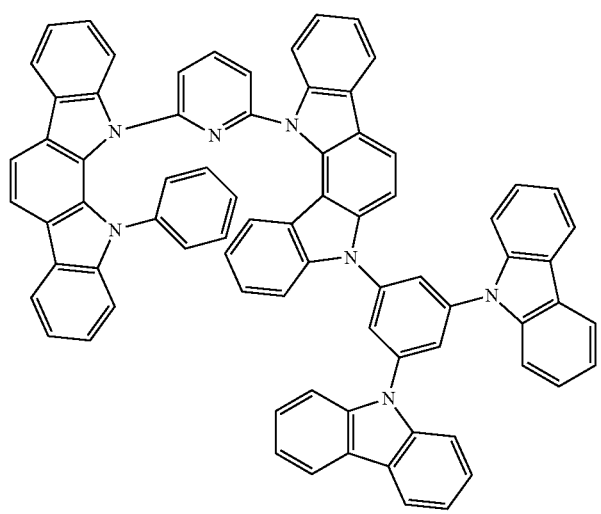
(584)
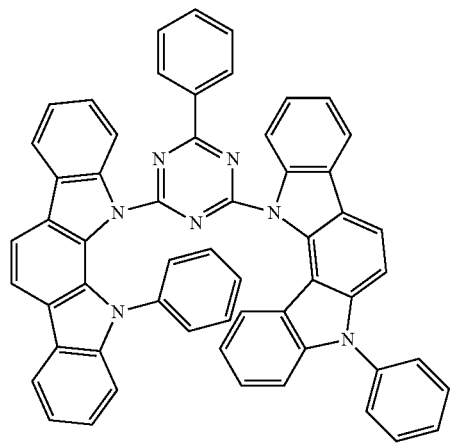
(585)
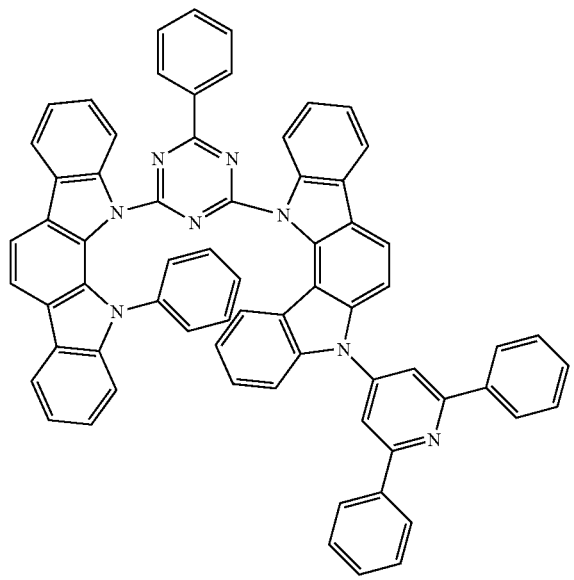

-continued
(586)
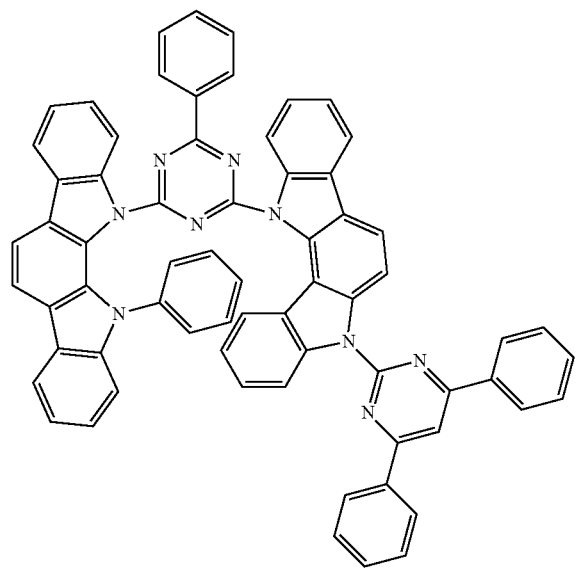
(587)
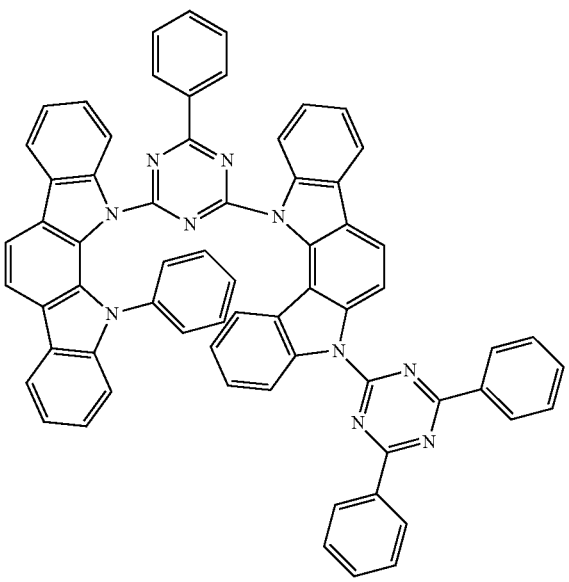
(588)
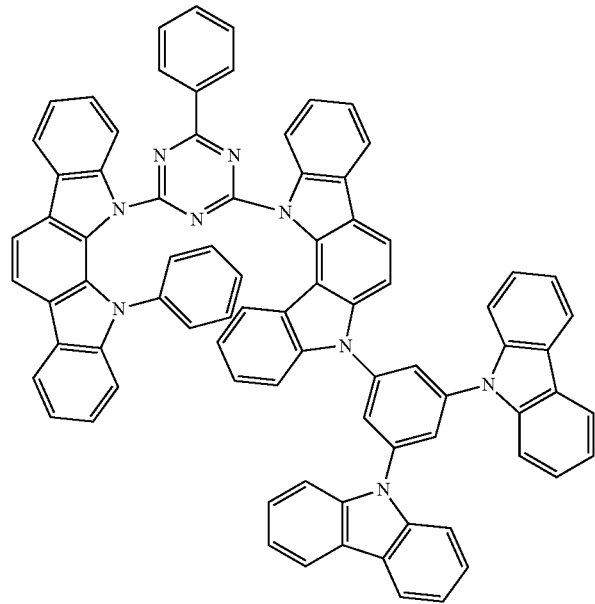
(589)
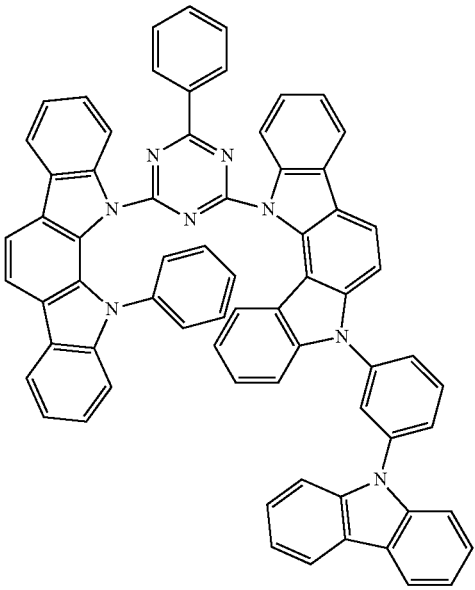

(590)
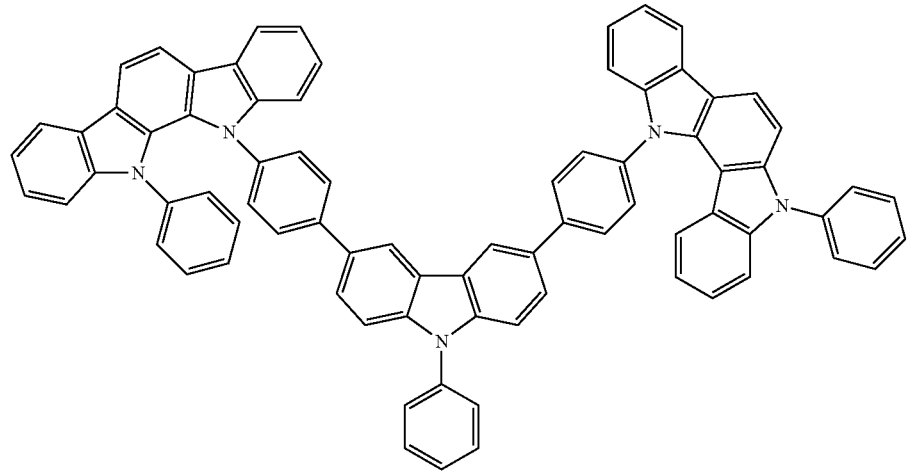
(591)
(592)
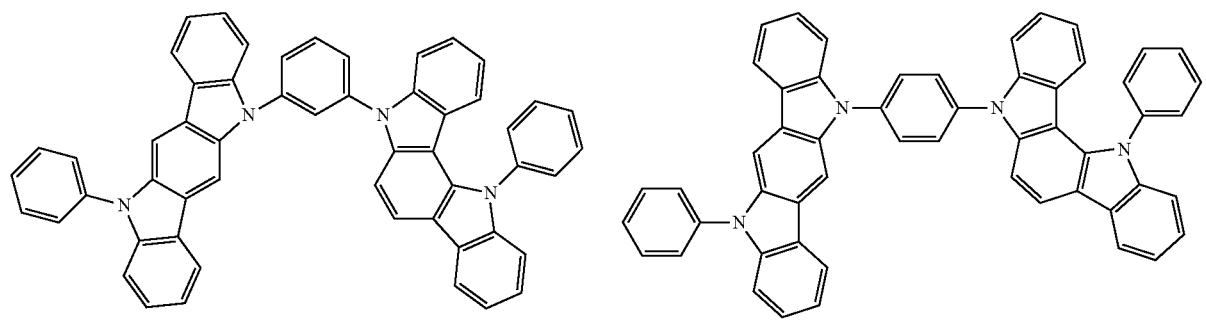
(593)
(594)
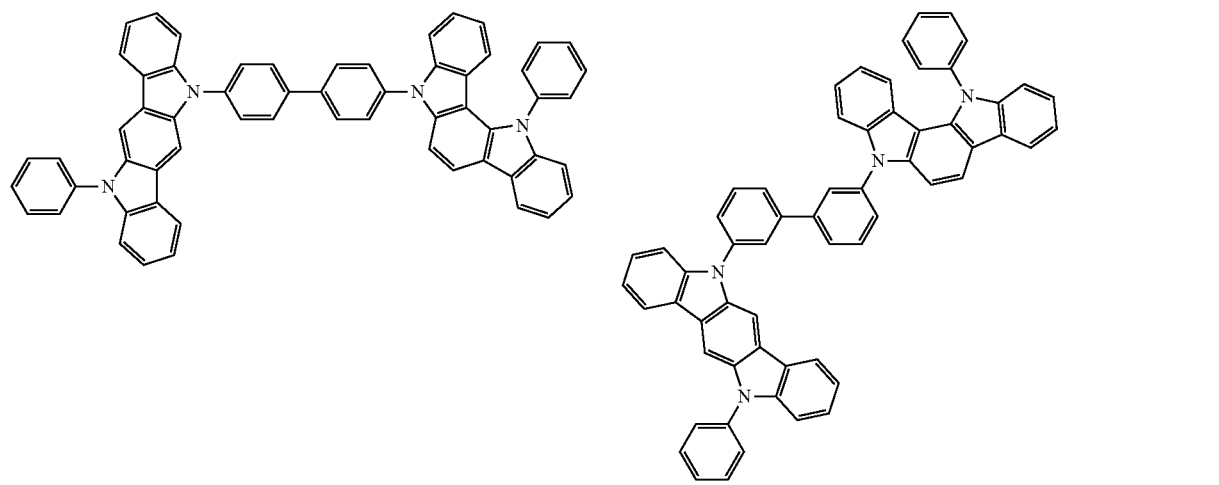
(595)
(596)
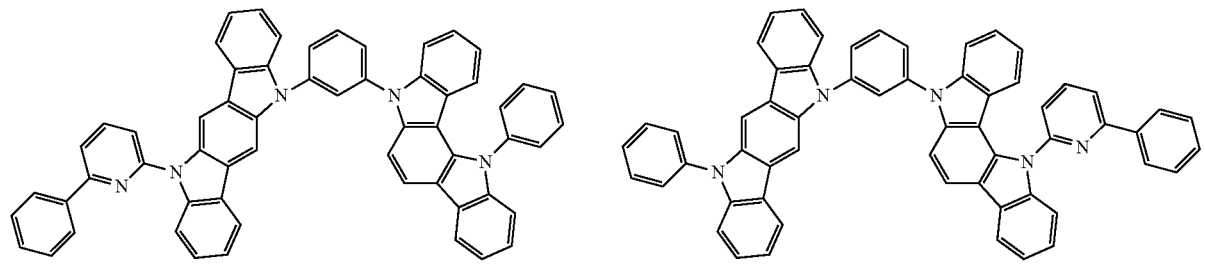

(597)
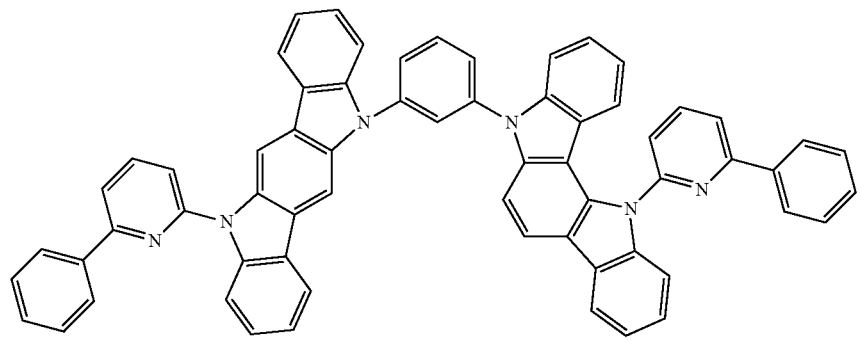
(598)
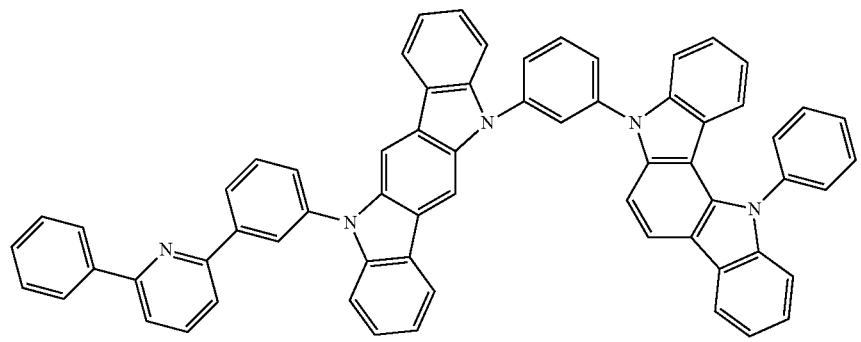
(599)
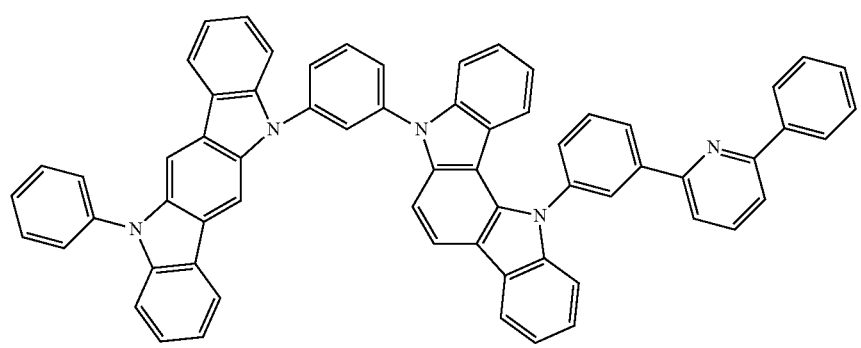
(600)
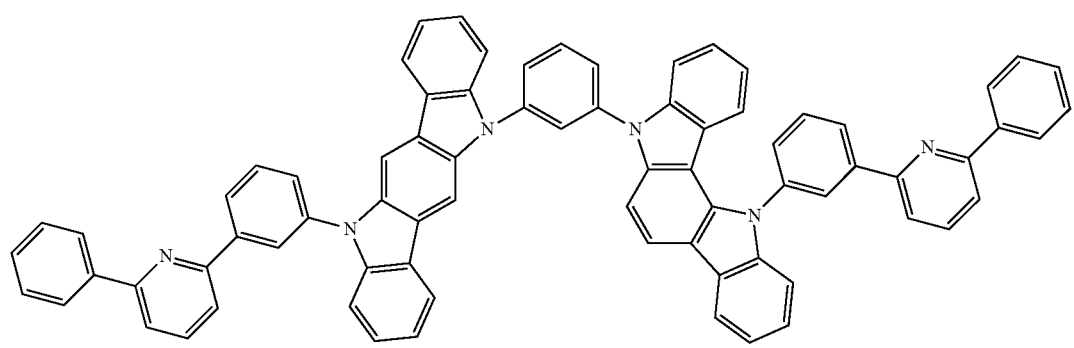

(601)
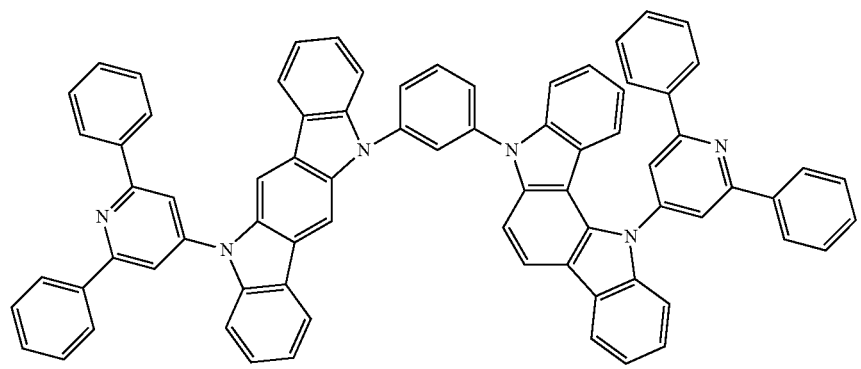
(602)
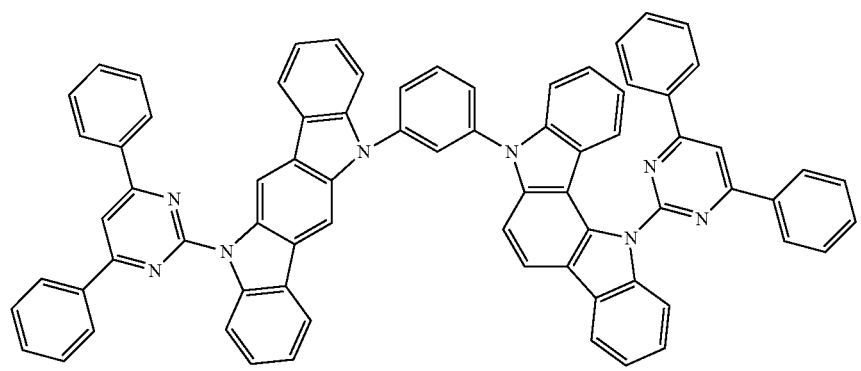
(603)
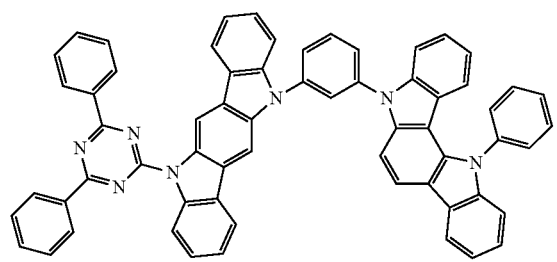
(604)
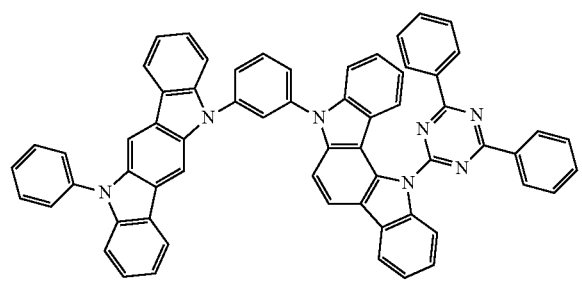
(605)
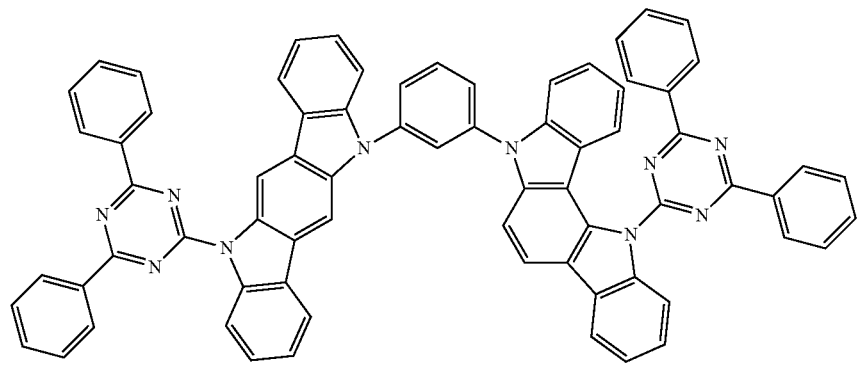

-continued
(606)
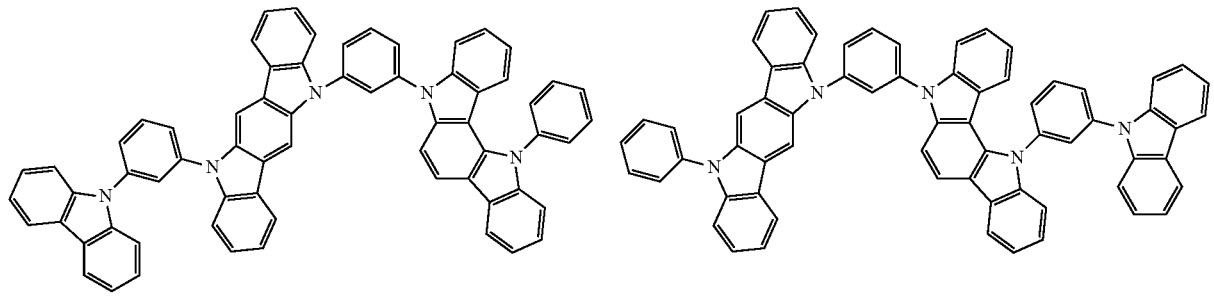
(607)
(608)
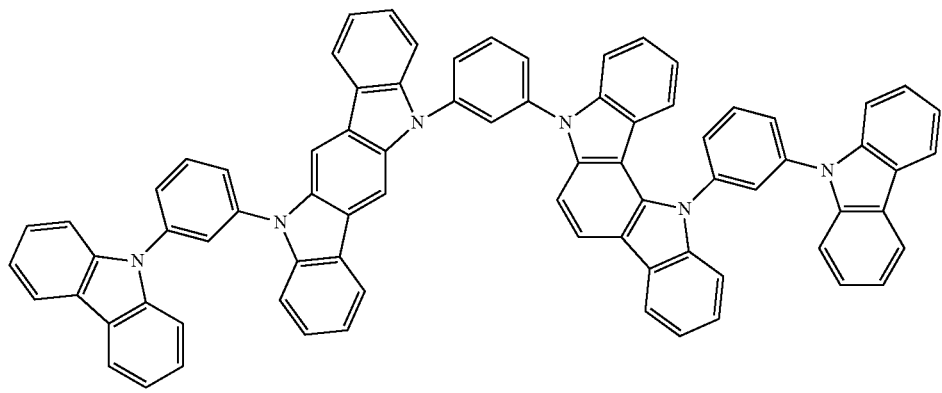
(609)
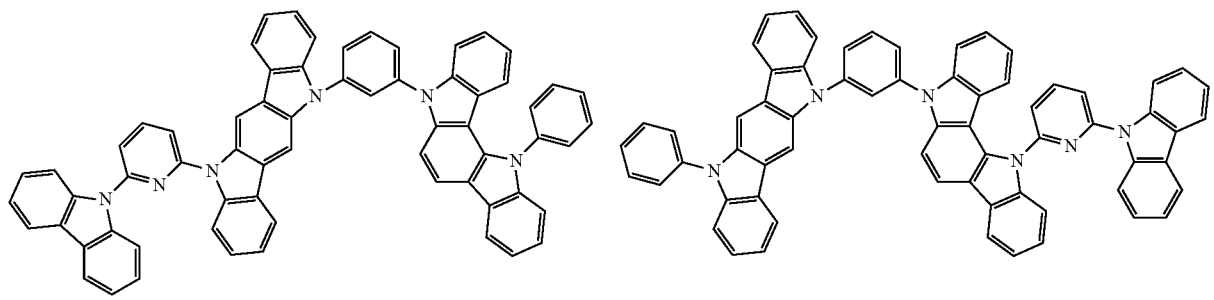
(610)
(611)
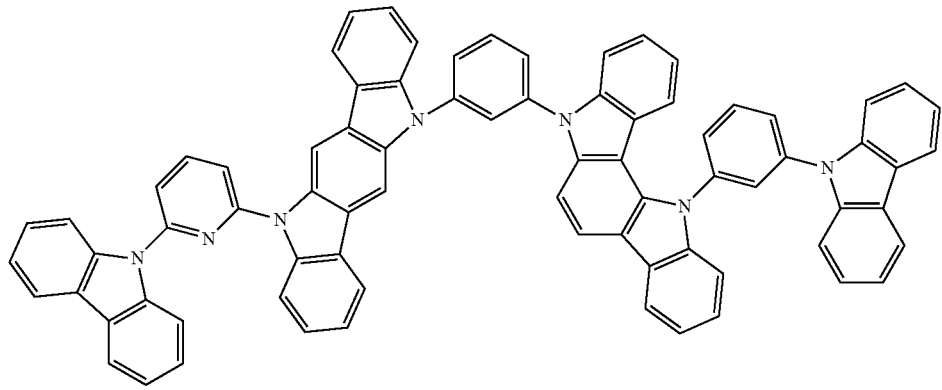

-continued
(612)
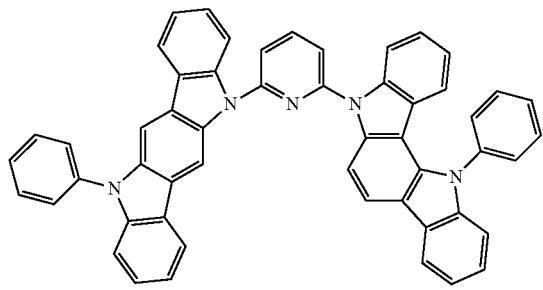
(613)
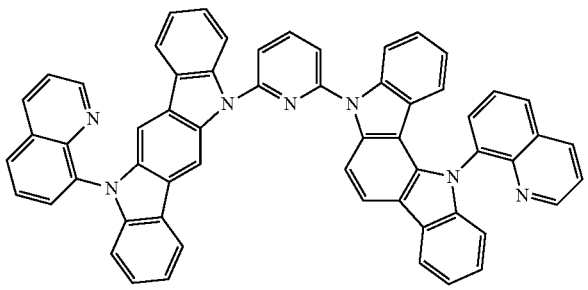
(614)
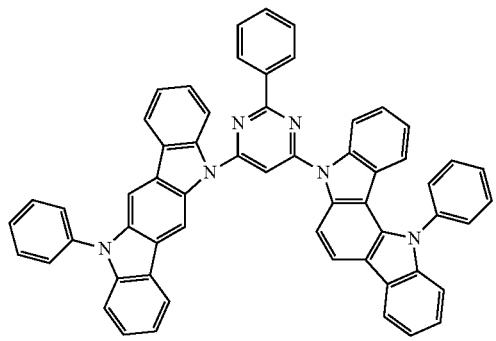
(615)
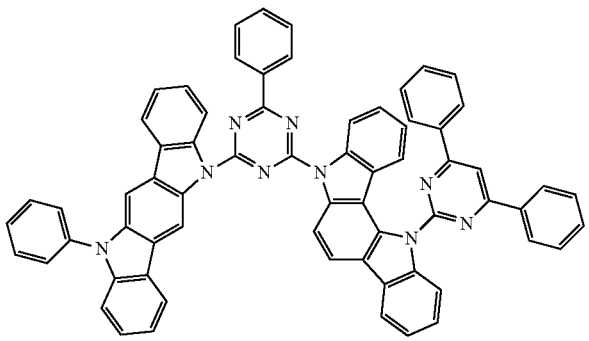
(616)
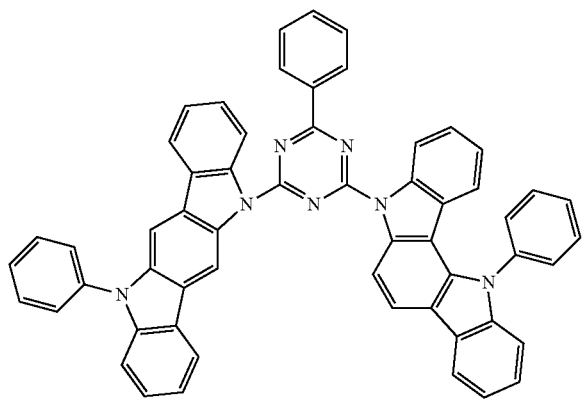
(617)
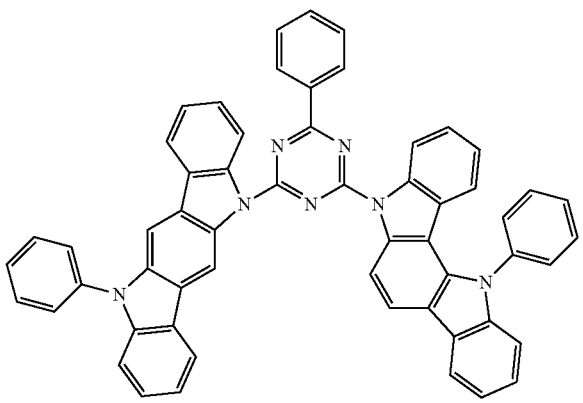
(618)
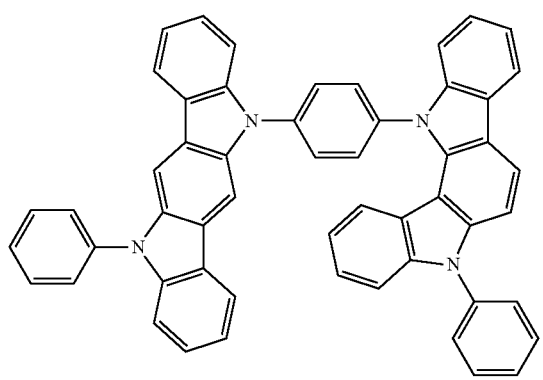
(619)
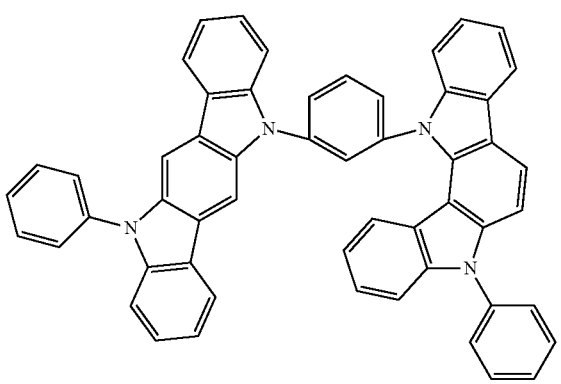

-continued
(620)
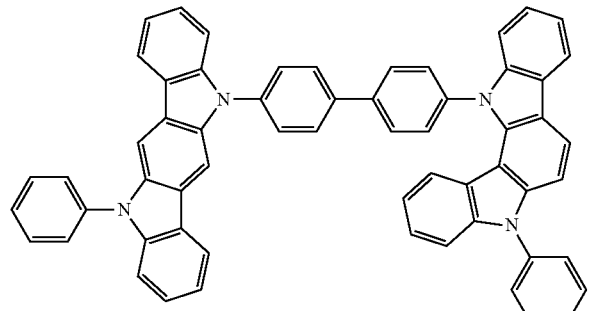
(621)
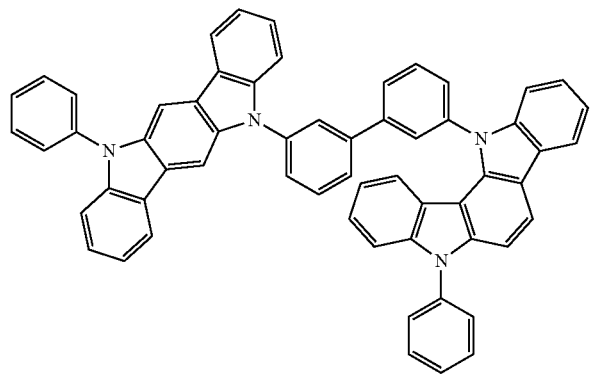
(622)
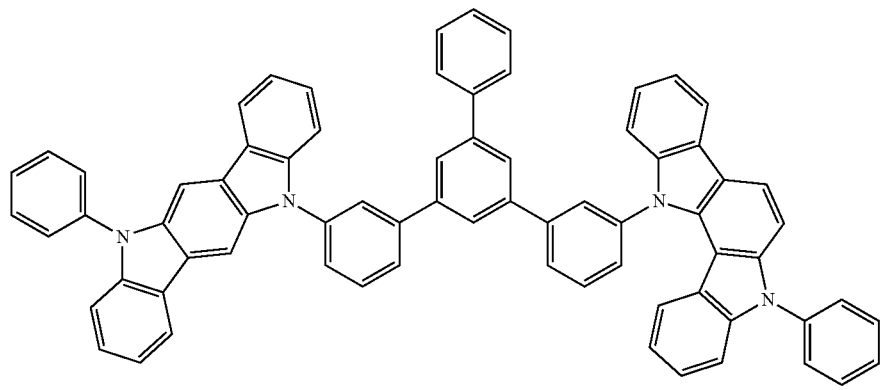
(623)
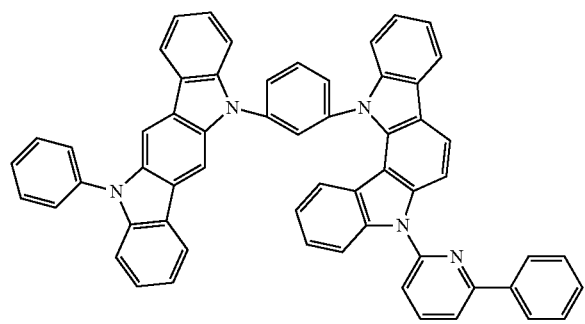
(624)
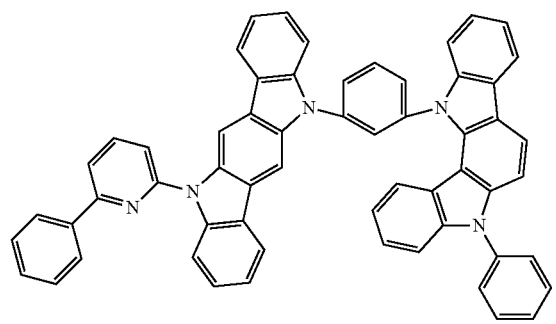
(625)
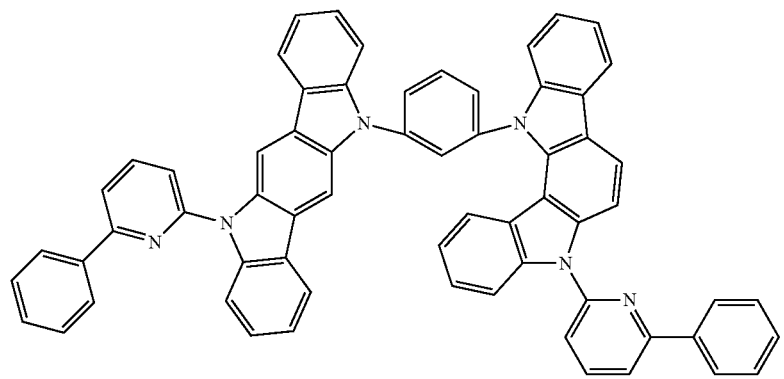

-continued
(626)
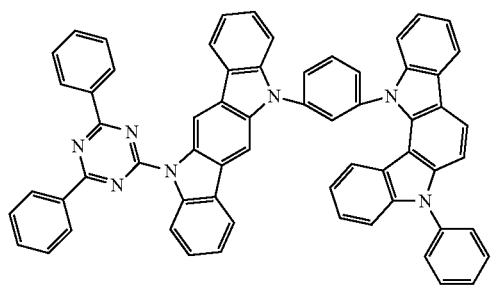
(627)
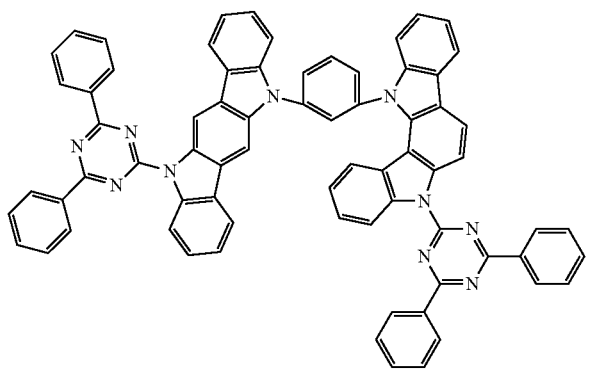
(628)
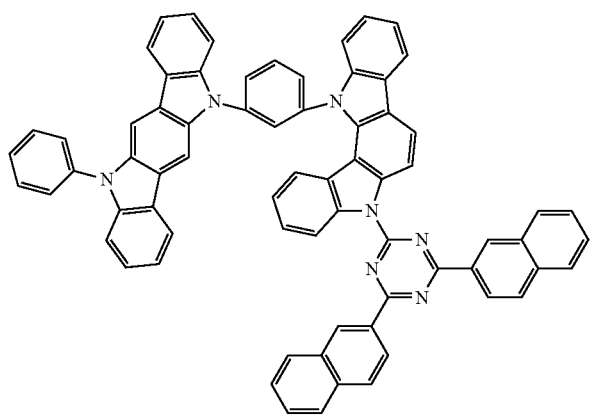
(629)
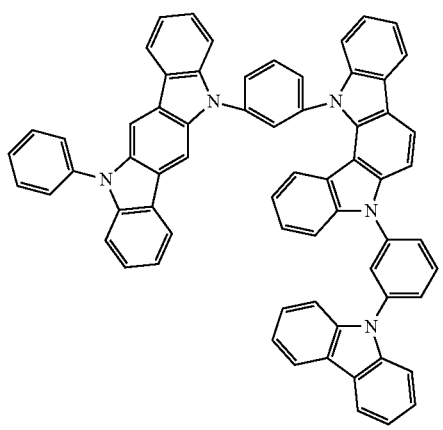
(630)
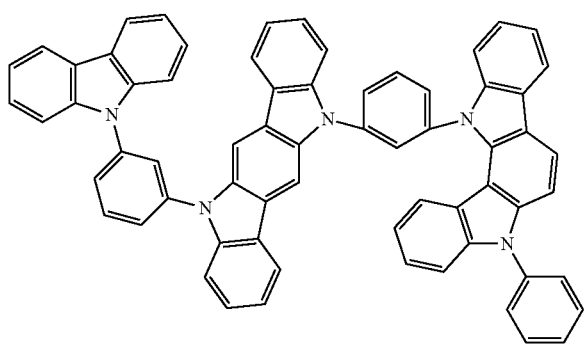
(631)
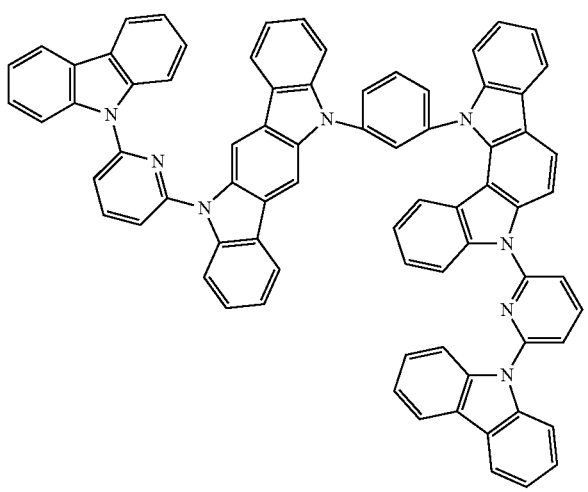

-continued
(632)
(633)
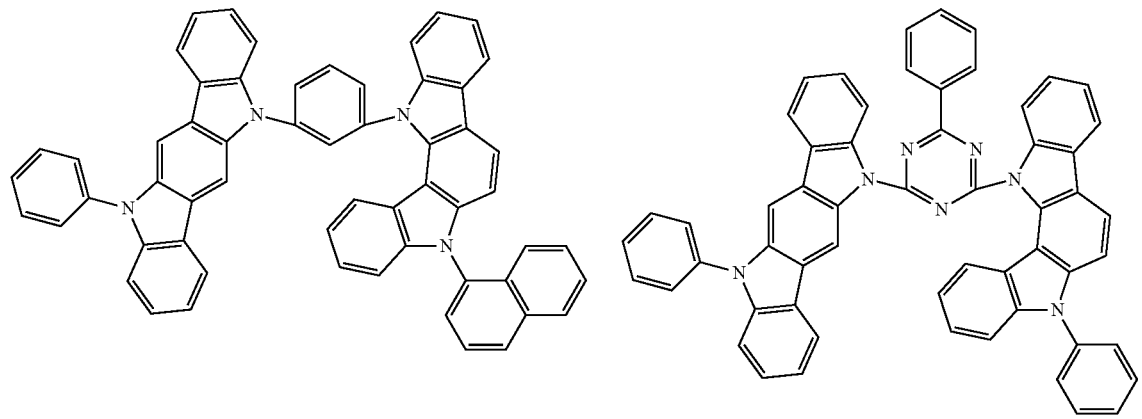
(634)
(635)
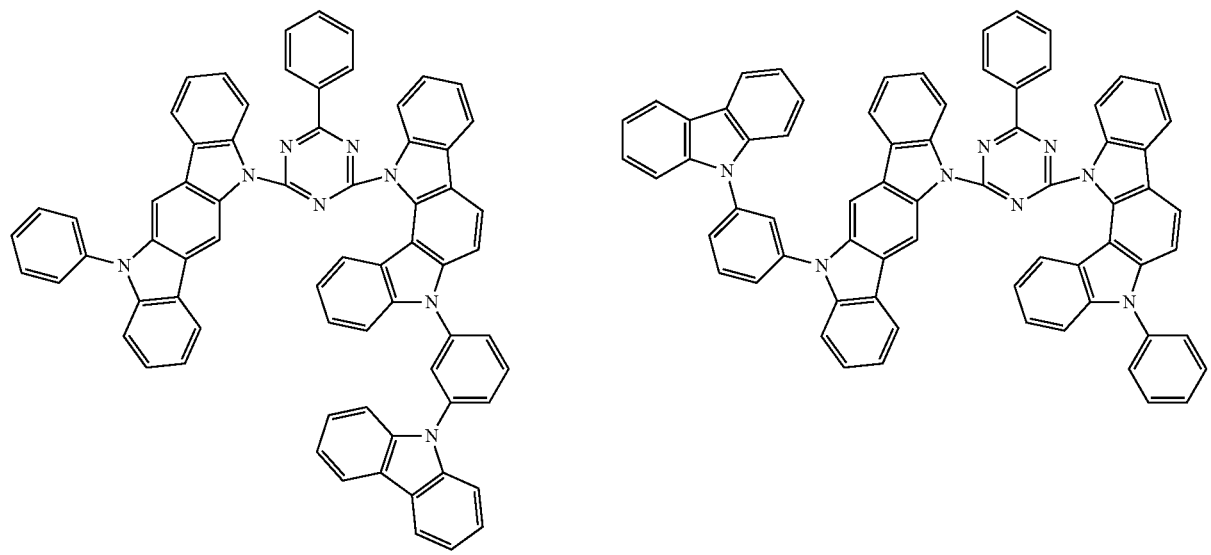
(636)
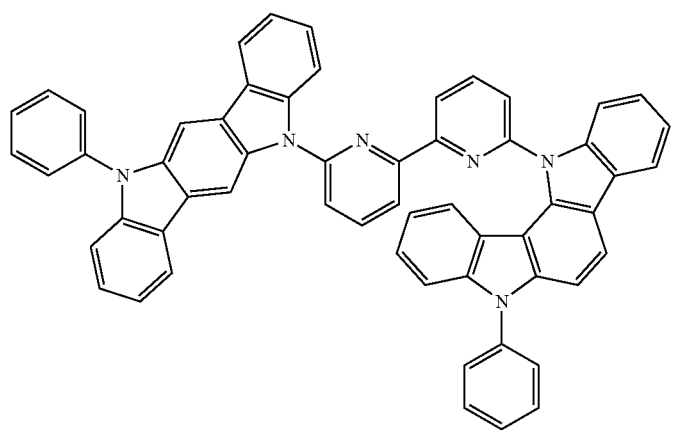

(637)
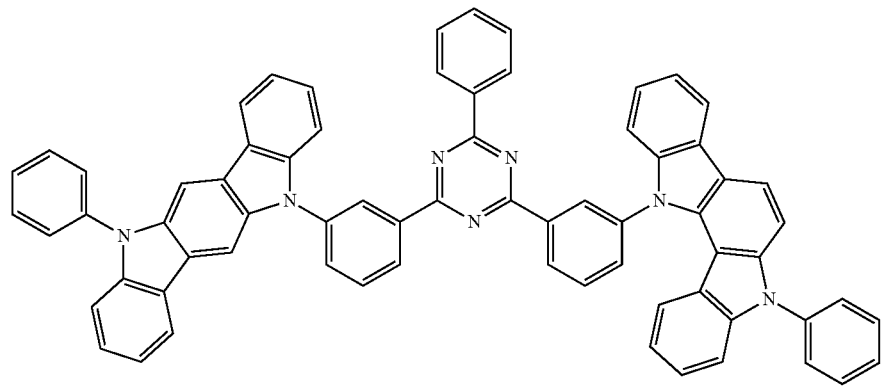
(638)
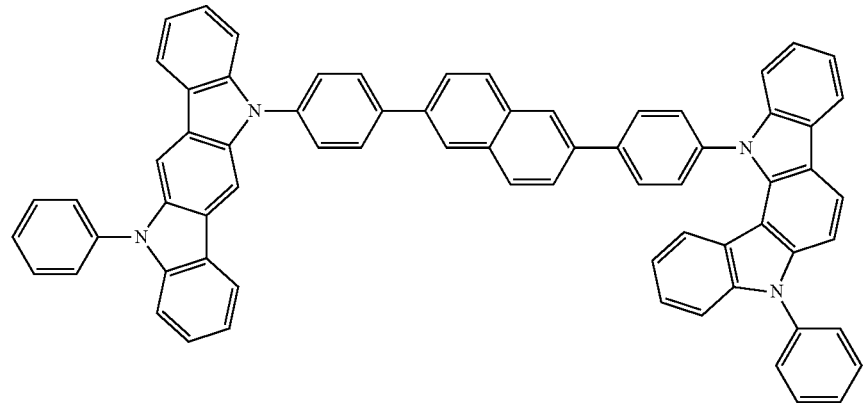
(639)
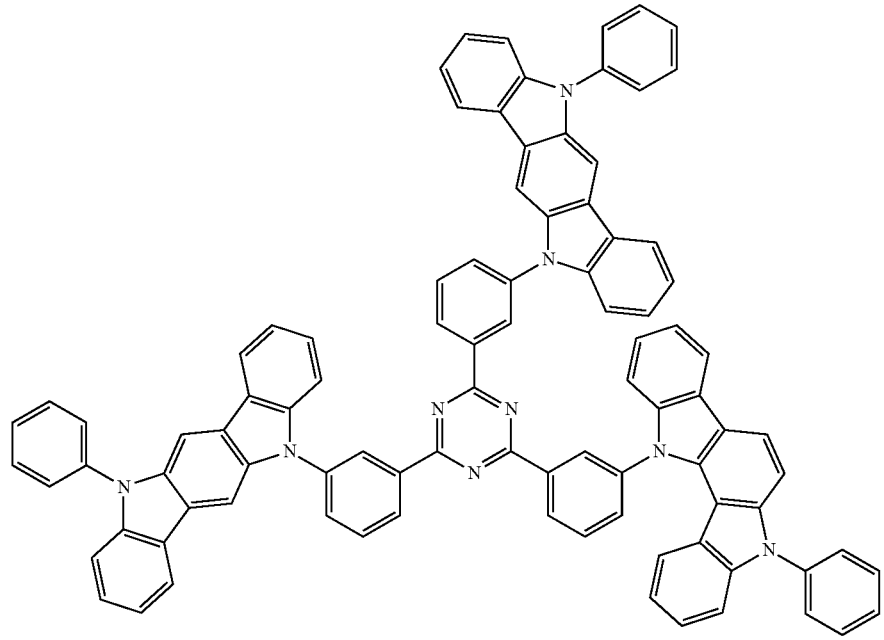

-continued
(640)
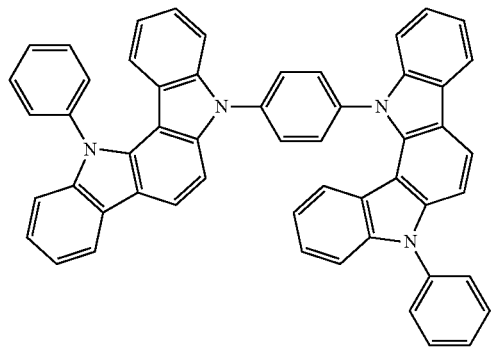
(641)
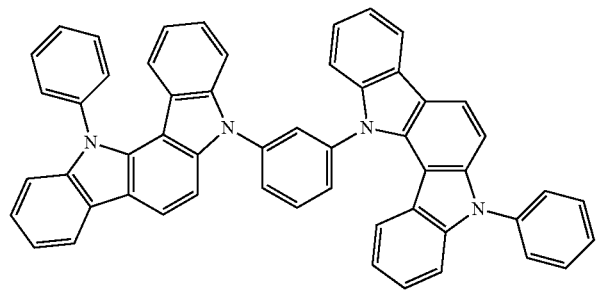
(642)
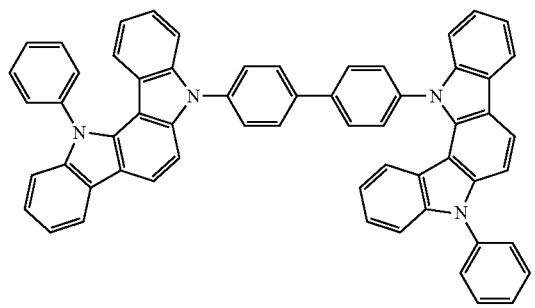
(643)
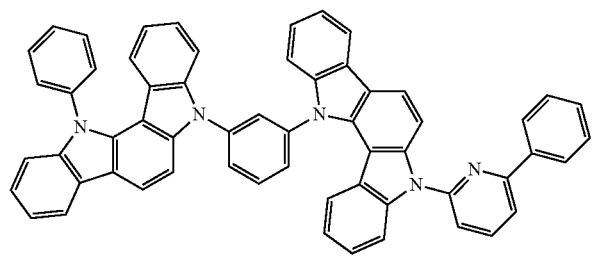
(644)
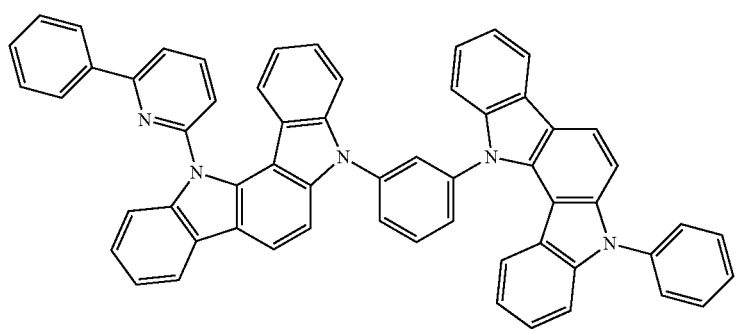
(645)
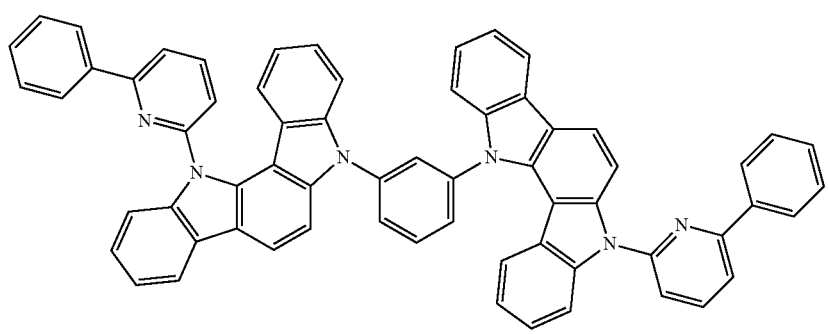

-continued
(646)
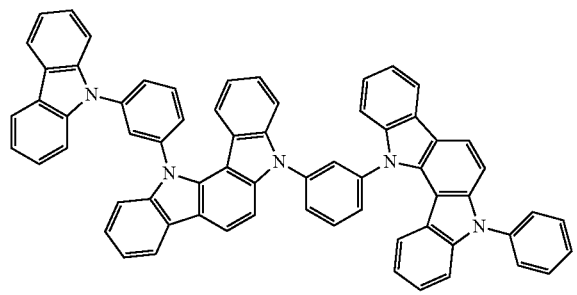
(647)
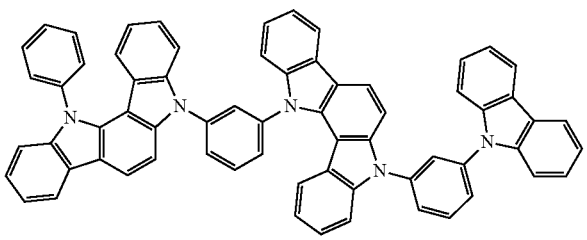
(648)
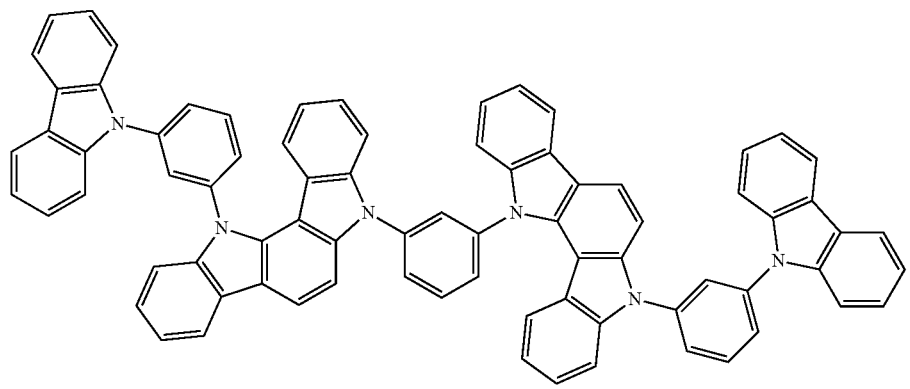
(649)
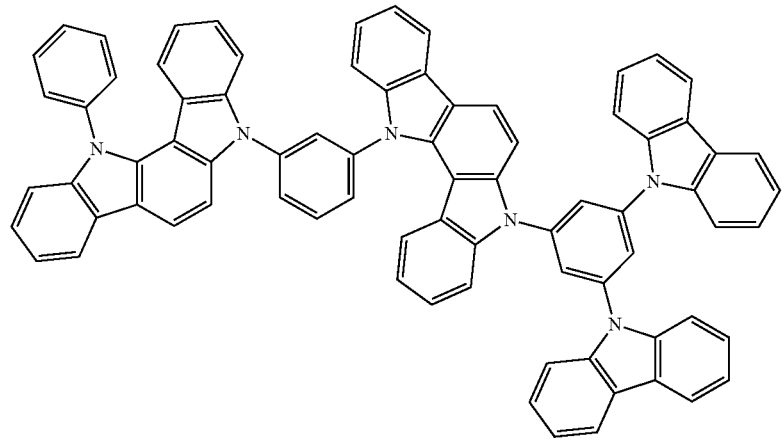
(650)
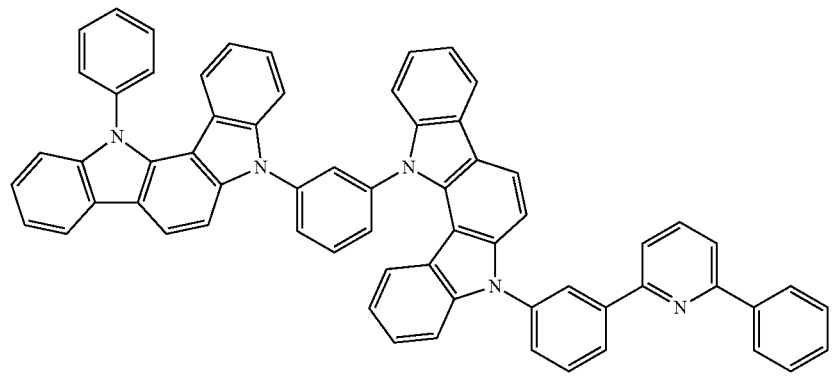

-continued
(651)
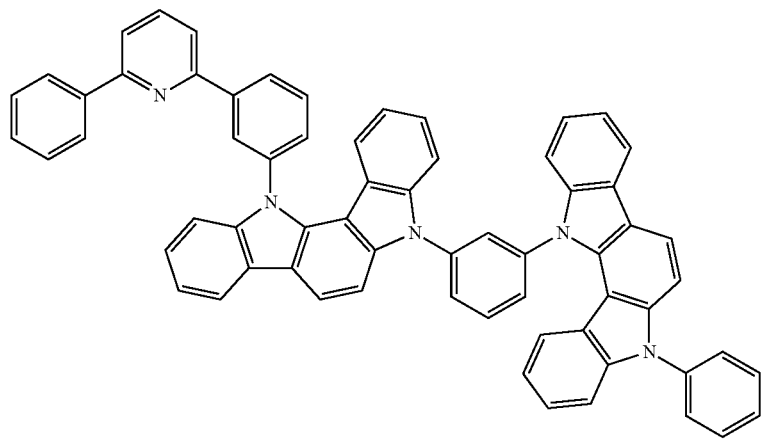
(652)
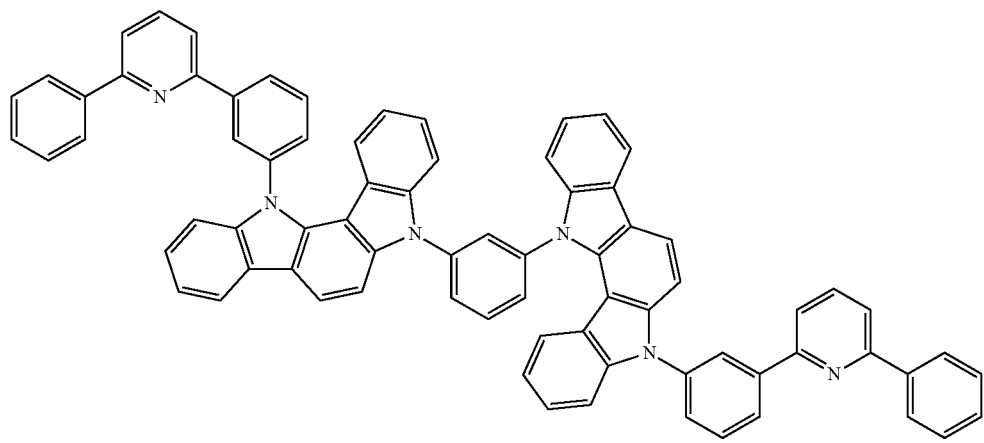
(653)
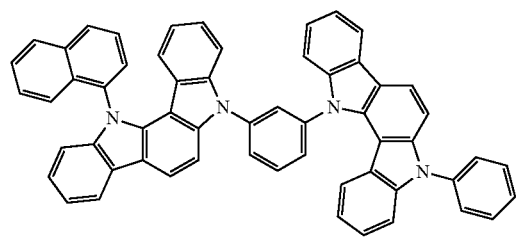
(654)
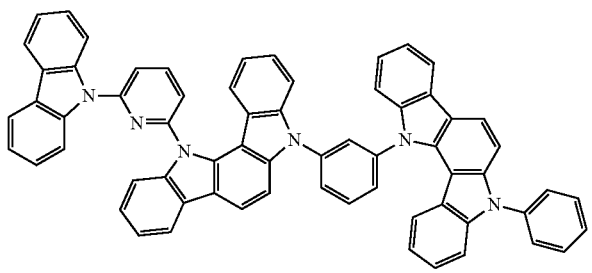
(655)
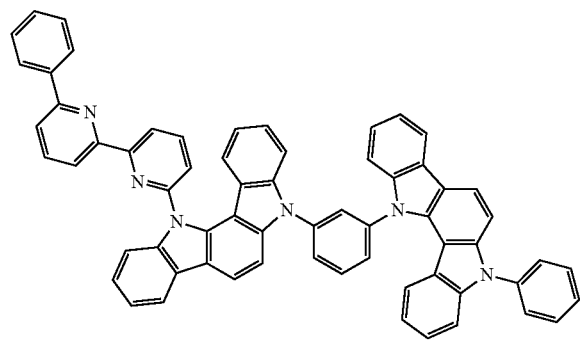
(656)
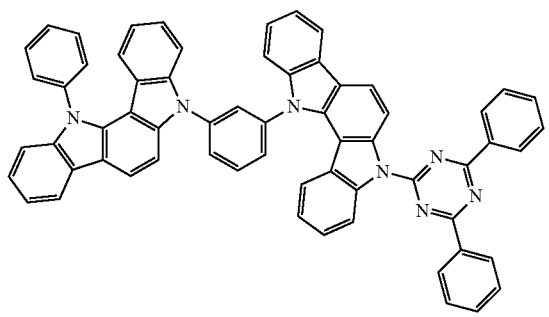

-continued
(657)
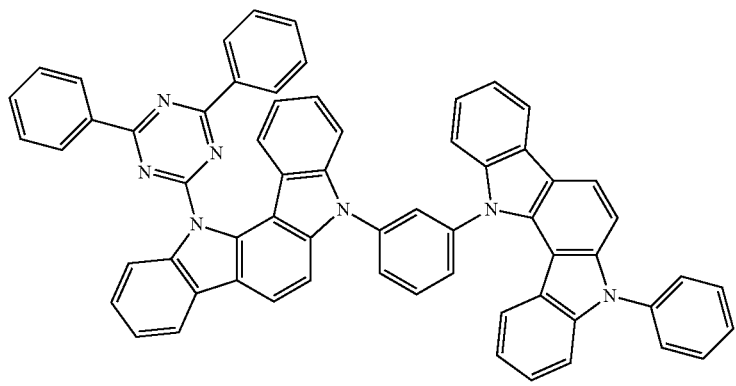
(658)
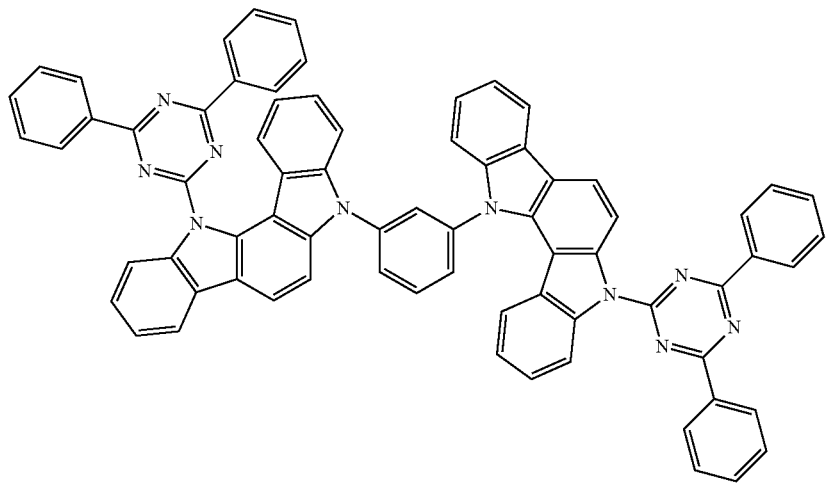
(659)
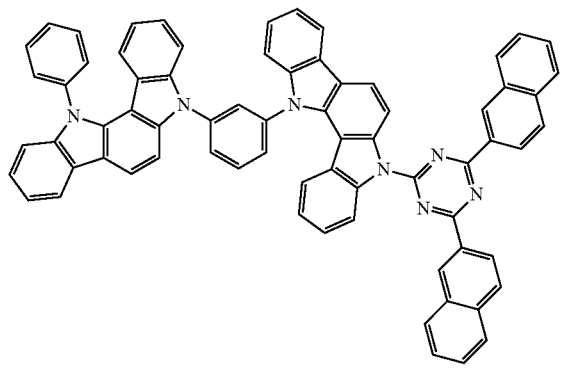
(660)
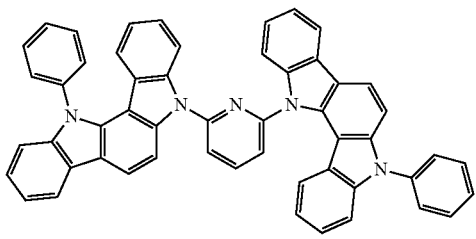

(661)
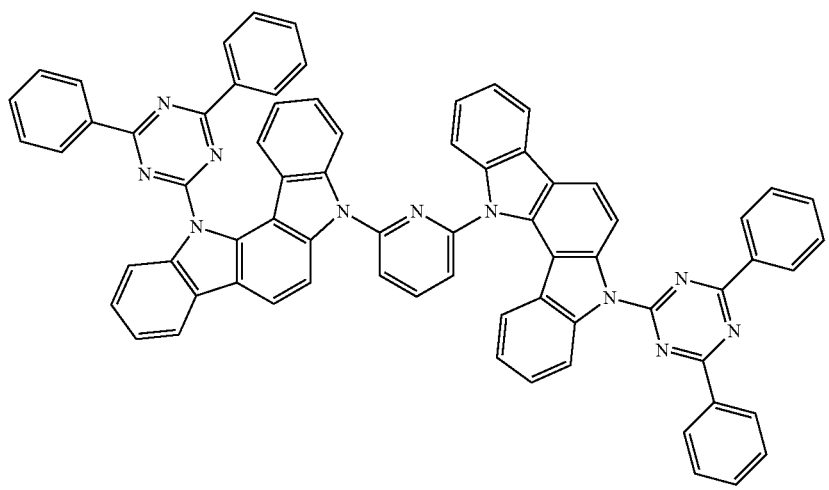
(662)
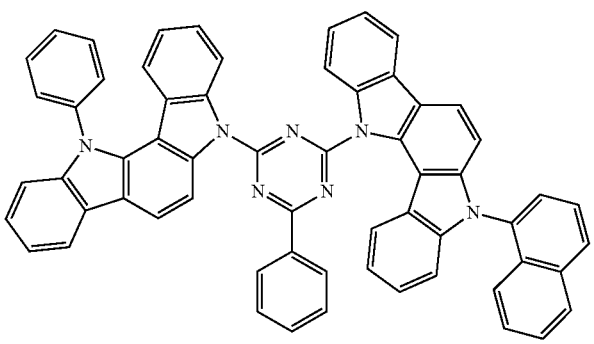
(663)
(664)
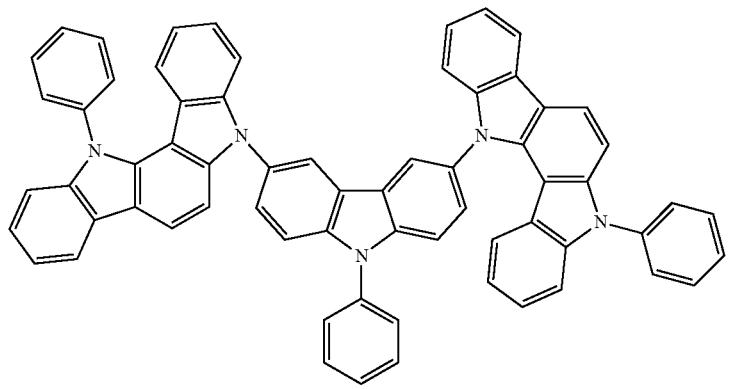
(665)
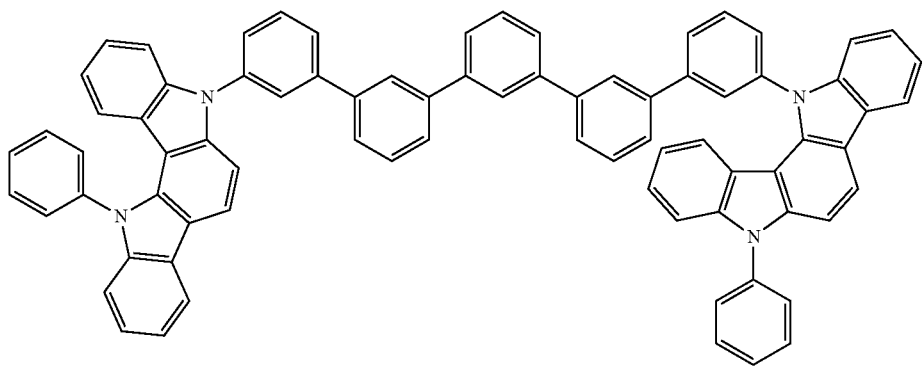

-continued
(666)
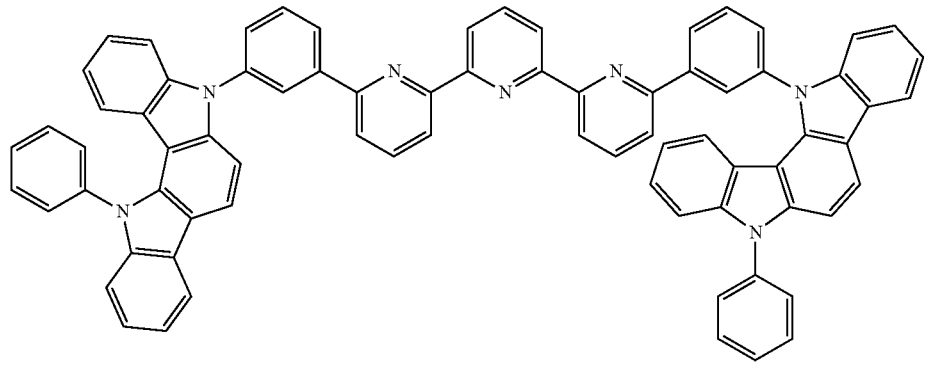
(667)
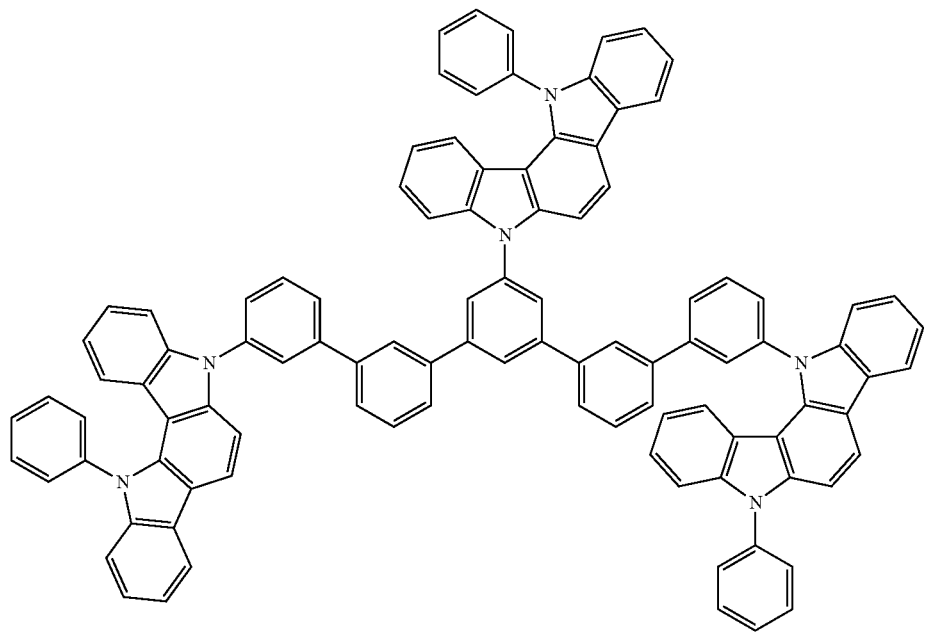
(668)
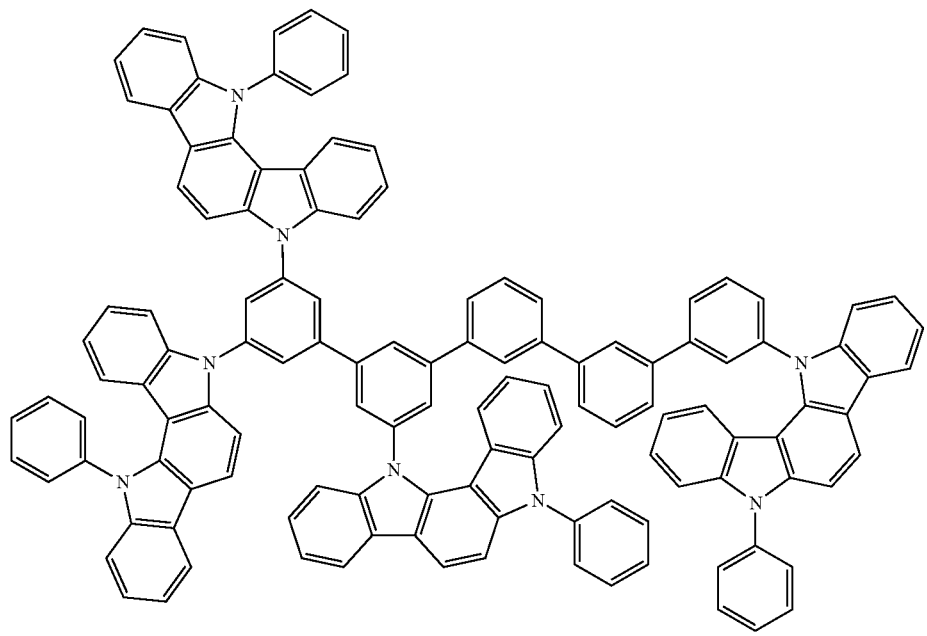

(669)
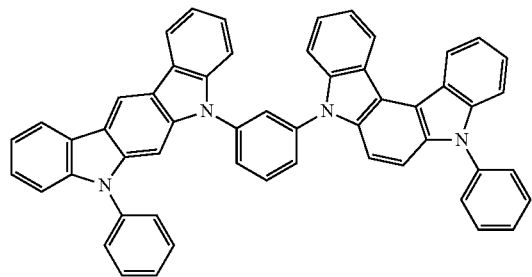
(670)
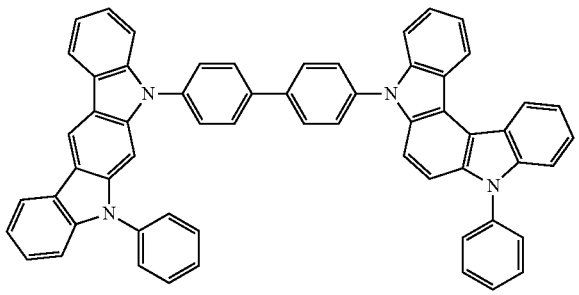
(671)
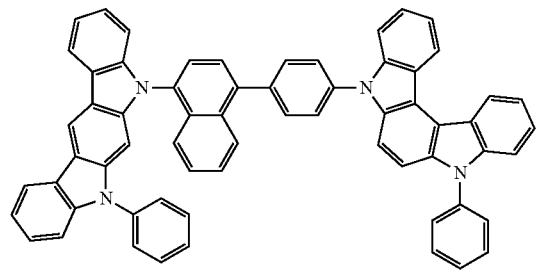
(672)
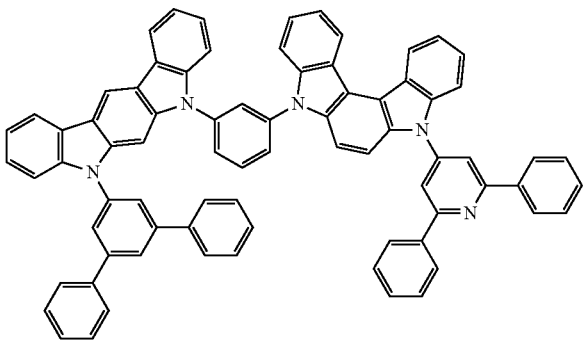
(673)
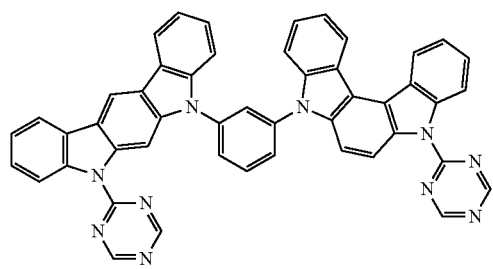
(674)
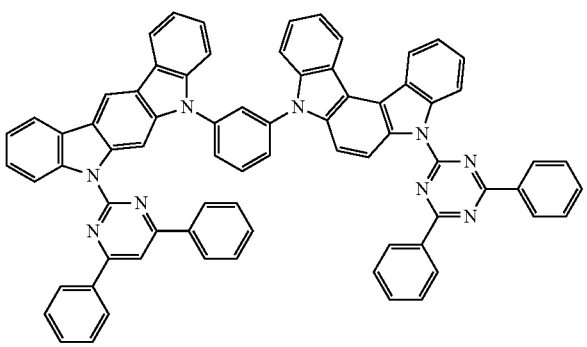
(675)
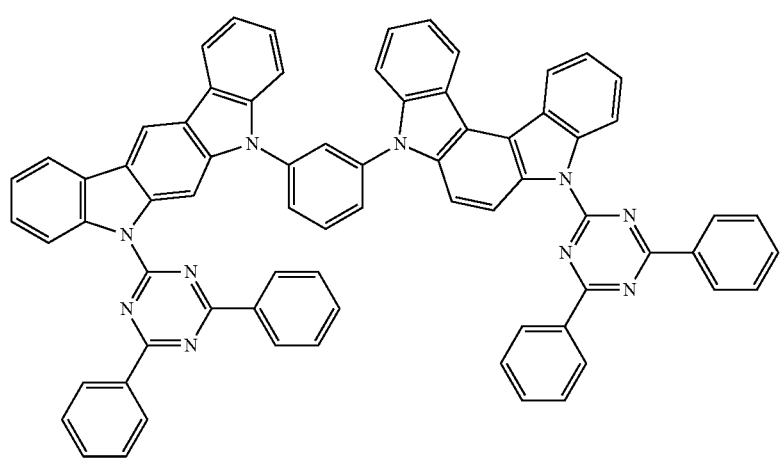

(676)
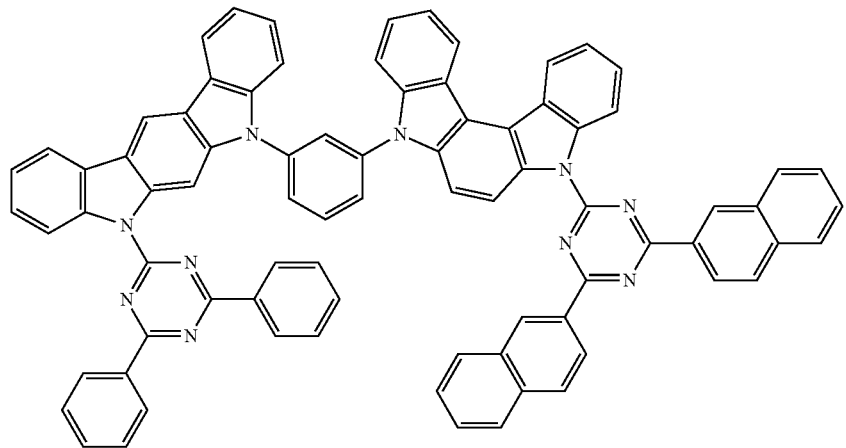
(677)
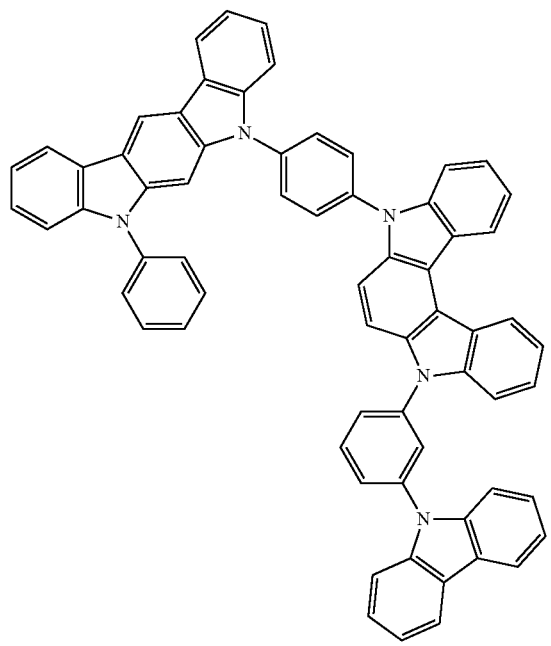
(678)
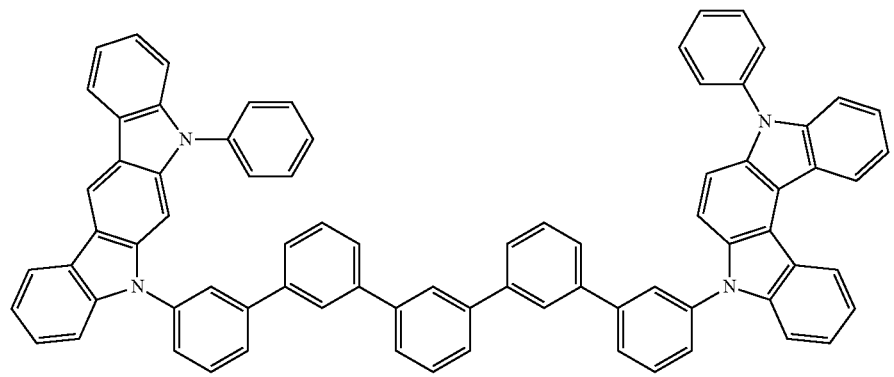

(679)
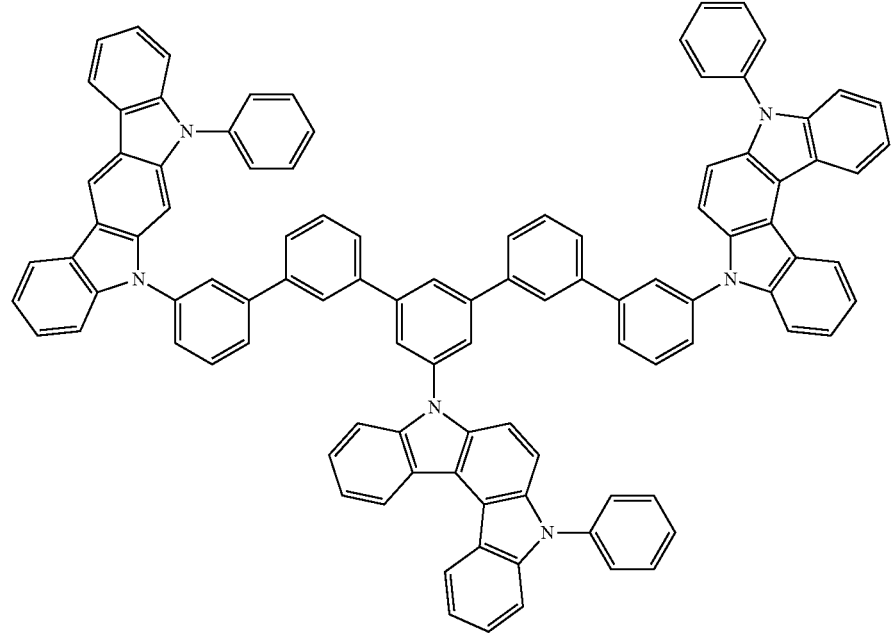
(680)
(681)
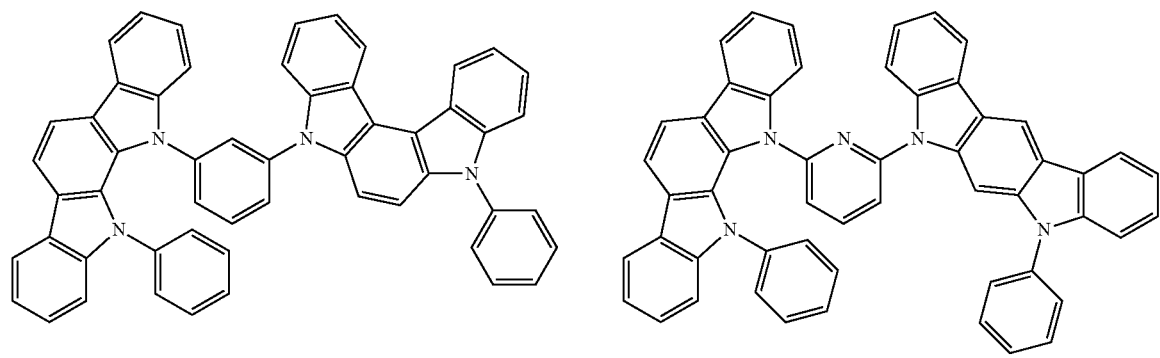
(682)
(683)
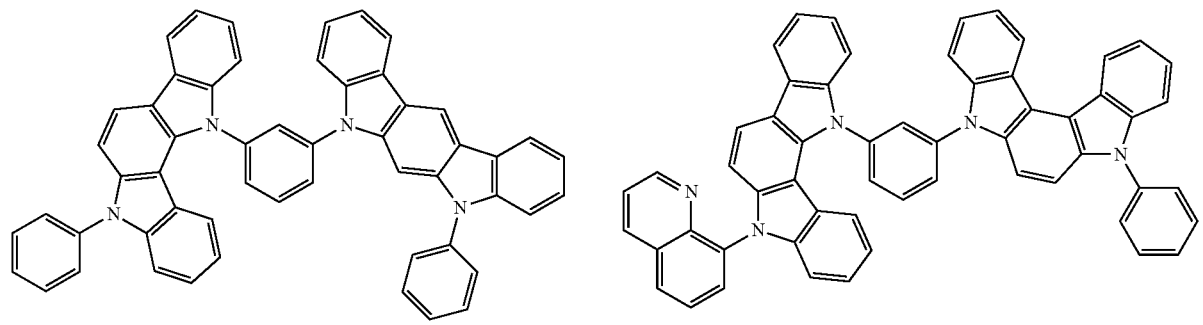

-continued
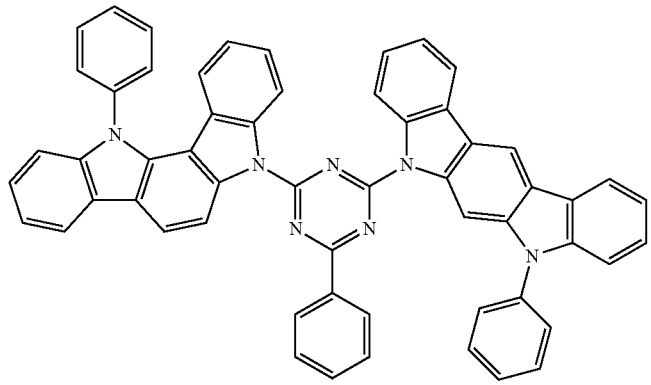
(684)
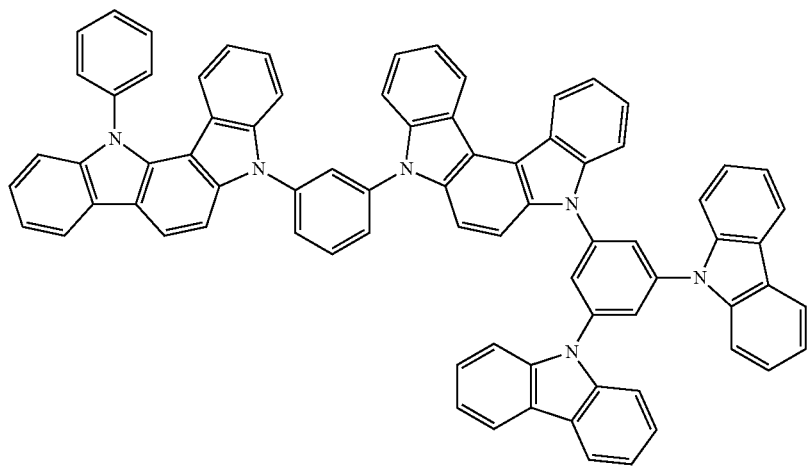
(685)
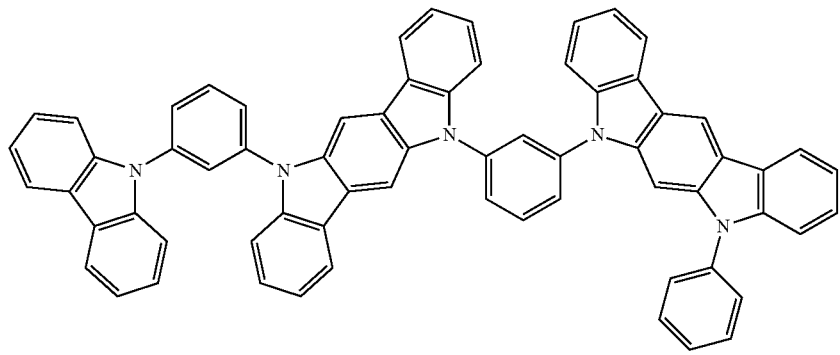
(686)
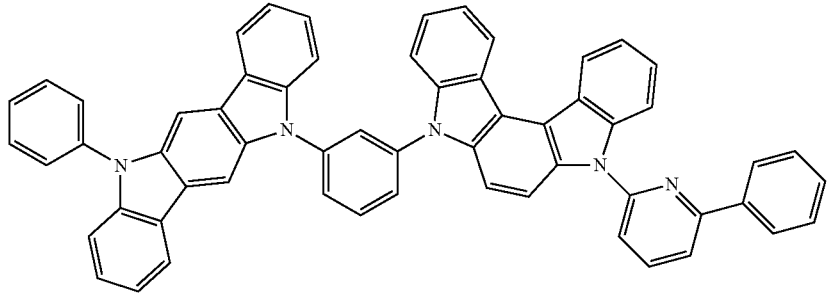
(687)

(688)
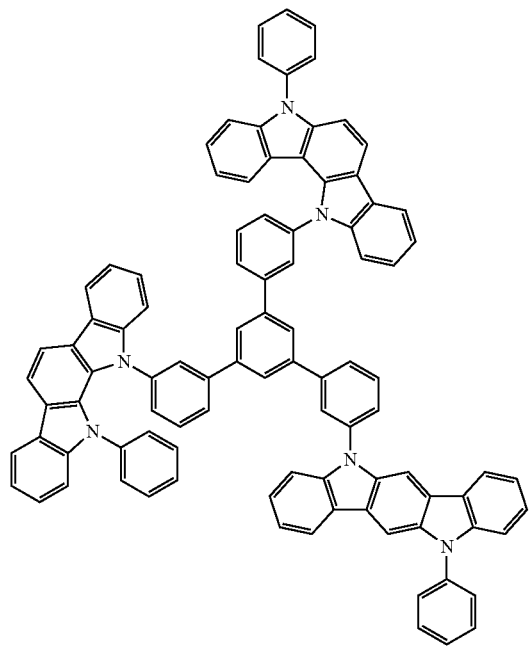
(689)
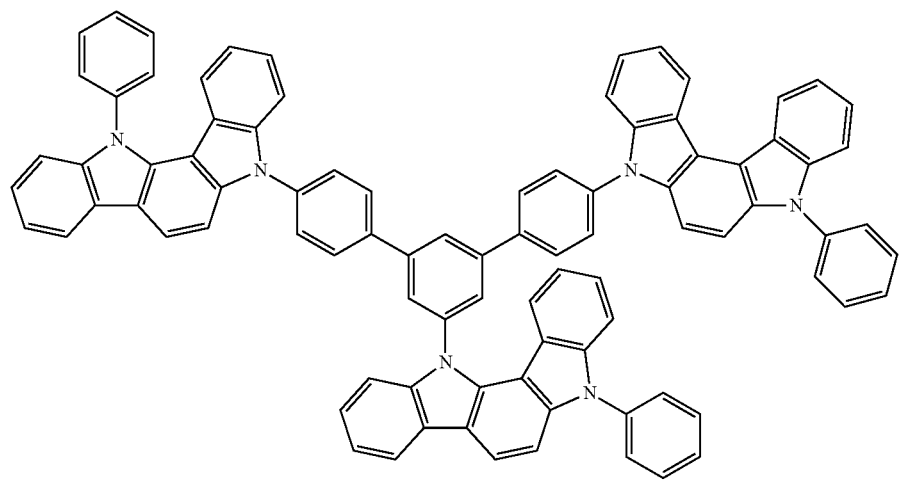

-continued
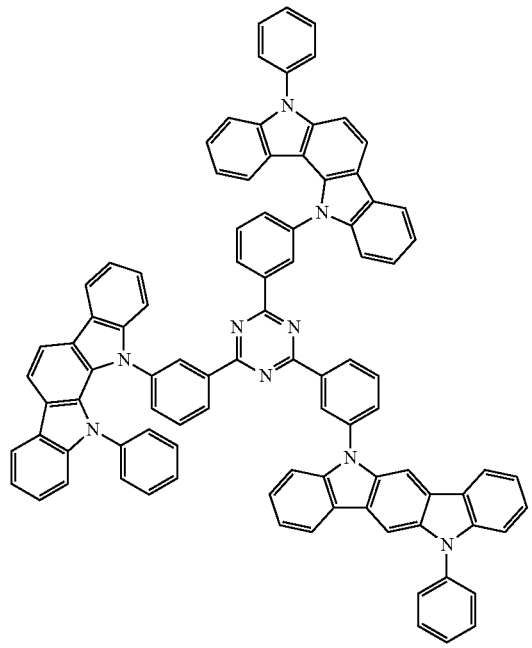
(690)
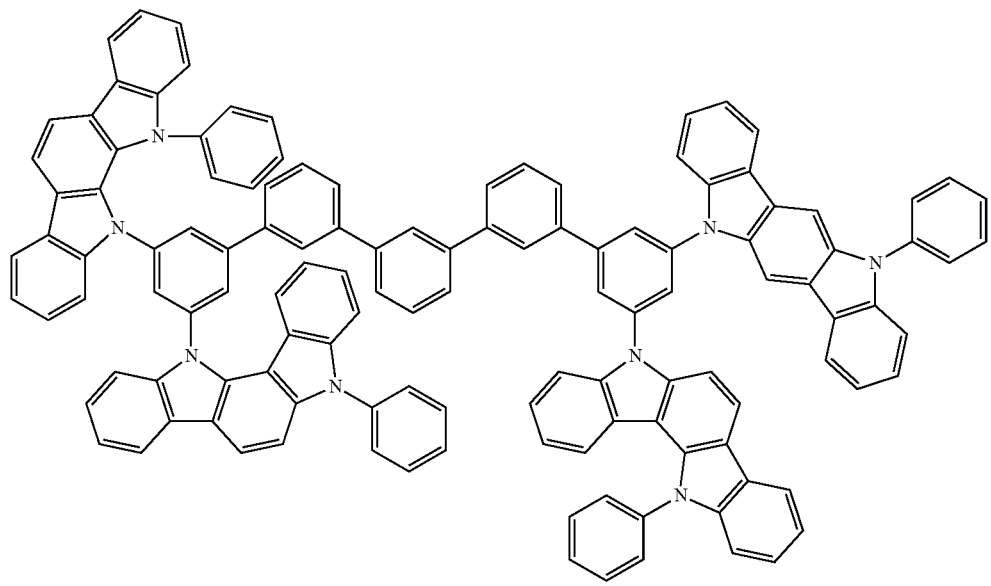
(691)

-continued
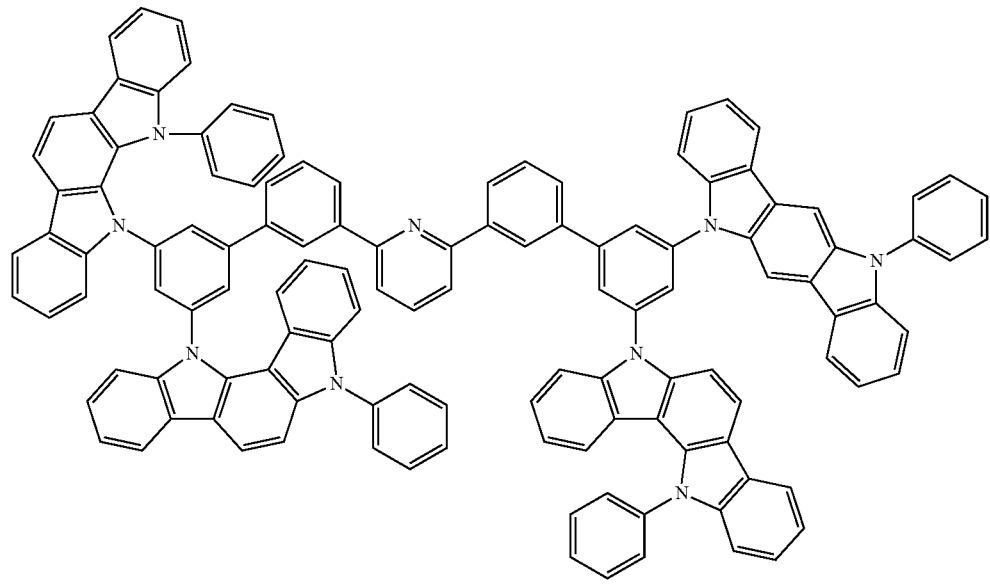
(692)
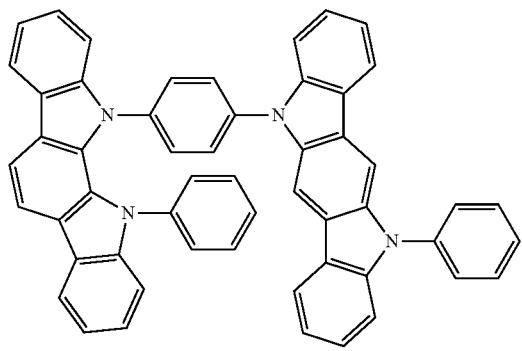
(693)
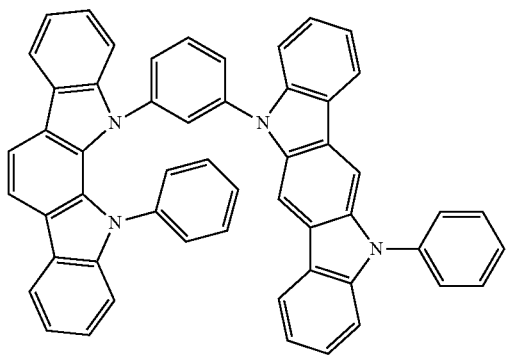
(694)
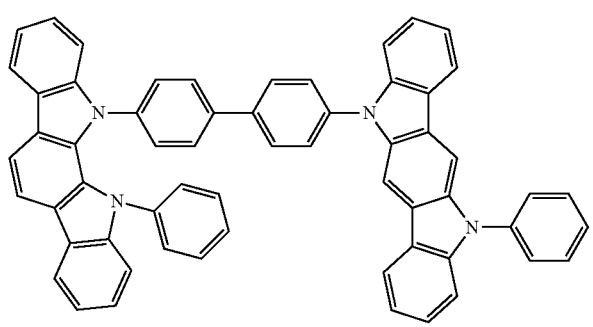
(695)
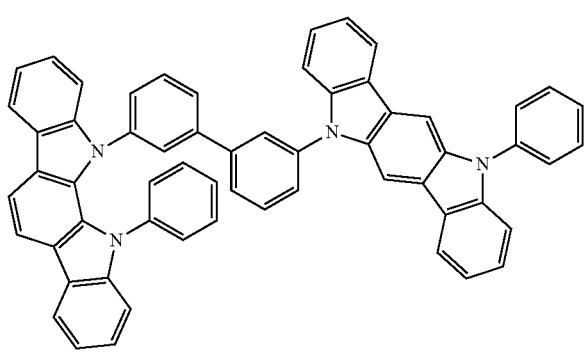
(696)

-continued
(697)
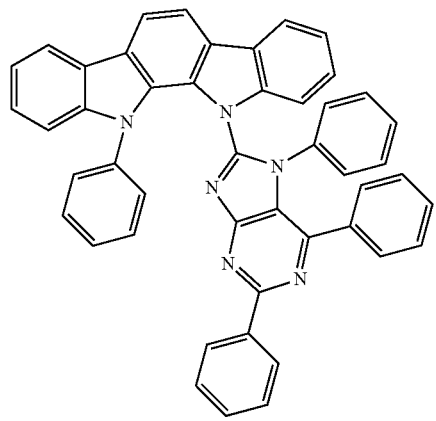
(698)
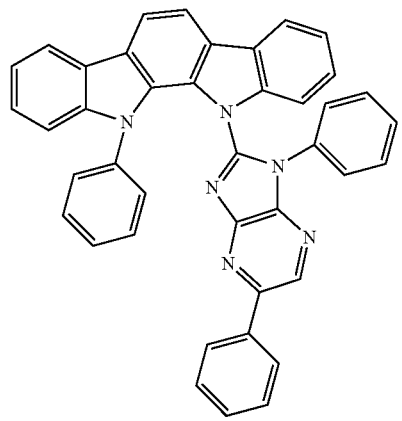
(699)
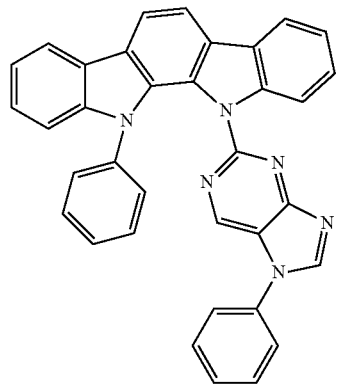
(700)
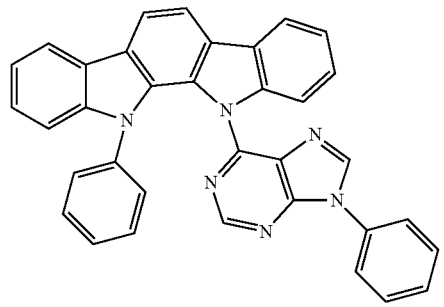
(701)
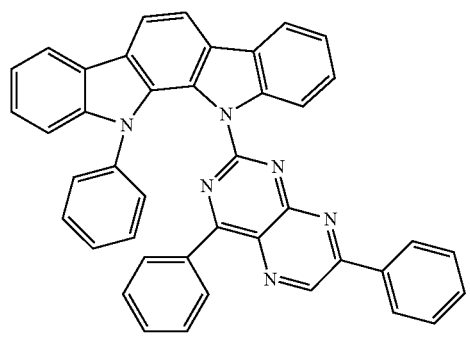
(702)
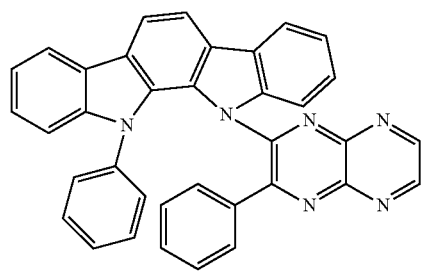
(703)
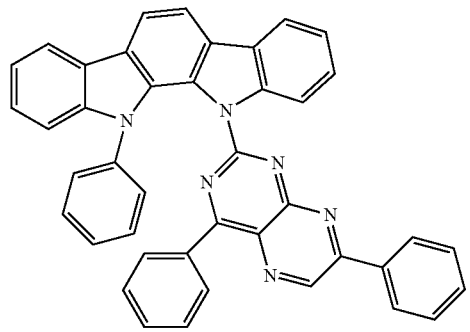
(704)
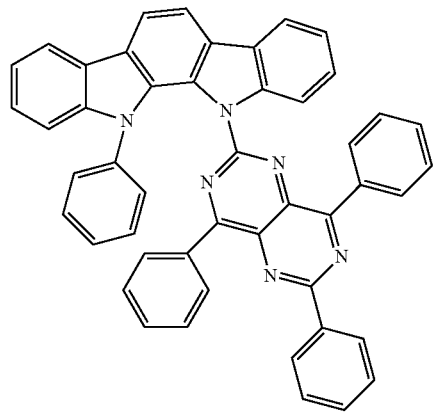

-continued
(705)
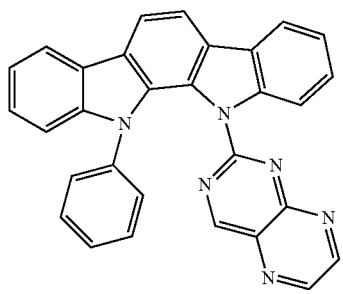
(706)
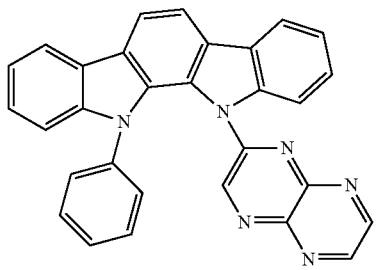
(707)
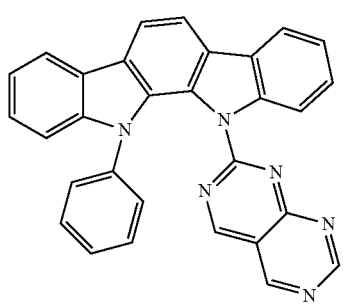
(708)
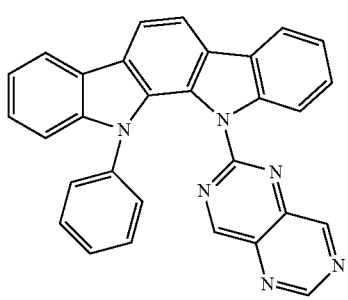
(709)
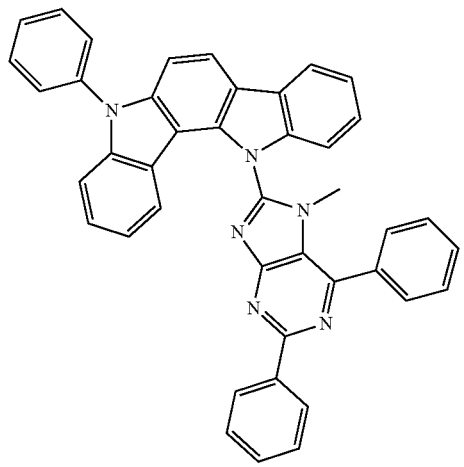
(710)
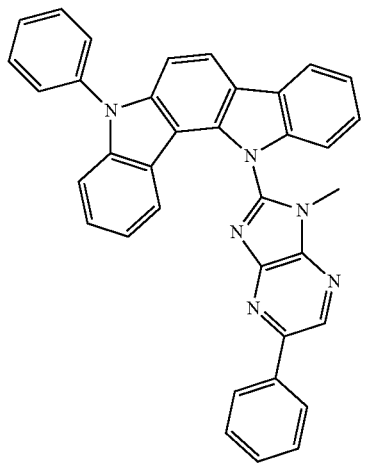
(711)
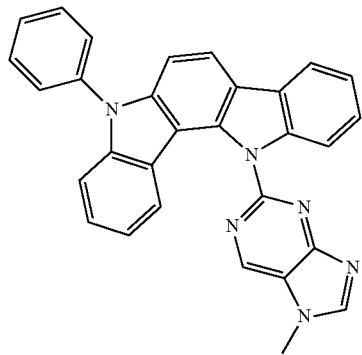
(712)
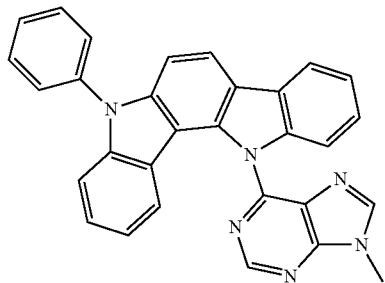

-continued
(713)
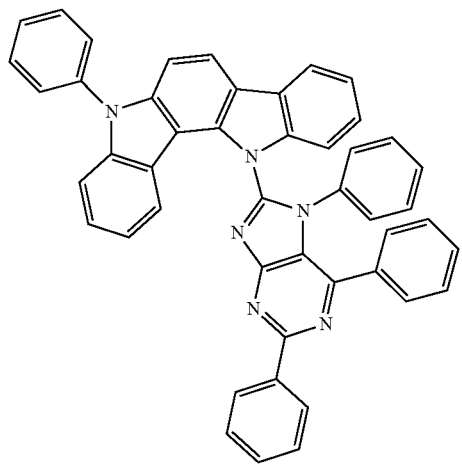
(714)
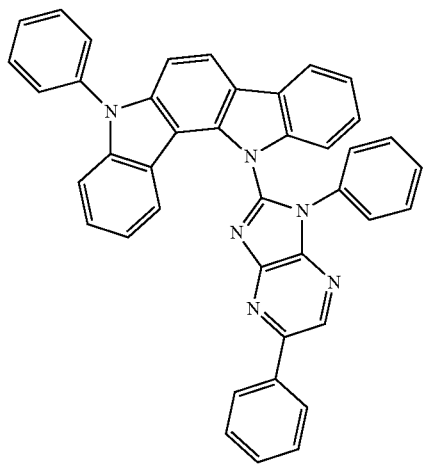
(715)
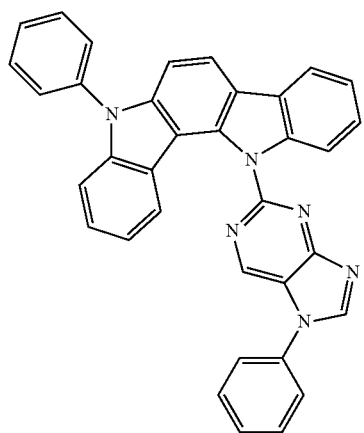
(716)
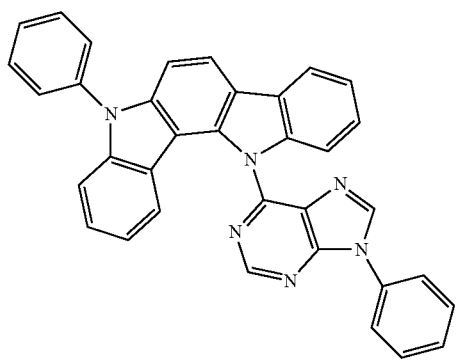
(717)
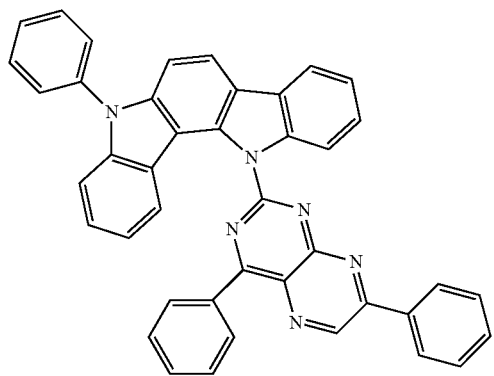
(718)
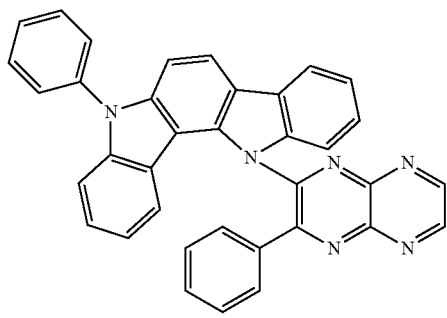

(719)
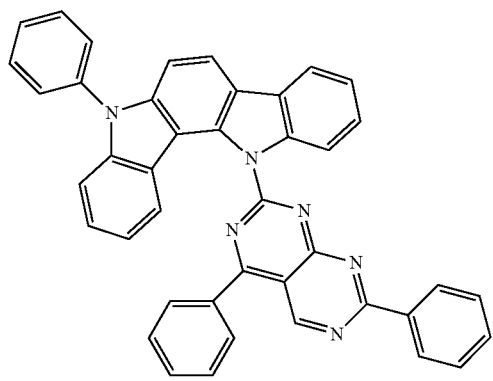
(720)
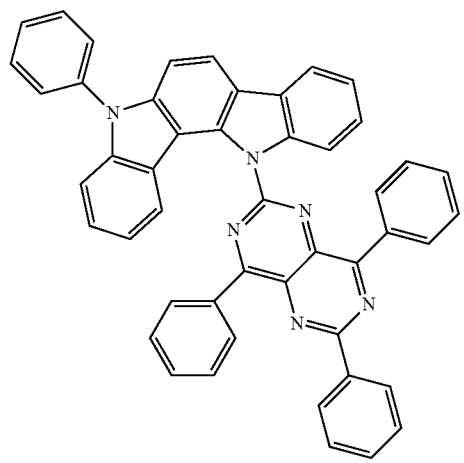
(721)
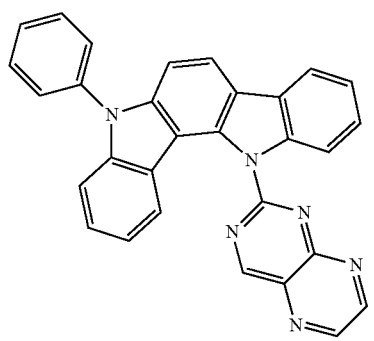
(722)
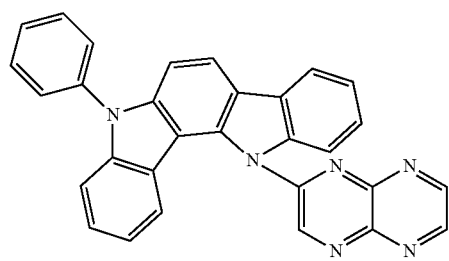
(723)
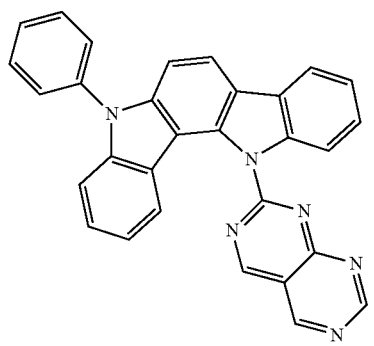
(724)
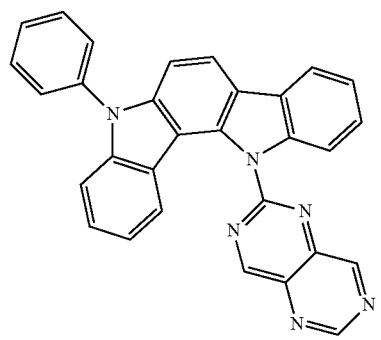

-continued
(725)
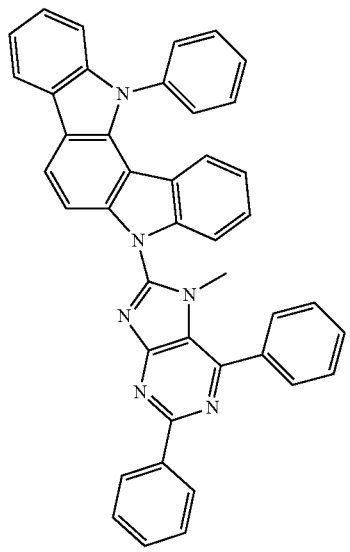
(726)
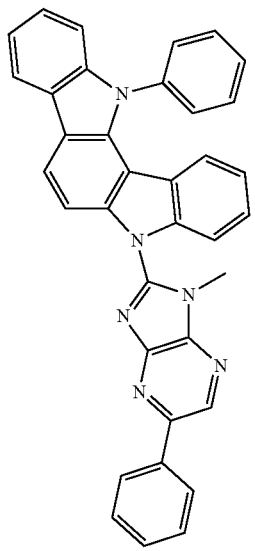
(727)
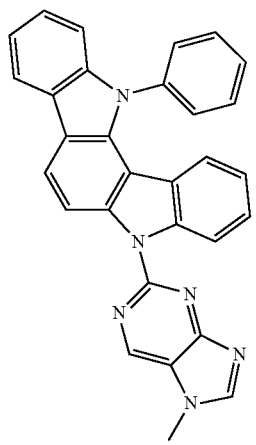
(728)
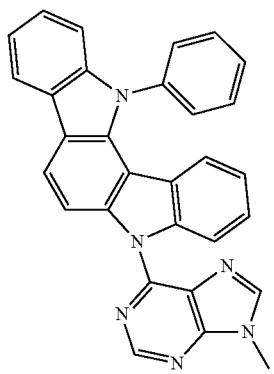
(729)
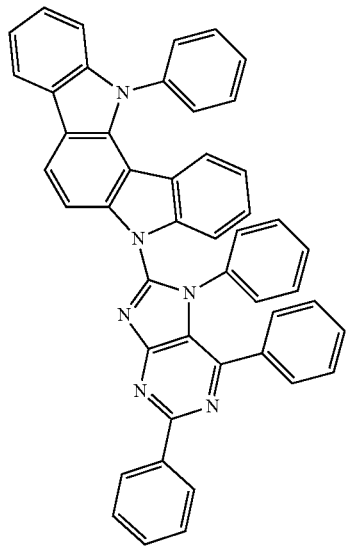
(730)
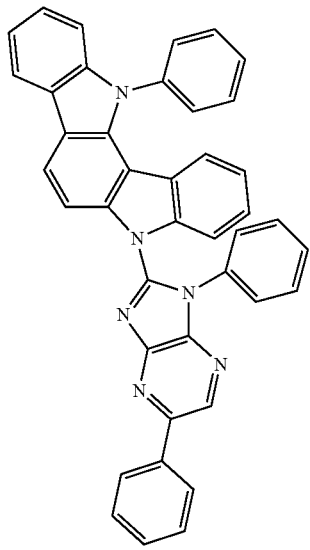

-continued
(731)
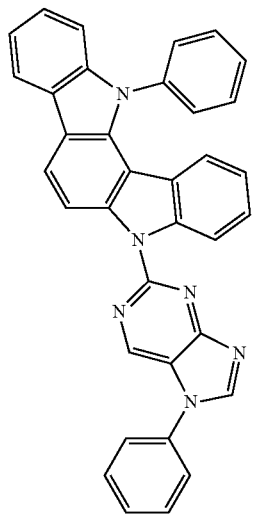
(732)
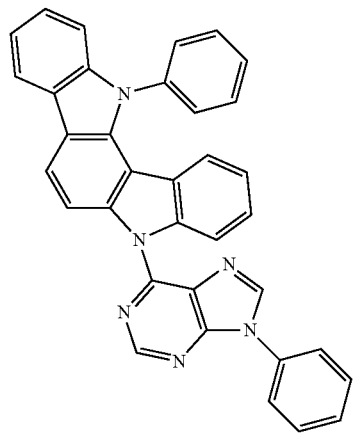
(733)
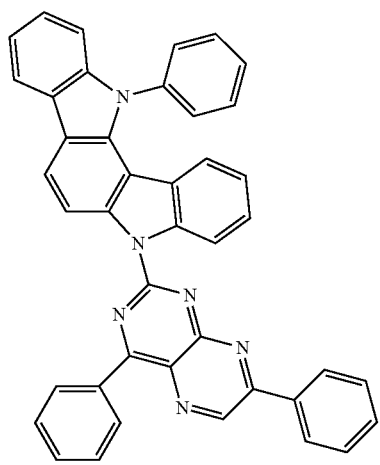
(734)
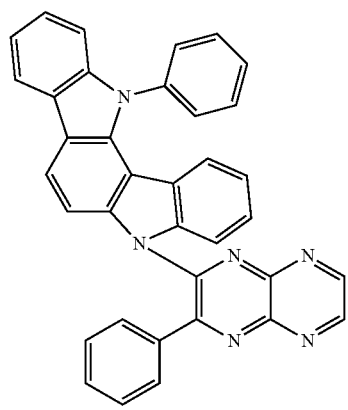
(735)
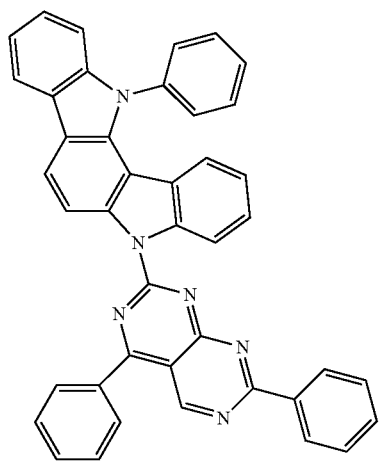
(736)
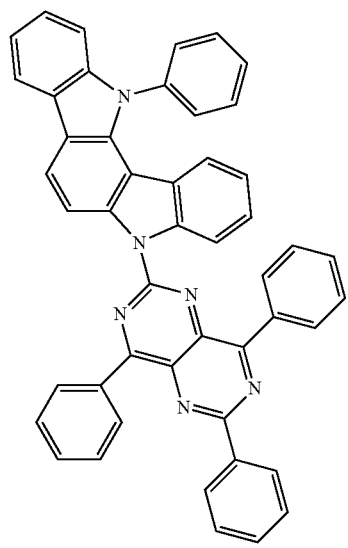

(737)
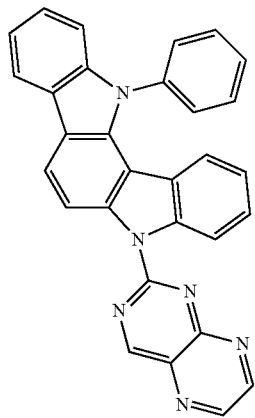
(738)
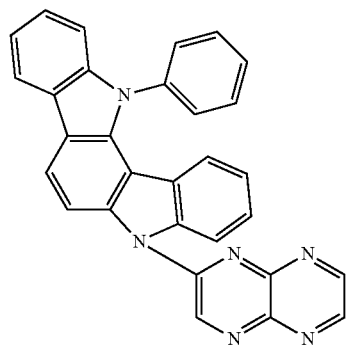
(739)
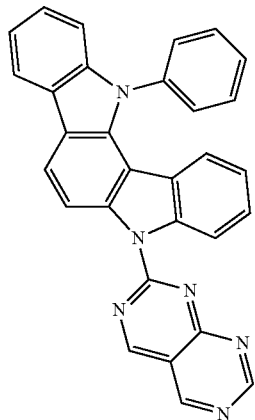
(740)
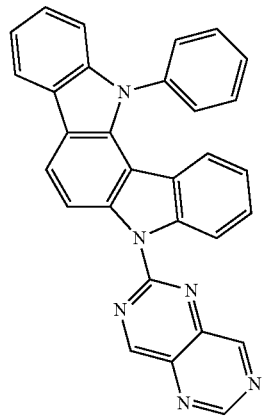
(741)
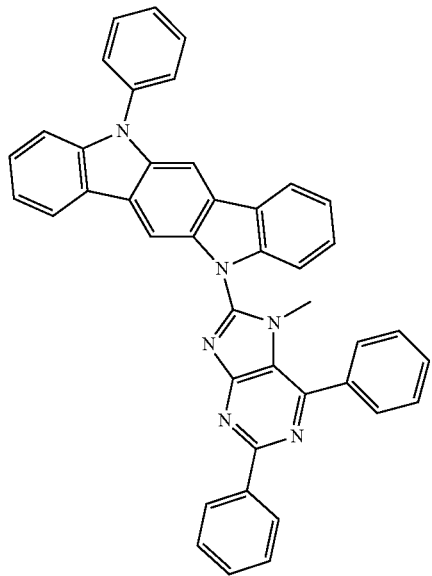
(742)
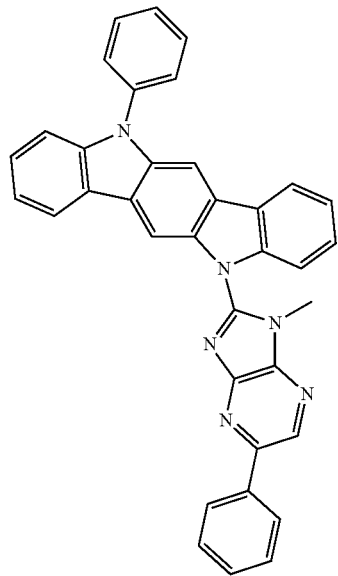

-continued
(743)
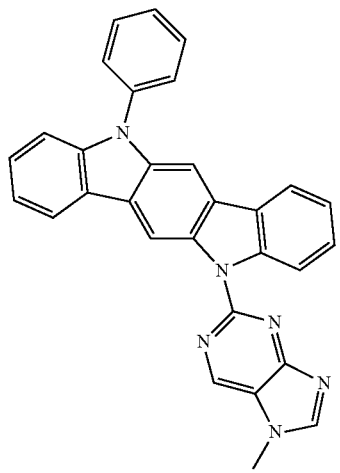
(744)
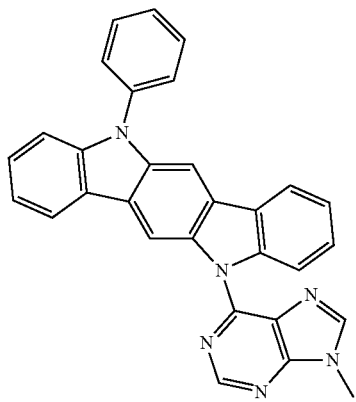
(745)
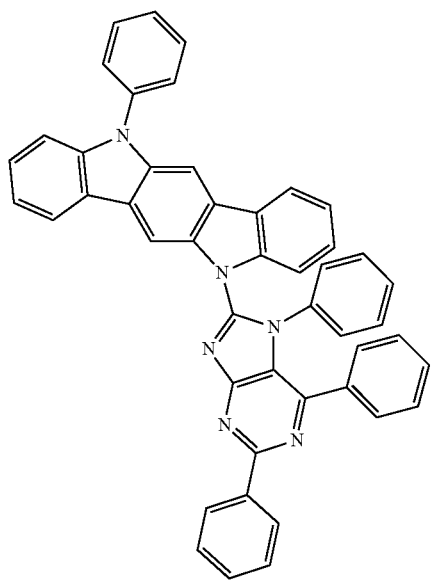
(746)
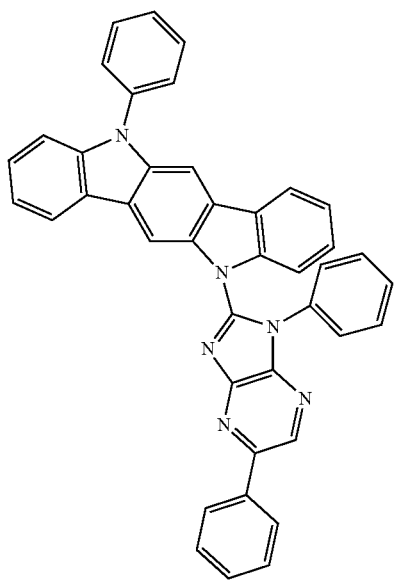
(747)
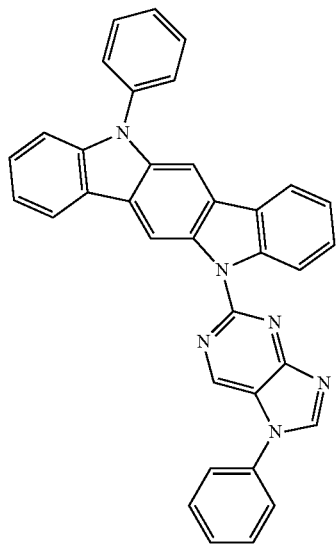
(748)
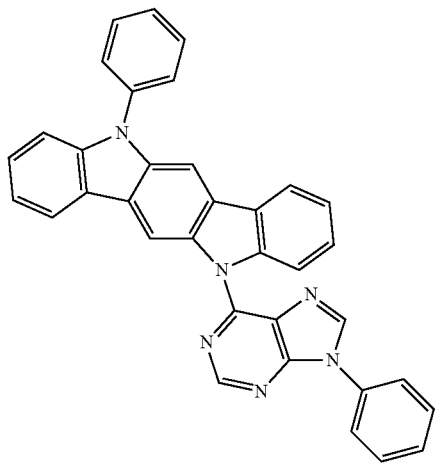

-continued
(749)
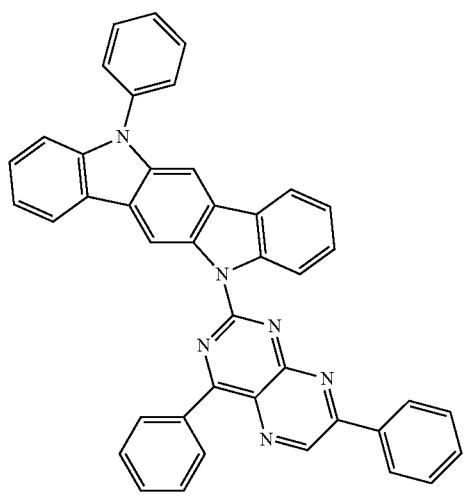
(750)
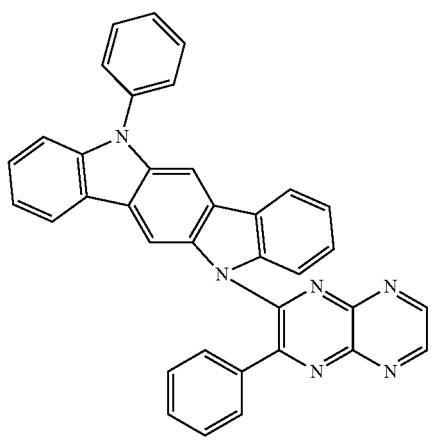
(751)
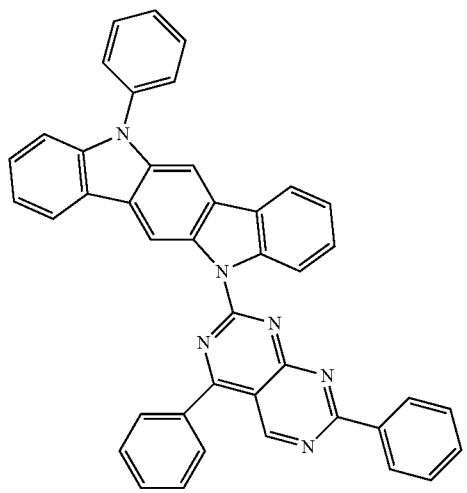
(752)
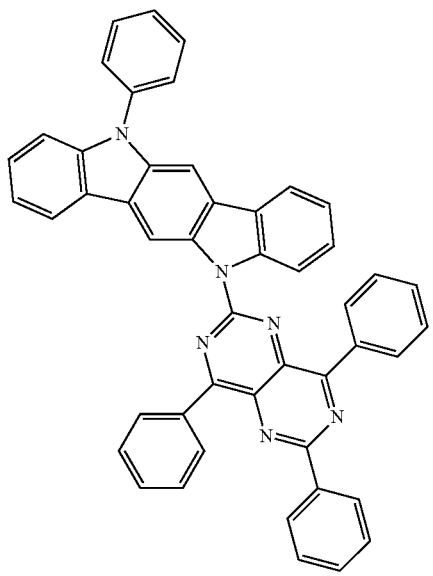
(753)
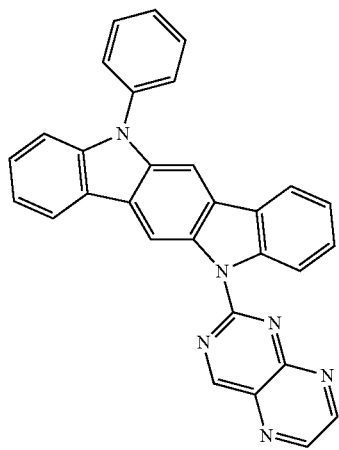
(754)
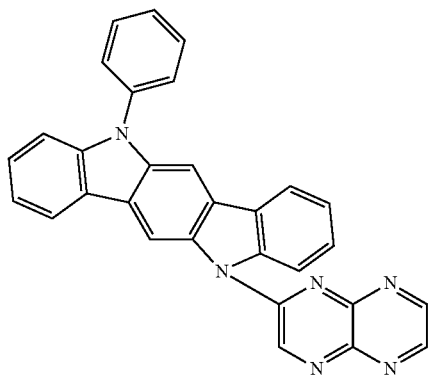

-continued
(755)
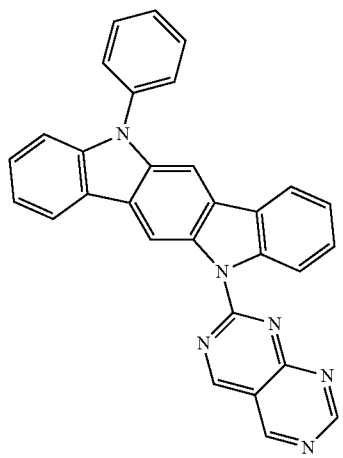
(756)
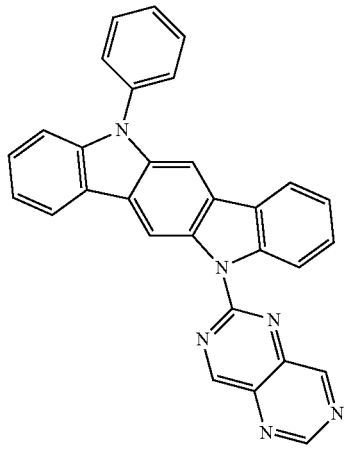
(757)
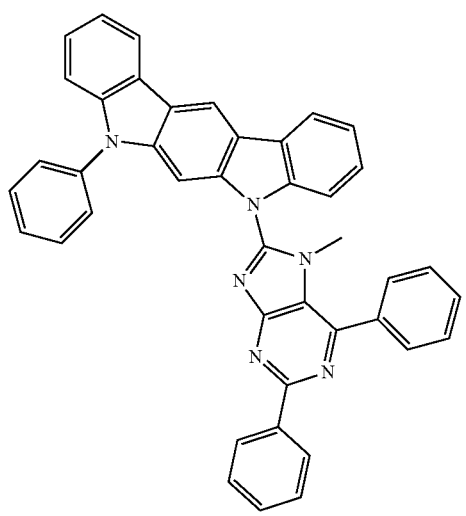
(758)
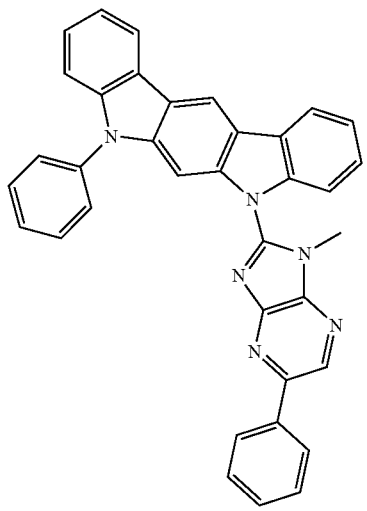
(759)
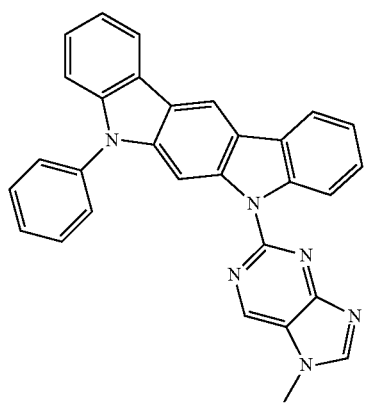
(760)
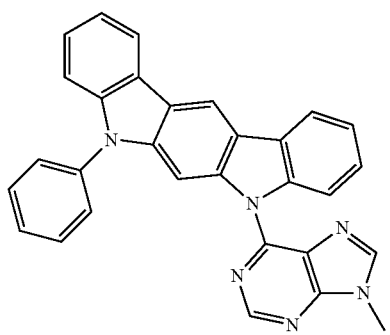

-continued
(761)
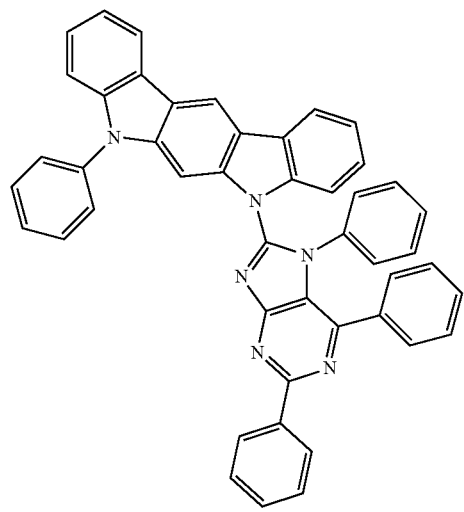
(762)
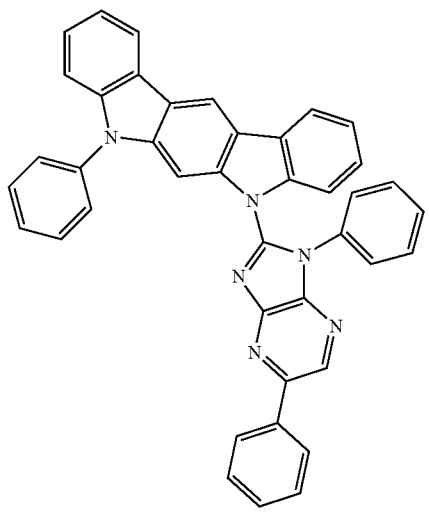
(763)
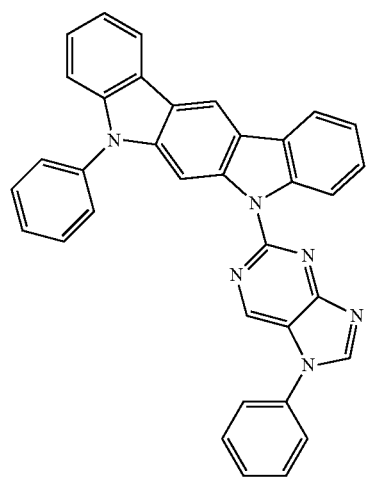
(764)
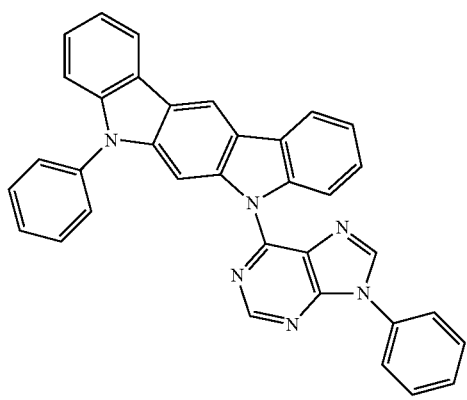
(765)
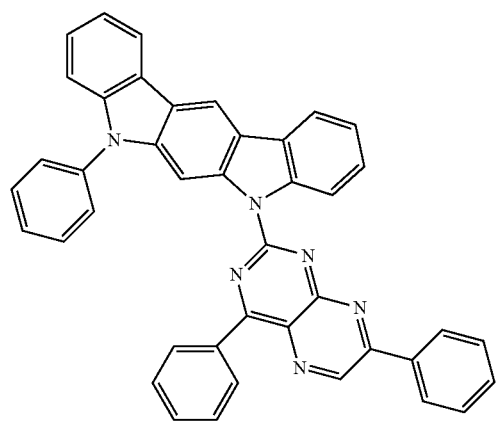
(766)
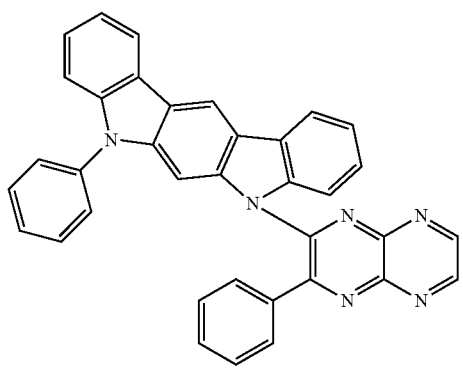

-continued
(767)
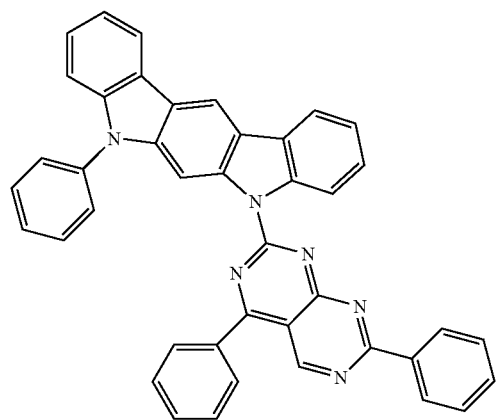
(768)
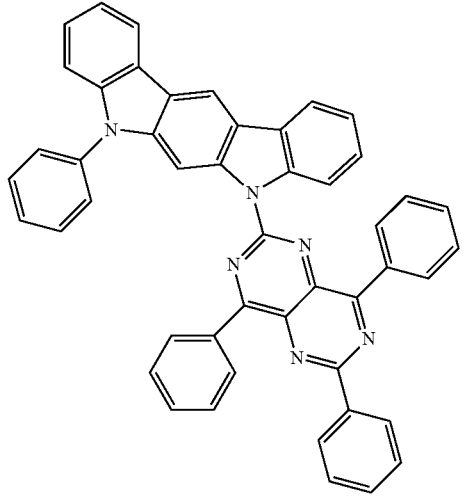
(769)
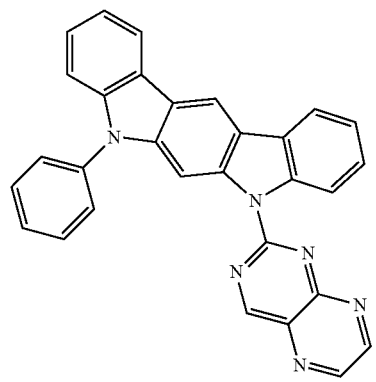
(770)
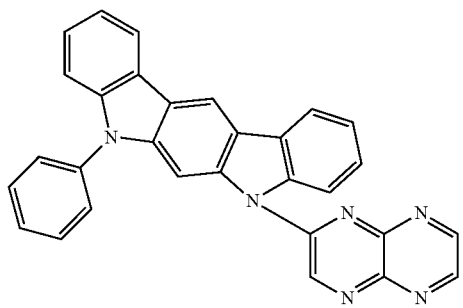
(771)
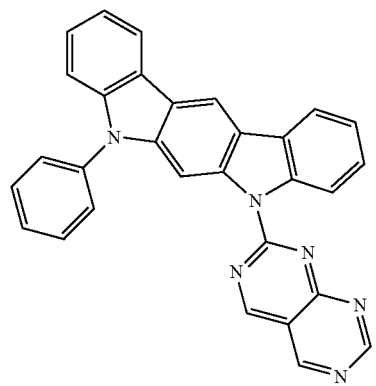
(772)
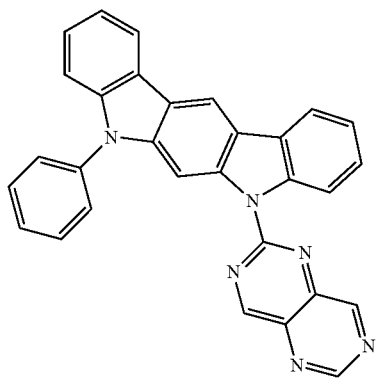

-continued
(773)
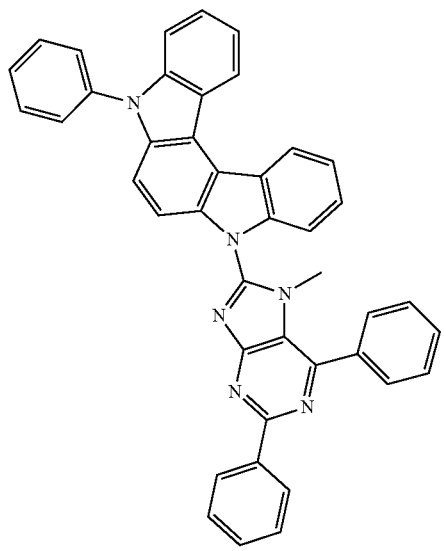
(774)
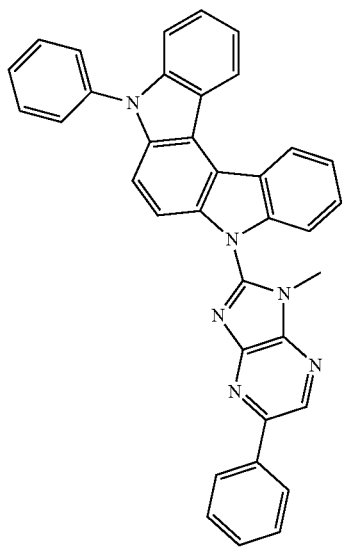
(775)
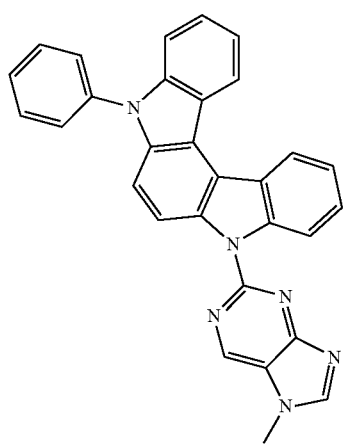
(776)
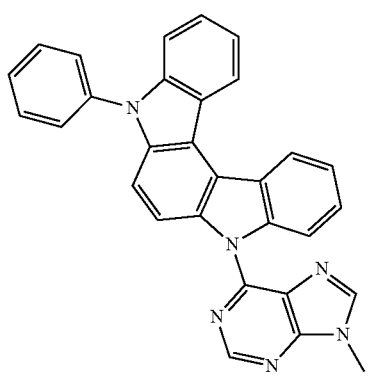
(777)
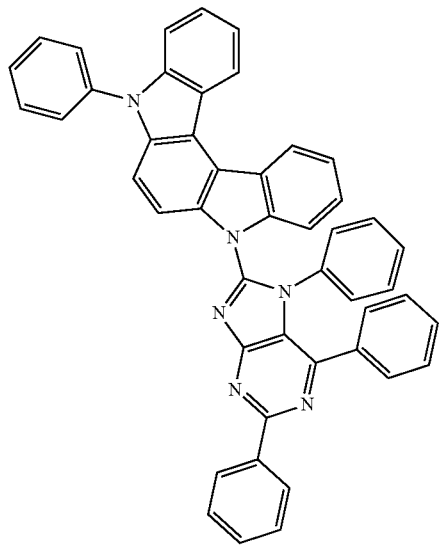
(778)
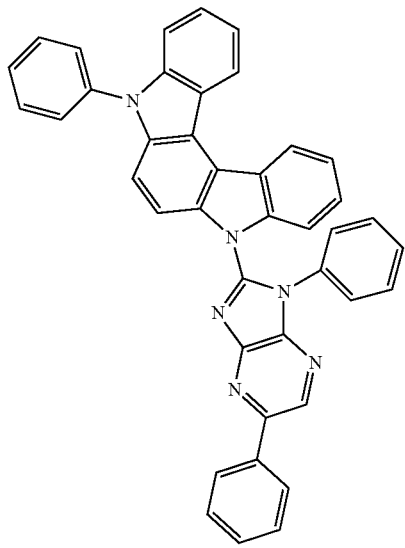

-continued
(779)
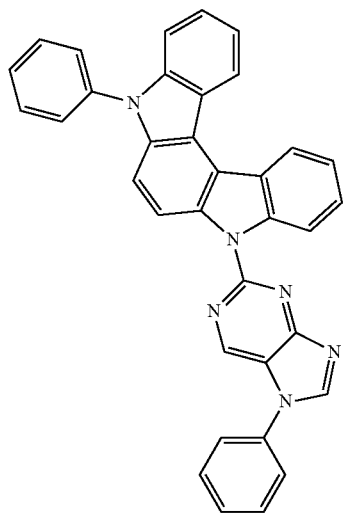
(780)
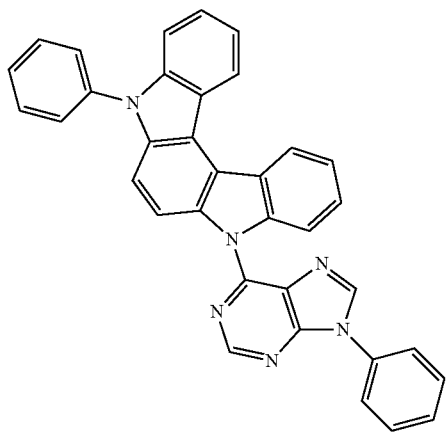
(781)
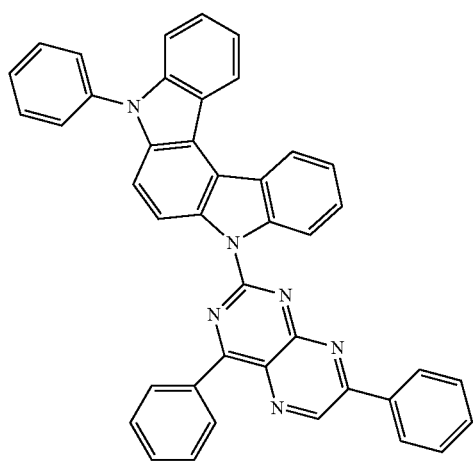
(782)
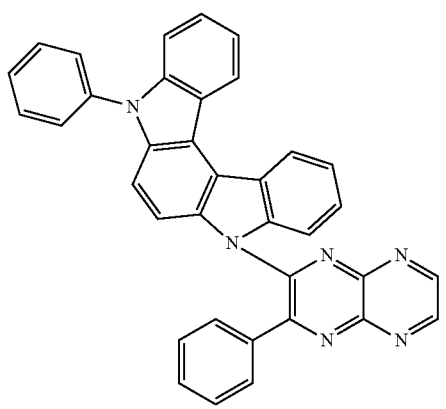
(783)
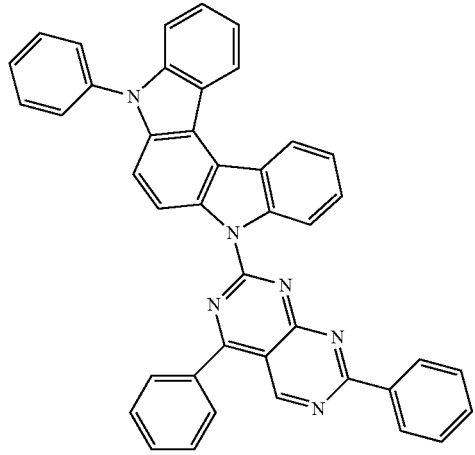
(784)
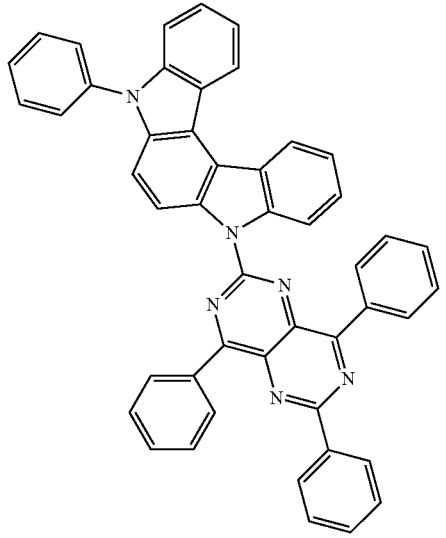

-continued
(785)
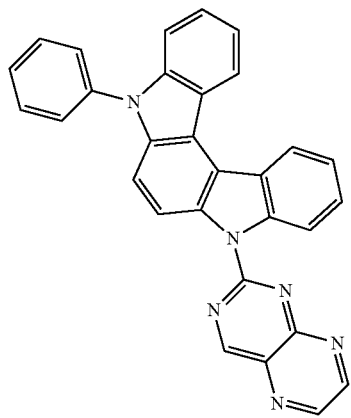
(786)
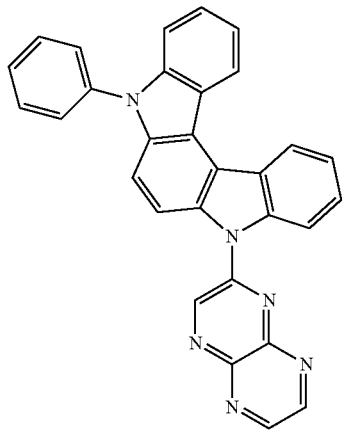
(787)
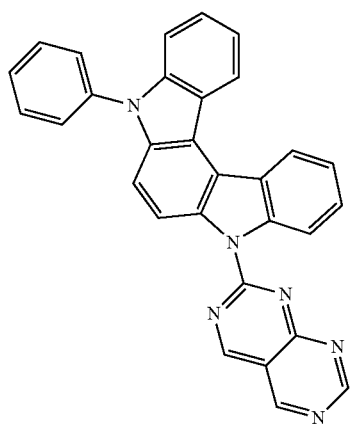
(788)
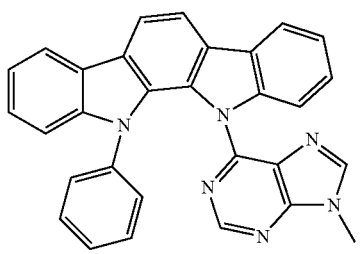
(789)
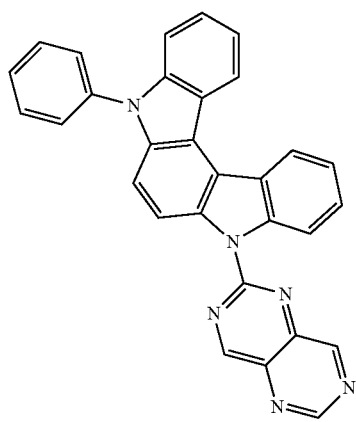
(790)
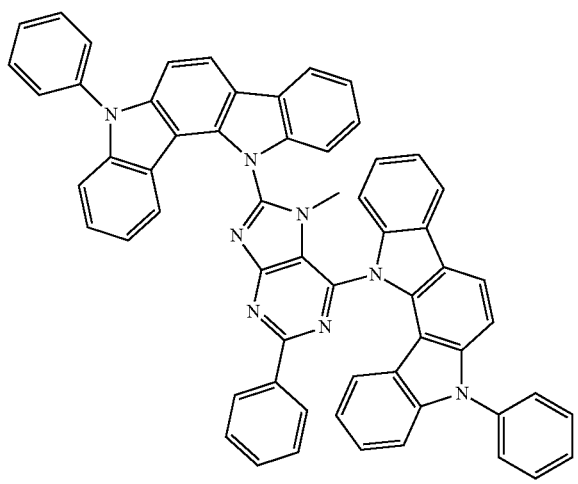

-continued
(791)
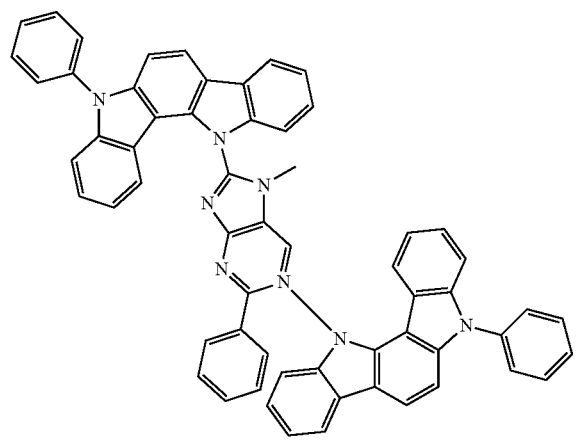
(792)
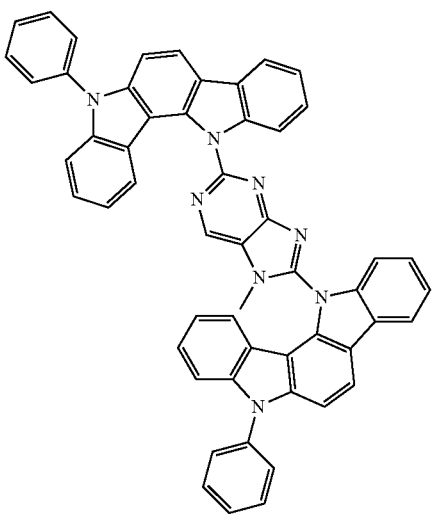
(793)
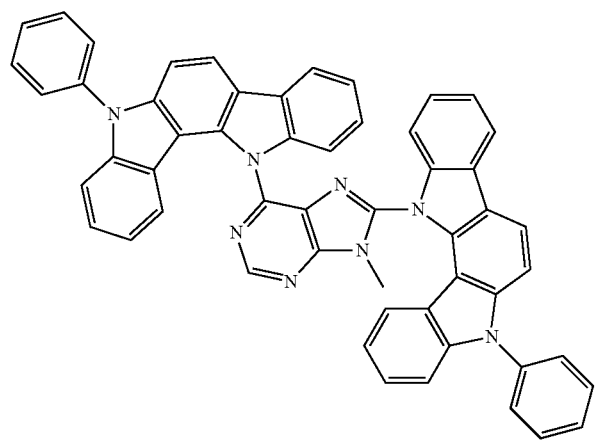
(794)
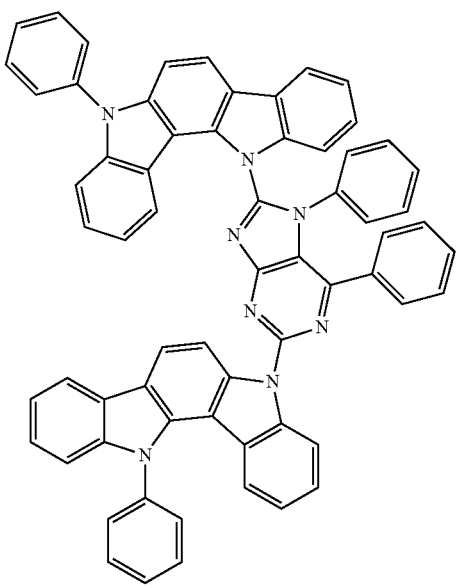

-continued
(795)
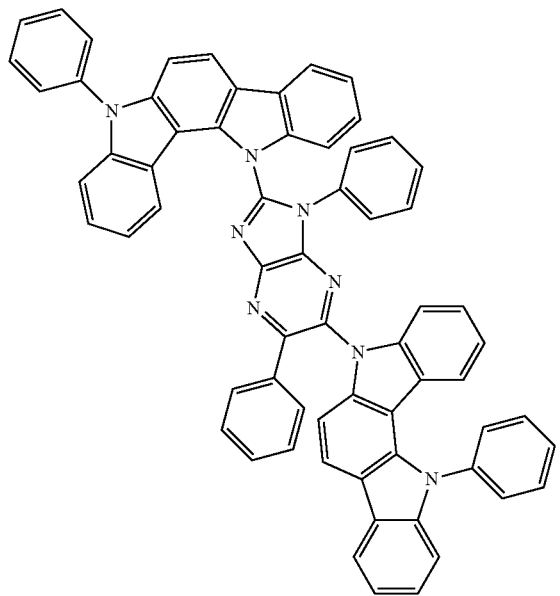
(796)
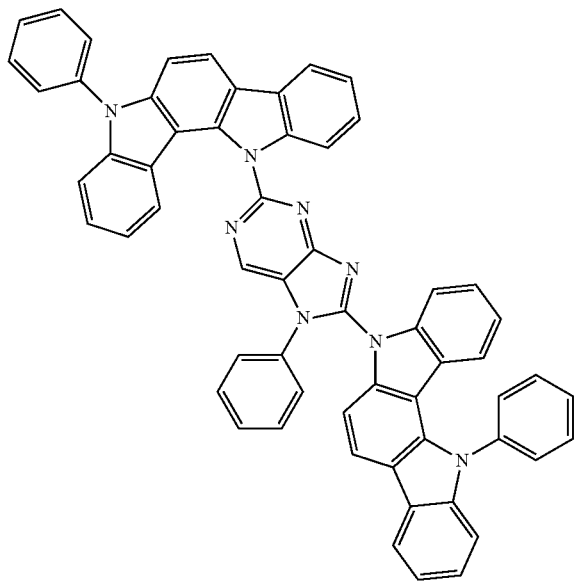
(797)
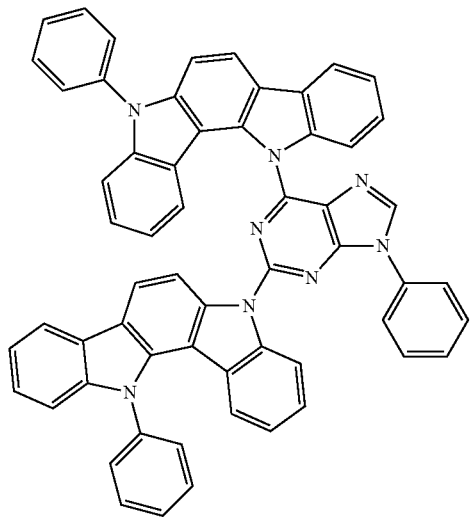
(798)
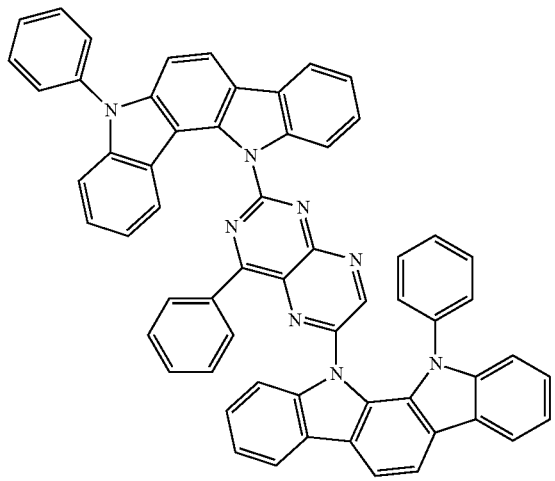

-continued
(799)
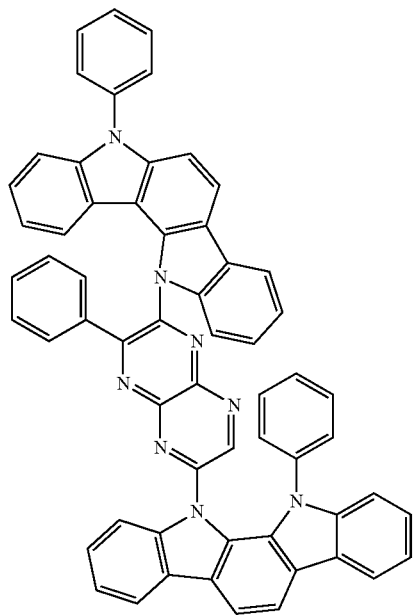
(800)
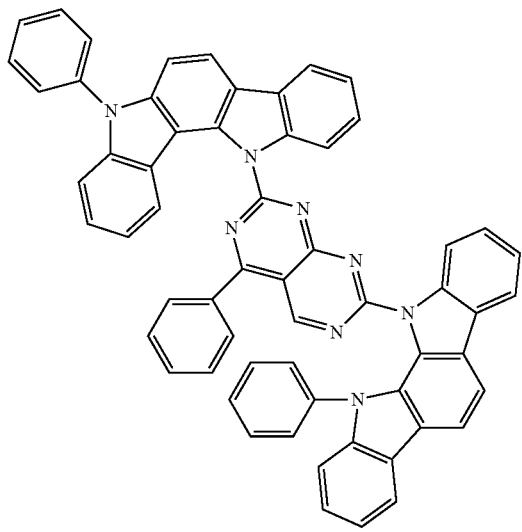
(801)
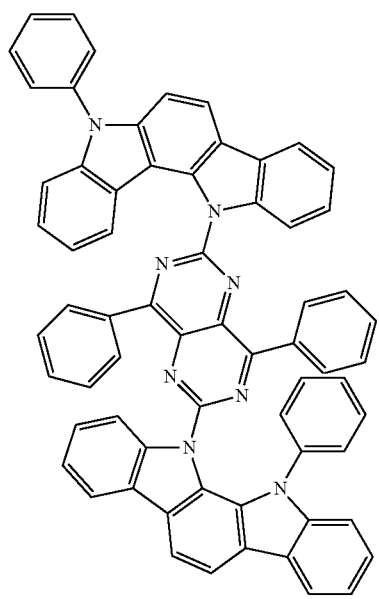
(802)
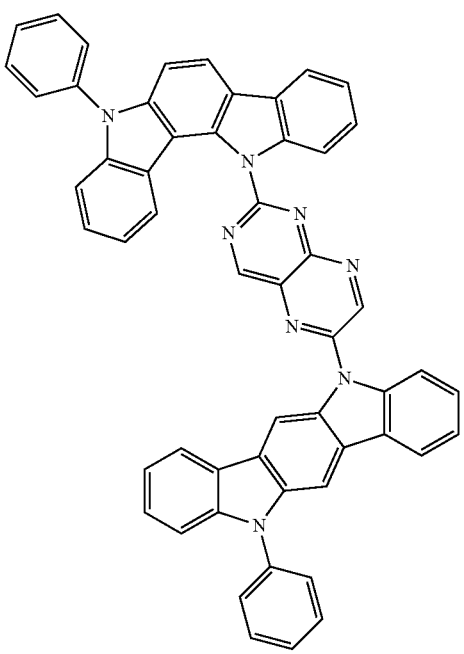

-continued
(803)
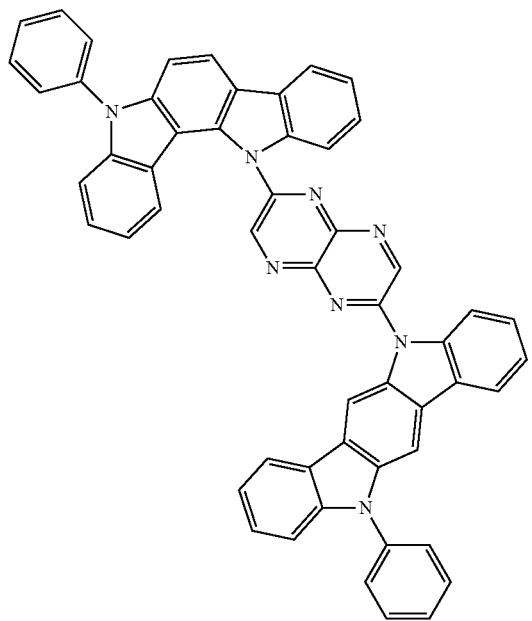
(804)
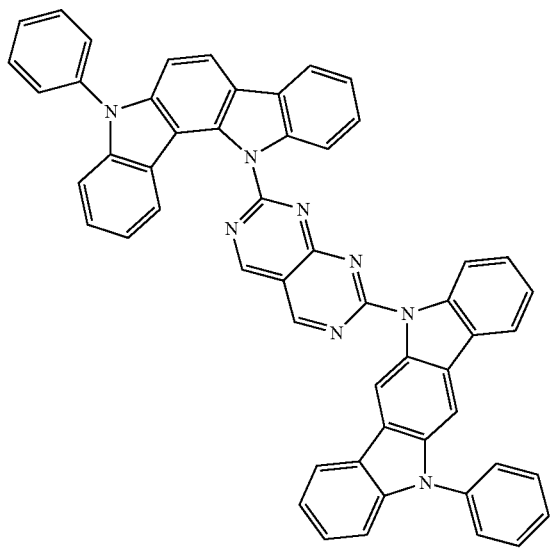
(805)
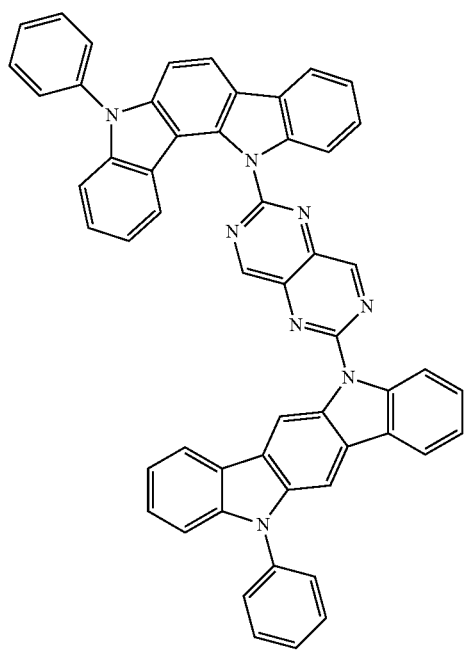
(806)
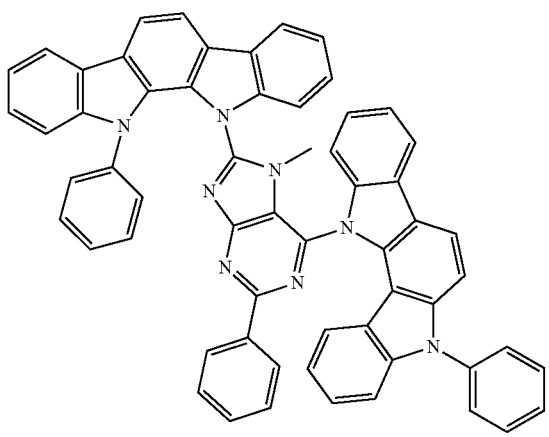

-continued
(807)
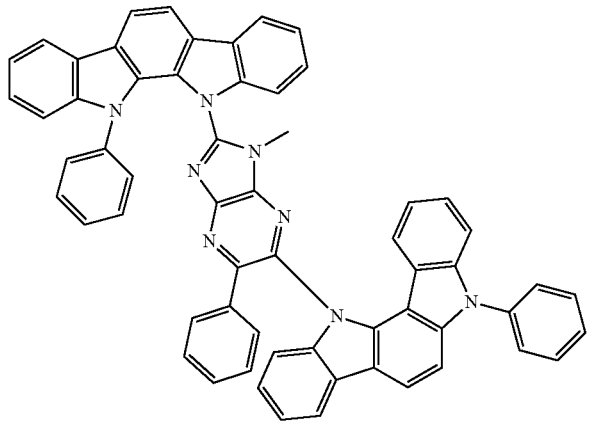
(808)
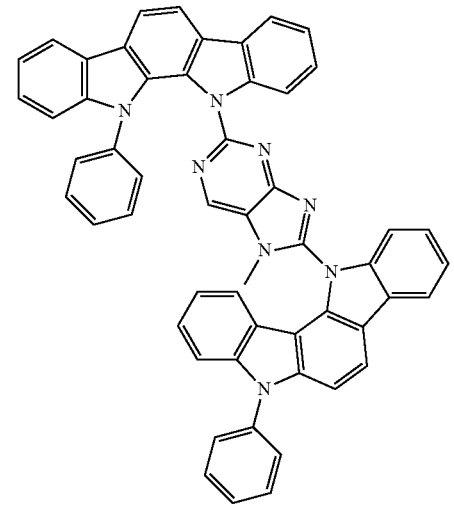
(809)
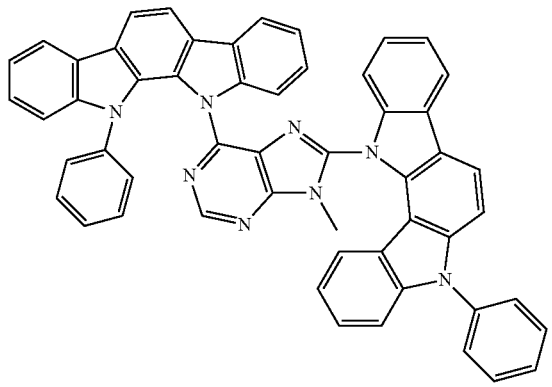
(810)
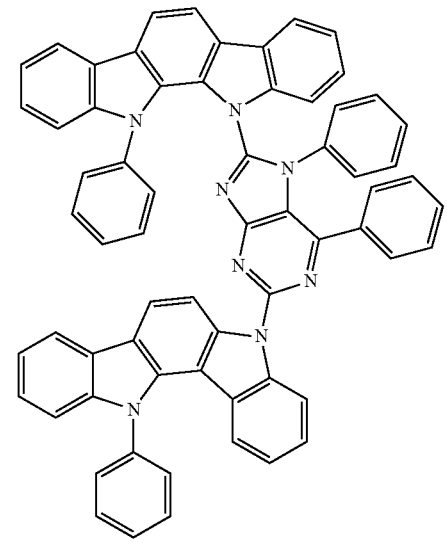
(811)
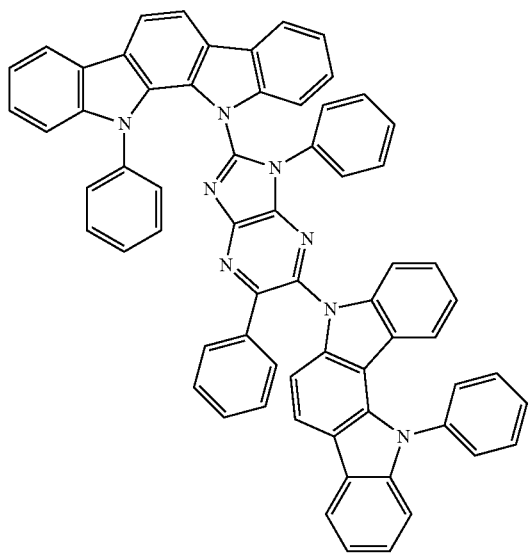
(812)
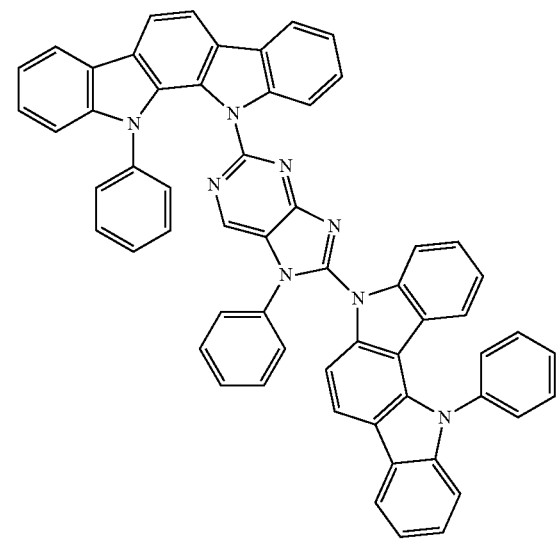

-continued
(813)
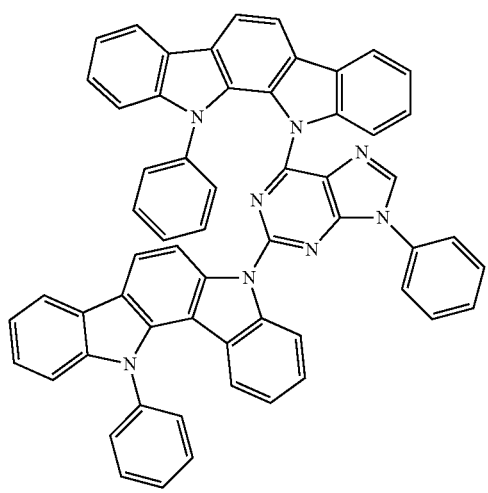
(814)
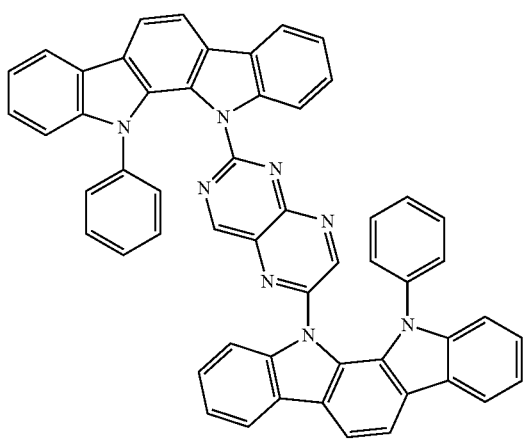
(815)
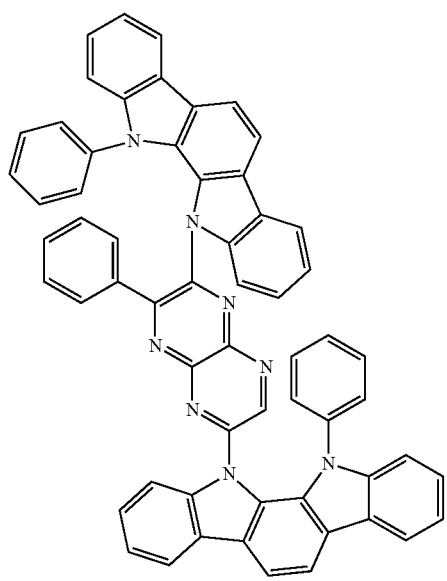
(816)
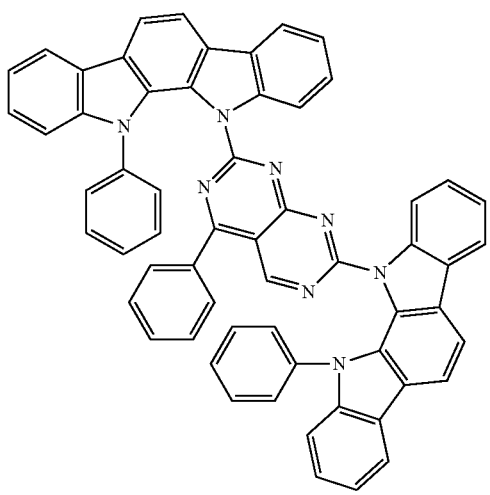
(817)
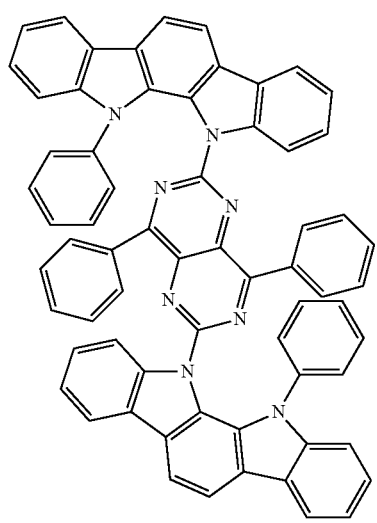
(818)
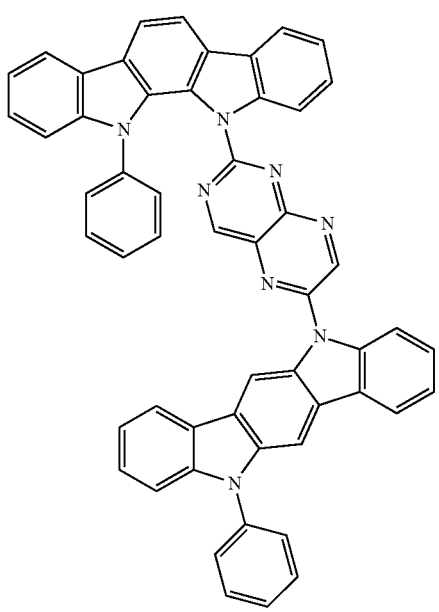

299
300
-continued
(819)
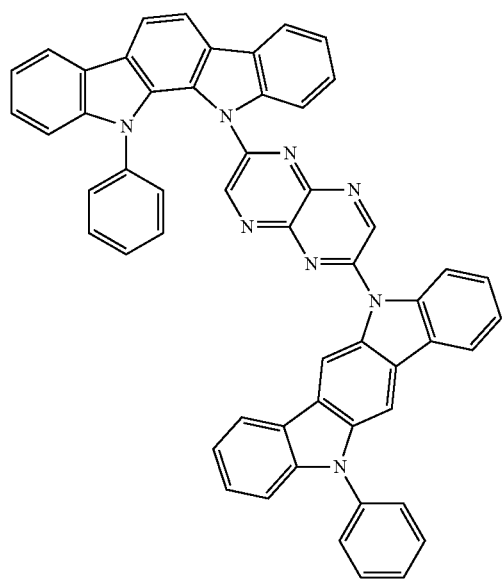
(820)
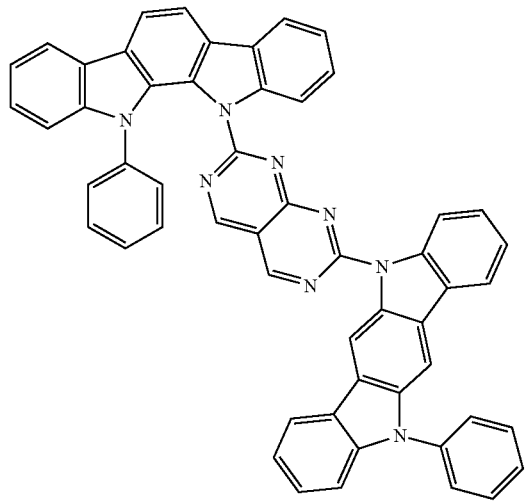
(821)
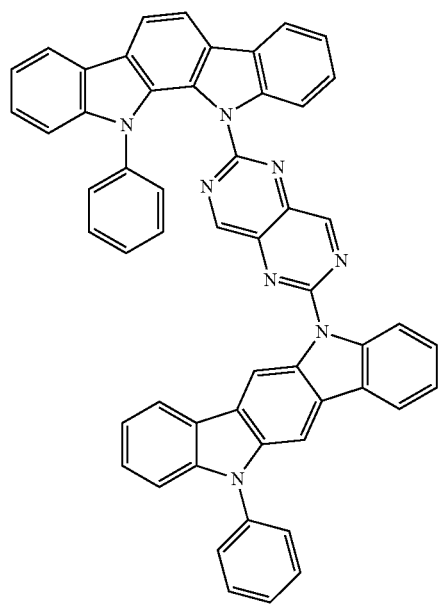
(822)
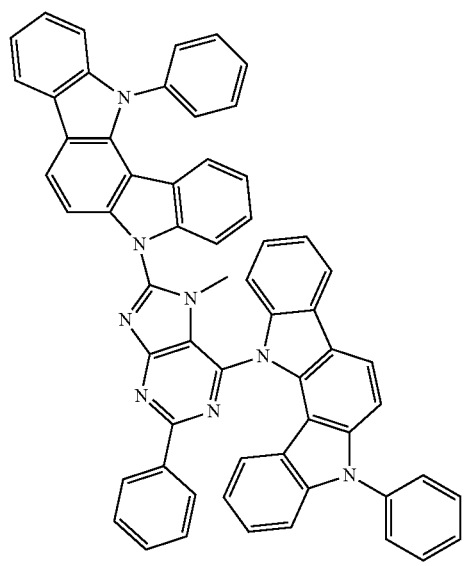

-continued
(823)
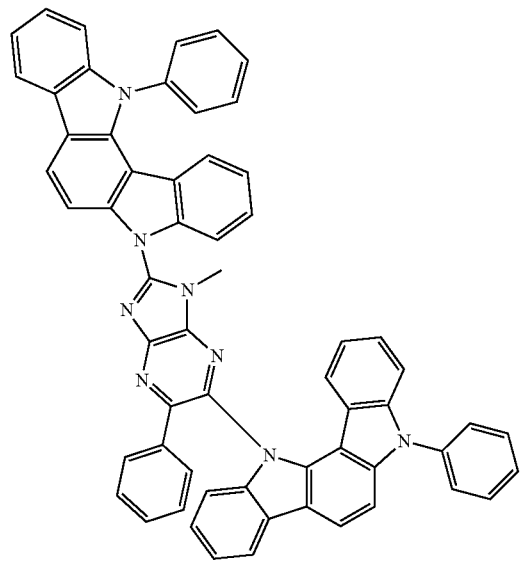
(824)
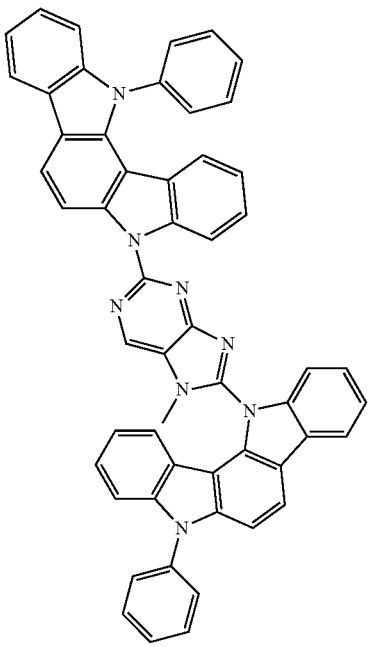
(825)
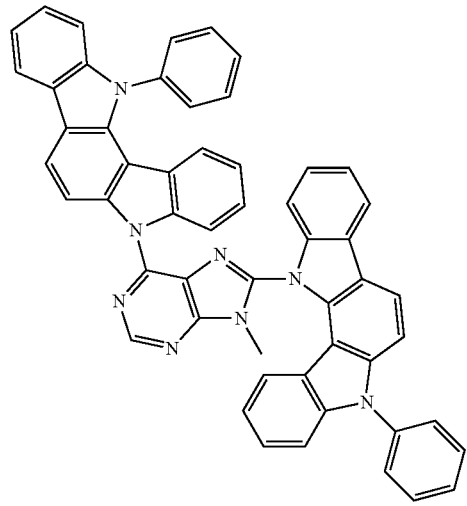
(826)
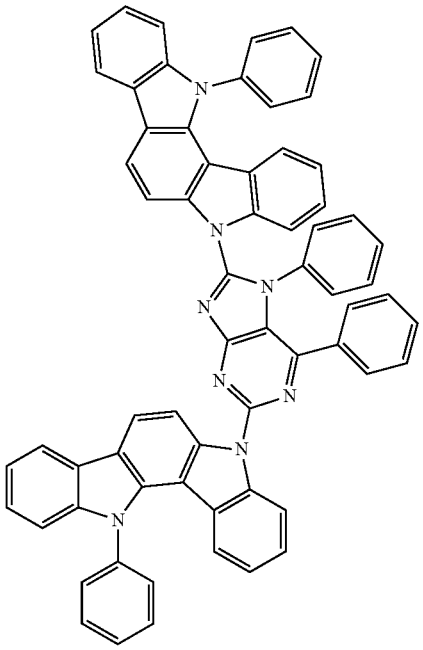

-continued
(827)
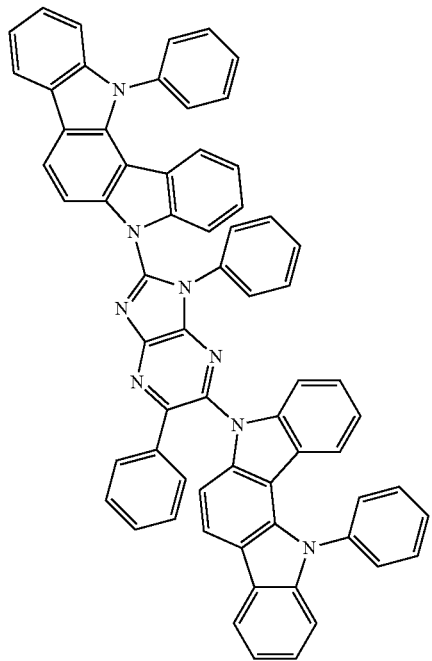
(828)
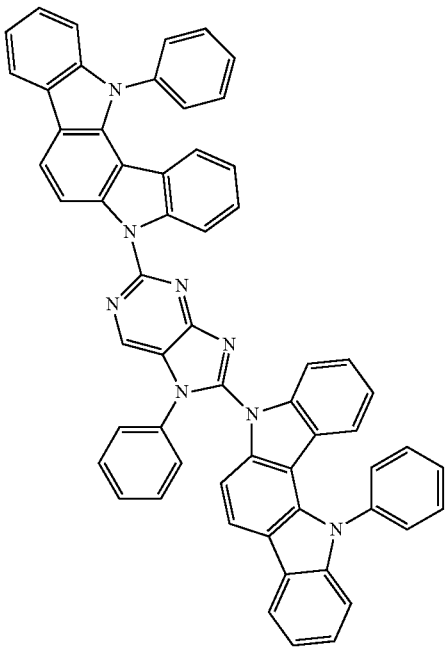
(829)
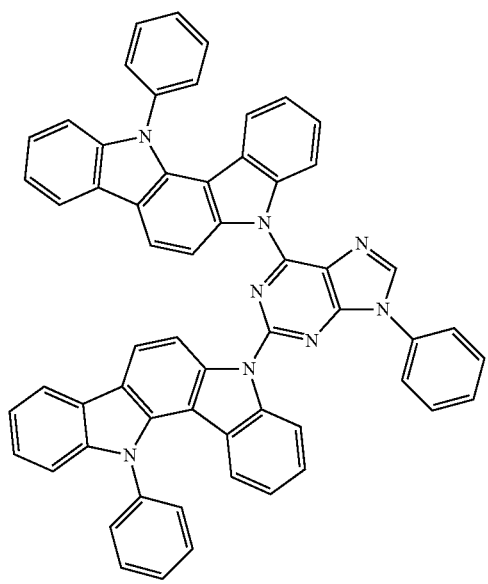
(830)
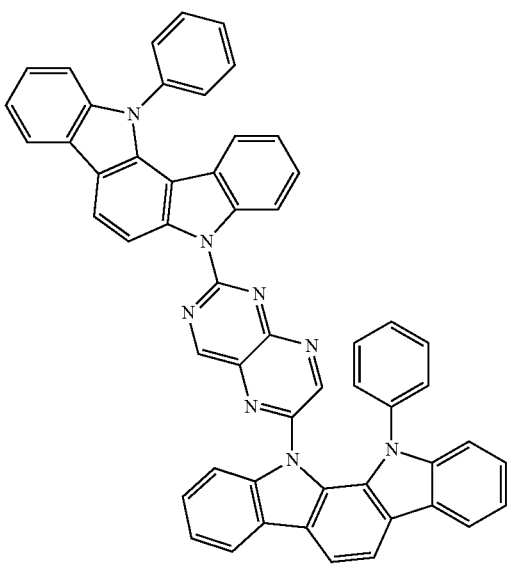

-continued
(831)
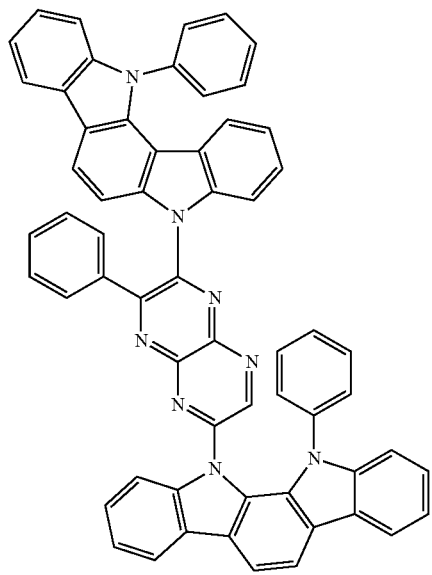
(832)
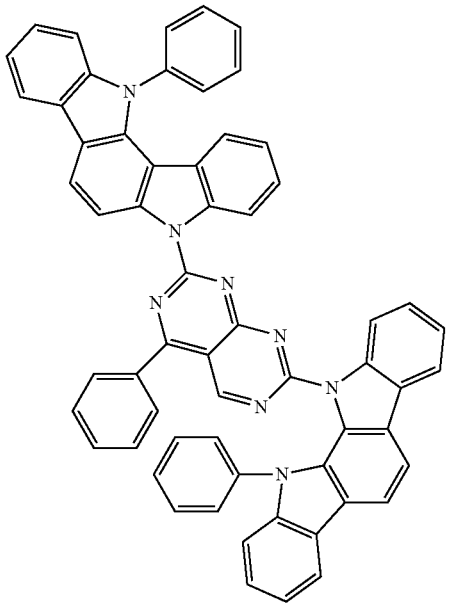
(833)
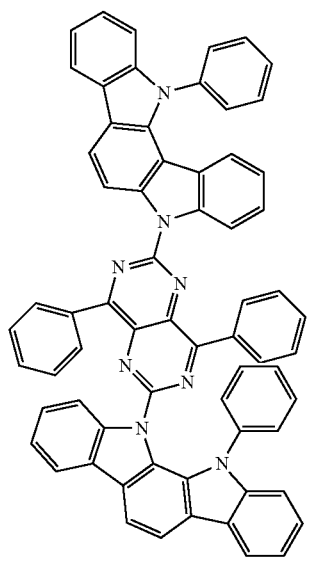
(834)
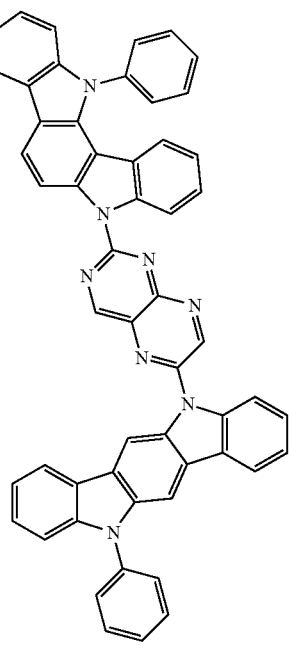

-continued
(835)
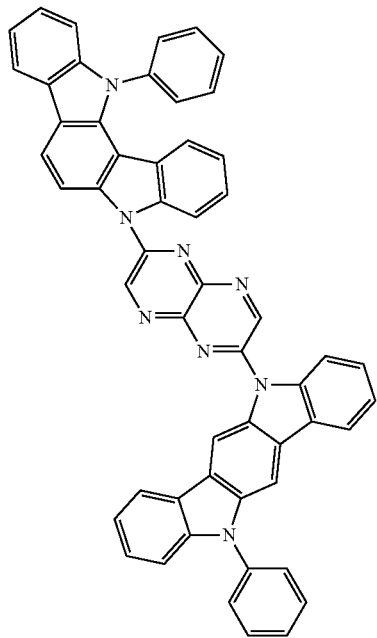
(836)
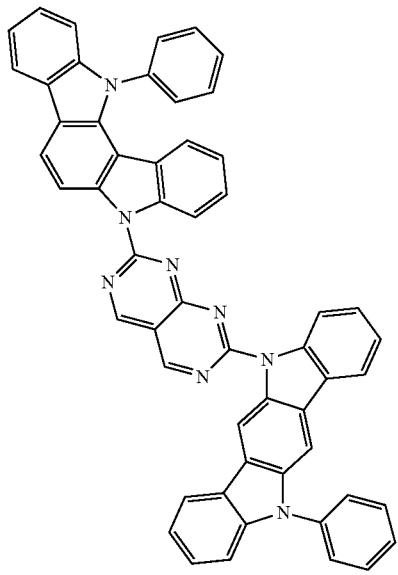
(837)
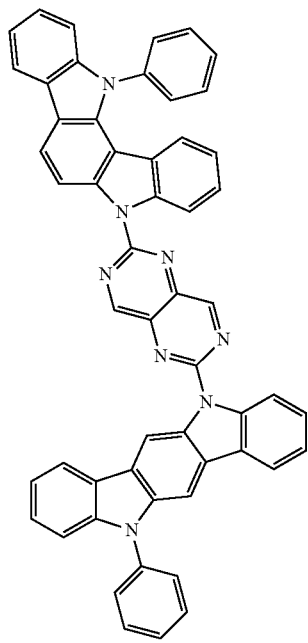
(838)
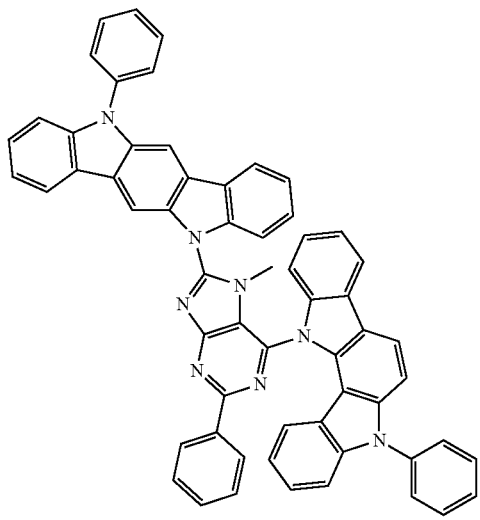

(839)
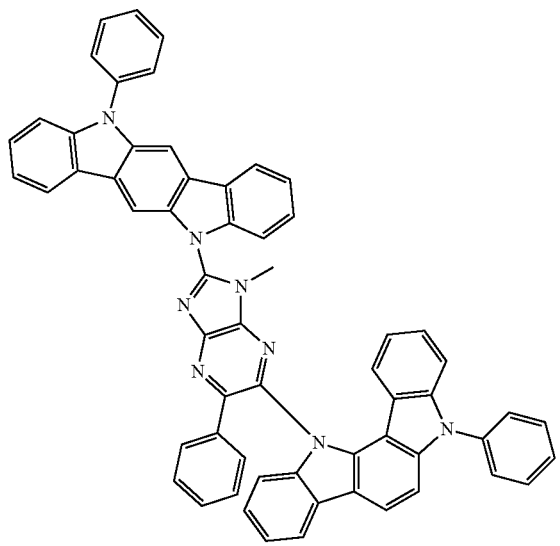
(840)
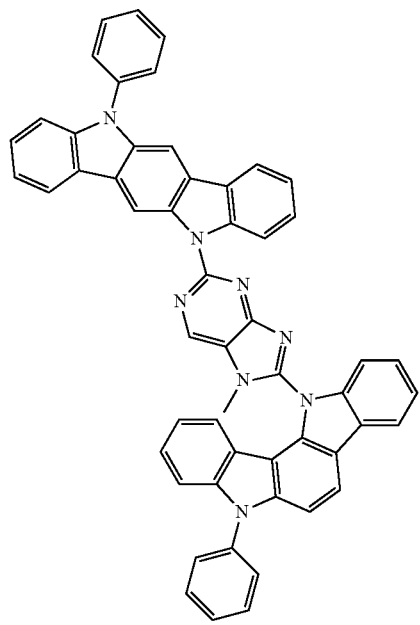
(841)
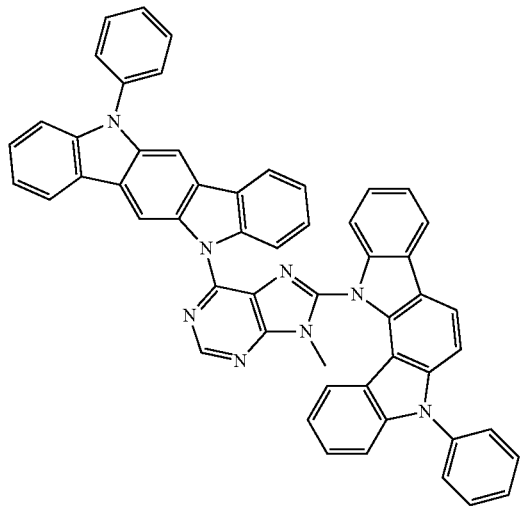
(842)
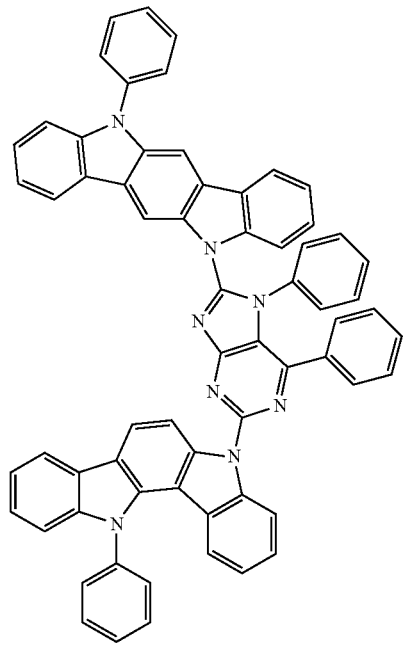

311
-continued
(843)
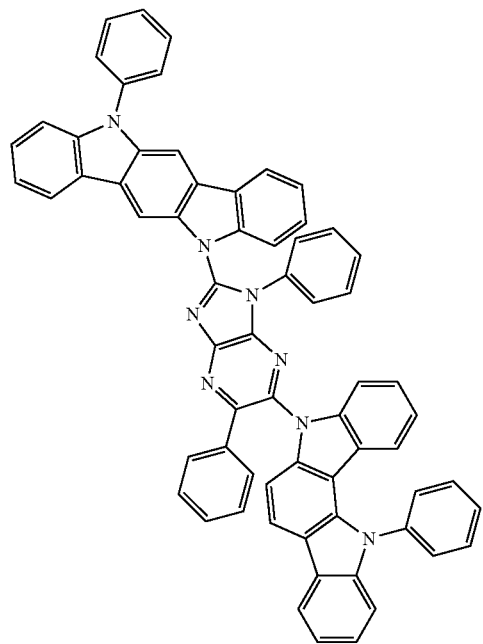
312
(844)
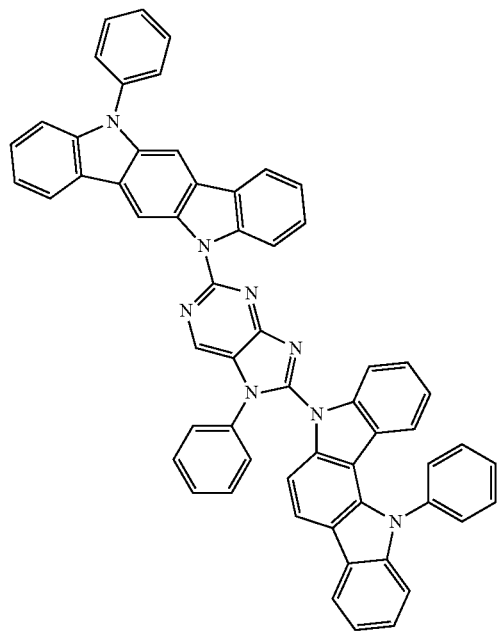
(845)
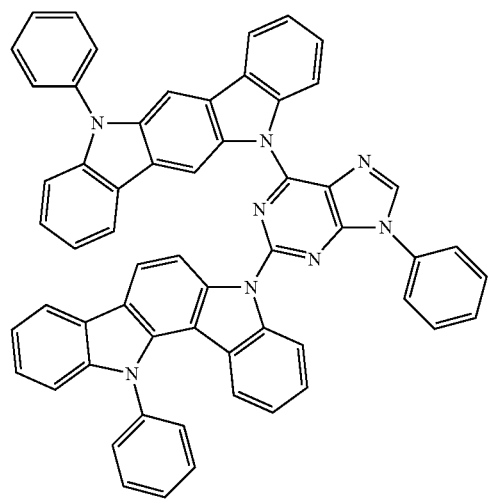
(846)
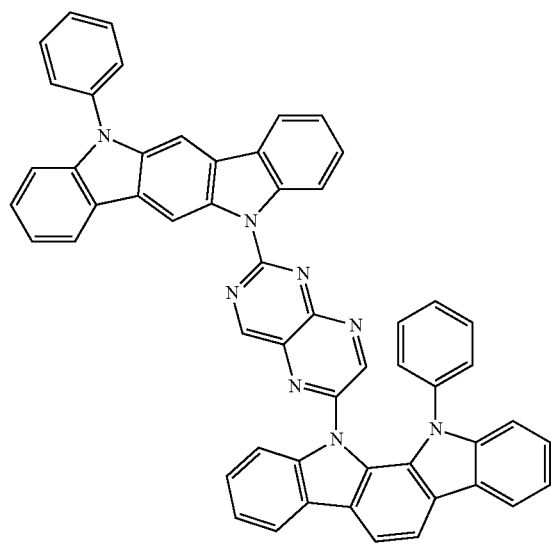

313
314
-continued
(847)
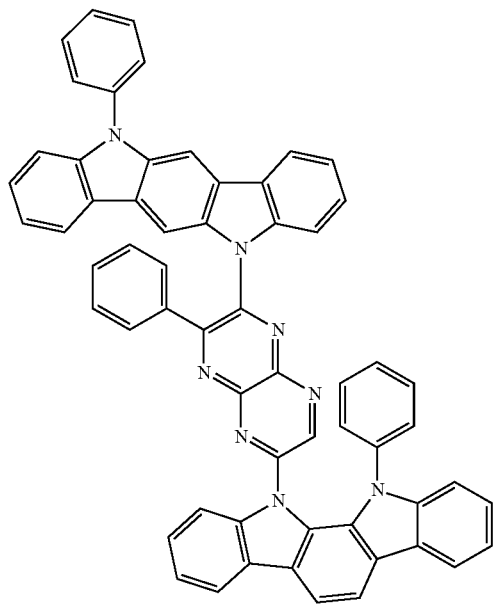
(848)
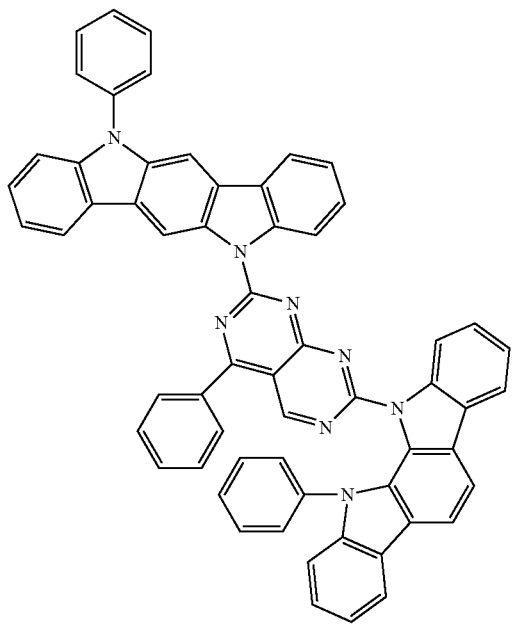
(849)
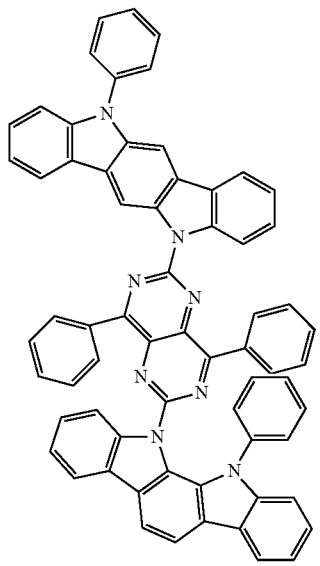
(850)
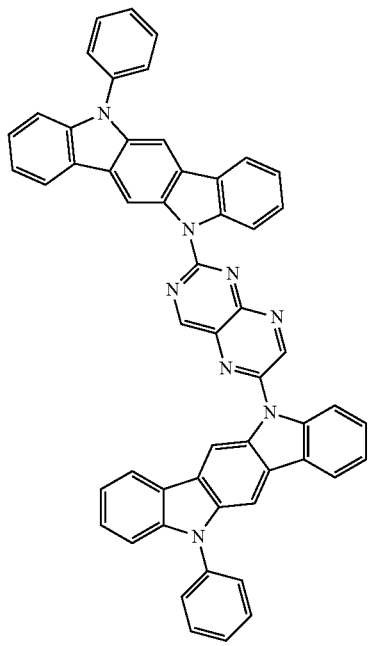

-continued
(851)
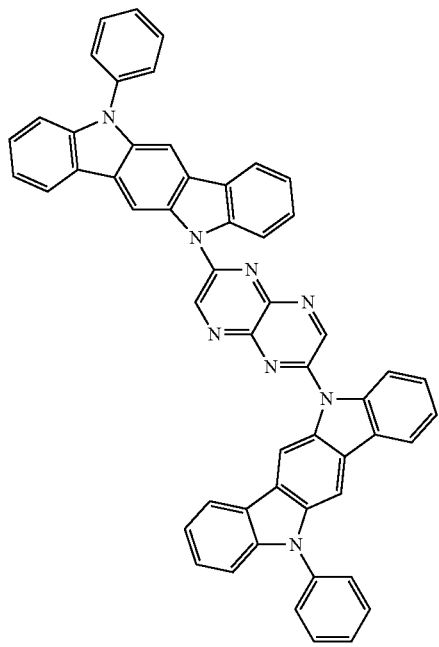
(852)
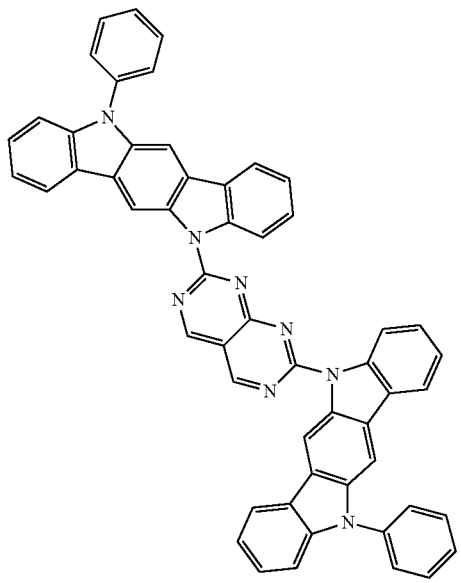
(853)
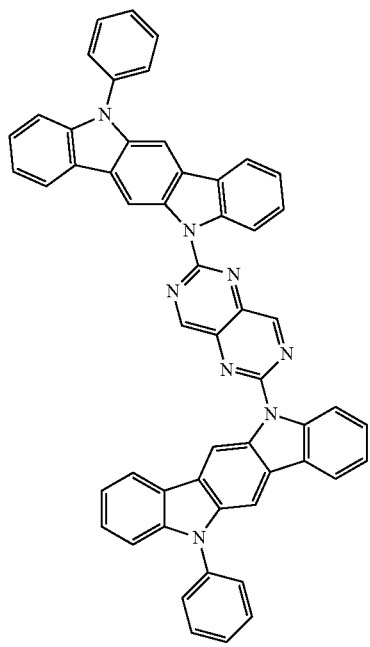
(854)
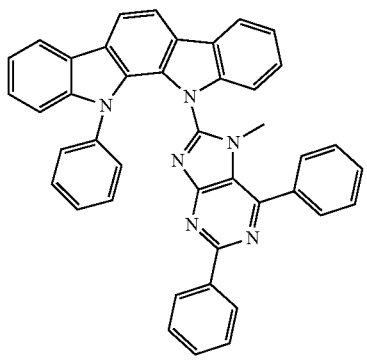

-continued
(855)
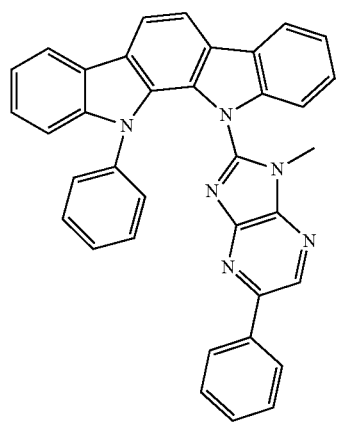
(856)
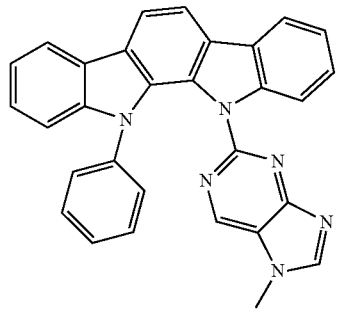
(857)
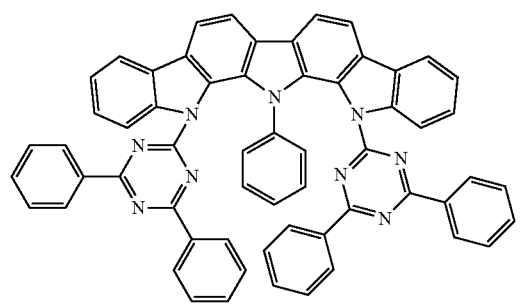
(858)
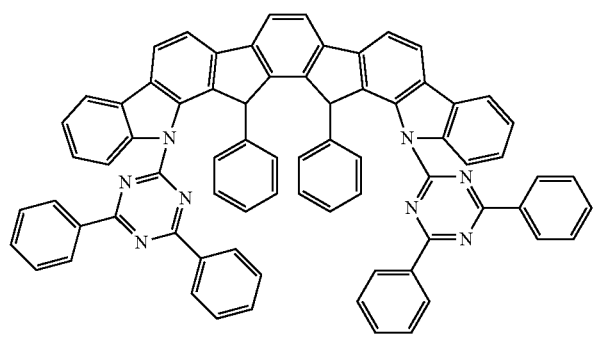
(859)
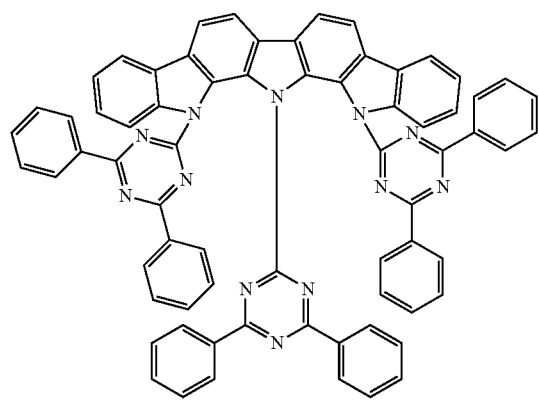
(860)
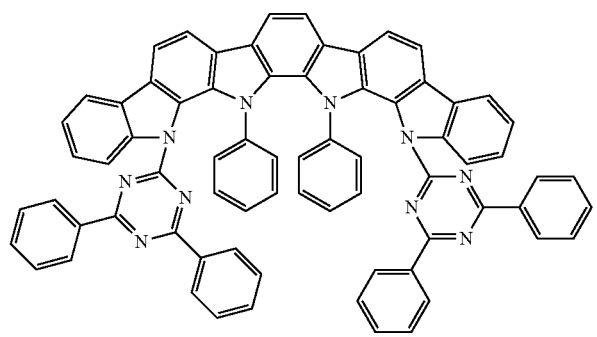
(861)
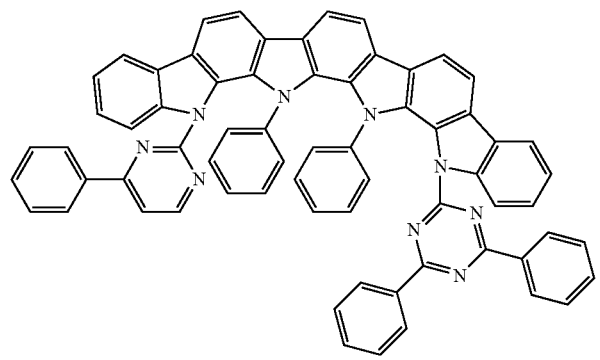
(862)
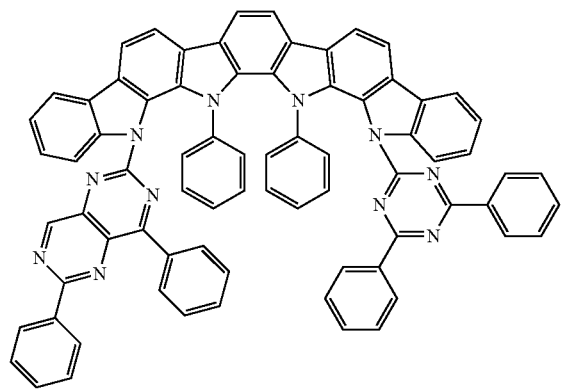

-continued
(863)
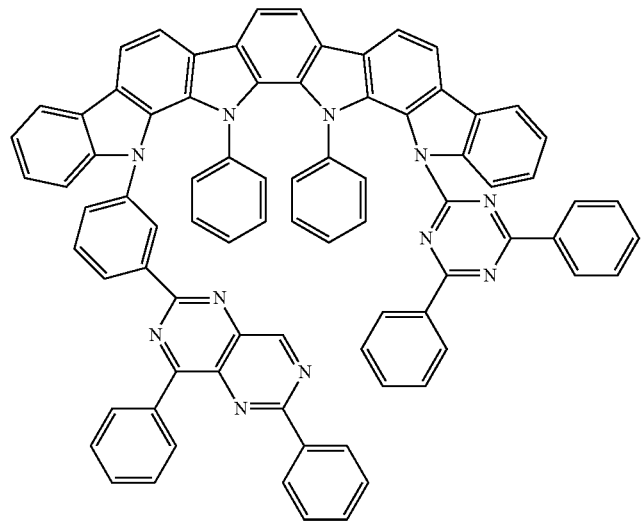
(864)
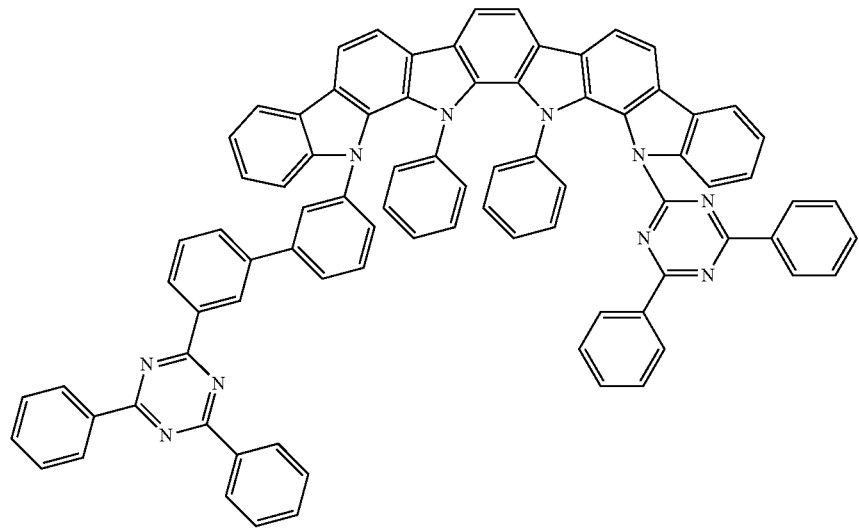
(865)
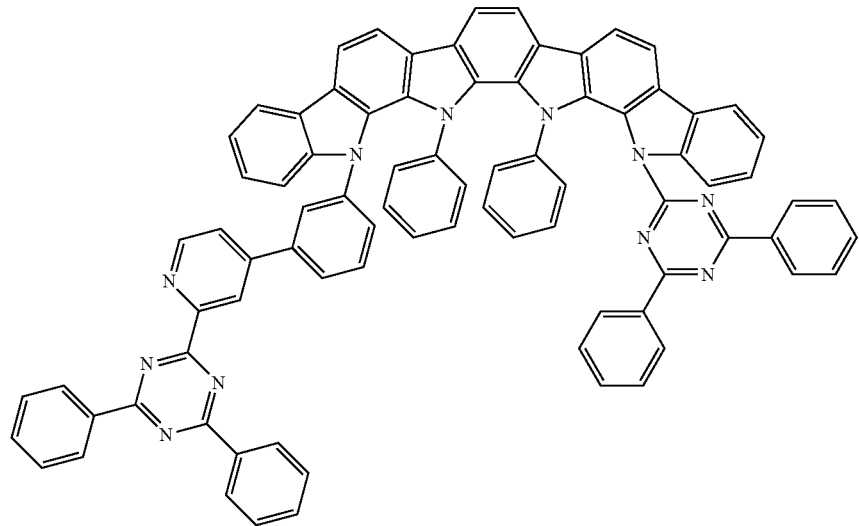

321
(866)
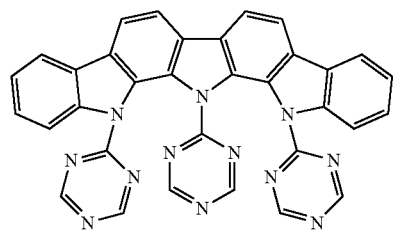
322
-continued
(867)
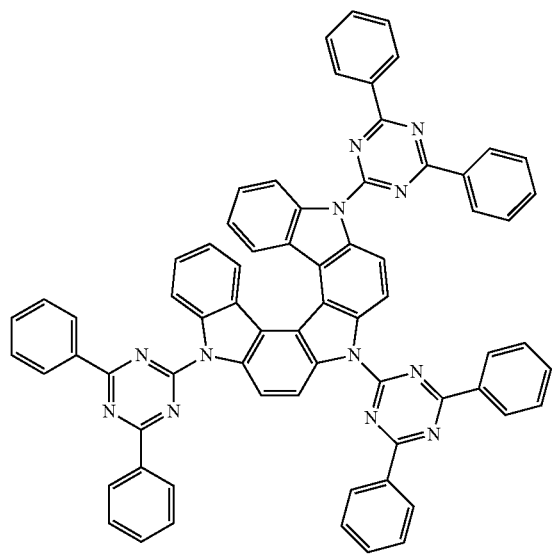
(868)
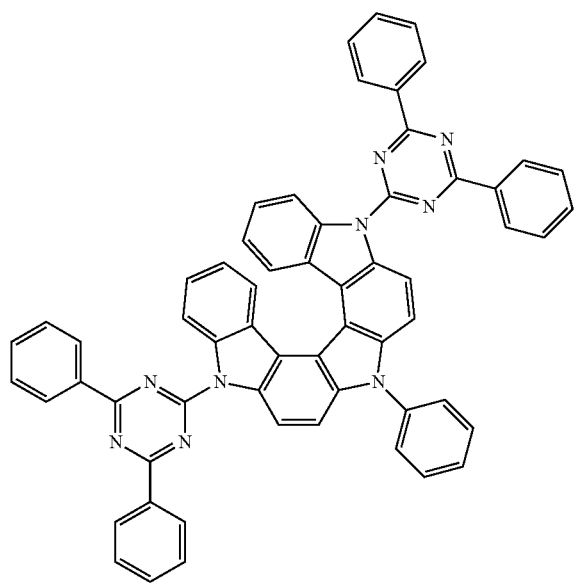
(869)
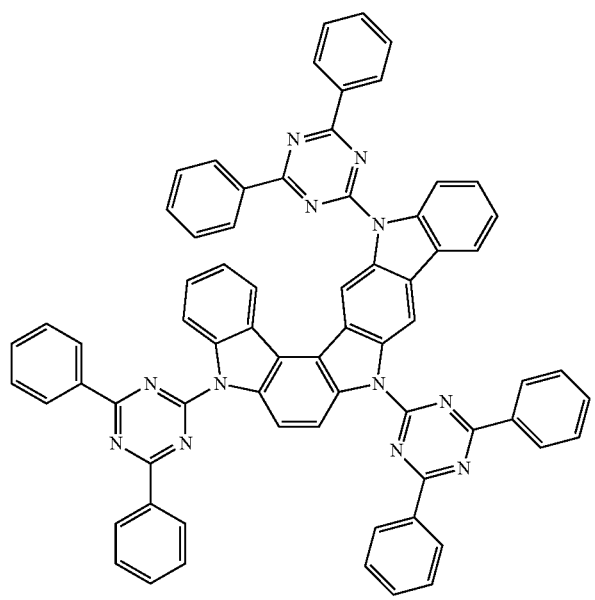

-continued
(870)
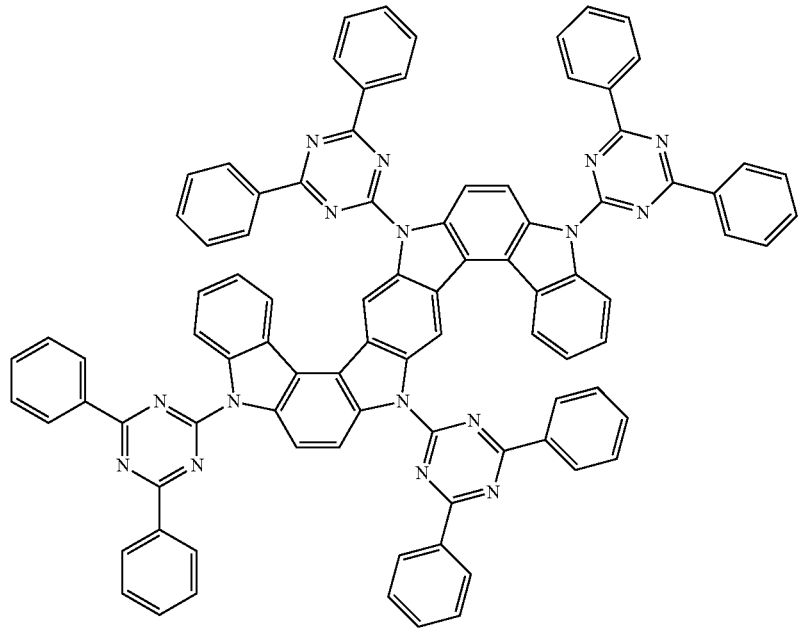
(871)
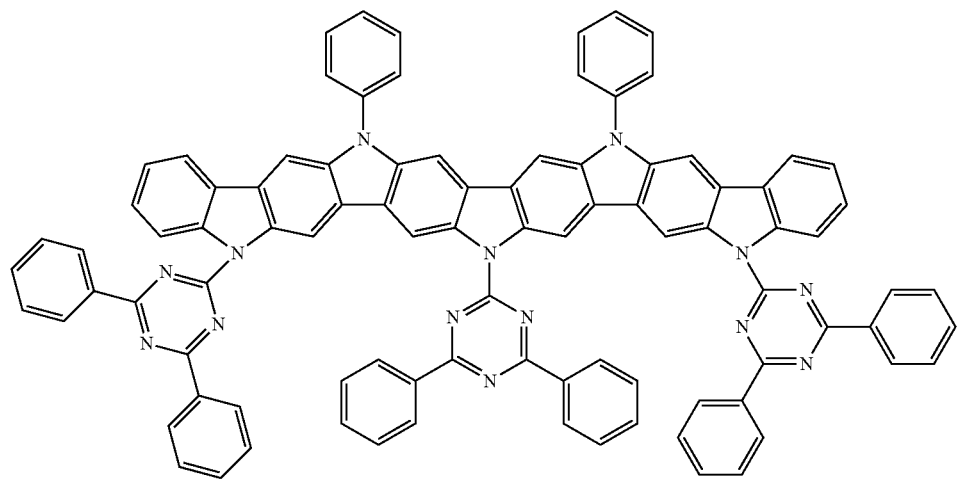
(872)
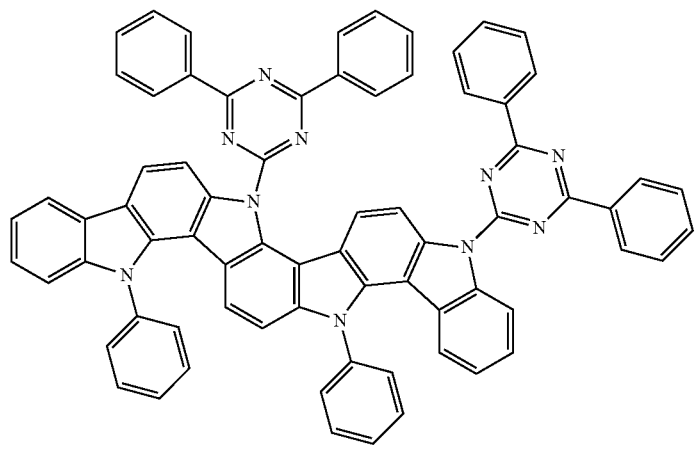

-continued
(873)
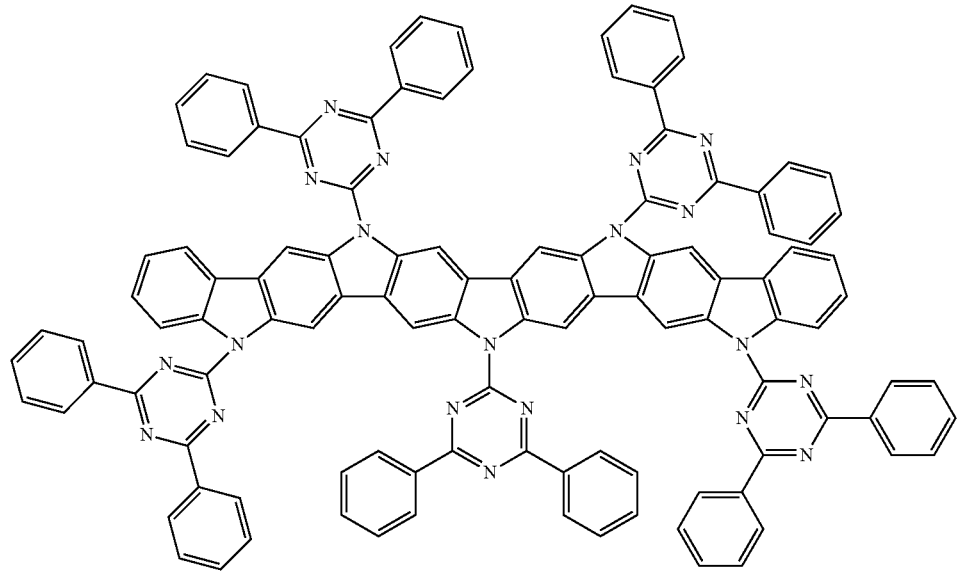
(874)
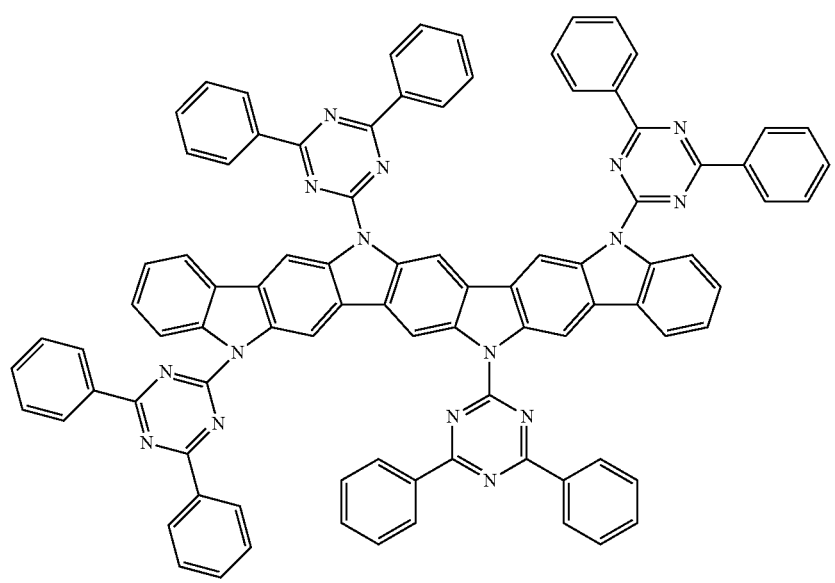

-continued
(875)
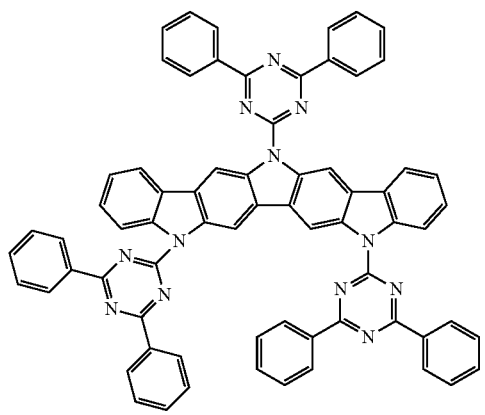
(876)
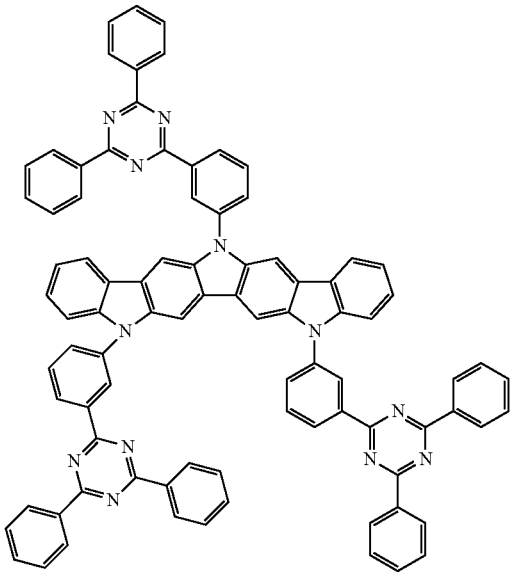
(877)
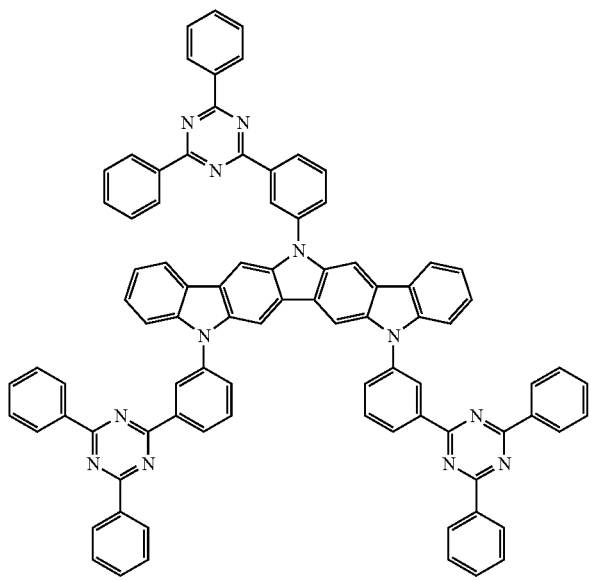
(878)
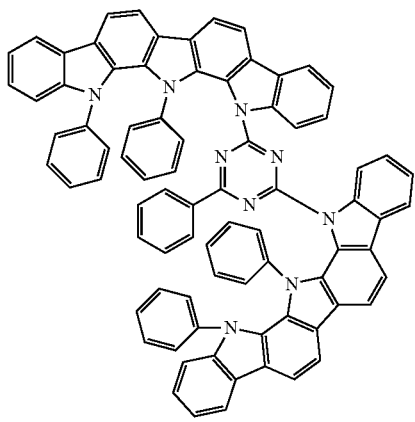
(879)
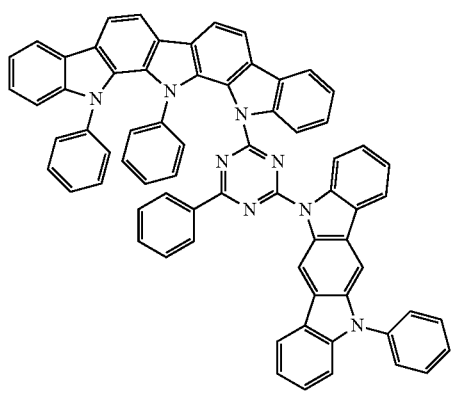
(880)
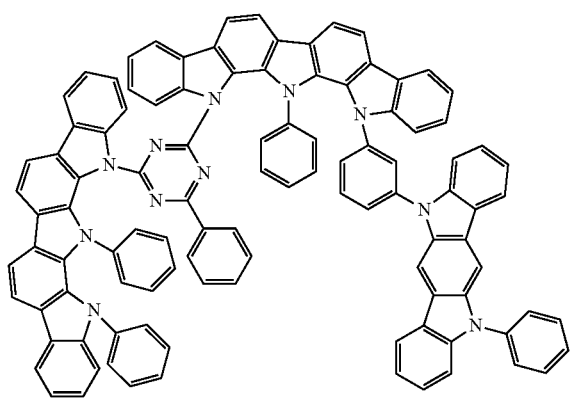

(881)
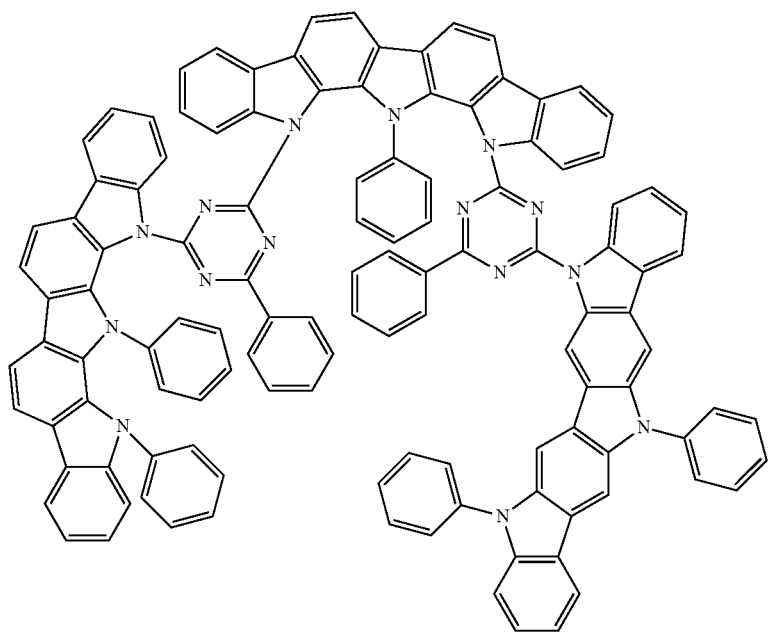
(882)
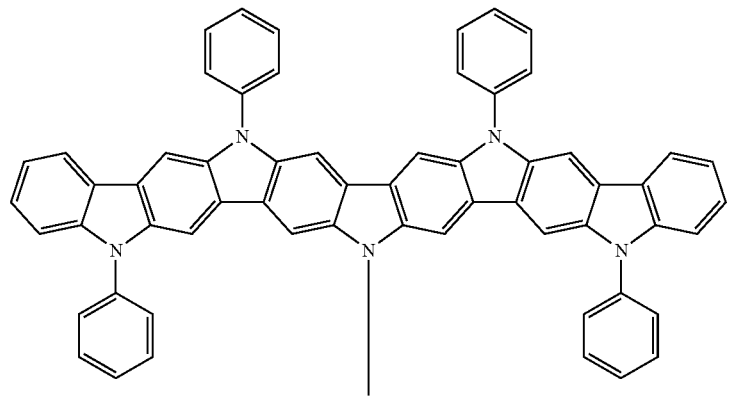

-continued
331
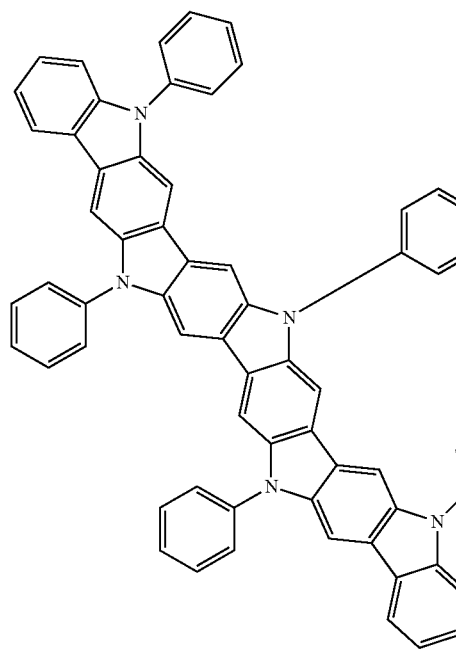
332
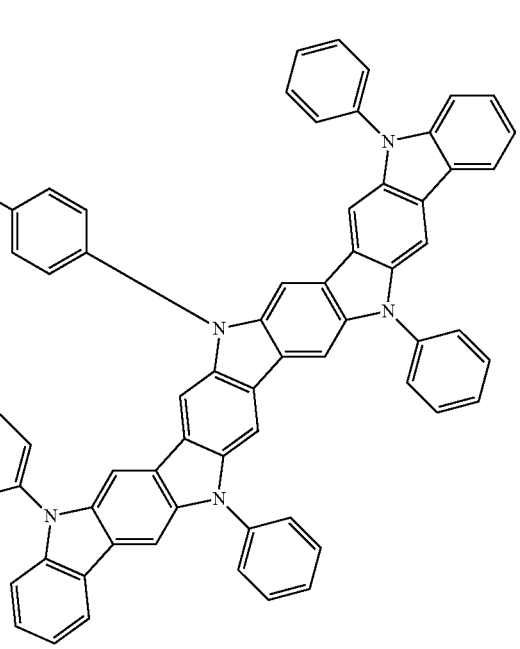
(883)
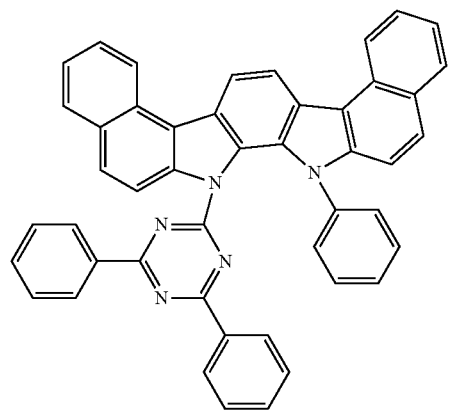
(884)
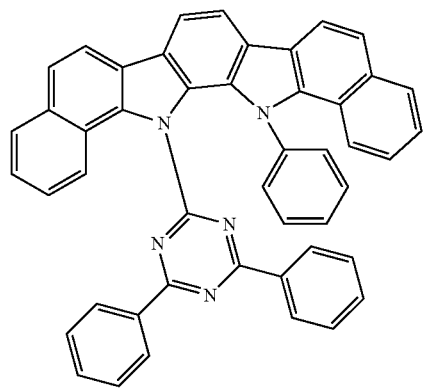
(885)
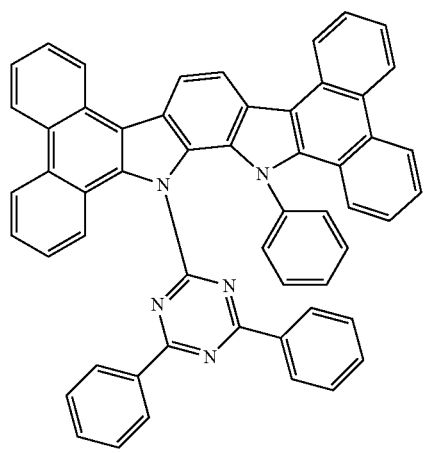
(886)
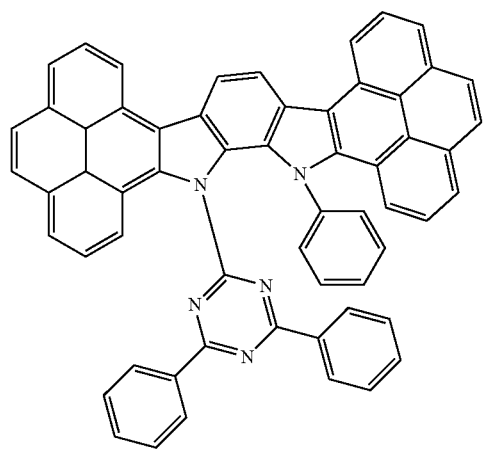

-continued
(887)
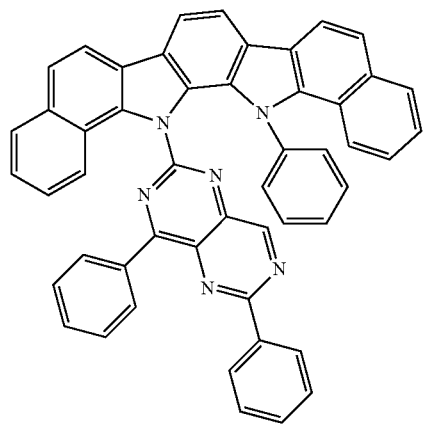
(888)
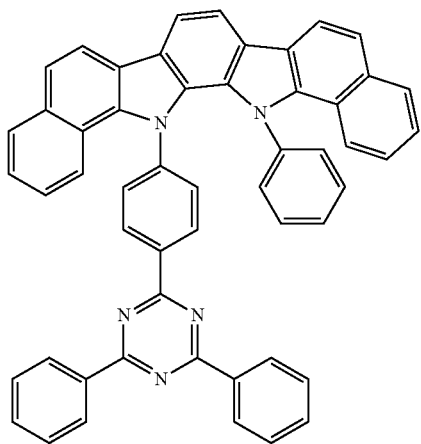
(889)
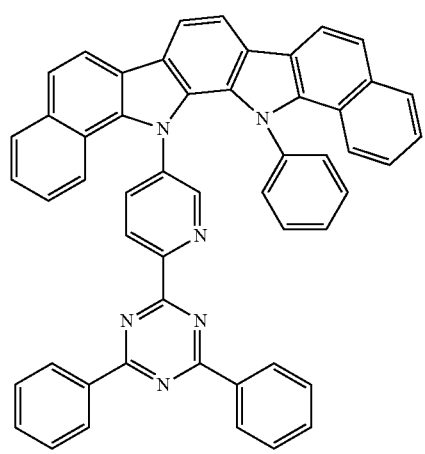
(890)
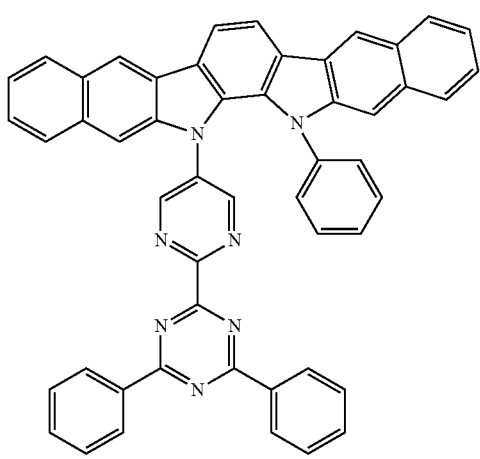
(891)
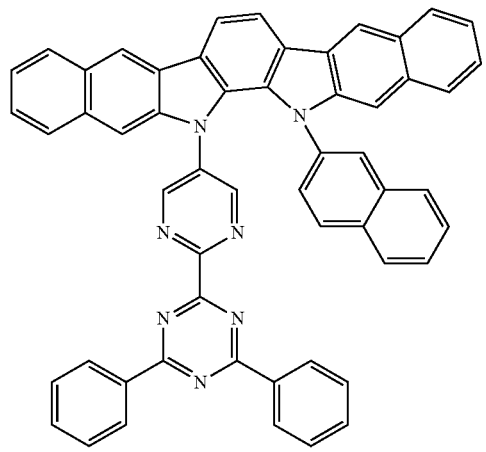
(892)
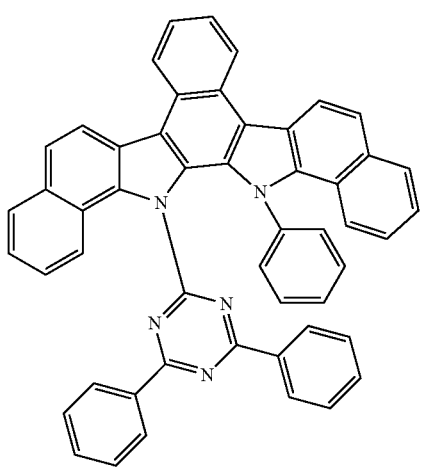

-continued
(893)
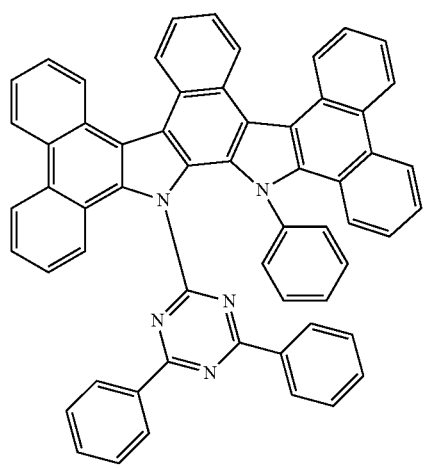
(894)
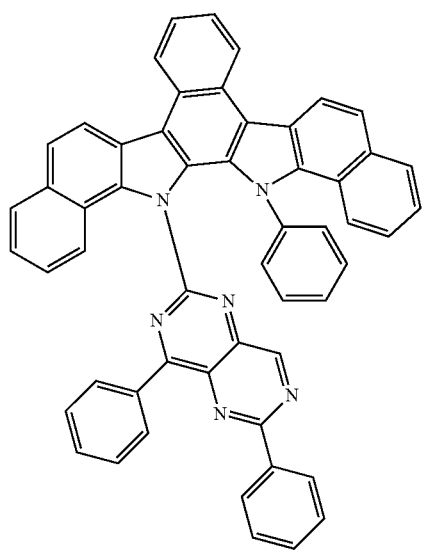
(895)
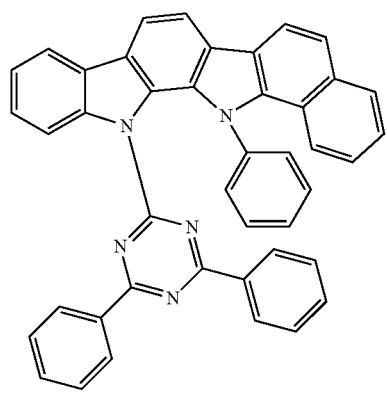
(896)
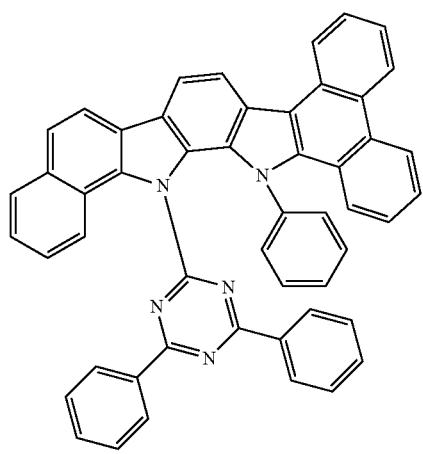
(897)
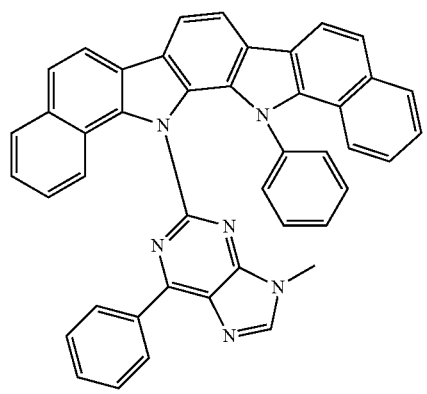
(898)
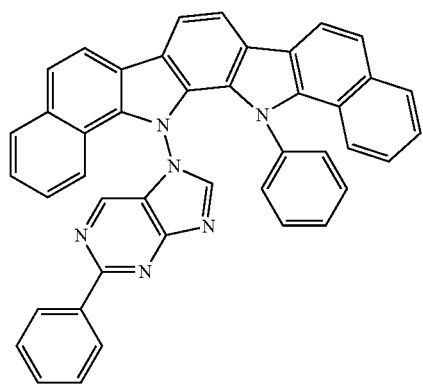

-continued
(899)
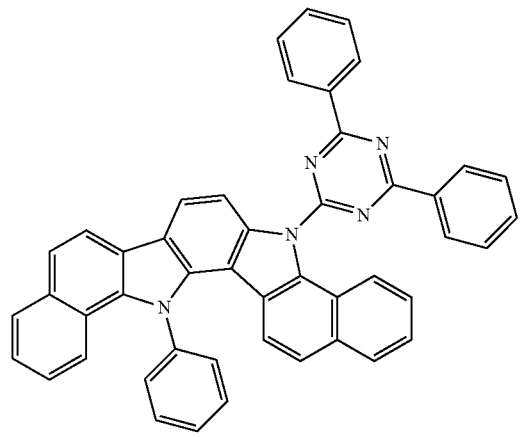
(900)
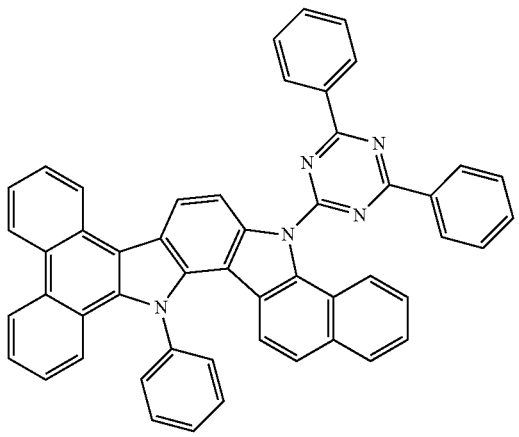
(901)
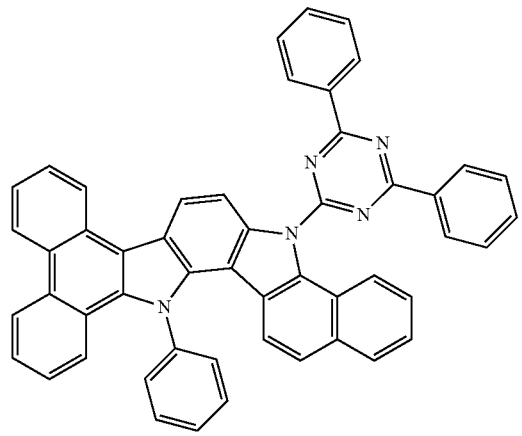
(902)
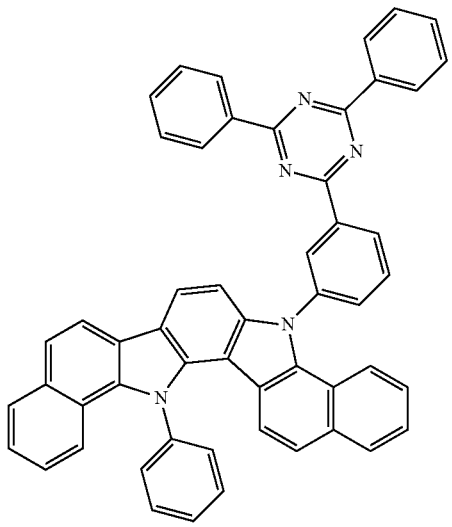
(903)
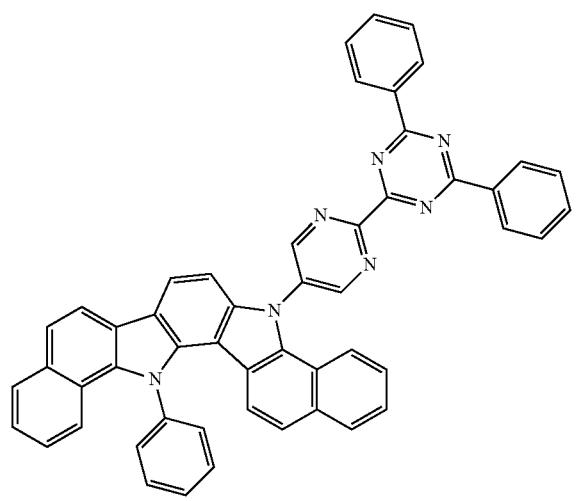
(904)
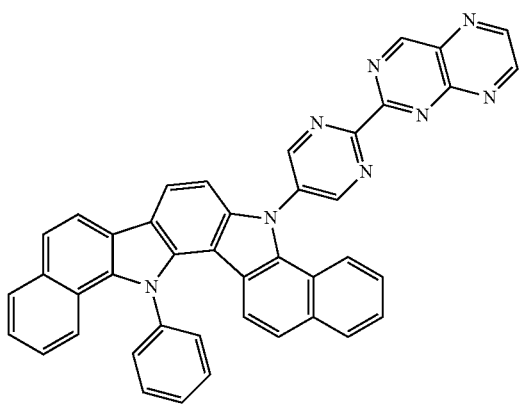

-continued
(905)
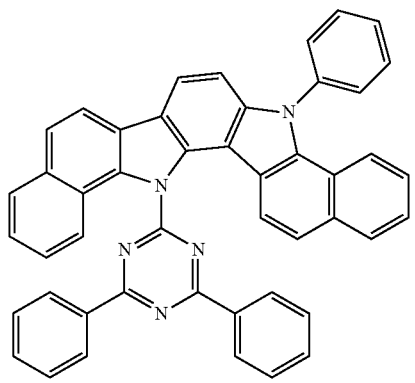
(906)
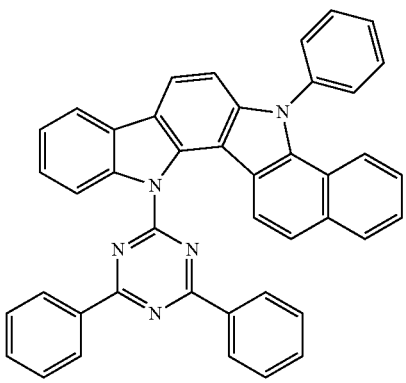
(907)
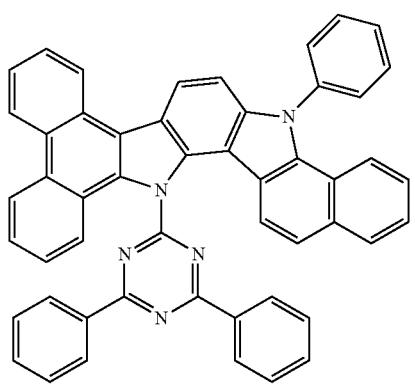
(908)
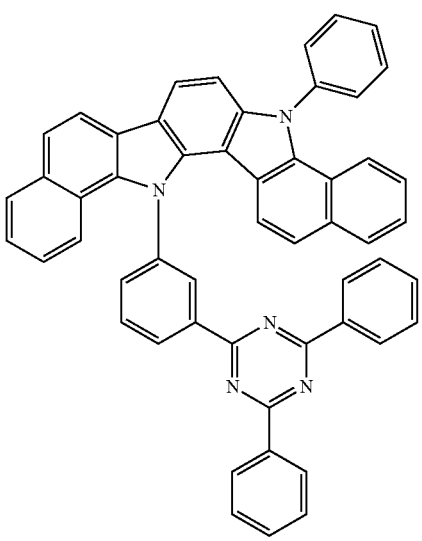
(909)
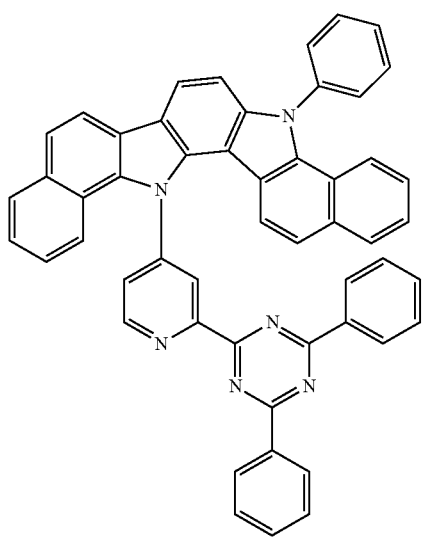
(910)
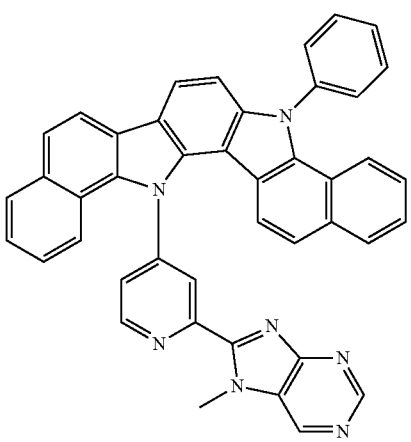

-continued
(911)
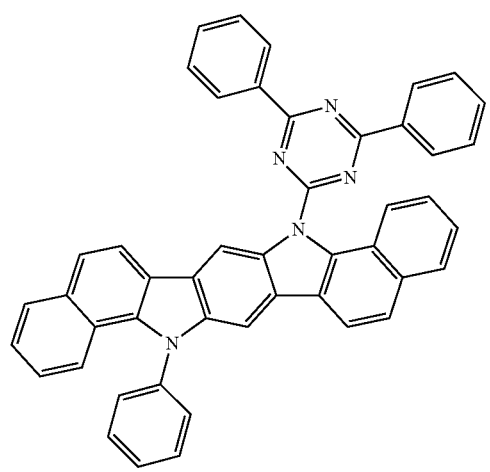
(912)
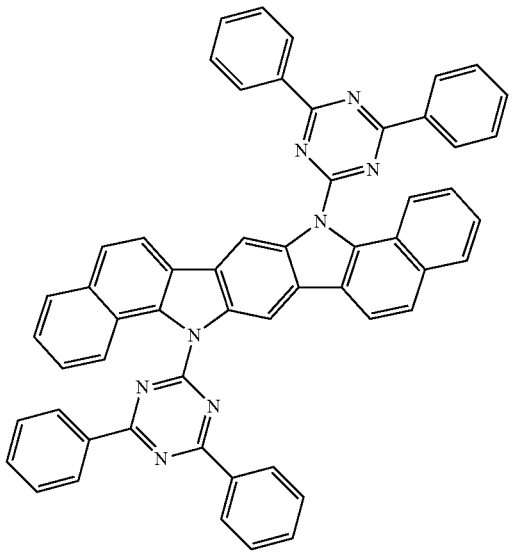
(913)
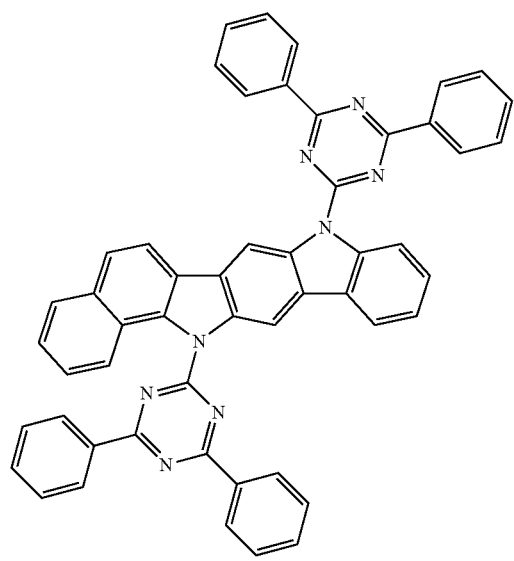
(914)
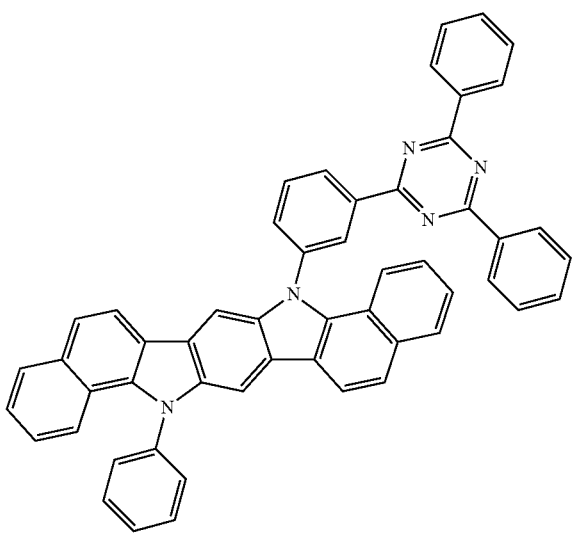

343
-continued
(915)
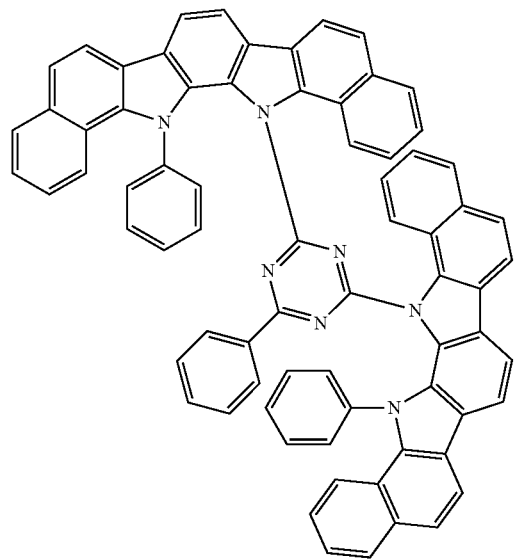
344
(916)
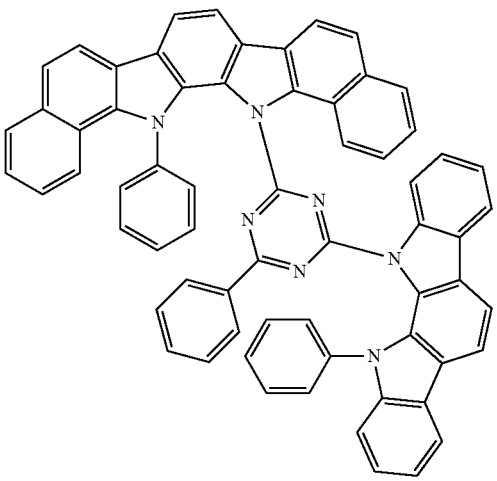
(917)
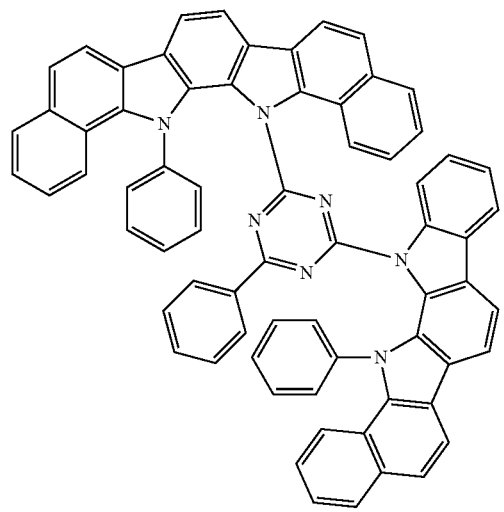
(918)
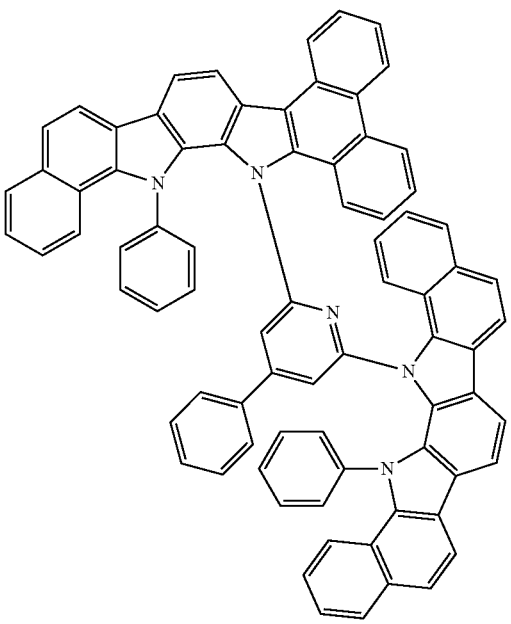

345
-continued
(919)
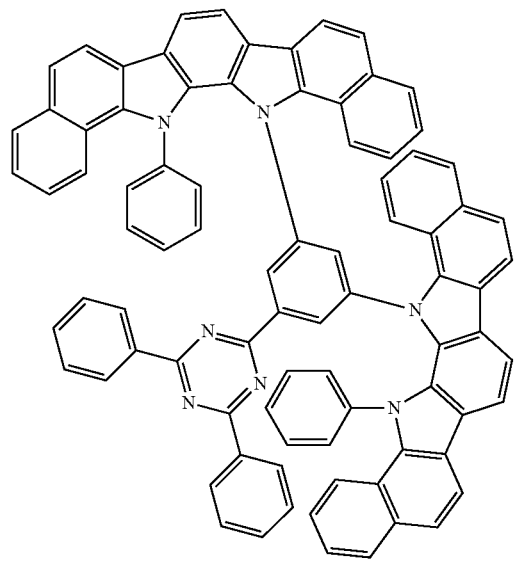
346
(920)
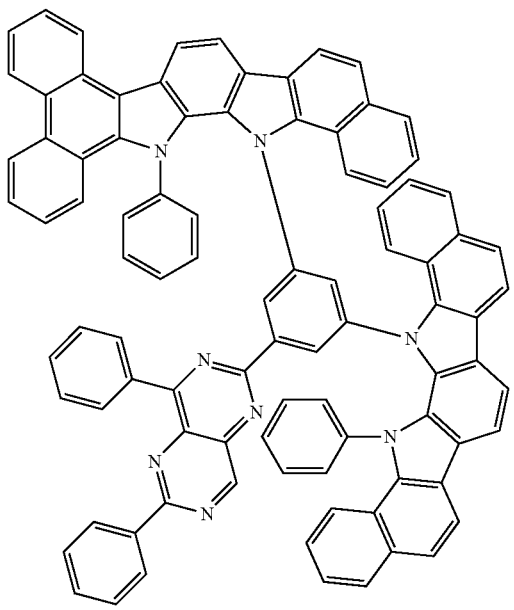
(921)
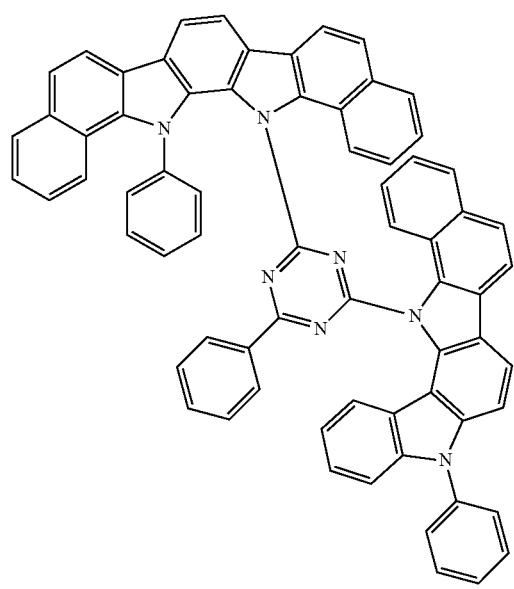
(922)
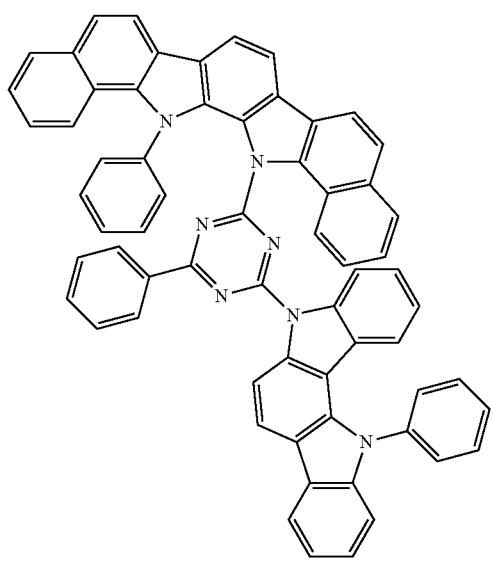

-continued
(923)
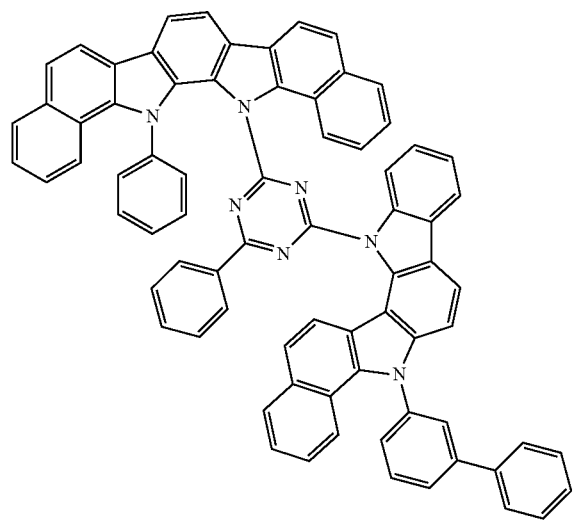
(924)
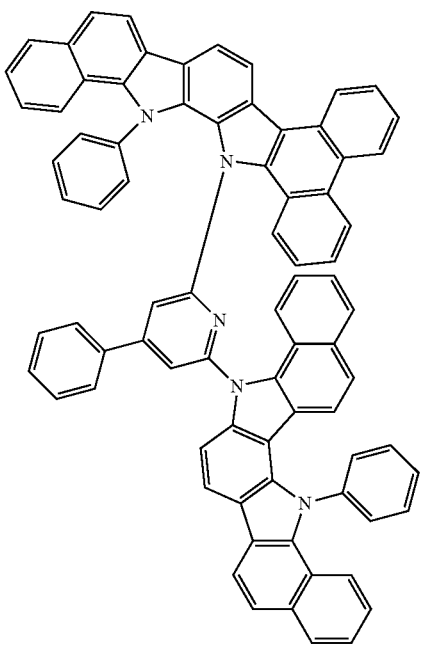
(925)
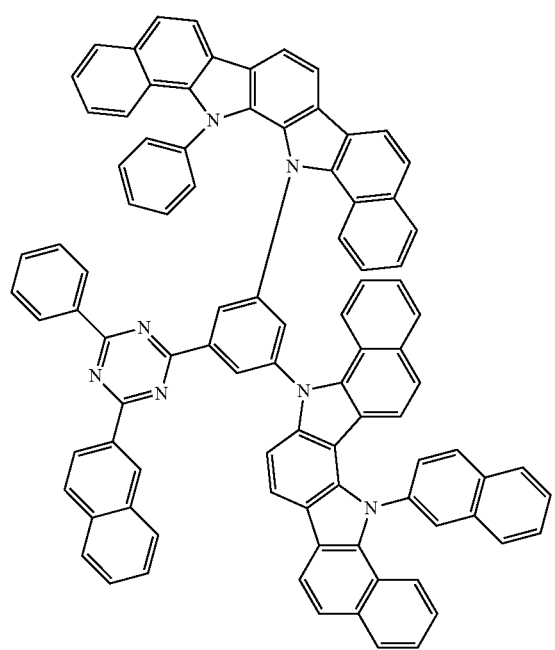
(926)
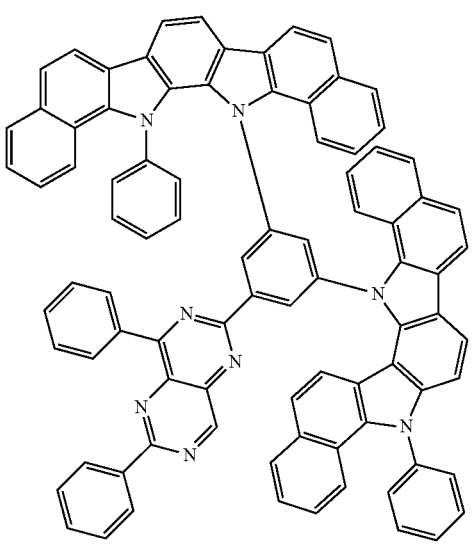

-continued
(927)
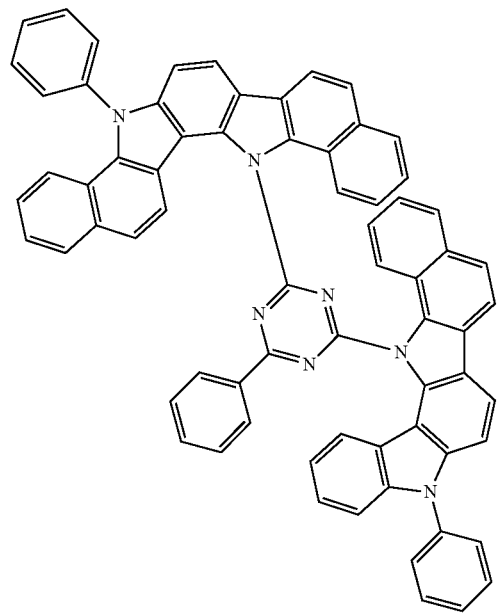
(928)
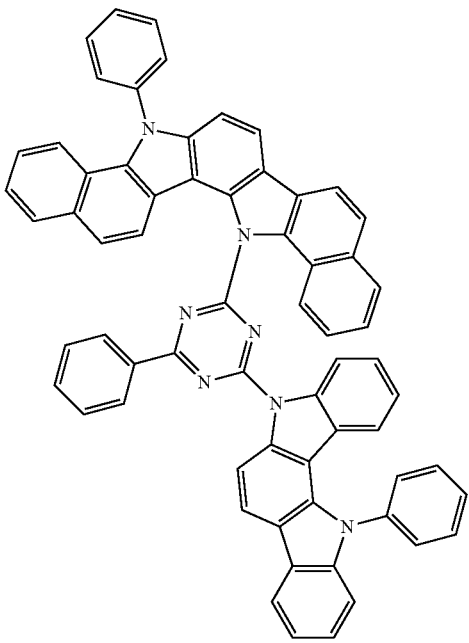
(929)
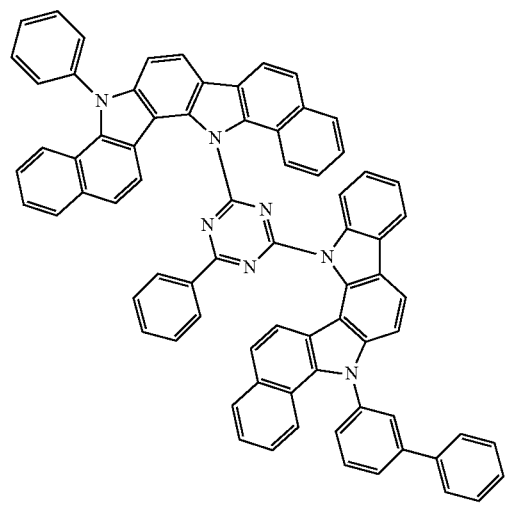
(930)
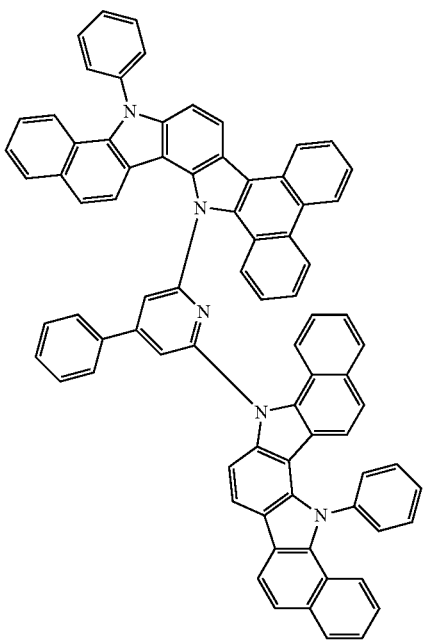

-continued
(931)
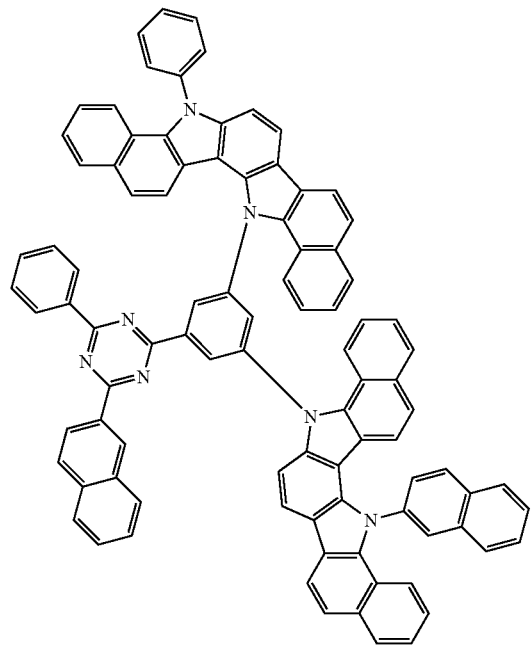
(932)
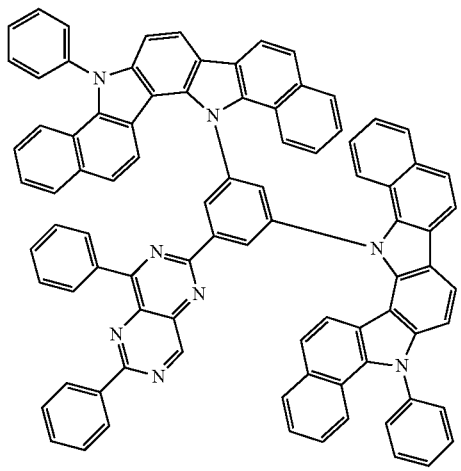
(933)
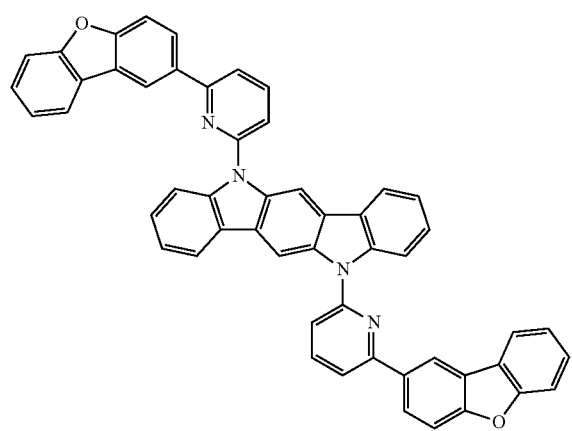
(934)
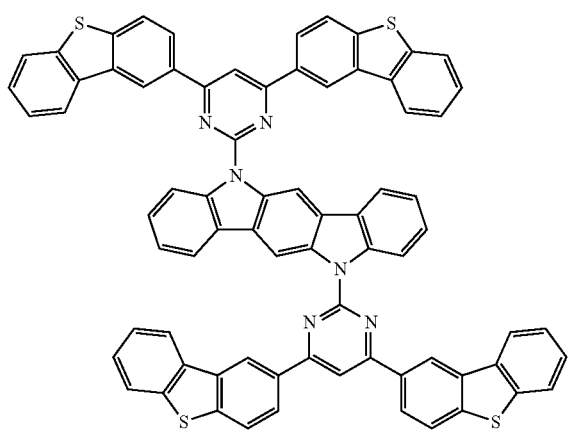

-continued
(935)
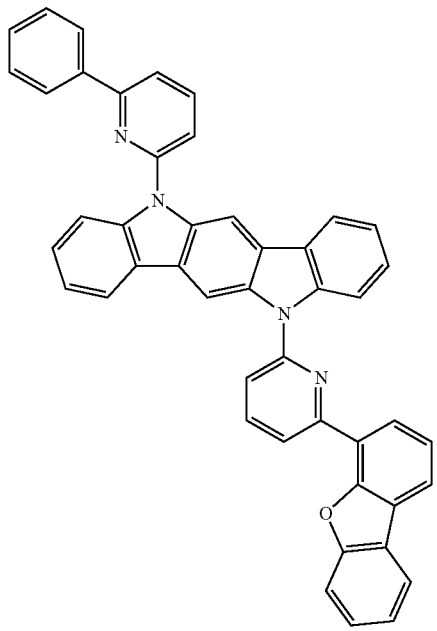
(936)
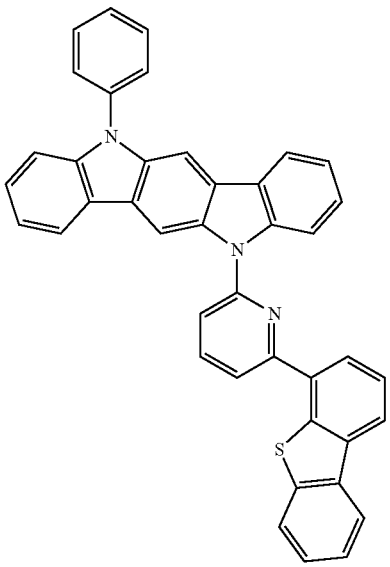
(937)
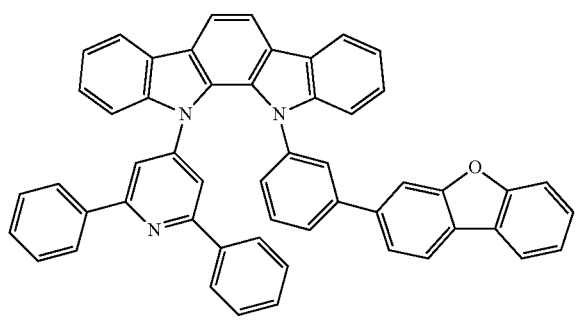
(938)
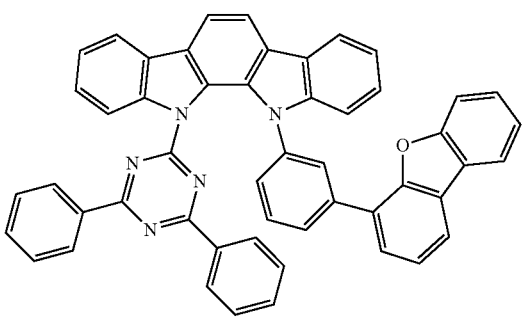
(939)
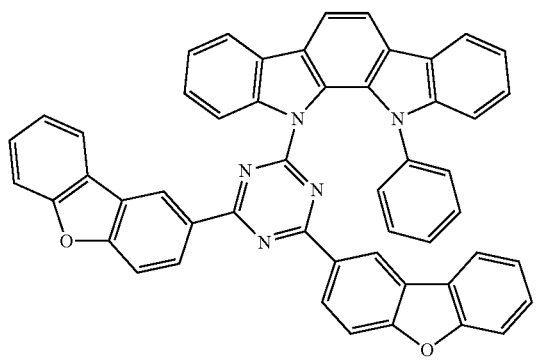
(940)
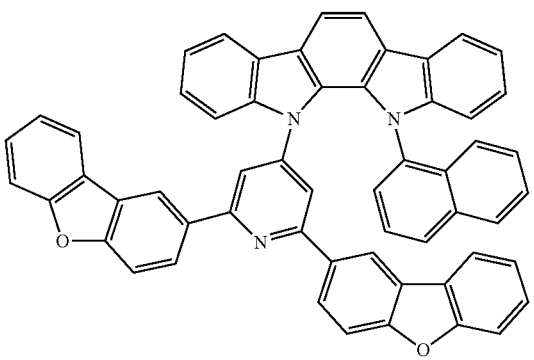
(941)
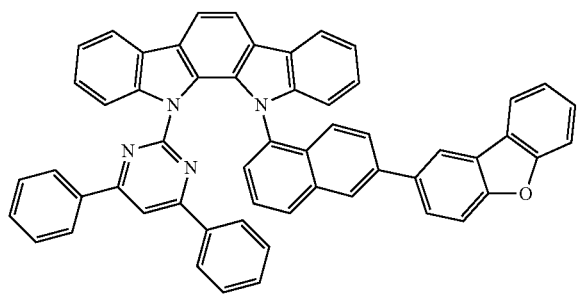
(942)
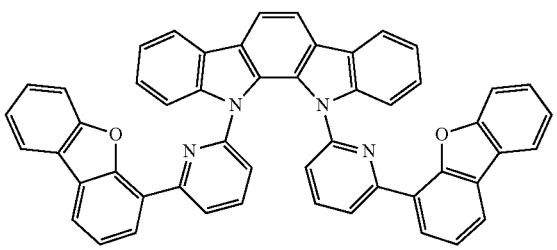

-continued
(943)
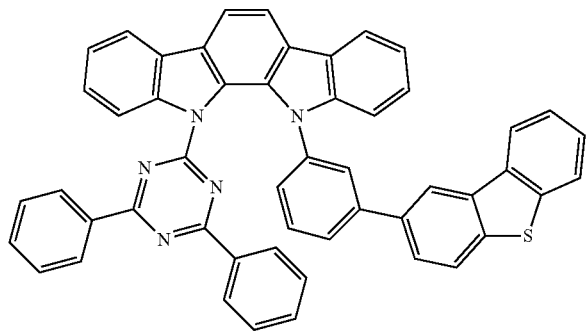
(944)
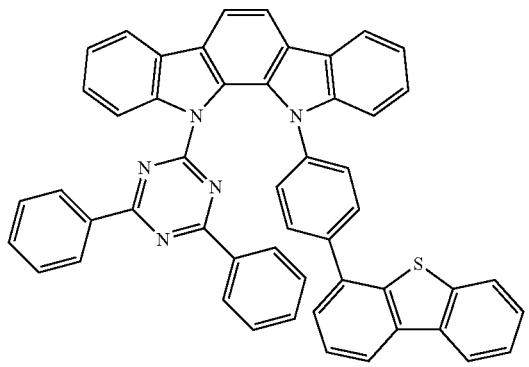
(945)
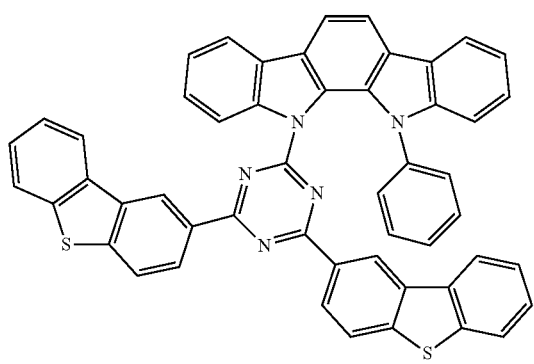
(946)
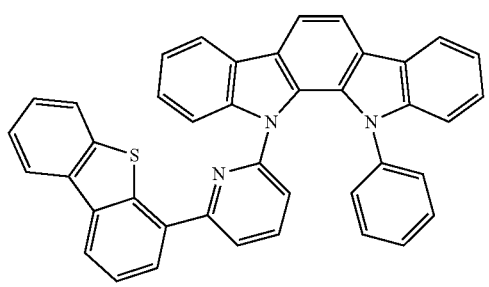
(947)
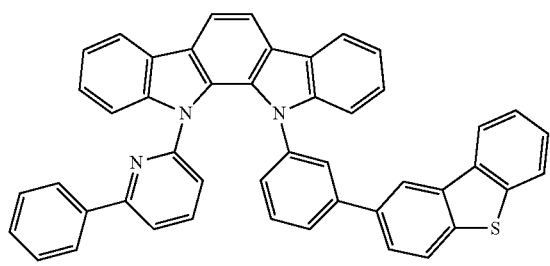
(948)
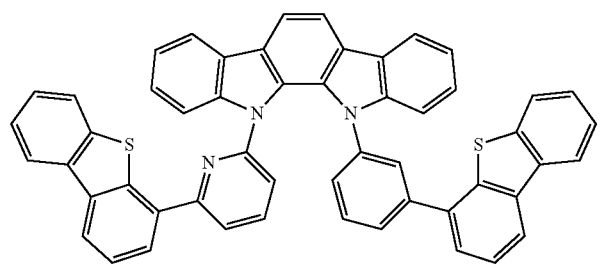
(949)
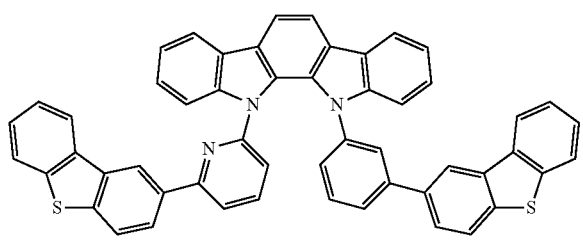
(950)
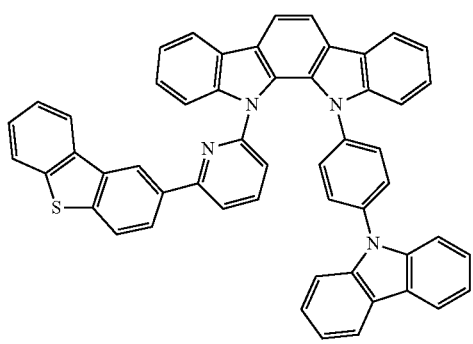

-continued
(951)
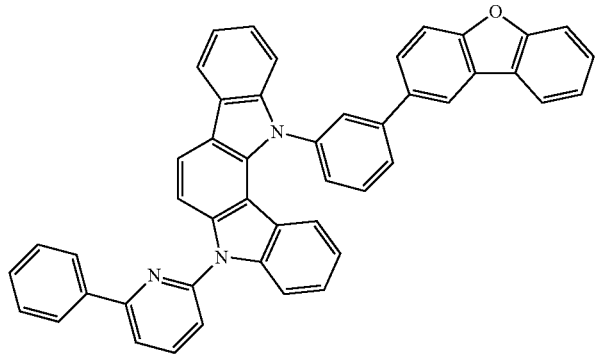
(952)
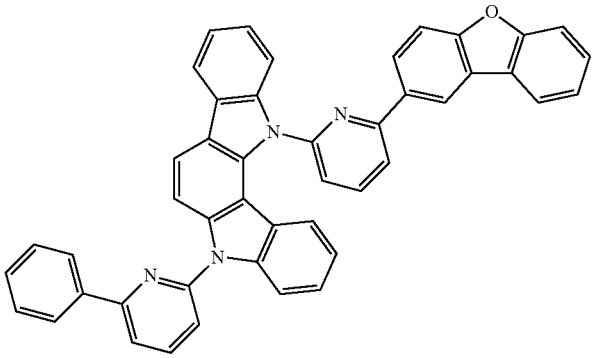
(953)
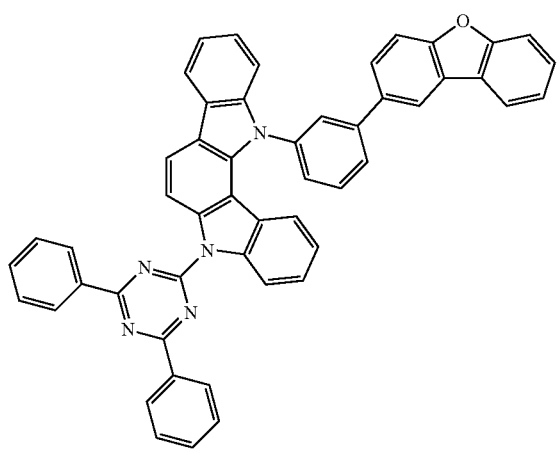
(954)
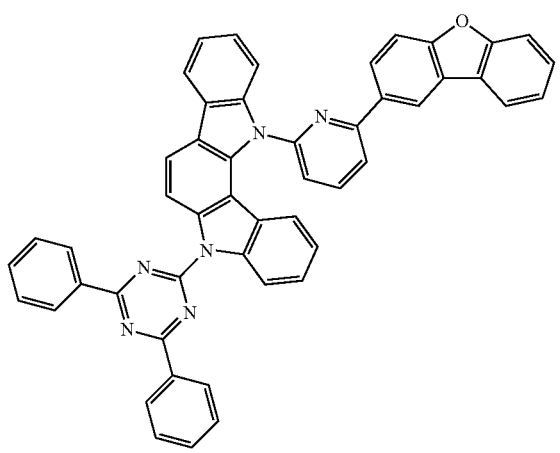
(955)
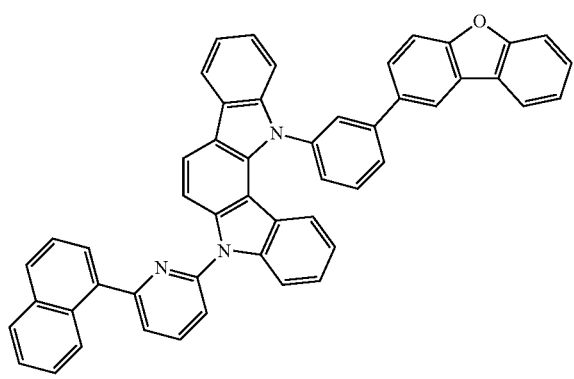
(956)
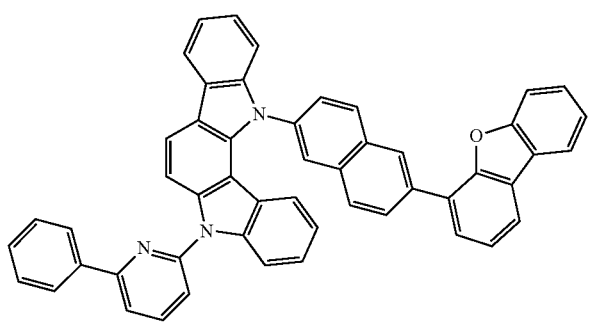
(957)
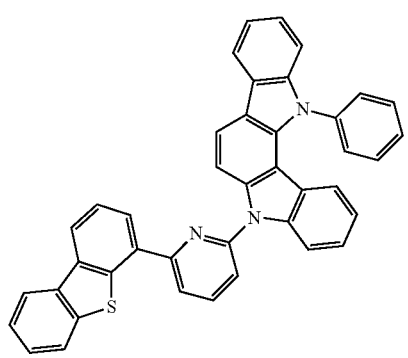
(958)
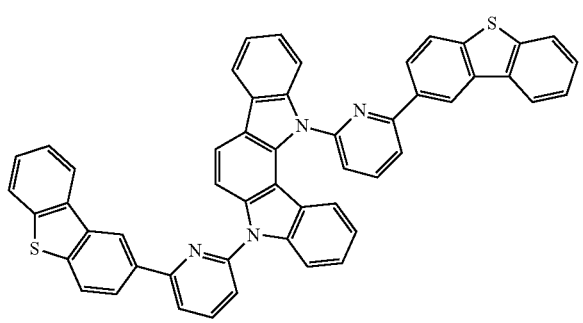

-continued
(959)
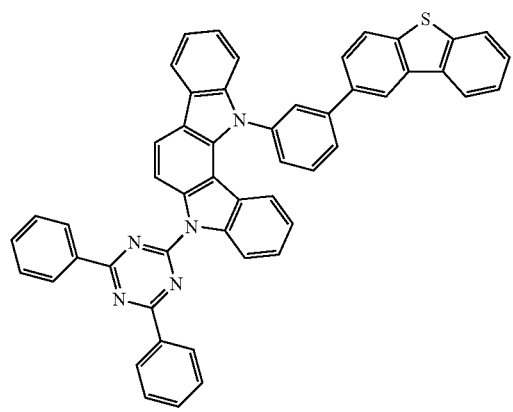
(960)
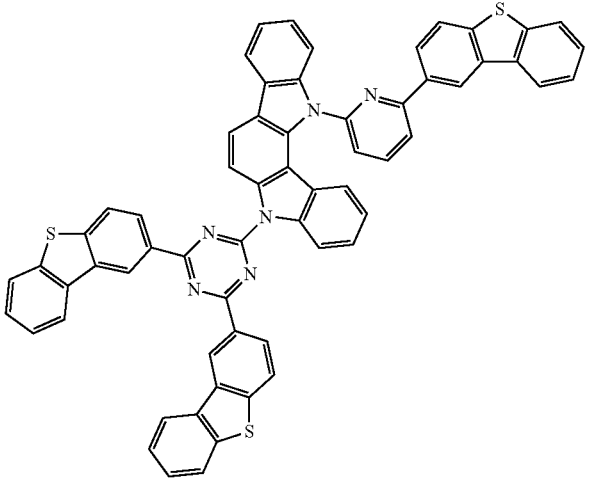
(961)
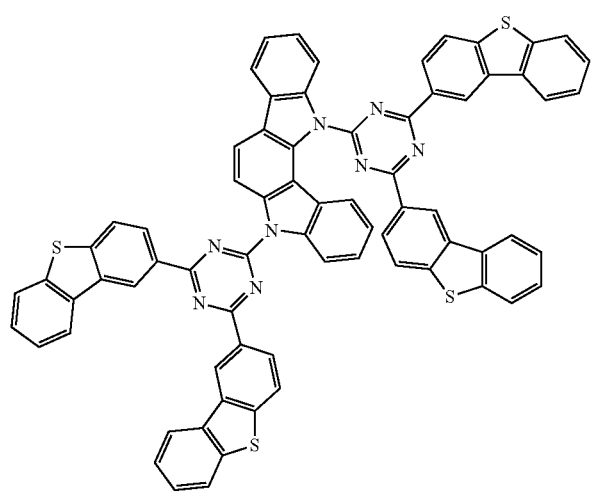
(962)
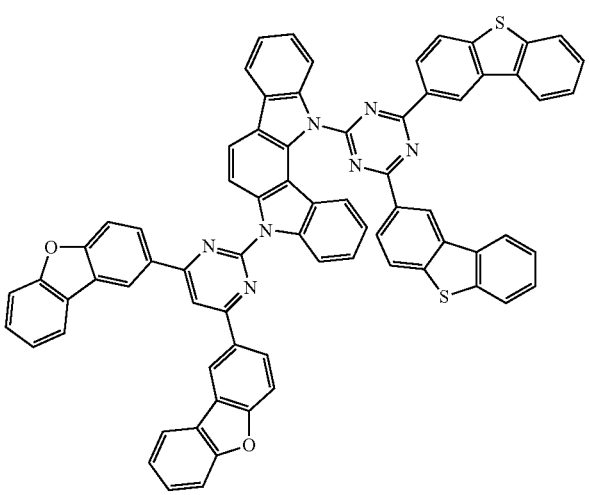
(963)
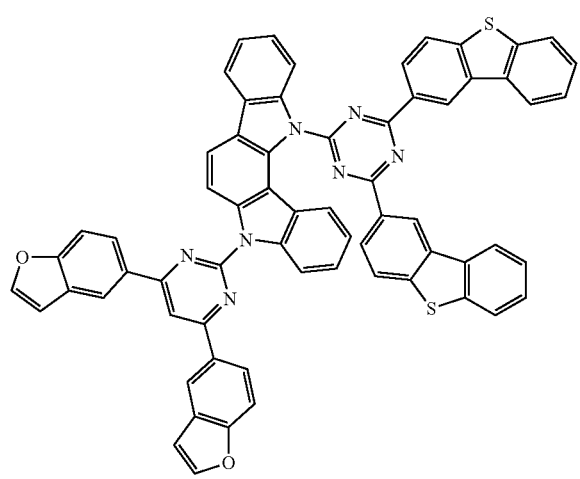
(964)
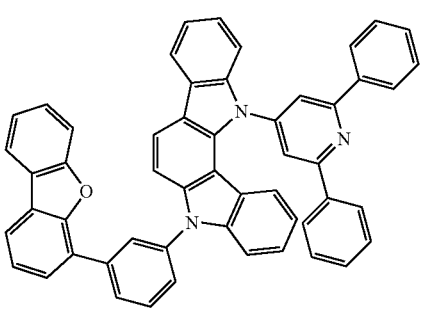

-continued
(965)
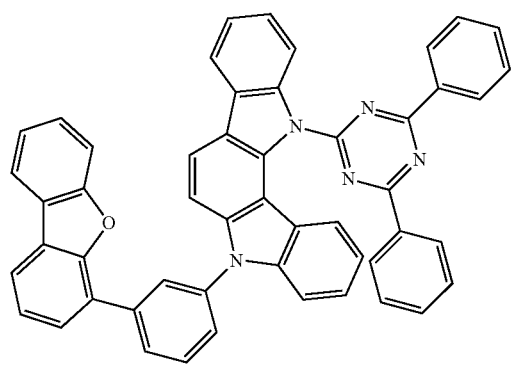
(966)
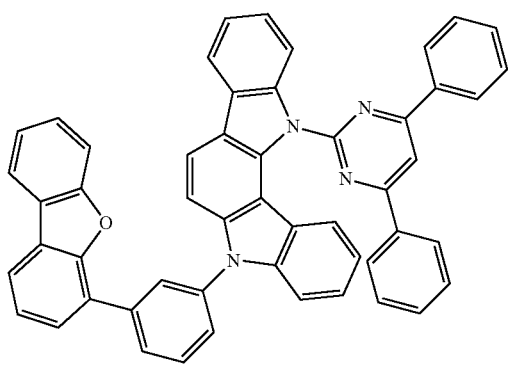
(967)
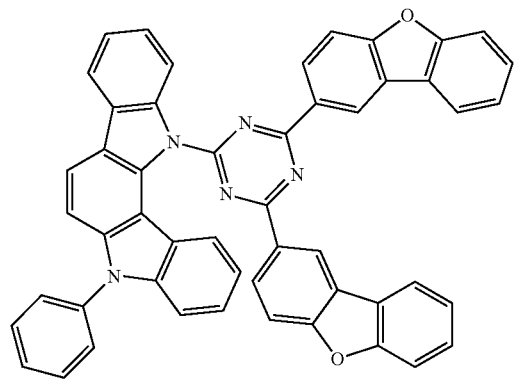
(968)
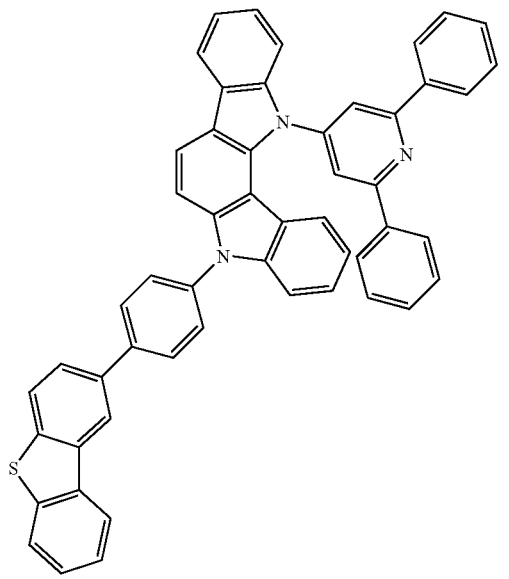
(969)
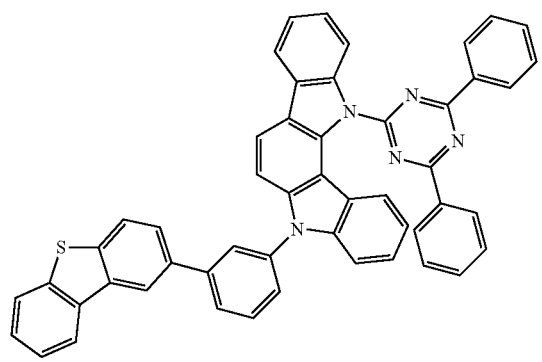
(970)
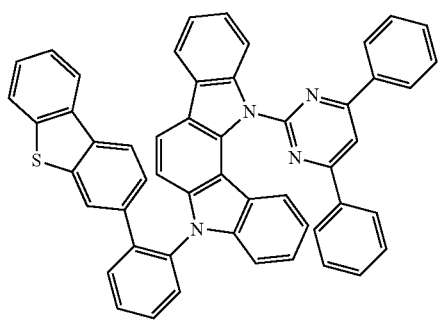

-continued
(971)
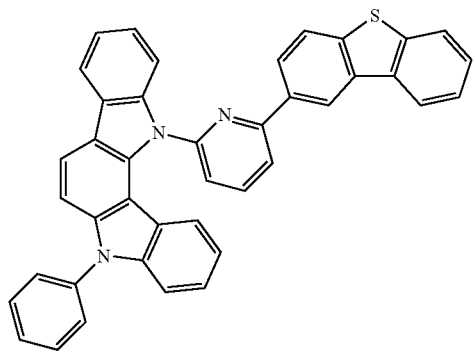
(972)
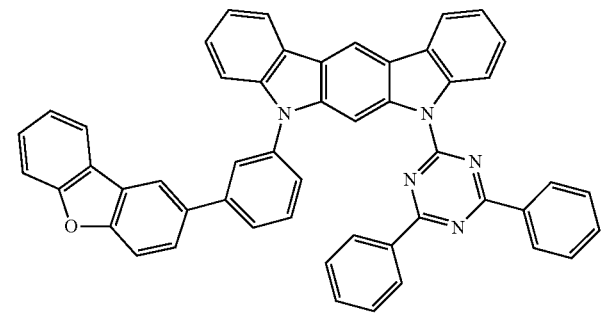
(973)
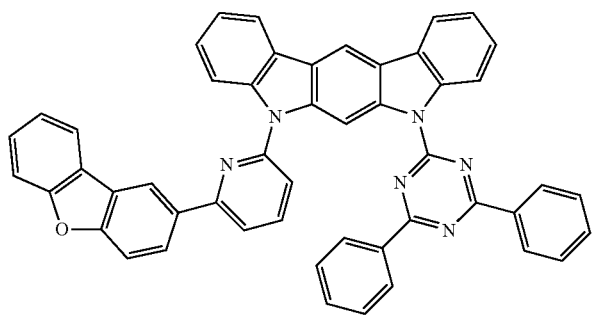
(974)
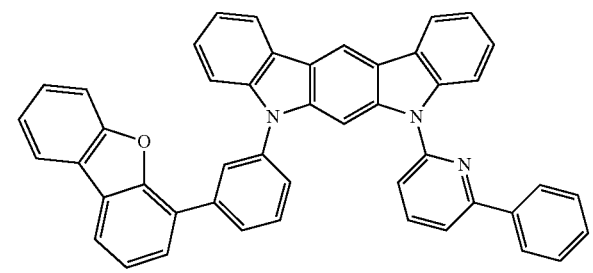
(975)
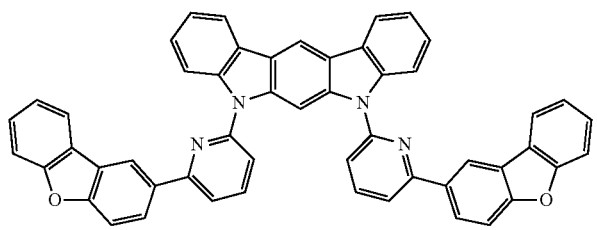
(976)
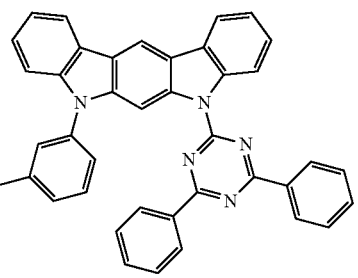
(977)
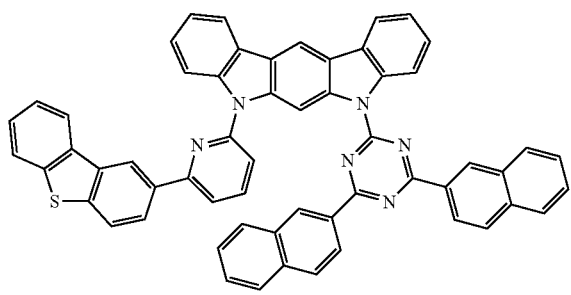
(978)
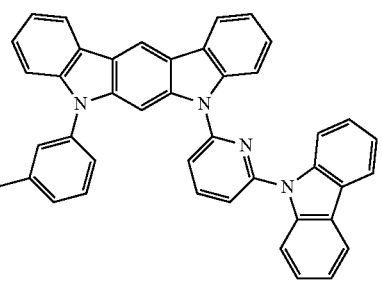
(979)
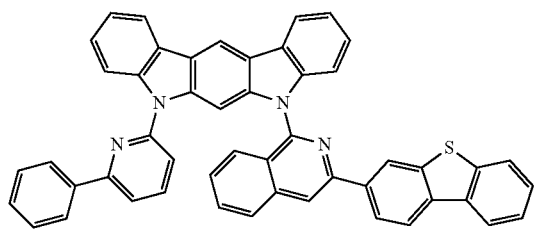
(980)
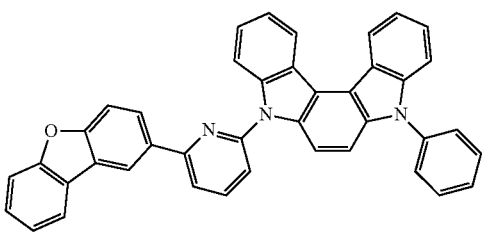

(981)
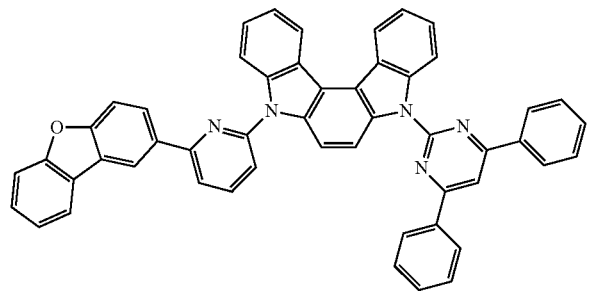

(982)
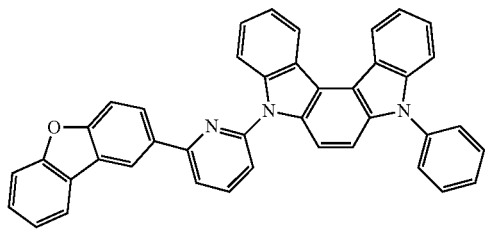

(983)
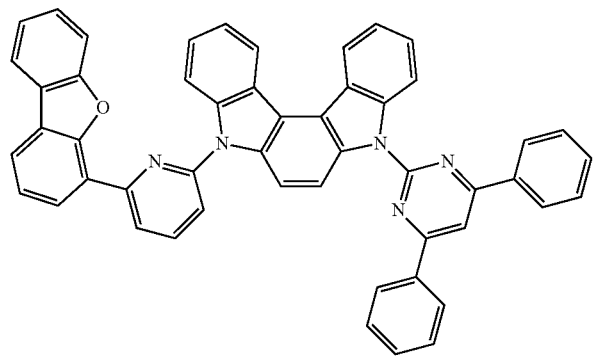

(984)
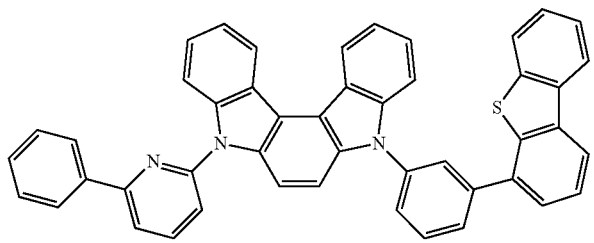

(985)
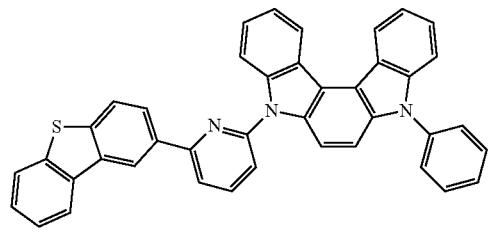

(986)
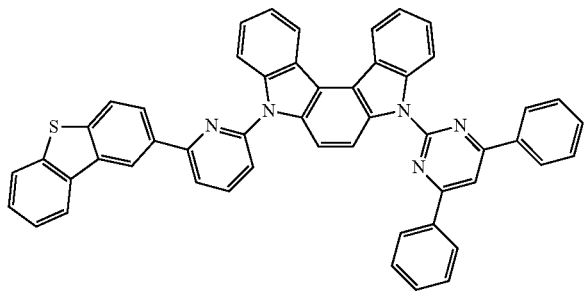

(987)
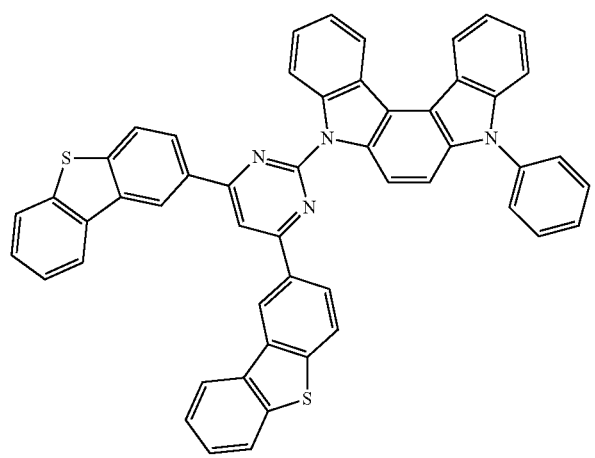

When the organic light-emitting material of the present invention is an organic light-emitting material which emits fluorescence and delayed fluorescence, the organic light-emitting material having a difference between excited singlet energy and excited triplet energy (ΔE) of 0.2 eV or less, the organic light-emitting material of the present invention may be a compound other than the compound represented by the general formula (1) but is preferably the compound represented by the general formula (1). ΔE described above is preferably 0.15 ev or less. Further, when the organic light-emitting material which emits fluorescence and delayed fluorescence of the present invention is the compound represented by the general formula (1), ΔE is not limited but preferably falls within the range described above.

The organic light-emitting material of the present invention is used as a material for an organic light-emitting element. The organic light-emitting material is incorporated into a light-emitting layer of an organic light-emitting element to provide an excellent organic light-emitting element such as an organic PL element or an organic EL element. The organic light-emitting material may be used alone in the light-emitting layer. However, as necessary, for the purpose of, for example, confining, in the organic light-emitting material, singlet excitons and triplet excitons generated in the organic light-emitting material, the organic light-emitting material of the present invention and an organic compound which has a higher value of at least any one of excited singlet energy and excited triplet energy than those of the organic light-emitting material and serves as a host material are preferably used in the light-emitting layer. At least any one of the excited singlet energy (S1h) and excited triplet energy (T1h) of the organic compound is preferably higher by 0.1 eV or more, particularly preferably higher by 0.2 eV or more than the excited singlet energy (S1g) and excited triplet energy (T1g) of the organic light-emitting material of the present invention. That is, it is preferred that one or both of (S1h)−(S1g)>0.1 eV and (T1h)−(T1g)>0.1 eV be satisfied and it is more preferred that one or both of (S1h)−(S1g)>0.2 eV and (T1h)−(T1g)>0.2 eV be satisfied.

Next, an organic light-emitting element of the present invention is described. The organic light-emitting element includes an organic PL element and an organic EL element. A structure of the organic EL element is described with reference to the drawings. However, the structure of the organic EL element of the present invention is by no means limited to one illustrated in the FIGURE.

FIG. 1 is a cross-sectional view schematically illustrating a structure example of a general organic EL element to be used in the present invention. In the FIGURE, a substrate is represented by 1, an anode is represented by 2, a hole-injecting layer is represented by 3, a hole-transporting layer is represented by 4, a light-emitting layer is represented by 5, an electron-transporting layer is represented by 6, and a cathode is represented by 7. The organic EL element of the present invention has, as essential layers, an anode, a hole-transporting layer, a light-emitting layer, and a cathode.

Further, as a structural example of an organic PL element, a construction including the substrate 1 and the light-emitting layer 5 in FIG. 1 is given as the simplest example. The description of each layer in the organic EL element may also be interpreted as the description of each layer in the organic PL element. However, the organic PL element has no electrode. Hence, layers required for both the elements are different from each other.

Further, the organic EL element of the present invention may have, as layers other than the essential layers, an electron-transporting layer, an electron-injecting layer, an electron-blocking layer, a hole-blocking layer, and an exciton element layer. In addition, the hole-transporting layer may be a hole-injecting/transporting layer having a hole-injecting function and the electron-transporting layer may be an electron-injecting/transporting layer having an electron-injecting function.

It should be noted that the organic EL element of the present invention may have an structure opposite to that illustrated in FIG. 1, that is, the cathode 7, the electron-transporting layer 6, the light-emitting layer 5, the hole-transporting layer 4, and the anode 2 may be laminated on the substrate 1 in the stated order. Also in this case, a layer may be added or omitted, as necessary.

Hereinafter, the respective members and the respective layers of the organic EL element are described.

—Substrate—

The organic EL element of the present invention is preferably supported by a substrate. The substrate is not particularly limited and may be any substrate which is conventionally used in an organic EL element. For example, a substrate formed of glass, transparent plastic, quartz, or the like may be used.

—Anode—

Preferably used as the anode in the organic EL element is one using, as an electrode substance, any of a metal, an alloy, an electrically conductive compound, and a mixture thereof with a high work function (4 eV or more). Specific examples of such electrode substance include metals such as Au and conductive transparent materials such as CuI, indium tin oxide (ITO), $SnO_2$, and ZnO. Further, a material capable of producing an amorphous transparent conductive film such as IDIXO ($In_2O_3$—ZnO) may be used. In the production of the anode, it is possible to form any of those electrode substances into a thin film by a method such as vapor deposition or sputtering, and then form a pattern having a desired shape by a photolithographic method. Alternatively, in the case of not requiring high pattern accuracy (about 100 μm or more), it is also possible to form a pattern via a mask having a desired shape during the vapor deposition or sputtering of any of the electrode substances. Alternatively, in the case of using a coatable substance such as an organic conductive compound, it is also possible to employ a wet film-forming method of a printing mode, a coating mode, or the like. When emitted light is extracted from the anode, the transmittance is desirably set to more than 10%, and the sheet resistance as the anode is preferably several hundred Ω/□ or less. In addition, the film thickness, which varies depending on materials, is selected in the range of generally 10 to 1,000 nm, preferably 10 to 200 nm.

—Cathode—

Meanwhile, used as the cathode is one using, as an electrode substance, any of a metal (referred to as electron-injecting metal), an alloy, an electrically conductive compound, and a mixture thereof with a low work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, from the viewpoints of electron-injecting property and durability against oxidation and the like, a mixture of an electron-injecting metal and a second metal, which has a work function value higher than that of the electron-injecting metal and is a stable metal, such as a magnesium/silver mixture, a magnesium/aluminum mixture, a magnesium/indium mixture, an aluminum/aluminum oxide ($Al_2O_3$) mixture, a lithium/aluminum mixture, or aluminum is suitable. The cathode may be produced by forming any of those electrode substances into a thin film by a method such as vapor deposition or sputtering. Further, the sheet resistance as the cathode is preferably several hundred Ω/□ or less, and the film thickness is selected in the range of generally 10 nm to 5 μm, preferably 50 to 200 nm. It should be noted that a case where any one of the anode and the cathode of the organic EL element is transparent or translucent in order to transmit emitted light is advantageous because light emission luminance is improved.

Further, when the conductive transparent material given in the description about the anode is used for the cathode, a transparent or translucent cathode may be produced. The application of this technique allows the production of an element in which both of the anode and the cathode each have transparency.

—Light-emitting Layer—

The light-emitting layer is a layer which emits light after excitons have been generated through the recombination of holes and electrons injected respectively from an anode and a cathode. The light-emitting layer may be formed through the use of an organic light-emitting material alone but preferably includes an organic light-emitting material and a host material. As the organic light-emitting material, there may be used one kind or two or more kinds selected from the organic light-emitting materials of the present invention. In order that each of the organic EL element and organic PL element of the present invention exhibits high luminous efficiency, it is important to confine, in the organic light-emitting material, singlet excitons and triplet excitons generated in the organic light-emitting material. Accordingly, it is preferred to use the host material in addition to the organic light-emitting material in the light-emitting layer. As the host material, there may be used an organic compound having a higher value of at least any one of excited singlet energy and excited triplet energy than those of the organic light-emitting material of the present invention. This allows singlet excitons and triplet excitons generated in the organic light-emitting material of the present invention to be confined in the molecule of the organic light-emitting material of the present invention and allows the luminous efficiency to be exhibited sufficiently. In the organic light-emitting element or organic EL element of the present invention, light is emitted from the organic light-emitting material of the present invention included in the light-emitting layer. The light emission includes both of fluorescence emission and delayed fluorescence emission. In this regard, however, part of the light emission may be derived from the host material.

In the case of using the host material, it is recommended that the content of the organic light-emitting material of the present invention in the light-emitting layer fall within the range of 1 to 50 wt %, preferably 1 to 20 wt %.

The host material in the light-emitting layer is preferably an organic compound which has a hole-transporting ability and an electron-transporting ability, prevents an emission wavelength from becoming longer, and has a high glass transition temperature.

—Injecting Layer—

The injecting layer refers to a layer to be provided between an electrode and an organic layer for the purposes of reducing a driving voltage and improving a light emission luminance. The injecting layer includes a hole-injecting layer and an electron-injecting layer, and may be provided between the anode and the light-emitting layer or the hole-transporting layer, and between the cathode and the light-emitting layer or the electron-transporting layer. The injecting layer may be provided as necessary.

—Blocking Layer—

The blocking layer is capable of blocking charges (electrons or holes) and/or excitons present in the light-emitting layer from diffusing to the outside of the light-emitting layer. The electron-blocking layer may be arranged between the light-emitting layer and the hole-transporting layer, and blocks electrons from passing through the light-emitting layer toward the hole-transporting layer. Similarly, the hole-blocking layer may be arranged between the light-emitting layer and the electron-transporting layer, and blocks holes from passing through the light-emitting layer toward the electron-transporting layer. The blocking layer may also be used for blocking excitons from diffusing to the outside of the light-emitting layer. That is, the electron-blocking layer and the hole-blocking layer may each have a function of an exciton-blocking layer as well. The electron-blocking layer or exciton-blocking layer as used herein is meant to include a layer having a function of an electron-blocking layer and an exciton-blocking layer in one layer.

—Hole-blocking Layer—

The hole-blocking layer has a function of the electron-transporting layer in a broad sense. The hole-blocking layer has a role in blocking holes from reaching the electron-transporting layer while transporting electrons. This can improve the probability of recombination of electrons and holes in the light-emitting layer. As a material for the hole-blocking layer, a material for the electron-transporting layer to be described below may be used as necessary.

—Electron-blocking Layer—

The electron-blocking layer has a function of transporting holes in a broad sense. The electron-blocking layer has a role in blocking electrons from reaching the hole-transporting layer while transporting holes. This can improve the probability of recombination of electrons and holes in the light-emitting layer.

—Exciton-blocking Layer—

The exciton-blocking layer refers to a layer for blocking excitons, which are generated by the recombination of holes and electrons in the light-emitting layer, from diffusing to a charge-transporting layer. The insertion of this layer allows excitons to be efficiently confined in the light-emitting layer, which can improve the luminous efficiency of an element. The exciton-blocking layer may be inserted on any of the anode side and the cathode side of the adjacent light-emitting layer, and may be simultaneously inserted on both of the sides. That is, when the exciton-blocking layer is provided on the anode side, the layer may be inserted between the hole-transporting layer and the light-emitting layer so as to be adjacent to the light-emitting layer. When the exciton-blocking layer is inserted on the cathode side, the layer may be inserted between the light-emitting layer and the cathode so as to be adjacent to the light-emitting layer. Further, the hole-injecting layer, the electron-blocking layer, and the like may be provided between the anode and the exciton-blocking layer adjacent to the anode side of the light-emitting layer, and the electron-injecting layer, the electron-transporting layer, the hole-blocking layer, and the like may be provided between the cathode and the exciton-blocking layer adjacent to the cathode side of the light-emitting layer. In the case of providing the blocking layer, it is preferred that at least any one of the excited singlet energy and excited triplet energy of a material to be used as the blocking layer be higher than the excited singlet energy and excited triplet energy of a light-emitting material.

—Hole-transporting Layer—

The hole-transporting layer is formed of a hole-transporting material having a function of transporting holes. The hole-transporting layer may be provided in a single layer or a plurality of layers.

The hole-transporting material has any of hole-injecting or -transporting property and electron-blocking property, and may be an organic material or an inorganic material. An applicable known hole-transporting material is exemplified by a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, or a conducting polymeric oligomer, particularly a thiophene oligomer. However, preferably used are a porphyrin compound, an aromatic tertiary amine compound, and a styrylamine compound, and more preferably used is an aromatic tertiary amine compound.

—Electron-transporting Layer—

The electron-transporting layer is formed of a material having a function of transporting electrons. The electron-transporting layer may be provided in a single layer or a plurality of layers.

An electron-transporting material (may also serve as a hole-blocking material) has only to have a function of transporting electrons, which are injected from the cathode, to the light-emitting layer. An applicable electron-transporting layer is exemplified by a nitro-substituted fluorene derivative, a diphenylquinone derivative, a thiopyran dioxide derivative, carbodiimide, a fluorenylidenemethane derivative, an anthraquinodimethane derivative, an anthrone derivative, or an oxadiazole derivative. In addition, in oxadiazole derivative, a thiadiazole derivative in which an oxygen atom of an oxadiazole ring is substituted by a sulfur atom, or a quinoxaline derivative having a quinoxaline ring known as an electron-withdrawing group may also be used as the electron-transporting material. In addition, a polymer material obtained by introducing any of those materials into a polymer chain, or a polymer material including any of those materials in a polymer main chain may also be used.

The organic EL element produced by the above-mentioned method emits light when an electric field is applied between an anode and a cathode of the resultant element. At this time, in the case of light emission based on excited singlet energy, lights having different wavelengths depending on the energy levels are observed as fluorescence emission and delayed fluorescence emission. Further, in the case of light emission based on excited triplet energy, a wavelength depending on the energy level is observed as phosphorescence. As for fluorescence, when general fluorescence emission occurs, the emission lifetime is 2 µS or less, whereas when delayed fluorescence emission occurs, an emission lifetime of more than 2 µS is observed as the emission lifetime. Thus, both the fluorescence emissions are distinguishable from each other.

On the other hand, as for phosphorescence, it is almost impossible to observe the phosphorescence at room temperature because the excited triplet energy of a general organic compound like the compound of the present invention is so unstable as to be converted to heat and the like and has so short lifetime as to be immediately inactivated. The excited triplet energy of the general organic compound may be measured by observing light emission under an extremely low temperature condition.

The organic EL element of the present invention may be applied to any of a single element, an element formed of a structure with arrangement in an array fashion, and a structure in which an anode and a cathode are arranged in an X-Y matrix fashion. According to the present invention, there is provided an element having significantly improved luminous efficiency as compared to a conventional element using light emission from a singlet state by incorporating the organic light-emitting material having a specific skeleton of the present invention into the light-emitting layer. The element can exhibit excellent performance when being applied to a full-color or multi-color panel. The element may also be utilized in a backlight, lighting, and the like.

EXAMPLES

Hereinafter, the present invention is described in more detail by way of examples. However, it should be understood that the present invention is by no means limited to these examples and can be carried out in various forms without departing from the gist of the present invention. It should be noted that compound numbers correspond to numbers attached to the above-mentioned chemical formulae. Further, Example in which an example number is followed by (R) means Reference Example or Comparative Example.

Synthetic Example 1

Synthesis of Compound (11)

33.3 g (297.0 mmol) of 1,2-cyclohexanedione and 86.0 g (594.7 mmol) of phenylhydrazine hydrochloride were loaded into a 2,000-ml three-necked flask subjected to degassing and nitrogen purging, 1,000 ml of ethanol were added thereto, and the mixture was stirred. After that, 3.0 g (30.6 mmol) of concentrated sulfuric acid were added dropwise to the flask over 5 minutes and the mixture was then heated to 65° C. and stirred for 4 hours. The resultant mixture was cooled to room temperature and the precipitated purple-brown crystal was then collected by filtration. The crystal collected by filtration was washed by reslurrying twice with 500 ml of ethanol. The resultant was dried under reduced pressure to afford 80.0 g (280.5 mmol, 96.3% yield) of a purple-brown powder.

Next, 72.0 g (261.5 mmol) of the purple-brown powder described above were loaded into a 1,000-ml three-necked flask, 720 g of acetic acid and 72.0 g of trifluoroacetic acid were added thereto, and the mixture was stirred. After that, the mixture was heated to 100° C. and stirred for 15 hours. The resultant mixture was cooled to room temperature and the precipitated yellow crystal was then collected by filtration. After that, the crystal collected by filtration was rinsed with 200 ml of acetic acid and then rinsed with 200 ml of hexane. The resultant was dried under reduced pressure to afford 28.0 g (109.4 mmol, 41.8% yield) of a white powder.

Next, 26.0 g (101.4 mmol) of the white powder obtained above, 122.7 g (601.4 mmol) of iodobenzene, 54.7 g (287.2 mmol) of copper iodide, and 66.7 g (482.6 mmol) of potassium carbonate were loaded into a 2,000-ml three-necked flask subjected to degassing and nitrogen purging, 800 ml of quinoline were added thereto, and the mixture was stirred. After that, the mixture was heated to 190° C. and stirred for 72 hours. The resultant mixture was cooled once to room temperature, 500 ml of water and 500 ml of dichloromethane were then added thereto, and the mixture was stirred. The precipitated yellow crystal was then collected by filtration. The filtrate was transferred to a 2,000-ml separating funnel and separated into an organic layer and an aqueous layer. The organic layer was washed three times with 500 ml of water. After that, the resultant organic layer was dried over magnesium sulfate. The magnesium sulfate was separated by filtration once and the solvent was then distilled off under reduced pressure. The residue was then purified by column chromatography to afford 12.7 g (38.3 mmol, 37.8% yield) of a white solid.

Next, 2.16 g (49.5 mmol) of 55% sodium hydride were loaded into a 500-ml three-necked flask subjected to degassing and nitrogen purging, 70 ml of dry N,N-dimethylformamide (DMF) were added thereto, and the mixture was stirred under a nitrogen stream. A solution of 12.7 g (38.3 mmol) of the white powder obtained above in 70 ml of dry DMF was added dropwise to the flask over 15 minutes. After the completion of the dropwise addition, stirring was continued for 1 hour. After that, a solution of 3.54 g (19.2 mmol) of cyanuric chloride in 70 ml of dry DMF was added dropwise to the flask over 15 minutes. After the completion of the dropwise addition, stirring was continued for 2 hours, 350 g of water were then added thereto, and the precipitated crystal was collected by filtration. The crystal collected by filtration was reslurried twice with 300 g of water and then reslurried with 300 g of methanol. The resultant was dried under reduced pressure and then purified by column chromatography to afford 11.3 g (14.5 mmol, 75.5% yield) of a white powder.

Next, 10.0 g (12.9 mmol) of the white powder obtained above, 3.25 g (16.4 mmol) of 4-biphenylboronic acid, and 1.5 g (1.3 mmol) of tetrakis(triphenylphosphine)palladium(0) were loaded into a 1,000-ml three-necked flask, 50 ml of ethanol and 100 ml of toluene were added thereto, and the mixture was stirred. After that, 6.5 g (47.0 mmol) of sodium carbonate were dissolved in 50 ml of water. The solution was added to the flask and the mixture was heated to 85° C. and stirred for 5 hours. The resultant mixture was cooled once to room temperature, 100 ml of water and 100 ml of toluene were then added thereto, and the mixture was stirred. Insoluble matter was then separated by filtration. The filtrate was transferred to a 1,000-ml separating funnel and separated into an organic layer and an aqueous layer. The organic layer was washed three times with 100 ml of water. After that, the resultant organic layer was dried over magnesium sulfate. The magnesium sulfate was separated by filtration once and the solvent was then distilled off under reduced pressure. The residue was then purified by column chromatography to afford 6.9 g (7.7 mmol, 59.7% yield) of Compound (11) as a yellow solid.

The EI-MS (M+1) of Compound (11) was 894 and the melting point of the compound was undetectable.

Example 1

On a glass substrate, Compound (11) was deposited from the vapor from a vapor deposition source under the condition of a degree of vacuum of $5.0\times10^{-4}$ Pa by a vacuum vapor deposition method so as to form a thin film having a thickness of 100 nm at a rate of 0.2 nm/sec. The produced thin film was irradiated with light having a wavelength of 337 nm with N2 laser. An emission spectrum from the thin film upon the irradiation was evaluated at a temperature of 5 K. As a result, fluorescence emission at 466 nm and phosphoresce emission at 486 nm were confirmed. Based on the wavelengths, the excited singlet energy and excited triplet energy of Compound (11) were found to be 2.66 eV and 2.55 eV, respectively. Further, a difference between the excited singlet energy and the excited triplet energy ($\Delta E$) was 0.11 eV.

Example 2(R)

On a glass substrate, 1,3-dicarbazolylbenzene (mCP) was deposited from a vapor deposition source under the condition of a degree of vacuum of $5.0\times10^{-4}$ Pa by a vacuum vapor deposition method so as to form a thin film having a thickness of 100 nm at a rate of 0.2 nm/sec. The produced thin film was irradiated with light having a wavelength of 337 nm with N2 laser. An emission spectrum from the thin film upon the irradiation was evaluated at a temperature of 5 K. As a result, fluorescence emission at 375 nm and phosphoresce emission at 420 nm were confirmed. Based on the wavelengths, the excited singlet energy and excited triplet energy of mCP were found to be 3.30 eV and 2.95 eV, respectively.

mCP is calculated to have excited singlet energy and excited triplet energy higher by 0.64 eV and higher by 0.4 eV, respectively, than the excited singlet energy and excited triplet energy of Compound (11).

Example 3

On a glass substrate, Compound (11) and mCP were deposited from the vapor from different vapor deposition sources under the condition of a degree of vacuum of $5.0\times10^{-4}$ Pa by a vacuum vapor deposition method so as to form a thin film containing Compound (11) at a concentration of 6.0 wt % and having a thickness of 100 nm at a rate of 0.3 nm/sec. Thus, an organic PL element was obtained. The element was irradiated with light at 337 nm with N2 laser through the use of a C9920-02 type absolute quantum yield measuring apparatus manufactured by Hamamatsu Photonics K.K. An emission spectrum from the thin film upon the irradiation was subjected to characteristic evaluation at 300 K. As a result, light emission at 478 nm derived from Compound (11) was confirmed and the external luminous efficiency in that case was 41%. Next, the element was irradiated with light at 337 nm with N2 laser and a time resolved spectrum upon the irradiation was evaluated with a C4334 type streak camera manufactured by Hamamatsu Photonics K.K. A component having an emission lifetime of 2 μS or less and a component having an emission lifetime of more than 2 μS were judged as fluorescence and delayed fluorescence, respectively. As a result, the light emission of the element included 35% of a fluorescence component and 65% of a delayed fluorescence component.

The PL element was evaluated at a temperature of 150 K, 200 K, or 250 K in the same manner as described above. Table 1 shows the results collectively.

TABLE 1

| Temperature | External luminous efficiency (%) | Fluorescence component (%) | Delayed fluorescence component (%) |
| --- | --- | --- | --- |
| 300 K | 41 | 35 | 65 |
| 250 K | 39 | 35 | 65 |
| 200 K | 43 | 33 | 67 |
| 150 K | 24 | 60 | 40 |

Example 4

An organic PL element was obtained in the same manner as in Example 3 except that the concentration of Compound (11) was changed to 2.0 wt %, 10.0 wt %, or 14.0 wt %. The organic PL element was evaluated at 150 K, 200 K, 250 K, and 300 K in the same manner as in Example 3. Table 2 shows the results.

TABLE 2

| Temperature | Concentration (wt %) | External luminous efficiency (%) | Fluorescence component (%) | Delayed fluorescence component (%) |
| --- | --- | --- | --- | --- |
| 300 K | 2 | 38 | 39 | 61 |
| 250 K | 2 | 28 | 44 | 56 |
| 200 K | 2 | 30 | 47 | 53 |
| 150 K | 2 | 30 | 64 | 36 |
| 300 K | 10 | 40 | 24 | 76 |
| 250 K | 10 | 43 | 24 | 76 |

TABLE 2-continued

| Temperature | Concentration (wt %) | External luminous efficiency (%) | Fluorescence component (%) | Delayed fluorescence component (%) |
|---|---|---|---|---|
| 200 K | 10 | 40 | 31 | 69 |
| 150 K | 10 | 32 | 35 | 65 |
| 300 K | 14 | 39 | 28 | 72 |
| 250 K | 14 | 31 | 29 | 71 |
| 200 K | 14 | 26 | 33 | 67 |
| 150 K | 14 | 24 | 53 | 47 |

Example 5

On a glass substrate, on which an anode being formed of ITO and having a thickness of 100 nm had been formed, the respective thin films were laminated at a degree of vacuum of $5.0 \times 10^{-4}$ Pa by a vacuum deposition method. First, molybdenum trioxide was formed into a film having a thickness of 0.7 nm on ITO. Next, diphenylnaphthyldiamine (NPD) was formed into a film having a thickness of 40 nm. Next, mCP was formed into a film having a thickness of 10 nm. Next, Compound (11) and mCP were co-deposited from different vapor deposition sources to form a film having a thickness of 20 nm. In this case, the concentration of Compound (11) was 6.0 wt %. Next, bathophenanthroline (BPhen) was formed into a film having a thickness of 40 nm. Then, cesium was formed into a film having a thickness of 0.5 nm. Finally, aluminum (Al) was formed into a film having a thickness of 70 nm to serve as an electrode. Thus, an organic EL element was produced.

The resultant organic EL element was subjected to characteristic evaluation at 300 K with a C9920-02 type absolute quantum yield measuring apparatus manufactured by Hamamatsu Photonics K.K while being connected to an external power source and applied with a DC voltage. As a result, light emission at 478 nm derived from Compound (11) was confirmed. The external luminous efficiency was 3.4% at a current density of 0.03 mA/cm$^2$. Next, a time resolved spectrum of the element was evaluated with a C4334 type streak camera manufactured by Hamamatsu Photonics K.K. A component having an emission lifetime of 2 μS or less and a component having an emission lifetime of more than 2 μS were judged as fluorescence and delayed fluorescence, respectively. As a result, the light emission of the element included 60% of a fluorescence component and 40% of a delayed fluorescence component.

The organic EL element was evaluated at 150 K, 200 K, 250 K, and 300 K in the same manner as described above except that the current density was set to 5 mA/cm$^2$. Table 3 shows the results collectively.

TABLE 3

| Temperature | External luminous efficiency (%) | Fluorescence component (%) | Delayed fluorescence component (%) |
|---|---|---|---|
| 300 K | 2.0 | 60 | 40 |
| 250 K | 1.9 | 52 | 48 |
| 200 K | 1.7 | 42 | 58 |
| 150 K | 1.6 | 45 | 55 |

Example 6(R)

10 mg of an octaethylporphyrin-tin fluoride complex (SnF$_2$(OEP)) were dissolved in a mixed solution of methanol/dichloromethane (weight ratio=1/9). The solution was impregnated into filter paper and then dried. The resultant thin film was irradiated with light at 337 nm with N2 laser and an emission spectrum from the thin film upon the irradiation was evaluated at 5 K. As a result, fluorescence emission at 570 nm and phosphorescence emission at 706 nm were confirmed. Based on the wavelengths, the excited singlet energy, excited triplet energy, and ΔE of SnF$_2$(OEP) were found to be 2.17 eV, 1.76 eV, and 0.41 eV, respectively.

Example 7(R)

A 5-wt % solution of polyvinylcarbazole (PVCz) in dichloromethane was used to form a thin film having a thickness of 100 nm on a glass substrate by a spin coating method. The produced thin film was irradiated with light at 337 nm with N2 laser and an emission spectrum from the thin film upon the irradiation was evaluated at 5 K. As a result, fluorescence emission at 376 nm and phosphorescence emission at 425 nm were confirmed. Based on the wavelengths, the excited singlet energy and excited triplet energy of PVCz were found to be 3.30 eV and 2.91 eV, respectively.

From comparisons with the results of measurement of the excited singlet energy and excited triplet energy of SnF$_2$(OEP) in Example 6, PVCz has excited singlet energy and excited triplet energy higher by 1.13 eV and higher by 1.15 eV, respectively, than those of SnF$_2$(OEP).

Example 8(R)

On a glass substrate by a spin coating method, a solution of 10 mg of SnF$_2$(OEP) and 500 mg of PVCz in 10 ml of dichloromethane was used to form a mixture of SnF$_2$(OEP) and PVCz into a thin film having a thickness of 100 nm on a glass substrate by a spin coating method. Thus, an organic PL element was produced. The organic PL element was subjected to characteristic evaluation at 300 K in the same manner as in Example 3. As a result, light emission at 570 nm derived from SnF$_2$(OEP) was confirmed. The external luminous efficiency was 1.4%. Further, the light emission of the element included 49% of a fluorescence component and 51% of a delayed fluorescence component.

Example 9(R)

On a glass substrate having formed thereon an anode formed of ITO having a film thickness of 100 nm, each thin film and a cathode were laminated by a spin coating method or a vacuum vapor deposition method. First, an aqueous solution of a mixture of polyethylene dioxythiophene and polystyrene sulfonic acid (PEDOT:PSS aqueous solution) was used to form a film having a thickness of 40 nm on the ITO. Next, a solution of 10 mg of SnF$_2$(OEP) and 500 mg of PVCz in 10 ml of dichloromethane was used to form a mixture SnF$_2$(OEP) and PVCz into a thin film having a thickness of 100 nm. Next, a magnesium-silver alloy (Mg/Ag=10/1) was formed into a film having a thickness of 100 nm to serve as an electrode. Finally, silver (Ag) was formed into a film having a thickness of 10 nm. Thus, an organic EL element was produced. The organic EL element was subjected to characteristic evaluation at 300 K in the same manner as in Example 5. As a result, light emission at 570 nm derived from SnF$_2$(OEP) was confirmed. The external luminous efficiency was 0.01%. Further, the light emission of the element included 48% of a fluorescence component and 52% of a delayed fluorescence component.

Example 10(R)

On a glass substrate, 4,4'-bis(carbazol-9-yl)biphenyl (CBP) was deposited from a vapor deposition source under the condition of a degree of vacuum of $5.0\times10^{-4}$ Pa by a vacuum vapor deposition method so as to form a thin film having a thickness of 100 nm at a rate of 0.2 nm/sec. The produced thin film was irradiated with light having a wavelength of 337 nm with N2 laser. An emission spectrum from the thin film upon the irradiation was evaluated at a temperature of 5 K. As a result, fluorescence emission at 393 nm and phosphoresce emission at 488 nm were confirmed. Based on the wavelengths, the excited singlet energy and excited triplet energy of the compound CBP were found to be 3.15 eV and 2.54 eV, respectively. From comparisons with the results of measurement of the excited singlet energy and excited triplet energy of Compound (11) in Example 1, CBP was found to have excited singlet energy and excited triplet energy higher by 0.49 eV and lower by 0.01 eV, respectively, than those of Compound (11).

Example 11

On a glass substrate, Compound (11) and CBP were deposited from different vapor deposition sources under the condition of a degree of vacuum of $5.0\times10^{-4}$ Pa by a vacuum vapor deposition method so as to form a thin film containing Compound (11) at a concentration of 6 wt % and having a thickness of 100 nm at a rate of 0.2 nm/sec. Thus, an organic PL element was obtained. The organic PL element was subjected to characteristic evaluation at 300 K in the same manner as in Example 3. As a result, light emission at 478 nm derived from Compound (11) was confirmed. The external luminous efficiency was 17%. Further, the light emission of the element included 45% of a fluorescence component and 55% of a delayed fluorescence component.

The organic PL element was evaluated at temperatures of 150 K, 200 K, and 250 K in the same manner as described above. Table 4 shows the results collectively.

TABLE 4

| Temperature | External luminous efficiency (%) | Fluorescence component (%) | Delayed fluorescence component (%) |
|---|---|---|---|
| 300 K | 17 | 45 | 55 |
| 250 K | 14 | 39 | 61 |
| 200 K | 10 | 41 | 59 |
| 150 K | 5 | 37 | 63 |

Example 12

On a glass substrate, on which an anode being formed of ITO and having a thickness of 100 nm had been formed, the respective thin films were laminated at a degree of vacuum of $5.0\times10^{-4}$ Pa by a vacuum deposition method. First, diphenylnaphthyldiamine (NPD) was formed into a film having a thickness of 40 nm on ITO. Next, mCP was formed into a film having a thickness of 10 nm. Next, Compound (11) and mCP were co-deposited from different vapor deposition sources to form a film having a thickness of 20 nm. In this case, the concentration of Compound (11) was 6.0 wt %.

Next, 3,3',5,5'-tetra[(m-pyridyl)-phen-3-yl]biphenyl (BP4 mPy) was formed into a film having a thickness of 40 nm. In addition, lithium fluoride was formed into a film having a thickness of 0.8 nm. Finally, aluminum (Al) was formed into a film having a thickness of 70 nm to serve as an electrode. Thus, an organic EL element was produced. The organic EL element was subjected to characteristic evaluation at 300 K in the same manner as in Example 5. As a result, light emission at 495 nm derived from Compound (11) was confirmed. The external luminous efficiency was 5.5% at a current density of 0.01 mA/cm$^2$. Further, the light emission of the element included 60% of a fluorescence component and 40% of a delayed fluorescence component.

The results reveal that the compound having a difference between excited singlet energy and excited triplet energy ΔE of 0.2 eV or less or the indolocarbazole compound of the present invention represented by the general formula (1) provides a highly efficient PL light-emitting element and EL light-emitting element as compared to SnF$_2$(OEP) known as a material which emits delayed fluorescence (ΔE of 0.41 eV).

Synthetic Example 2

Synthesis of Compound (31)

Under a nitrogen atmosphere, 33.3 g (0.30 mol) of 1,2-cyclohexanedione, 86.0 g (0.60 mol) of phenylhydrazine hydrochloride, and 1,000 ml of ethanol were stirred at room temperature, and to the stirred mixture was added dropwise over 5 minutes 3.0 g (0.031 mol) of concentrated sulfuric acid. After that, the mixture was stirred for 4 hours while being heated at 65° C. The reaction solution was cooled to room temperature. The precipitated crystal was then collected by filtration and washed with ethanol (2×500 ml) to afford 80.0 g of a purple-brown crystal. 72.0 g (0.26 mol) of the crystal, 72.0 g of trifluoroacetic acid, and 720.0 g of acetic acid were stirred for 15 hours while being heated at 100° C. The reaction solution was cooled to room temperature. The precipitated crystal was then collected by filtration and washed with acetic acid (200 ml). The resultant was purified by reslurrying to afford 30.0 g (45% yield) of (B-1) as a white crystal.

Under a nitrogen atmosphere, 26.0 g (0.10 mol) of (B-1), 122.7 g (0.60 mol) of iodobenzene, 54.7 g (0.29 mol) of copper iodide, 66.7 g (0.48 mol) of potassium carbonate, and 800 ml of quinoline were stirred for 72 hours while being heated at 190° C. The reaction solution was cooled to room temperature. Distilled water (500 ml) and dichloromethane (500 ml) were then added thereto while being stirred. The precipitated crystal was separated by filtration and the organic layer was then washed with distilled water (3×500 ml). The organic layer was dried over anhydrous magnesium sulfate, the magnesium sulfate was then separated by filtration, and the solvent was distilled off under reduced pressure. The resultant residue was purified by silica gel column chromatography to afford 13.7 g (41% yield) of (B-2) as a white solid.

72.2 g (0.392 mol) of cyanuric chloride and 500 ml of dry tetrahydrofuran (THF) were added to a 2,000-ml three-necked flask subjected to degassing and nitrogen purging and the mixture was stirred. While the temperature of the liquid contained in the flask was kept at −20° C. or less, 500 ml of a 1 mol/l solution of phenyl magnesium bromide in THF were added dropwise to the flask over 2 hours and stirring was then continued for 0.5 hour. After that, 300 ml of toluene and 500 ml of 2N hydrochloric acid were added to the flask while the temperature of the liquid contained in the flask was kept at 5° C. or less. The liquid contained in the flask was transferred to a 2,000-ml separating funnel and separated into an organic layer and an aqueous layer. The organic layer was washed twice with 300 ml of water and washed once with brine. The organic layer was then dried over magnesium sulfate. The magnesium sulfate was separated by filtration. The filtrate was then transferred to a 2,000-ml recovery flask and the solvent was distilled off under reduced pressure. 1.0 kg of n-hexane was added to the resultant pale yellow crystal and the mixture was heated and stirred. After that, the resultant mixture was cooled and the precipitated needle crystal was collected by filtration and dried to afford 50.9 g (0.225 mol, 57.4% yield) of (B-3).

1.64 g of 56% sodium hydride and 50 ml of dry DMF were added to a 500-ml three-necked flask subjected to degassing and nitrogen purging and the mixture was stirred. Next, a solution prepared by dissolving 10.0 g (30.1 mmol) of (B-2) in 60 ml of dry DMF was added dropwise to the flask over 30 minutes. After that, stirring was continued for 1 hour. Next, a solution prepared by dissolving 7.00 g (30.9 mmol) of (B-3) in 60 ml of dry DMF was added dropwise to the flask over 30 minutes. After that, stirring was continued the whole day and night. Next, 300 g of water were added to the flask and the precipitated yellow crystal was collected by filtration. The yellow crystal collected by filtration was reslurried with methanol and dried to afford 15.0 g (28.7 mmol, 95.6% yield) of (B-4).

The reaction formulae are shown below.

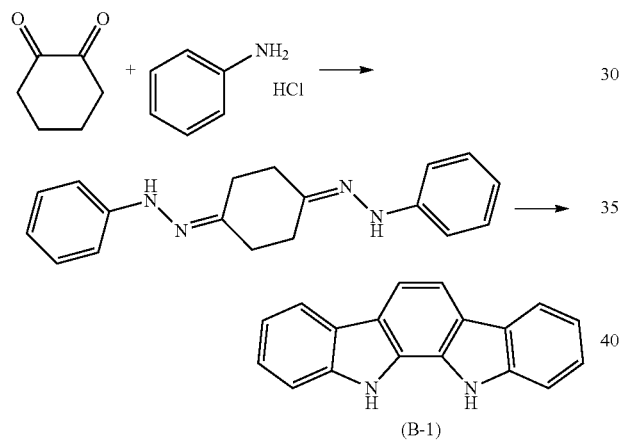

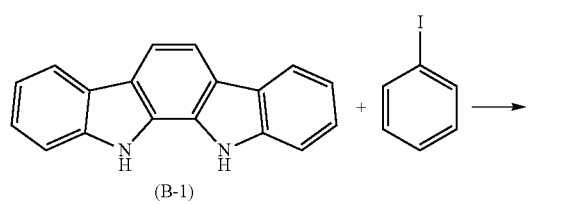

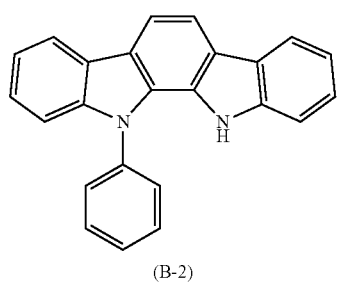

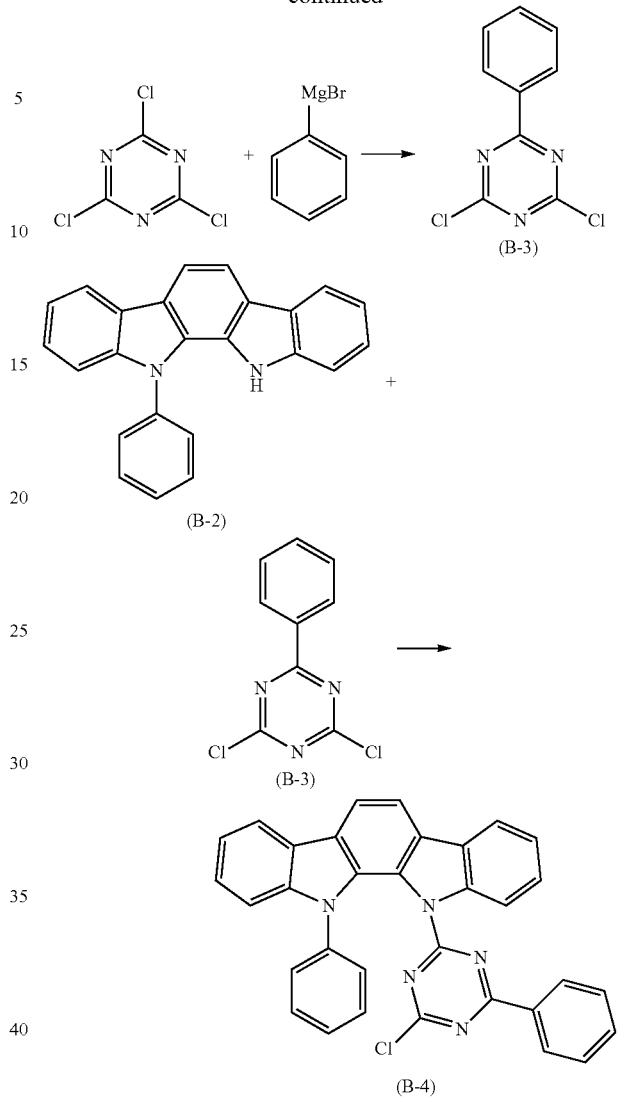

Under a nitrogen atmosphere, 50 g (177 mmol) of p-bromoiodobenzene, 30.0 g (179.4 mmol) of carbazole, 1.0 g (5.25 mmol) of copper iodide, 187.5 g (885 mmol) of tripotassium phosphate, and 500 ml of 1,4-dioxane were added and stirred. 6.0 g (52.5 mmol) of trans-1,2-cyclohexanediamine were added thereto and the mixture was heated to 110° C. and stirred for 4 hours. The reaction solution was cooled to room temperature, inorganic matter was then separated by filtration, and the solvent was distilled off under reduced pressure. 600 ml of methanol were added to the resultant residue and the residue was reslurried with heating for 2 hours. The resultant was cooled and the precipitate was then collected by filtration and then dried under reduced pressure to afford 50 g (140.0 mmol, 78.9% yield) of (B-5) as a pale brown crystal.

Under a nitrogen atmosphere, 3.6 g (149 mmol) of magnesium and 150 ml of dry THF were added to a flask and heated to reflux. A solution prepared by dissolving 40.0 g (124 mmol) of (B-5) in 150 ml of dry THF was added dropwise to the flask over 30 minutes. After that, stirring was continued for 2 hours. After the confirmation of disappearance of the raw materials, the mixture was cooled (liquid A).

Under a nitrogen atmosphere, 19.3 g (186 mmol) of trimethoxyborane and 200 ml of dry THF were added to a flask.

The flask was placed in an ice bath and the internal temperature was set to 0° C. or less. The liquid A described above was added dropwise thereto over 45 minutes and stirring was then continued for 1 hour. 12 ml of methanol were added to the flask to quench the reaction. After that, 130 ml of 2M HCl were added and stirring was continued at room temperature for 2 hours. The precipitated crystal was collected by filtration. THF was distilled off under reduced pressure from the filtrate, and the residue was extracted three times with toluene. Magnesium sulfate was added to the toluene layer for drying, and the magnesium sulfate was then separated by filtration. The filtrate was concentrated under reduced pressure. 300 g of ethyl acetate were added to the resultant solid and the mixture was reslurried with heating for 1 hour. The resultant was cooled to room temperature and the precipitate was filtered. After that, the precipitate was dried under reduced pressure to afford 25.7 g (89.5 mmol, 72.2% yield) of (B-6) as a gray solid.

6.7 g (12.9 mmol) of (B-4) obtained above, 4.1 g (14.2 mmol) of (B-6), 1.5 g (1.3 mmol) of tetrakis(triphenylphosphine)palladium(0), 50 ml of ethanol, and 100 ml of toluene were added to a 300-ml three-necked flask subjected to degassing and nitrogen purging and stirred. After that, 6.5 g (47.0 mmol) of potassium carbonate were dissolved in 50 ml of water. The solution was added to the flask and the mixture was heated to 85° C. and stirred for 5 hours. The resultant mixture was cooled once to room temperature, 100 ml of water and 100 ml of toluene were then added thereto, and the mixture was stirred. Insoluble matter was then separated by filtration once. The filtrate was transferred to a 1,000-ml separating funnel and separated into an organic layer and an aqueous layer. The organic layer was washed three times with 100 ml of water. After that, the resultant organic layer was dried over magnesium sulfate. The magnesium sulfate was separated by filtration once and the solvent was then distilled off under reduced pressure. The residue was then purified by column chromatography to afford 6.9 g (9.5 mmol, 73.6% yield) of Compound (31) as a yellow solid. The EI-MS (M+1) of the compound was 729.

The reaction formulae are shown below.

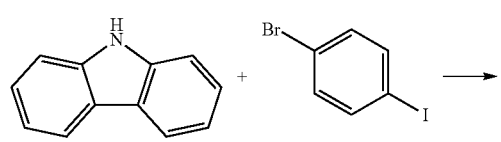

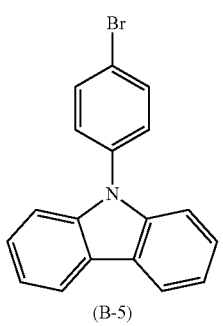

(B-5)

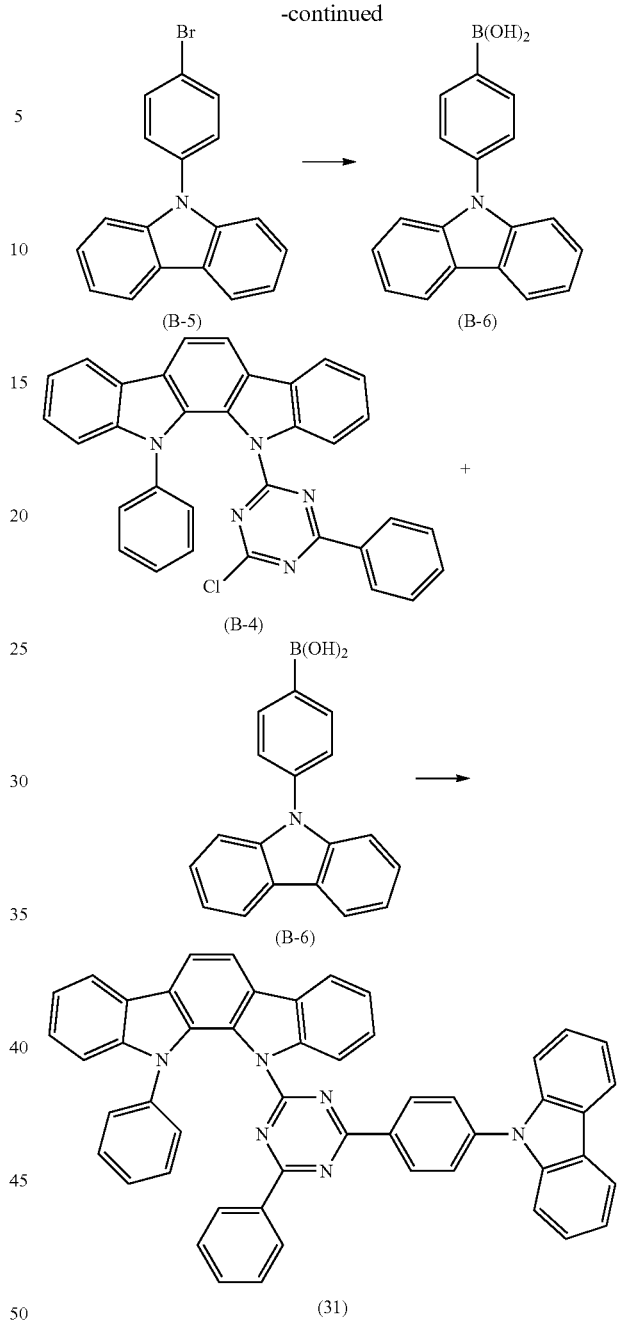

Synthetic Example 3

Synthesis of Compound (130)

Under a nitrogen atmosphere, a solution of 20.0 g (0.17 mol) of indole in 300 ml of dry diethyl ether was stirred at room temperature, and the stirred solution was bubbled with a hydrogen chloride gas generated by adding dropwise over 1 hour 112.0 g (1.10 mol) of concentrated hydrochloric acid to 211.7 g (2.16 mol) of concentrated sulfuric acid. The reaction solution was stirred at room temperature for 15 hours. To the mixture were then added 121.0 g of ethyl acetate and 303.2 g of a saturated sodium bicarbonate aqueous solution. The aqueous layer was extracted with ethyl acetate (2×100 ml) and the organic layer was then washed with a saturated sodium bicarbonate aqueous solution (100 ml) and distilled water (2×100 ml). The organic layer was dried over anhydrous magnesium sulfate. The magnesium sulfate was then separated by filtration and the solvent was distilled off under reduced pressure. The resultant residue was dissolved in 150 ml of toluene, 2.5 g of palladium/activated carbon were added thereto, and the mixture was then stirred for 3 hours while being heated to reflux at 111° C. The reaction solution was cooled to room temperature. The palladium/activated carbon was then separated by filtration and the solvent was distilled off under reduced pressure. The residue was purified by recrystallization to afford 14.7 g (37% yield) of (F-1) as a white crystal.

Under a nitrogen atmosphere, 14.1 g (0.061 mol) of (F-1), 11.4 g (0.071 mol) of N,N'-dimethylaminoacetaldehyde diethylacetal, and 110.0 g of acetic acid were stirred for 8 hours while being heated to reflux at 118° C. The reaction solution was cooled to room temperature. The precipitated crystal was then collected by filtration and washed with acetic acid (30 ml). The resultant crystal was purified by reslurrying to afford 10.4 g (67% yield) of (F-2) as a white crystal.

Under a nitrogen atmosphere, 10.0 g (0.039 mol) of (F-2), 39.8 g (0.20 mol) of iodobenzene, 6.2 g (0.098 mol) of copper, 8.1 g (0.059 mol) of potassium carbonate, and 200 ml of tetraglyme were added and stirred. After that, the mixture was heated to 190° C. and stirred for 24 hours. The reaction solution was cooled to room temperature and copper and inorganic matter were then separated by filtration. 200 ml of distilled water were added to the filtrate and the mixture was stirred. The precipitated crystal was separated by filtration. The resultant crystal was dried under reduced pressure and then purified by column chromatography to afford 9.7 g (0.029 mol, 75% yield) of (F-3) as a white powder.

The reaction formulae are shown below.

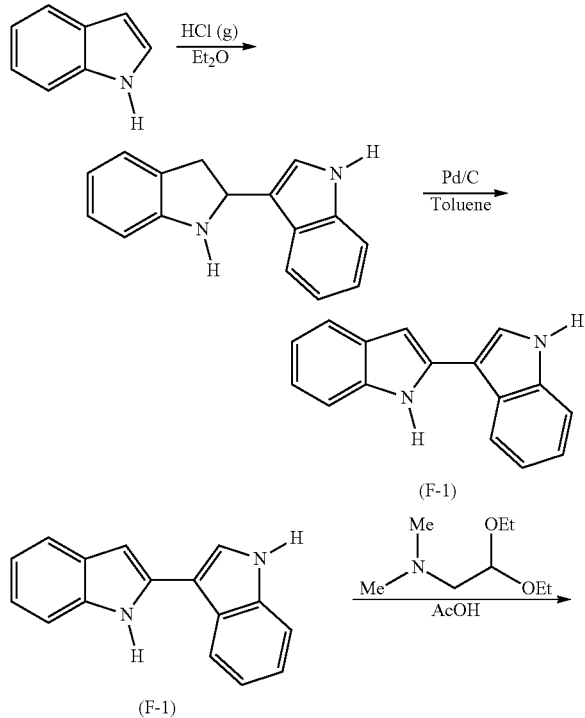

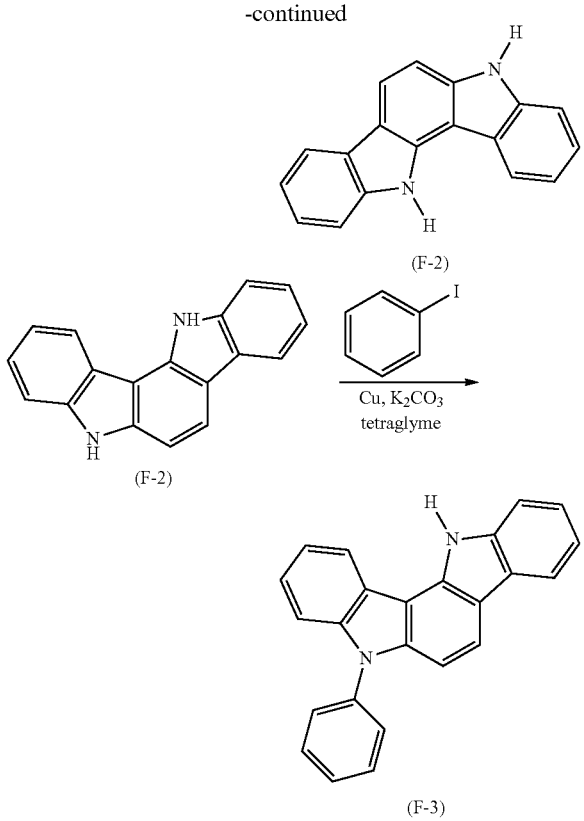

Next, 12.5 g (0.068 mol) of cyanuric chloride and 55 ml of dry THF were added to a 200-ml three-necked flask subjected to degassing and nitrogen purging and the mixture was stirred under a nitrogen stream in an ice bath. After that, 105.6 g (0.186 mol) of a 32% solution of phenyl magnesium bromide in THF were added dropwise to the flask over 2 hours. The temperature was kept at 15° C. or less during the dropwise addition. After the completion of the dropwise addition, stirring was continued for 1.5 hours. After that, 80 g of toluene were added to the flask. The flask was then cooled in an ice bath and 76.5 g (0.254 mol) of a 12% HCl aqueous solution were added dropwise to the flask over 15 minutes. The temperature was kept at 30° C. or less during the dropwise addition. The contents in the flask were transferred to a 500-ml separating funnel and separated into an organic layer and an aqueous layer. The organic layer was washed three times with 100 ml of water. The resultant organic layer was then dried over magnesium sulfate. The magnesium sulfate was separated by filtration once and the solvent was then distilled off reduced pressure. 110 g of methanol were added to the resultant residue and the mixture was stirred for 1 hour. The precipitate was then separated by filtration and dried under reduced pressure with a vacuum dryer to afford 14.5 g (6.5 mmol, 50.2% yield) of (F-4).

2.18 g (50.0 mmol) of 55% sodium hydride and 70 ml of dry DMF were added to a 2,000-ml three-necked flask subjected to degassing and nitrogen purging and the mixture was stirred under a nitrogen stream. 150 ml of dry DMF were added to 13.5 g (40.6 mmol) of (F-3) to prepare a solution. The solution was then added dropwise to the flask over 10 minutes. After the completion of the dropwise addition, stirring was continued for 1 hour. Next, a solution of 10.4 g (39.0 mmol) of (F-4) in 150 ml of dry DMF was added dropwise to the flask over 1 hour. After the completion of the dropwise addition, stirring was continued for 3 hours. After that, 600 g of water were added thereto and the precipitated crystal was collected by filtration. The crystal collected by filtration was reslurried twice with 300 g of water and then reslurried with 300 g of methanol. The resultant crystal was purified by column chromatography to afford 13.1 g (23.2 mmol, 57.2% yield) of Compound (130) as a yellow solid. The EI-MS (M+1) of Compound (130) was 564.

The reaction formulae are shown below.

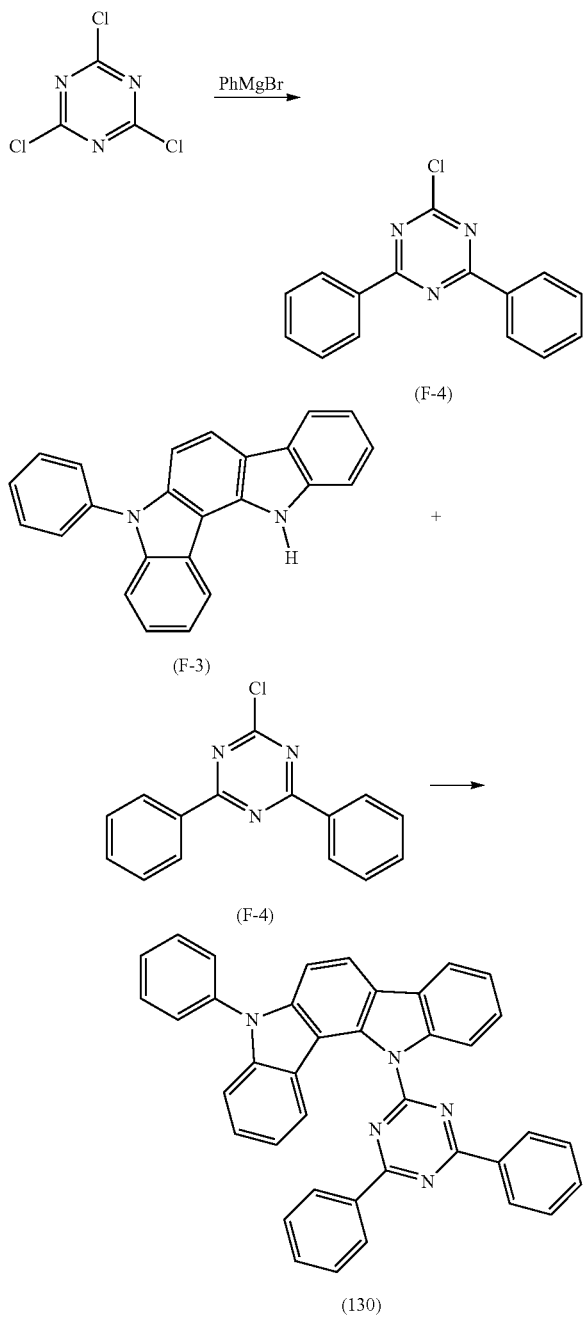

Synthesis Example 4

Synthesis of Compound (183)

2.16 g (49.5 mmol) of 55% sodium hydride and 70 ml of dry DMF were added to a 500-ml three-necked flask subjected to degassing and nitrogen purging and the mixture was stirred under a nitrogen stream. 13.7 g (41.2 mmol) of (B-2) obtained by the method described in Synthesis Example 2 were added to 70 ml of dry DMF to prepare a solution. The solution was then added dropwise to the flask over 15 minutes. After the completion of the dropwise addition, stirring was continued for 1 hour. After that, 3.76 g (20.4 mmol) of cyanuric chloride were added to 70 ml of dry DMF to prepare a solution. The solution was then added dropwise to the flask over 15 minutes. After the completion of the dropwise addition, stirring was continued for 2 hours, 350 g of water were then added thereto, and the precipitated crystal was collected by filtration. The crystal collected by filtration was reslurried twice with 300 g of water and then reslurried with 300 g of methanol. The resultant was dried under reduced pressure and then purified by column chromatography to afford 10.9 g (14.0 mmol, 70.0% yield) of (B-7) as a white powder.

10.0 g (12.9 mmol) of (B-7), 2.0 g (16.4 mmol) of phenylboronic acid, 1.5 g (1.3 mmol) of tetrakis(triphenylphosphine)palladium(0), 50 ml of ethanol, and 100 ml of toluene were added to a 300-ml three-necked flask and stirred. After that, 6.5 g (47.0 mmol) of sodium carbonate were dissolved in 50 ml of water. The solution was added to the flask and the mixture was heated to 85° C. and stirred for 5 hours. The resultant mixture was cooled once to room temperature, 100 ml of water and 100 ml of toluene were then added thereto, and the mixture was stirred. Insoluble matter was then separated by filtration once. The filtrate was transferred to a 1,000-ml separating funnel and separated into an organic layer and an aqueous layer. The organic layer was washed three times with 100 ml of water. After that, the resultant organic layer was dried over magnesium sulfate. The magnesium sulfate was separated by filtration once and the solvent was then distilled off under reduced pressure. The residue was then purified by column chromatography to afford 5.3 g (6.5 mmol, 50.2% yield) of Compound (183) as a yellow solid. The EI-MS (M+1) of Compound (183) was 818.

The reaction formulae are shown below.

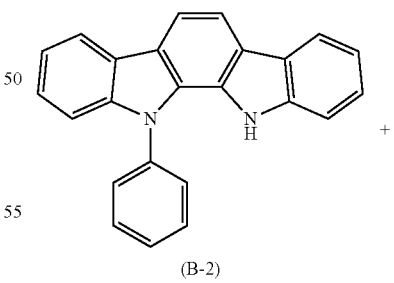

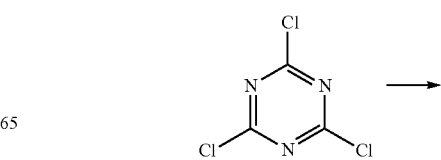

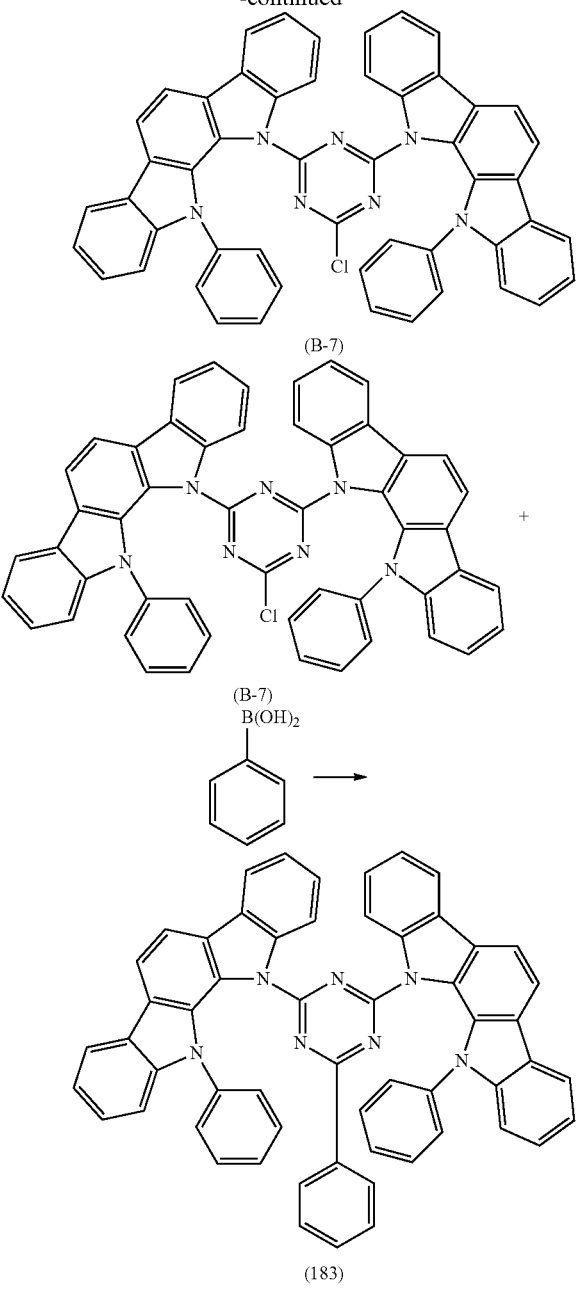

(B-7)

(B-7)

(183)

Synthetic Example 5

Compound (192) was synthesized in accordance with the reaction formula shown below.

10.0 g (12.9 mmol) of (B-7), 4.5 g (16.4 mmol) of (3,5-diphenyl)boronic acid, 1.5 g (1.3 mmol) of tetrakis(triphenylphosphine)palladium(0), 50 ml of ethanol, and 100 ml of toluene were added to a 300-ml three-necked flask and stirred. After that, 6.5 g (47.0 mmol) of sodium carbonate were dissolved in 50 ml of water. The solution was added to the flask and the mixture was heated to 85° C. and stirred for 5 hours. The resultant mixture was cooled once to room temperature, 100 ml of water and 100 ml of toluene were then added thereto, and the mixture was stirred. Insoluble matter was then separated by filtration once. The filtrate was transferred to a 1,000-ml separating funnel and separated into an organic layer and an aqueous layer. The organic layer was washed three times with 100 ml of water. After that, the resultant organic layer was dried over magnesium sulfate. The magnesium sulfate was separated by filtration once and the solvent was then distilled off under reduced pressure. The residue was then purified by column chromatography to afford 4.7 g (4.8 mmol, 37.5% yield) of Compound (192) as a yellow solid. The EI-MS (M+1) of Compound (192) was 971.

The reaction formula is shown below.

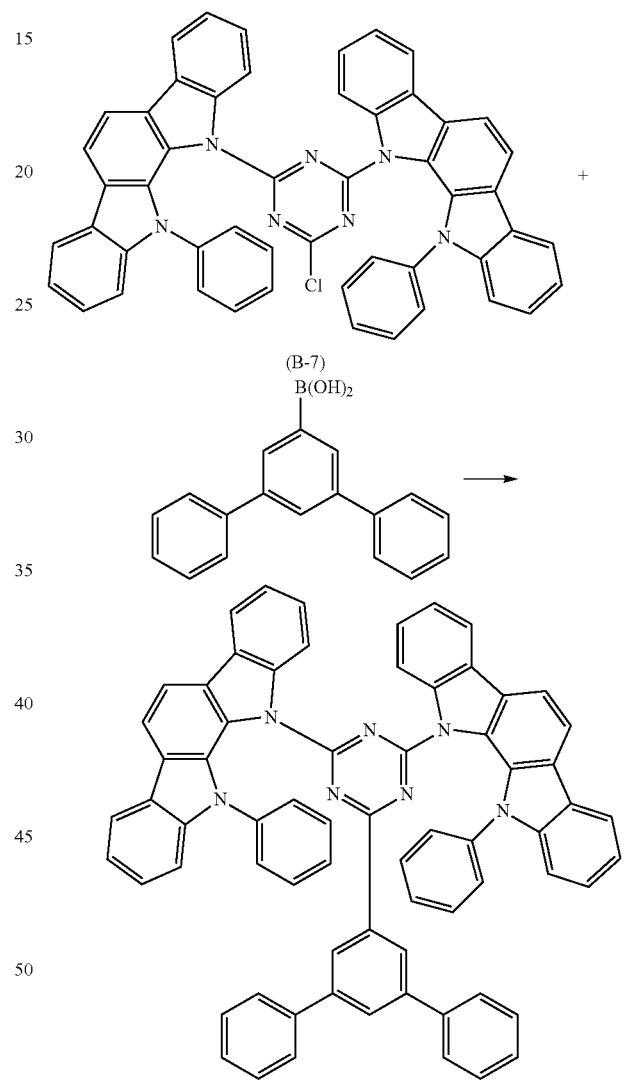

(B-7)

(B-7)
B(OH)$_2$ (192)

Example 13

A thin film was formed in the same manner as in Example 1 except that Compound (31), (130), (183), or (192) was used in place of Compound (11). In the same manner as in Example 1, the produced thin film was irradiated with light at 337 nm with N2 laser and an emission spectrum from the thin film upon the irradiation was evaluated at a temperature of 5 K. Fluorescence emission and phosphorescence emission were confirmed. The excited singlet energy (S1) and excited triplet energy (T1) of each compound were determined based on a fluorescence emission wavelength (Fλ) and a phosphorescence emission wavelength (Pλ). Further, a difference between (S1) and (T1) (ΔE) was determined. Table 5 shows the results.

TABLE 5

| Compound | Fλ nm | Pλ nm | S1 eV | T1 eV | ΔE eV |
|---|---|---|---|---|---|
| 31 | 503 | 521 | 2.47 | 2.38 | 0.09 |
| 130 | 500 | 500 | 2.48 | 2.48 | 0.00 |
| 183 | 456 | 470 | 2.72 | 2.64 | 0.08 |
| 192 | 468 | 479 | 2.65 | 2.59 | 0.06 |

Examples 14 to 17

An organic PL element was obtained in the same manner as in Example 3 except that Compound (31), (130), (183), or (192) was used in place of Compound (11). The PL element was subjected to characteristic evaluation at 150 K to 350 K in the same manner as in Example 3. Table 6 shows the results.

TABLE 6

| Compound | Temperature K | External luminous efficiency (%) | Fluorescence component (%) | Delayed fluorescence component (%) |
|---|---|---|---|---|
| 31 | 350 | 30 | 13 | 87 |
| 31 | 325 | 27 | 14 | 86 |
| 31 | 300 | 33 | 13 | 87 |
| 31 | 250 | 35 | 10 | 90 |
| 31 | 200 | 35 | 10 | 90 |
| 31 | 150 | 42 | 9 | 91 |
| 130 | 325 | 23 | 30 | 70 |
| 130 | 300 | 30 | 16 | 84 |
| 130 | 250 | 40 | 15 | 85 |
| 130 | 200 | 47 | 16 | 84 |
| 130 | 150 | 50 | 21 | 79 |
| 183 | 350 | 36 | 58 | 42 |
| 183 | 325 | 41 | 58 | 42 |
| 183 | 300 | 46 | 52 | 48 |
| 183 | 250 | 44 | 54 | 46 |
| 183 | 200 | 48 | 53 | 47 |
| 183 | 150 | 57 | 61 | 39 |
| 192 | 350 | 29 | 55 | 45 |
| 192 | 325 | 39 | 45 | 55 |
| 192 | 300 | 45 | 39 | 61 |
| 192 | 250 | 41 | 43 | 57 |
| 192 | 200 | 45 | 41 | 59 |
| 192 | 150 | 60 | 49 | 51 |

Example 18

An organic EL element was produced in the same manner as in Example 12 except that Compound (31) was used in place of Compound (11), BPhen was used in place of BP4mPy, and the film thickness of aluminum (Al) was set to 100 nm. In the same manner as in Example 12, the resultant organic EL element was subjected to characteristic evaluation at 300 K through the use of a C9920-02 type absolute quantum yield measuring apparatus manufactured by Hamamatsu Photonics K.K. while being connected to an external power source and applied with a DC voltage. As a result, light emission at 520 nm derived from Compound (31) was confirmed. The external luminous efficiency was 5.6% at a current density of 0.1 mA/cm$^2$. Further, a time resolved spectrum of the element was evaluated in the same manner as in Example 12. As a result, the light emission of the element included 44% of a fluorescence component and 56% of a delayed fluorescence component.

Example 19

An organic EL element was produced in the same manner as in Example 18 except that Compound (130) was used in place of Compound (31). The resultant organic EL element was subjected to characteristic evaluation at 300 K in the same manner as in Example 18. As a result, light emission at 500 nm derived from Compound (130) was confirmed. The external luminous efficiency was 4.1% at a current density of 0.2 mA/cm$^2$. The light emission of the element included 61% of a fluorescence component and 38% of a delayed fluorescence component.

Example 20

An organic EL element was produced in the same manner as in Example 18 except that Compound (183) was used in place of Compound (31). The resultant organic EL element was subjected to characteristic evaluation at 300 K in the same manner as in Example 18. As a result, light emission at 490 nm derived from Compound (183) was confirmed. The external luminous efficiency was 4.4% at a current density of 0.01 mA/cm$^2$. The light emission of the element included 59% of a fluorescence component and 41% of a delayed fluorescence component.

Example 21

An organic EL element was produced in the same manner as in Example 18 except that Compound (192) was used in place of Compound (31). The resultant organic EL element was subjected to characteristic evaluation at 300 K in the same manner as in Example 18. As a result, light emission at 493 nm derived from Compound 192 was confirmed. The external luminous efficiency was 3.7% at a current density of 0.01 mA/cm$^2$. The light emission of the element included 53% of a fluorescence component and 47% of a delayed fluorescence component.

Example 22

On a glass substrate, on which an anode being formed of ITO and having a thickness of 100 nm had been formed, the respective thin films were laminated at a degree of vacuum of 5.0×10$^{-4}$ Pa by a vacuum deposition method. First, diphenylnaphthyldiamine (NPD) was formed into a film having a thickness of 40 nm on ITO. Next, mCP was formed into a film having a thickness of 10 nm. Next, Compound (130) was formed into a film having a thickness of 20 nm. Next, Bphen was formed into a film having a thickness of 40 nm. Then, lithium fluoride was formed into a film having a thickness of 0.8 nm. Finally, aluminum (Al) was formed into a film having a thickness of 100 nm to serve as an electrode. Thus, an organic EL element was produced.

The resultant organic EL element was subjected to characteristic evaluation at 300 K in the same manner as in Example 5 while being connected to an external power source and applied with a DC voltage. As a result, light emission at 525 nm derived from Compound (130) was confirmed. The external luminous efficiency was 5.8% at a current density of 0.03 mA/cm². The light emission of the element included 59% of a fluorescence component and 41% of a delayed fluorescence component.

INDUSTRIAL APPLICABILITY

The fluorescence and delayed fluorescence type organic light-emitting element using the organic light-emitting material of the present invention can emit light with high luminance and high efficiency. The organic EL element of the present invention can emit light with high luminance and high efficiency at a low voltage. Therefore, potential applications of the organic EL element of the present invention include a flat panel display (such as a display for an OA computer or a wall-hung TV), an on-vehicle display element, a cellular phone display, a light source utilizing the feature of the element as a planar light emitter (such as a light source for a copying machine or a backlight source for liquid crystal displays and meters), a display board, and the field of lighting such as a marker lamp. Accordingly, the element has a large technical value.

The invention claimed is:

1. A fluorescence and delayed fluorescence type organic light-emitting element, comprising:
a substrate; and
at least one light-emitting layer comprising (i) an organic light-emitting material having no metal atom in the molecule, which light-emitting material emits fluorescence and delayed fluorescence and which has a difference between excited singlet energy (S1) and excited triplet energy (T1) of 0.2 eV or less, the light-emitting layer being provided on the substrate, and (ii) a host material having at least any one of excited singlet energy (S1) and excited triplet energy (T1) higher than those of the organic light-emitting material.

2. The fluorescence and delayed fluorescence-type organic light-emitting element according to claim 1, wherein the light-emitting material has a difference between excited singlet energy (S1) and excited triplet energy (T1) of 0.15 eV or less.

3. The fluorescence and delayed fluorescence-type organic light-emitting element according to claim 1, wherein the excited singlet energy (S1) of the host material is higher than the excited singlet energy (S1) of the organic light-emitting material by 0.1 eV or more, and/or the excited triplet energy (T1) of the host material is higher than the excited triplet energy (T1) of the organic light-emitting material by 0.1 eV or more.

4. The fluorescence and delayed fluorescence-type organic light-emitting element according to claim 1, wherein the excited singlet energy (S1) of the host material is higher than the excited singlet energy (S1) of the organic light-emitting material by 0.2 eV or more, and/or the excited triplet energy (T1) of the host material is higher than the excited triplet energy (T1) of the organic light-emitting material by 0.2 eV or more.

5. A fluorescence and delayed fluorescence organic light-emitting element, comprising:
a substrate;
an anode;
a hole-transporting layer;
at least one light-emitting layer comprising an organic light-emitting material having no metal atom in the molecule, which light-emitting material emits fluorescence and delayed fluorescence, the organic light-emitting material having a difference between excited singlet energy (S1) and excited triplet energy (T1) of 0.2 eV or less, the light-emitting layer being provided on the substrate, wherein light emission form the light-emitting layer consists substantially of fluorescence and delayed fluorescence which is generated substantially only by the organic light-emitting material; and
a cathode.

6. The fluorescence and delayed fluorescence-type organic light-emitting element according to claim 5, wherein the light-emitting material has a difference between excited singlet energy (S1) and excited triplet energy (T1) of 0.15 eV or less.

7. A fluorescence and delayed fluorescence-type organic light-emitting element, comprising:
a substrate; and
at least one light-emitting layer comprising an organic light-emitting material which has a difference between excited singlet energy (S1) and excited triplet energy (T1) of 0 to 0.2 eV, the organic light-emitting material having no metal atom in the molecule, the light-emitting layer being provided on the substrate, wherein the light emission of the element includes 36% or more of a delayed fluorescence component.

8. The fluorescence and delayed fluorescence-type organic light-emitting element according to claim 7, wherein the light-emitting material has a difference between excited singlet energy (S1) and excited triplet energy (T1) of 0.15 eV or less.

9. A fluorescence and delayed fluorescence-type organic light-emitting element, comprising:
a substrate; and
at least one light-emitting layer comprising an organic light-emitting material represented by the general formula (1):

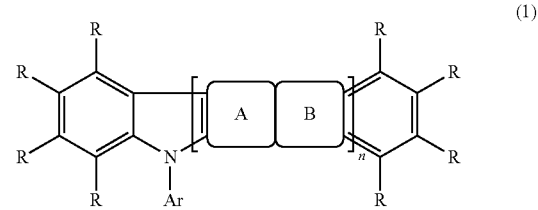

(1)

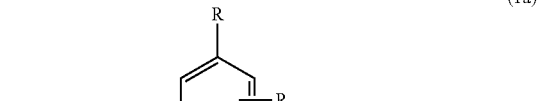

(1a)

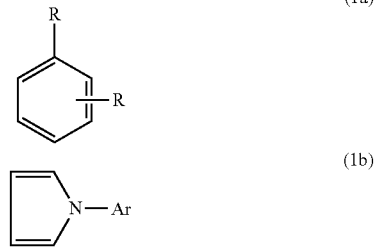

(1b)

in which: a ring A represents an aromatic ring represented by the formula (1a) to be fused with an adjacent ring at an arbitrary position; a ring B represents a heterocycle represented by the formula (1b) to be fused with an adjacent ring at an arbitrary position; Ar's in the formulae (1) and (1b) each independently represent an aromatic hydrocarbon group or an aromatic heterocyclic group; R's in the formulae (1) and (1a) each independently represent hydrogen or a monovalent substituent selected from the group consisting of an alkyl group having 1 to 10 carbon atoms, an alkoxy group having 1 to 10 carbon atoms, an alkylthio group having 1 to 10 carbon atoms, an alkylamino group having 1 to 10 carbon atoms, an acyl group having 2 to 10 carbon atoms, an aralkyl group having 7 to 20 carbon atoms, a substituted or unsubstituted aromatic hydrocarbon group having 6 to 30 carbon atoms, and a substituted or unsubstituted aromatic six-membered heterocyclic group having 3 to 30 carbon atoms, provided that adjacent substituents may together form a ring; and n represents an integer of 1 or more and 4 or less, the light-emitting layer being provided on the substrate, wherein the light emission of the element includes 36% or more of a delayed fluorescence component.

10. A fluorescence and delayed fluorescence type organic light-emitting element, comprising:
a substrate; and
at least one light-emitting layer comprising an organic light-emitting material which emits fluorescence and delayed fluorescence and which has a difference between excited singlet energy (S1) and excited triplet energy (T1) of 0.2 eV or less, the light-emitting layer being provided on the substrate,
wherein the organic light-emitting material comprises a compound represented by the following general formula (1):

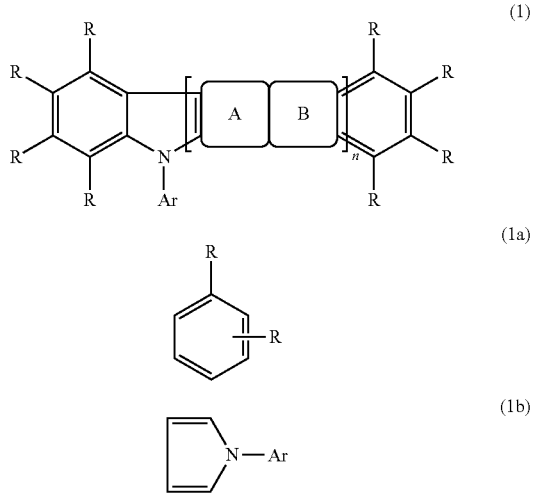

in which: a ring A represents an aromatic ring represented by the formula (1a) to be fused with an adjacent ring at an arbitrary position; a ring B represents a heterocycle represented by the formula (1b) to be fused with an adjacent ring at an arbitrary position; Ar's in the formulae (1) and (1b) each independently represent an aromatic hydrocarbon group or an aromatic heterocyclic group; R's in the formulae (1) and (1a) each independently represent hydrogen or a monovalent substituent selected from the group consisting of an alkyl group having 1 to 10 carbon atoms, an alkoxy group having 1 to 10 carbon atoms, an alkylthio group having 1 to 10 carbon atoms, an alkylamino group having 1 to 10 carbon atoms, an acyl group having 2 to 10 carbon atoms, an aralkyl group having 7 to 20 carbon atoms, a substituted or unsubstituted aromatic hydrocarbon group having 6 to 30 carbon atoms, and a substituted or unsubstituted aromatic six-membered heterocyclic group having 3 to 30 carbon atoms, provided that adjacent substituents may together form a ring; and n represents an integer of 1 or more and 4 or less.

11. A fluorescence and delayed fluorescence type organic light-emitting element, comprising:
a substrate; and
at least one light-emitting layer comprising (i) an organic light-emitting material which emits fluorescence and delayed fluorescence and which has a difference between excited singlet energy (S1) and excited triplet energy (T1) of 0.2 eV or less, the light-emitting layer being provided on the substrate, and (ii) a host material having at least any one of excited singlet energy (S1) and excited triplet energy (T1) higher than those of the organic light-emitting material,
wherein the organic light-emitting material comprises a compound represented by the following general formula (1):

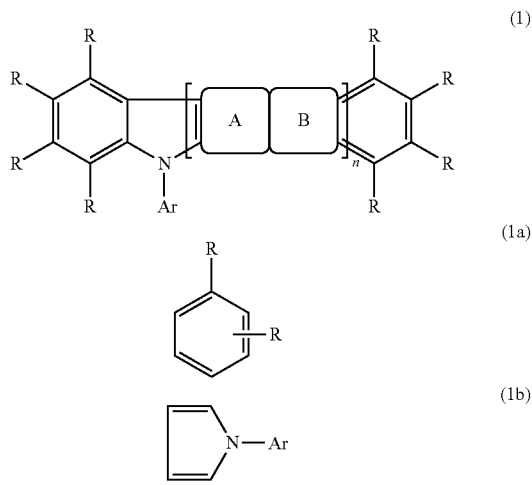

in which: a ring A represents an aromatic ring represented by the formula (1a) to be fused with an adjacent ring at an arbitrary position; a ring B represents a heterocycle represented by the formula (1b) to be fused with an adjacent ring at an arbitrary position; Ar's in the formulae (1) and (1b) each independently represent an aromatic hydrocarbon group or an aromatic heterocyclic group; R's in the formulae (1) and (1a) each independently represent hydrogen or a monovalent substituent selected from the group consisting of an alkyl group having 1 to 10 carbon atoms, an alkoxy group having 1 to 10 carbon atoms, an alkylthio group having 1 to 10 carbon atoms, an alkylamino group having 1 to 10 carbon atoms, an acyl group having 2 to 10 carbon atoms, an aralkyl group having 7 to 20 carbon atoms, a substituted or unsubstituted aromatic hydrocarbon group having 6 to 30 carbon atoms, and a substituted or unsubstituted aromatic six-membered heterocyclic group having 3 to 30 carbon atoms, provided that adjacent substituents may together form a ring; and n represents an integer of 1 or more and 4 or less.

12. The fluorescence and delayed fluorescence-type organic light-emitting element according to claim 11, wherein n in the general formula (1) represents 1.

13. The fluorescence and delayed fluorescence-type organic light-emitting element according to claim 11, wherein at least one of Ar in the general formula (1) represents an aromatic heterocyclic group.

14. The fluorescence and delayed fluorescence-type organic light-emitting element according to claim 11, wherein at least one of Ar in the general formula (1) represents a group represented by the following general formula (2):

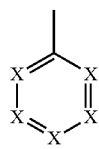

(2)

where: X's each independently represent N, C—H, or C—Ar$_1$ and at least one of X's represents N; and Ar$_1$'s each independently represent an aromatic hydrocarbon group or an aromatic heterocyclic group, provided that when X represents C—Ar$_1$, Ar$_1$ and a ring comprising X may have a side in common to form a fused ring.

15. An organic light-emitting element according to claim 11, wherein the organic light-emitting element comprises an organic electroluminescence element comprising:
   a substrate;
   an anode;
   a cathode; and
   at least one light-emitting layer comprising the organic light-emitting material, the anode and the cathode being provided on the substrate and the light-emitting layer being sandwiched between the anode and the cathode.

16. The fluorescence and delayed fluorescence-type organic light-emitting element according to claim 11, wherein a light emission from a light-emitting layer comprises fluorescence and delayed fluorescence, and the light emission includes 36% or more of a delayed fluorescence component.

* * * * *